(12) United States Patent
Oberegger et al.

(10) Patent No.: US 7,241,805 B2
(45) Date of Patent: Jul. 10, 2007

(54) MODIFIED RELEASE FORMULATIONS OF A BUPROPION SALT

(75) Inventors: Werner Oberegger, Mississauga (CA); Fang Zhou, Davie, FL (US); Paul Maes, Toronto, CA (US); Stefano Turchetta, Rome (IT); Graham Jackson, Kildare (IE); Pietro Massardo, Rome (IT); Mohammad Ashty Saleh, Oakville (CA)

(73) Assignee: Biovail Laboratories, Inc., Mississauga, Ontario (CA)

(*) Notice: Subject to any disclaimer, the term of this patent is extended or adjusted under 35 U.S.C. 154(b) by 0 days.

(21) Appl. No.: 11/475,252

(22) Filed: Jun. 27, 2006

(65) Prior Publication Data

US 2007/0027213 A1 Feb. 1, 2007

Related U.S. Application Data

(60) Provisional application No. 60/693,906, filed on Jun. 27, 2005.

(51) Int. Cl.
*A61K 31/195* (2006.01)
*A61K 9/48* (2006.01)

(52) U.S. Cl. ...................... 514/463; 424/464
(58) Field of Classification Search ................. 424/464
See application file for complete search history.

(56) References Cited

U.S. PATENT DOCUMENTS

| | | | |
|---|---|---|---|
| 3,819,706 A | 6/1974 | Nairman | |
| 4,021,492 A | 5/1977 | Linder | |
| 4,177,291 A | 12/1979 | Lindberg | |
| 4,308,400 A | 12/1981 | Felder | |
| 4,347,257 A | 8/1982 | Stern | |
| 4,393,078 A | 7/1983 | Peck | |
| 4,425,363 A | 1/1984 | Stern | |
| 4,435,449 A | 3/1984 | Stern | |
| 4,507,323 A | 3/1985 | Stern | |
| 4,816,489 A | 3/1989 | Lafon | |
| 4,980,377 A | 12/1990 | Lafon | |
| RE33,994 E | 7/1992 | Baker | |
| 5,358,970 A | 10/1994 | Ruff | |
| 5,427,798 A | 6/1995 | Ludwig | |
| 5,731,000 A * | 3/1998 | Ruff et al. ................. | 424/451 |
| 5,753,712 A | 5/1998 | Pinsker | |
| 5,968,553 A | 10/1999 | Maitra | |
| 6,110,973 A | 8/2000 | Young | |
| 6,150,420 A | 11/2000 | Houdi | |
| 6,153,223 A | 11/2000 | Apelian | |
| 6,197,827 B1 | 3/2001 | Cary | |
| 6,210,716 B1 | 4/2001 | Chen | |
| 6,221,917 B1 * | 4/2001 | Maitra et al. .............. | 514/649 |
| 6,280,763 B1 | 8/2001 | Midha | |
| 6,306,436 B1 | 10/2001 | Chungi | |
| 6,333,332 B1 | 12/2001 | Han | |
| 6,337,328 B1 | 1/2002 | Fang | |
| 6,458,374 B1 | 10/2002 | McCullough | |
| 6,589,553 B2 * | 7/2003 | Li et al. ..................... | 424/461 |
| 6,652,882 B1 | 11/2003 | Odidi | |
| 6,734,213 B2 | 5/2004 | Partridge | |
| 6,780,871 B2 | 8/2004 | Glick | |
| 6,869,942 B2 * | 3/2005 | Trofast et al. .............. | 514/171 |
| 6,893,660 B2 | 5/2005 | Li | |
| 6,932,971 B2 | 8/2005 | Bachmann | |
| 2001/0011103 A1 | 8/2001 | McCullough | |
| 2001/0031784 A1 * | 10/2001 | Petersen et al. ............ | 514/469 |
| 2002/0173551 A1 | 11/2002 | Reindler | |
| 2003/0035840 A1 | 2/2003 | Li | |
| 2003/0073872 A1 | 4/2003 | Atwood | |
| 2004/0059094 A1 | 3/2004 | Bachmann | |
| 2004/0102440 A1 | 5/2004 | Wong et al. | |
| 2004/0115263 A1 | 6/2004 | Robertson | |
| 2004/0225020 A1 | 11/2004 | McCullough | |
| 2005/0031670 A1 | 2/2005 | Jamerson | |
| 2005/0143322 A1 | 6/2005 | Gadde | |
| 2005/0176680 A1 | 8/2005 | Lalji | |
| 2005/0238718 A1 | 10/2005 | Oberegger | |
| 2005/0250838 A1 | 11/2005 | Challapalli | |
| 2006/0099262 A1 | 5/2006 | Chow | |

FOREIGN PATENT DOCUMENTS

| | | | |
|---|---|---|---|
| WO | WO 99/38502 | | 8/1999 |
| WO | WO 01/68627 | * | 9/2001 |
| WO | WO 03/040121 | * | 5/2003 |
| WO | WO 2004/024674 | | 3/2004 |
| WO | WO 2004/089873 | | 10/2004 |

OTHER PUBLICATIONS

Fava et al. "15 Years of Clinical Experience with Bupropion HCl:From Bupropion to Bupropion SR to Bupropion XL". Prim. Care Companion J Clin Psychiatry 2005; 7 (3) pp. 106-113.*

(Continued)

*Primary Examiner*—Thurman K. Page
*Assistant Examiner*—MLouisa Lao
(74) *Attorney, Agent, or Firm*—Hunton & Williams LLP

(57) ABSTRACT

The present invention relates to pharmaceutical compositions, formulations and medicaments comprising a bupropion salt, in particular, modified-release tablets comprising an effective amount of bupropion hydrobromide, and the use of the bupropion salt to prepare a medicament to treat a condition.

9 Claims, 71 Drawing Sheets

OTHER PUBLICATIONS

Berge et al. "Pharmaceutical Salts". J. Pharm Sci. Jan. 1977; vol. 66 (1).*

Stahl et al. "A Review of the Neuropharmacology of Bupropion, a Dual Norepinephrine and Dopamine Reuptake Inhibitor". Prim Care Companion, J Clin Psychiatry 2004; 6(4) pp. 159-166.*

"CITALOPRAM". http://www.answers.com/citalopram 4pages.*

Remington's Pharmaceutical Sciences, 17th ed. 1985 p. 1418.*

Wikipedia® i Wikimedia Foundation, Inc http://en.wikipedia.org/wiki/Bupropion#History 20:57, Apr. 8, 2007.*

Murray, et al., "Interaction of Dextrorotary Opioids with Phencyclidine Recognition Sites in Rat Brain Membranes", Life Sci., vol. 34, p. 1899-1911, 1984.

Nishikawa, et al., "Evidence for, and Nature of, the Tonic Inhibitory of Habenulointerpeduncular Pathways upon Cerebral Dopaminergic Transmissionin the Rat", Brian Res., vol. 373, p. 324-336, 1986.

Koyuncuoglu, et al., "The Treatment of Heroin Addicts with Dextromethorphan: A Double-blind Comparison of Dextromethrophan with Chlorpromazine", Int. J. Clin. Pharmacol. Ther., vol. 28, p. 147-152, 1990.

Glick, et al., "Effects and aftereffects of ibogaine on morphine self-administration in rats", Europ. J. Pharmacol., vol. 195, p. 341-345, 1991.

Flores, et al., "A Subtype of Nicotinic Cholinergic Receptor in Rat Brain is Comprised of 4 and 2 Subunits and is Up-regulated by Chronic Nicotine Treatment", Mol. Pharmacol., vol. 41, p. 31-37, 1992.

Koyuncuoglu, "The combination of tizanidine markedly improves the treatment with dextromethorphan of heroin addicted outpatients", Int. J. Clin. Pharmacol. Ther., vol. 33, No. 1, p. 13-19, Jan. 1995.

Popik, et al., "NMDA antagonist properties of the putative antiaddictive drug, ibogaine", Pharmacology and Experimental Therapeutics, vol. 275, No. 2, p. 753-760, 1995.

Sweetnam, et al., "Receptor Binding Profile Siggest Multiple Mechanisms of Action Are Responsible for Ibogaine's Putative Anti-addictive Activity", Psychopharmacology, vol. 118, p. 369-376, 1995.

Chen, et al., "Ibogaine block of the NDMA Receptor: in vitro and in vivo studies", Neuropharmacology, vol. 35, No. 4, p. 423-431, Apr. 1996.

Glick, et al., "18-Methoxycoronaridine, a non-toxic iboga alkaloid congener: effects on morphine and cocaine self-administration and on mesolimbic dopamine release in rats", Brain Res., vol. 719, vol. 1-2, p. 29-35, May 6, 1996.

Badio, et al., "Ibagaine: A Potent Noncopetitive Blocker of Ganglionic/Neuronal Nicotinic Receptors", Molec. Pharmacol., vol. 51, p. 1-5, 1997.

Pulvirenti, et al., "Dextromethorphan reduces intravenous cocaine self-administration in the rat", Eur. J. Pharmacol., vol. 321, No. 3, p. 279-283, Mar. 5, 1997.

Rezvani, et al., "Attenuation of Alcohol consumption by a novel nontoxic ibogaine analogue (18-methoxycoronaridine) in alcohol-preferring rats", Pharmacol. biochem. behav., vol. 58, No. 2, p. 615-619, 1997.

Ebert, et al. "Opioid Analgesics as noncompetitive N-mthyl-D-asparate (NMDA) Antagonists", Biochem Pharmacol., vol. 56, No. 5, p. 553-559, Sep. 1, 1998.

Glick, et al., "Mechanism of Antiaddictive Actions of Ibogaine", Annals of the New York Academy of Sciences, vol. 844, p. 214, 1998.

Mah, et al., "Ibogaine acts at the Nicotinic acetylcholine receptor to inhibit catecholamine release", Brain Res., vol. 797, No. 1, p. 173-180, Jun. 22, 1998.

Fryer, et al., "Noncopetitive Functional Inhibition at Diverse, Human Nicotinic Acetylcholine Receptor Subtypes by Bupropion, Phencyclidine, and Ibogaine", Pharmacology and Experimental Therapeutics, vol. 288, No. 1, p. 88-92, 1999.

Lukas, et al., "International Union of Pharmacology. XX. Current Status of the Nomenclature for Nicotinic Acetylcholine Receptors and their Subunits", Pharmacology and Experimental Therapeutics, vol. 51, No. 2, p. 397-401, 1999.

Maisonneuve, et al., "Attenuation of the Reinforcing efficacy of morphine by 18-methoxycoronaridine", Eur. J. Pharmacol., vol. 383, No. 1, p. 15-21, 1999.

Quick, et al., "3 4 Subunit-containing Nicotinic Receptors Dominate Function in Rat Medial Habenula Neurons", Neuropsychopharmacology, vol. 38, p. 769-783, 1999.

Reid, et al., "A Nicotine antagonist, Mecamylamine, reduces cue-induced cocaine craving in cocaine-dependent subjects", Neuropsychopharmacology, vol. 20, No. 3, p. 297-307, Mar. 1999.

Glick, et al., "18-MC reduces Methamphetamine and nicotine self-administration in rats", Neuroreport, vol. 11, No. 9, p. 2013-2015, 2000.

Glick, et al., "18-Methoxycoronaridine (18-MC) and Ibogaine: Comparison of Antiaddictive Efficacy, Toxicity, and Mechanisms of Action", Annals of the New York Academy of Sciences, vol. 914, 369-386, 2000.

Glick, et al., "Development of Novel Medication for Drug Addiction: The Legacy of an African Shrub", Annals of the New York Academy of Sciences, vol. 909, p. 88-103, 2000.

Hernandez, et al., "Dextromethorphan and its Metabolite Dextrorphan Block 3 4 Neuronal Nicotinic Receptors", J. Pharmacol, Exp. Ther., vol. 293, p. 962-967, 2000.

Jun, et al., "Dextromethorphan Alters methamphetamine self-administration in the rat", Pharmacol. Biochem. Behav., vol. 67, No. 3, p. 405-409, Nov. 2000.

Levin, et al., "Mecamylamine Preferentially Inhibits Cocaine Versus Food self-administration in Rats", Soc. Neurosci. Abstr., vol. 26, p. 1821, 2000.

Glick, et al., "Comparative Effects of dextromethorphan and dextrorphan on morphine, methamphetamine, and nicotine self-administration in Rats", Eur. J. Pharamcol., vol. 422, No. 1-3, p. 87-90, Jun. 22, 2001.

Klink, et al., "Molecular and Physiological Diversity of Nicotinic Acetylcholine Receptors in the Midbrain Dopaminergic Nuclei", The Journal of Neuroscience, vol. 21, No. 5, p. 1452-1463, Mar. 1, 2001.

Papke, et al., "Analysis of Mecamylamine Stereoisomers on Human Nicotinic Receptor Subtypes", Pharmacology and Experimental Therapeutics, vol. 297, No. 2, p. 646-656, 2001.

* cited by examiner

PXRD of Bupropion Hydrobromide Polymorphic Form I

DSC of Bupropion Hydrobromide Polymorphic Form I

PXRD of Bupropion Hydrobromide Polymorphic Form II

DSC of Bupropion Hydrobromide Polymorphic Form II

PXRD of Bupropion Hydrobromide Polymorphic Form III

DSC of Bupropion Hydrobromide Polymorphic Form III

PXRD of Bupropion Hydrobromide Form I after 6 months in ICH Conditions (40°C, 75% R.H.)

PXRD of Bupropion Hydrobromide Polymorphic Form II after 1 month in ICH Conditions (40°C, 75% R.H.)

PXRD of Bupropion Hydrobromide Polymorphic Form III after 1 month in ICH Conditions (40°C, 75% R.H.)

| PROJECT: BUP 10121 | | PROJECT: BUPROPION HBr XL TABLETS 348MG | | | | LOT NO.: BUP-HBr-XL-348-025-5 | |
|---|---|---|---|---|---|---|---|
| ACTIVE DRUG MFG SITE: | NA | PRODUCT MFG SITE: | NA | PACKG. SITE: | NA | EXPIRY DATE: NA | |
| ACTIVE DRUG MFG DATE: | NA | PRODUCT MFG DATE: | NA | CONTAINER: | BOTTLE | STABILITY STUDY #: STAB-05/064 | |
| ACTIVE DRUG LOT#: | NA | PRODUCT BATCH SIZE: | NA | CLOSURE: | NA | STABILITY PROGRAM: LONG TERM | |
| ACTIVE DRUG EXPIRY DATE: | NA | PRODUCT DESCRIPTION: | NA | DESICCANT: | NA | STORAGE CONDITIONS: 25°C/60%RH | |
| | | | | COUNT: | 90S | SCHEDULE: INITIAL, 3M, 6M, 9M, 12M | |

| TEST & METHODS | SPECIFICATIONS | INITIAL DATE: MAY 20/05 | 3 MONTHS DATE: AUG 20/05 | 6 MONTHS DATE: NOV 20/05 | 9 MONTHS DATE: FEB 20/06 | 12 MONTHS DATE: MAY 20/06 |
|---|---|---|---|---|---|---|
| | LAB SAMPLE # | E05-71 | H05-35 | K05-51 | B06-51 | |
| DESCRIPTION | REPORT RESULTS | OFF-WHITE COLOUR, ROUND TABLETS | CONFORMS | CONFORMS | CONFORMS | |
| ASSAY (%) | REPORT RESULTS | 99.6 | 99.4 | 97.4 | 96.8 | |
| IMPURITIES (%) | | | | | | |
| 3-CBA | NMT 0.7% | 0.012 | 0.046 | 0.071 | 0.172 | |
| 852U77 | NMT 1.0% | 0.028 | 0.138 | 0.185 | 0.207 | |
| 20U78/DILUENT | NMT 0.3% | 0.034 | 0.051 | 0.040 | 0.046 | |
| 827U76 | NMT 0.4% | ND | 0.011 | 0.018 | 0.010 | |
| MAJOR UNKNOWN | REPORT RESULTS | 0.253 (RRT 0.14) | 0.186 (RRT 0.13) | 0.657 (RRT 0.09) | 0.177 (RRT 0.15) | |
| TOTAL UNKNOWN | REPORT RESULTS | 0.376 | 0.342 | 1.055 | 0.280 | |
| TOTAL IMPURITIES | REPORT RESULTS | 0.45 | 0.59 | 1.37 | 0.72 | |
| KF (%) | REPORT RESULTS | 0.62 | 0.85 | 0.42 | 0.49 | |
| DISSOLUTION* | | | | | | |
| 2H | NMT 20% | 14 - 19 (16) | 13 - 17 (15) | 12 - 17 (14) | 12 - 20 (16) | - |
| 4H | 20 - 45% | 33 - 40 (36) | 30 - 35 (32) | 29 - 36 (32) | 29 - 40 (34) | - |
| 8H | 65 - 85% | 64 - 72 (68) | 57 - 64 (61) | 54 - 63 (58) | 55 - 68 (61) | - |
| 16H | NLT 80% | 92 - 101 (98) | 91 - 98 (94) | 89 - 97 (93) | 92 - 100 (96) | - |

*TENTATIVE SPECIFICATION

FIG. 63

| PROJECT: BUP 10121 | | PROJECT: BUPROPION HBr EA TABLETS 300MG | | | | LOT NO.: BUP-HBr-EA-300-001-5 | |
|---|---|---|---|---|---|---|---|
| ACTIVE DRUG MFG SITE: | N/A | PRODUCT MFG SITE: | N/A | PACKG. SITE: | N/A | EXPIRY DATE: | N/A |
| ACTIVE DRUG MFG DATE: | N/A | PRODUCT MFG DATE: | APR 19/05 | CONTAINER: | BOTTLE | STABILITY STUDY #: | STAB-05/072 |
| ACTIVE DRUG LOT #: | N/A | PRODUCT BATCH SIZE: | N/A | CLOSURE: | N/A | STABILITY PROGRAM: | ACCELERATED |
| ACTIVE DRUG EXPIRY DATE: | N/A | PRODUCT DESCRIPTION: | COATED TABLETS - 54MG WT GAIN | COUNT: | 90 COUNTS | STORAGE CONDITIONS: | 40°C/75%RH |
| | | | | DESICCANT: | N/A | SCHEDULE: INITIAL, 1M, 2M, 3M, 6M | |

| TEST & METHODS | SPECIFICATIONS | INITIAL | 1 MONTH | 2 MONTHS | 3 MONTHS | 6 MONTHS |
|---|---|---|---|---|---|---|
| | | DATE: JUN 13/05 | DATE: JUL 13/05 | DATE: AUG 13/05 | DATE: SEP 13/05 | DATE: DEC 13/05 |
| | LAB SAMPLE # | F05-5 | G05-10 | H05-24 | I05-13 | L05-23 |
| DESCRIPTION | REPORT RESULTS | CONFORMS | CONFORMS | CONFORMS | CONFORMS | CONFORMS |
| ASSAY (%) | REPORT RESULTS | 102.3 | 99.6 | 98.0 (*) | 101.8 | 101.0 |
| IMPURITIES (%) | | | | | | |
| 3-CBA | NMT 0.7% | 0.017 | 0.052 | 0.180 | 0.170 | 0.318 |
| 852U77 | NMT 1.0% | 0.023 | 0.221 | 0.438 | 0.256 | 0.221 |
| 20U78/DILUENT | NMT 0.3% | 0.044 | 0.036 | 0.032 | 0.057 | 0.059 |
| 827U76 | NMT 0.4% | 0.013 | 0.043 | 0.032 | 0.030 | 0.037 |
| MAJOR UNKNOWN | REPORT RESULTS | 0.623 (RRT 0.10) | 0.315 (RRT 0.10) | 0.205 (RRT 0.13) | 0.245 (RRT 0.14) | 0.651 (RRT 0.10) |
| TOTAL UNKNOWN | REPORT RESULTS | 1.054 | 0.675 | 0.381 | 0.421 | 1.125 |
| TOTAL IMPURITIES | REPORT RESULTS | 1.15 | 1.03 | 1.06 | 0.93 | 1.76 |
| KF (%) | REPORT RESULTS | 1.02 | 0.81 | 1.39 | 0.79 | 0.42 |
| DISSOLUTION* | | | | | | |
| 2H | NMT 20% | 13 - 15 (14) | 14 - 17 (16) | 15 - 17 (16) | 14 - 18 (16) | 12 - 13 (13) |
| 4H | 20 - 45% | 32 - 35 (33) | 33 - 37 (35) | 35 - 38 (36) | 33 - 38 (35) | 28 - 31 (30) |
| 8H | 65 - 85% | 64 - 69 (66) | 64 - 69 (67) | 65 - 71 (68) | 62 - 68 (65) | 55 - 59 (57) |
| 16H | NLT 80% | 96 - 101 (98) | 97 - 100 (98) | 97 - 102 (99) | 95 - 99 (97) | 90 - 92 (91) |

*TENTATIVE SPECIFICATION

FIG. 64-1

| PROJECT: BUP 10121 | | PROJECT: BUPROPION HBr EA TABLETS 300MG | | | | LOT NO.: | BUP-HBr-EA-300-001-5 |
|---|---|---|---|---|---|---|---|
| | | | | | | EXPIRY DATE: | N/A |
| ACTIVE DRUG MFG SITE: | N/A | PRODUCT MFG SITE: | N/A | PACKG SITE: | N/A | STABILITY STUDY #: | STAB-05/072 |
| ACTIVE DRUG MFG DATE: | N/A | PRODUCT MFG DATE: | APR 19/05 | CONTAINER: | BOTTLE | STABILITY PROGRAM: | ACCELERATED |
| ACTIVE DRUG LOT #: | N/A | PRODUCT BATCH SIZE: | N/A | CLOSURE: | N/A | STORAGE CONDITIONS: | 40°C/75%RH |
| ACTIVE DRUG EXPIRY DATE: | N/A | PRODUCT DESCRIPTION: | COATED TABLETS - 54MG WT GAIN | COUNT: | 90 COUNTS | SCHEDULE: | INITIAL, 1M, 2M, 3M, 6M |
| | | | | | | APPROVED BY / DATE: | |

FIG. 64-2

BUPROPION HBr XL 174MG CORE, LOT# BUP-HBr-XL-004-5 CORE

| TESTS | INITIAL | OPEN-CLOSED BOTTLE STABILITY (40C/75% RH) | | | |
|---|---|---|---|---|---|
| | | 10 DAYS-OPEN | 10 DAYS-CLOSED | 20 DAYS-OPEN | 20 DAYS-CLOSED |
| %ASSAY | 100.1 | 98.7 | 98.2 | 99.2 | 97.6 |
| %IMPURITIES | | | | | |
| 3-CBZ | 0.010 | 0.179 | 0.184 | 0.276 | 0.465 |
| 852U77 | 0.019 | 0.209 | 0.268 | 0.248 | 0.416 |
| 20U78/DILU | 0.054 | 0.055 | 0.060 | 0.058 | 0.063 |
| 827U76 | 0.026 | 0.131 | 0.308 | 0.102 | 0.497 |
| TOTAL UNKNOWN | 0.054 | 0.043 | 0.075 | 0.042 | 0.038 |
| TOTAL | 016 | 0.62 | 0.89 | 0.73 | 1.48 |

BUPROPION HBr XL 348MG CORE, LOT# BUP-HBr-XL-009-5 CORE

| TESTS | INITIAL | OPEN-CLOSED BOTTLE STABILITY (40C/75% RH) | | | |
|---|---|---|---|---|---|
| | | 10 DAYS-OPEN | 10 DAYS-CLOSED | 20 DAYS-OPEN | 20 DAYS-CLOSED |
| %ASSAY | 98.3 | 97.8 | 95.6 | 96.9 | 98.0 |
| %IMPURITIES | | | | | |
| 3-CBZ | 0.016 | 0.106 | 0.121 | 0.146 | 0.166 |
| 852U77 | 0.091 | 0.391 | 0.411 | 0.414 | 0.483 |
| 20U78/DILU | 0.054 | 0.051 | 0.055 | 0.056 | 0.055 |
| 827U76 | 0.020 | 0.077 | 0.102 | 0.059 | 0.119 |
| TOTAL UNKNOWN | 0.053 | 0.126 | 0.156 | 0.124 | 0.142 |
| TOTAL | 0.23^ | 0.74 | 0.84 | 0.80 | 0.97 |

FIG. 65A

BUPROPION HCl XL 150MG CORE, LOT# 05E056

| TESTS | INITIAL | OPEN-CLOSED BOTTLE STABILITY (40C/75% RH) | | | |
|---|---|---|---|---|---|
| | | 10 DAYS-OPEN | 10 DAYS-CLOSED | 20 DAYS-OPEN | 20 DAYS-CLOSED |
| %ASSAY | 97.5 | 98.4 | 97.5 | 98.1 | 97.6 |
| %IMPURITIES | | | | | |
| 3-CBZ | 0.006 | 0.079 | 0.052 | 0.185 | 0.238 |
| 852U77 | 0.043 | 0.406 | 0.342 | 0.520 | 0.685 |
| 20U78DILU | 0.044 | 0.046 | 0.046 | 0.059 | 0.052 |
| 827U76 | 0.028 | 0.050 | 0.074 | 0.069 | 0.127 |
| TOTAL UNKNOWN | 0.058 | 0.051 | 0.066 | 0.044 | 0.040 |
| TOTAL | 0.18 | 0.63 | 0.58 | 0.88 | 1.14 |

BUPROPION HCl XL 300MG CORE, LOT# 05D380

| TESTS | INITIAL | OPEN-CLOSED BOTTLE STABILITY (40C/75% RH) | | | |
|---|---|---|---|---|---|
| | | 10 DAYS-OPEN | 10 DAYS-CLOSED | 20 DAYS-OPEN | 20 DAYS-CLOSED |
| %ASSAY | 99.2 | 99.1 | 98.4 | 96.8 | 97.1 |
| %IMPURITIES | | | | | |
| 3-CBZ | 0.006 | 0.100 | 0.016 | 0.245 | 0.171 |
| 852U77 | 0.037 | 0.409 | 0.274 | 0.564 | 0.515 |
| 20U78DILU | 0.044 | 0.045 | 0.046 | 0.051 | 0.050 |
| 827U76 | 0.015 | 0.058 | 0.039 | 0.099 | 0.105 |
| TOTAL UNKNOWN | 0.044 | 0.038 | 0.045 | 0.032 | 0.052 |
| TOTAL | 0.15 | 0.65 | 0.42 | 0.99 | 0.90 |

FIG. 65B

USP-3 DIFFERENT MEDIA (SGF pH 1.2, ACETATE BUFFER pH 4.5 & PHOSPHATE BUFFER pH 6.8)
BUPROPION HBr XL 348MG TABLETS (FINAL LOT# BUP-HBr-XL-012-5 (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 9.0 | 8.3 | 8.9 | 11.6 | 8.8 | 8.6 | 9.2 |
| ACETATE BUFFER pH 4.5 | 2HRS | 15.8 | 15.0 | 19.3 | 18.5 | 17.5 | 18.2 | 17.4 |
| PHOSPHATE BUFFER SIF pH 6.8 | 2HRS | 26.8 | 25.4 | 24.9 | 33.3 | 27.7 | 24.2 | 27.1 |
| | 2HRS | 24.2 | 15.5 | 24.8 | 31.9 | 37.8 | 15.3 | 24.9 |
| | 2HRS | 22.5 | 19.5 | 16.6 | 1.4 | 2.4 | 25.8 | 14.7 |
| | 6HRS | 1.0 | 11.6 | 0.8 | 0.2 | 0.2 | 6.1 | 3.3 |
| TOTAL % RELEASED | | 99.3 | 95.3 | 95.3 | 96.9 | 94.4 | 98.2 | 96.6 |

WELLBUTRIN XL 300MG TABLETS (FINAL LOT# 05A116 (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 3.1 | 2.7 | 2.1 | 1.8 | 2.8 | 2.6 | 2.5 |
| ACETATE BUFFER pH 4.5 | 2HRS | 53.0 | 38.8 | 32.6 | 10.7 | 20.1 | 38.8 | 32.3 |
| PHOSPHATE BUFFER SIF pH 6.8 | 2HRS | 30.8 | 36.4 | 37.0 | 47.8 | 46.1 | 33.5 | 38.6 |
| | 2HRS | 5.6 | 15.2 | 25.0 | 22.4 | 22.8 | 19.6 | 18.4 |
| | 2HRS | 2.2 | 3.1 | 1.6 | 13.7 | 2.8 | 0.8 | 4.0 |
| | 6HRS | 0.9 | 0.3 | 0.2 | 0.9 | 0.2 | 0.1 | 0.4 |
| TOTAL % RELEASED | | 95.7 | 96.3 | 98.4 | 97.3 | 94.8 | 95.2 | 96.3 |

FIG. 66A

BUPROPION HBr XL 348MG TABLETS EC) LOT# BUP-HBr-XL-012-5 (EC 32MG WG.) (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 47.6 | 45.7 | 45.0 | 51.3 | 42.7 | 48.0 | 46.7 |
| ACETATE BUFFER pH 4.5 | 2HRS | 38.0 | 37.9 | 37.3 | 37.9 | 36.0 | 38.0 | 37.5 |
| PHOSPHATE BUFFER SIF pH 6.8 | 2HRS | 13.0 | 13.9 | 16.0 | 10.3 | 15.8 | 12.3 | 13.5 |
|  | 2HRS | 1.9 | 2.1 | 3.1 | 0.9 | 3.5 | 1.5 | 2.2 |
|  | 2HRS | 0.4 | 0.5 | 0.9 | 0.2 | 1.0 | 0.3 | 0.6 |
|  | 6HRS | 0.2 | 0.2 | 0.4 | 0.1 | 0.4 | 0.1 | 0.2 |
| TOTAL % RELEASED | | 100.9 | 100.3 | 102.7 | 100.6 | 99.4 | 100.2 | 100.7 |

WELLBUTRIN XL 300MG TABLETS (EC)-LOT# 05D047 (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 63.1 | 61.5 | 58.9 | 58.2 | 57.9 | 60.8 | 60.1 |
| ACETATE BUFFER pH 4.5 | 2HRS | 32.9 | 35.4 | 36.6 | 38.2 | 37.2 | 35.3 | 35.9 |
| PHOSPHATE BUFFER SIF pH 6.8 | 2HRS | 0.6 | 0.9 | 1.0 | 1.0 | 1.1 | 0.9 | 0.9 |
|  | 2HRS | 0.0 | 0.1 | 0.1 | 0.1 | 0.1 | 0.1 | 0.1 |
|  | 2HRS | 0.0 | 0.0 | 0.0 | 0.0 | 0.0 | 0.0 | 0.0 |
|  | 6HRS | 0.0 | 0.1 | 0.1 | 0.1 | 0.1 | 0.0 | 0.0 |
| TOTAL % RELEASED | | 96.7 | 97.9 | 96.6 | 97.6 | 96.3 | 97.1 | 97.0 |

FIG. 66B

MODIFIED RELEASE FORMULATIONS OF A BUPROPION SALT

RELATED APPLICATIONS

The present application claims priority from U.S. provisional application 60/693,906 filed Jun. 27, 2005, the contents of which is incorporated by reference in their entirety.

FIELD OF THE INVENTION

There is a need for dosage forms comprising a pharmaceutically acceptable salt of bupropion that is more stable than bupropion hydrochloride. Accordingly, the present invention relates to dosage forms comprising an effective amount of a pharmaceutically acceptable salt of bupropion that is more stable than bupropion hydrochloride. The present invention also relates to the use of such dosage forms for the treatment of one or more conditions in a subject suitable for treatment by bupropion or pharmaceutically acceptable salts thereof such as depression, nicotine addiction and obesity.

BACKGROUND

Bupropion is an antidepressant chemically unrelated to tricyclics, tetracyclics, selective serotonin re-uptake inhibitors (SSRIs), or other known antidepressant agents. The drug resembles a psycho stimulant in terms of its netirochemical and behavioral profiles in vivo, but it does not reliably produce stimulant-like effects in humans at clinically prescribed doses. Its structure closely resembles that of diethyipropion and it is related to phenylethylamines. It is designated as ($\pm$)-1-(3-chlorophenyl)-2-[(1,1-dimethylethyl)arnino]-1-propanone hydrochloride and by its generic name amfebutarnone hydrochloride. Bupropion hydrochloride is commercially available as an immediate release form (WELLBUTRIN®) and a sustained release form (WELUBUTRIN® SR and ZYBAN®). Both WELLBUTRIN® SR AND ZYBAN® are chemically and pharmaceutically identical.

The neurochemical mechanism of the antidepressant effcct of bupropion is not well known. Bupropion does not inhibit monoamine oxidase. Bupropion affects chemicals within the brain that nerves use to send messages to each other. These chemical messengers are called neurotransmitters. The neurotransmitters that are released by nerves are taken up again by the nerves that release them for reuse (this is referred to as reuptake). Many experts believe that depression is caused by an imbalance among the amounts of neurotransmitters that are released. It is believed that bupropion works by inhibiting the reuptake of the neurotransmitters dopamine, serotonin, and norepinephrine, an action which results in more dopamine, serotonin, and norepinephrine made available to transmit messages to other nerves. Accordingly, bupropion is unique in that its major effect is on dopamine, an effect which is not shared by the SSRIs (e.g. paroxetine (PAXIL®), fluoxetine (PROZAC®), scrtraline (ZOLOFT®)) or the tricyclic antidepressants or TCAs (e.g. amitriptyline (ELAVIL®). imipramine (TOFRANIL®), desiprarnine (NORPRAMIN®)).

WELLBUTRIN® and WELLBUTRN® SR are used for the management of depression. ZYBAN® has been approved as an aid to patients wanting to quit smoking. WELLBUTRIN®, the immediate release formulation of bupropion, is dosed three tunes a day, suitably with 6 or more hours in between doses. For patients requiring more than 300 mg bupropion a day. each dose should not exceed 150 mg. This requires administration of the tablets at least 4 times a day with at least 4 hours in between doses. The immediate release formulation results in more than a 75% release of the bupropion into the dissolution media in 45 minutes, and one of the major side effects of bupropion has been the incidence of seizures, which in part appears to be strongly associated with the immediate release of the bupropion into the system. Accordingly, sustained release products were developed to avoid the incidence of seizures. The sustained release products are dosed twice daily.

In general, patient compliance is a problem with medications that require a multiple dosing regimen and is especially problematic with depressed individuals. While sustained release formulations have simplified the dosing regimen and increased patient compliance, there is still room for further simplifying the dosing regimen and further improving patient adherence to the dosing regimen. The development of an approved stable once daily modified-release bupropion formulation would be an advance in the art.

The selection of a suitable salt for a drug candidate is recognized as an important step in the preclinical phase of drug development; however, the scientific literature on this topic is rather limited. Changing the salt form of a drug is a recognized means of modifying its chemical and biological properties without modifying its structure. As yet, there is no reliable way of predicting exactly what effect changing the salt form of an active drug will have on its biological activity. A decision to change the salt form at a later stage introduces the need to repeat toxicological, formulation and stability tests, with obvious implications for the overall development and production time for the new pharmaceutical product.

In general, a few of the factors that should be considered during a salt selection include: What is the effect of the salt on the chemical stability of the drug substance and the drug product? Does the salt form a hydrate? What is the solubility of the salt and is it appropriate for in vivo administration? What is the quality of the salt with regard to processing, issues with scale up, safety, etc.?

According to the CHEMICAL ABSTRACTS REGISTRY® Database, the only salts of bupropion that have been previously reported are the hydrochloride (HCl), (2Z)-2-butenedioate, (2E)-2-butenedioate, methane sulfonate, formic acid, 2-hydroxy-1,2,3-propanetricarboxylate, phosphate and trifluoromethanesulfonate salts.

There is a need for a once daily formulation of a pharmaceutically acceptable salt of bupropion with enhanced stability.

SUMMARY

The present invention relates to dosage forms comprising an effective amount of a pharmaceutically acceptable salt of bupropion (bupropion hydrobromide) which is more stable than bupropion hydrochloride. In particular such bupropion compositions are more stable than otherwise equivalent bupropion hydrochloride compositions when stored for at least 3 months and/or at least 6 months at 40 degrees C. and 75% relative humidity ("accelerated storage conditions") as evidenced by a reduced amount of at least one moiety characteristic of bupropion degradation and/or exhibit less fluctuation or reduction in potency after being stored for at least 3 months and/or at least 6 months under accelerated storage conditions relative to an otherwise similar bupropion hydrochloride composition as evidenced e.g., by less fluctuation in the in vitro dissolution profile in at least one dissolution medium over a 24 hour period.

The present invention also relates to the use of such more stable bupropion hydrobromide dosage forms for the treatment of one or more conditions in a subject.

The dosage forms of the present invention comprise a compound of formula I (bupropion hydrobromide):

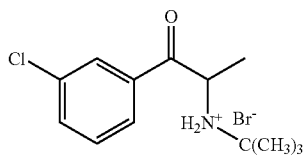

(I)

and pharmaceutically acceptable carriers, excipients and/or diluents, said composition having greater stability than a corresponding pharmaceutical composition comprising bupropion hydrochloride and pharmaceutically acceptable carriers, excipients and/or diluents.

In other embodiments of the present invention, the bupropion salt can be in the form of its anhydrous, hydrated, and solvated forms, in the form of prodrugs, and in the individually optically active enantiomers of the bupropion salt, such as for example (+)-bupropion and (−)-bupropion. Suitable pharmaceutically acceptable salts of bupropion for use in the present invention are more stable than bupropion hydrochloride. Suitable salts of bupropion also include for example, pharmaceutically acceptable acid addition salts. In certain embodiments, the acid addition salt of bupropion can be indirectly obtained by the separate addition of bupropion and an acid to the core formulation.

Another embodiment of the present invention contemplates the use of bupropion hydrobromide to prepare a medicament to treat a condition which can benefit from administration of bupropion, wherein said medicament has greater stability than a corresponding medicament comprising bupropion hydrochloride. Herein enhanced stability means that the salt or a composition containing is more stable after being stored for at least 3 months and/or 6 months at 40 degrees C. and 75% relative humidity (accelerated storage conditions) as evidenced by a lesser amount of at least one moiety characteristic of bupropion degradation and/or a reduction or fluctuation in potency evidenced e.g., by a greater fluctuation in the in vitro dissolution profile over at least a 12 or a 24 hour period in at least one dissolution medium relative and under the same conditions to an otherwise equivalent bupropion hydrobromide composition stored for the same length of time under the same accelerated storage conditions.

As discussed infra and generally known in the art appropriate dissolution medium and appropropriate conditions for assaying the dissolution characteristics of pharmaceutical dosage forms such as tablets are well known in the art and are contained in the United States Pharmacopoiea and its European or Japanese counterparts and include by way of example dissolution in USP Type 1 apparatus (Rotating Basket Method) in 900 ml water; 0.1 N HCl; 0.1N HCl+ 0.1% Cetrimide; USP buffer pH 1.5; Acetate buffer pH 4.5; Phosphate Buffer pH 6.5; or Phosphate Buffer pH 7.4 at 75 RPM at 37 degrees C.+/−0.5 degrees C.

Additionally, other disolution media include USP-3 media and USP-3 dissolution conditions i.e., SGF pH 1.2; Acetate buffer pH 4.5 and Phosphate Buffer pH 6.8.

In another embodiment of the present invention, the dosage forms comprising bupropion hydrobromide can be used to treat a condition which can benefit from administration of bupropion such as depression, seasonal effective disorder, smoking cessation or obesity.

Another embodiment of the present invention contemplates the use of bupropion hydrobromide to prepare a modified-release tablet of bupropion hydrobromide with enhanced stability. The tablets of the present invention, comprising bupropion hydrobromide, have unexpected enhanced stability compared to the prior art bupropion hydrochloride tablets.

In another embodiment the present invention contemplates the use of bupropion hydrobromide to produce once-daily administrable tablets or other dosage forms that are bioequivalent to WELBUTRIN™ or ZYBAN/WELLBUTRIN™ SR tablets as defined by FDA criteria when administered once daily to a subject in need thereof. In particular at least one of the Tmax, Cmax, and AUC profile are within 80-125% of WELLBUTRIN™ and ZYBAN™/ WELLBUTRIN™ when administered once daily to a subject in need thereof. Preferably, these formulations also will be free of any significant food effect.

In addition the present invention provivdes bupropion hydrobromide dosage forms containing at least one coating, e.g., tablets, which are resistant to dose dumping in high alcohol, e.g., 40% ethanol, because of the presence of an appropriate coating, i.e., a SMARTCOAT.™

Another embodiment of the present invention further contemplates a method of preparing a medicament for the treatment of a condition which can benefit from the administration of bupropion comprising bringing an effective amount of bupropion hydrobromide into contact with one or more pharmaceutically acceptable carriers, diluents and/or excipients.

Another embodiment of the present invention contemplates a method of treating a condition which can benefit from the administration of bupropion comprising administering an effective amount of bupropion hydrobromide to a subject. For example, such conditions which can benefit from administration of bupropion hydrobromide include but are not limited to depression, including seasonal effective disorder, cognitive symptoms in depression, bipolar depression, post partum depression, minor depression, lack of energy in depression, suicidal depression, anxiety disorders, generalized anxiety disorder, social anxiety disorder, obsessive compulsive disorder, post traumatic stress disorder (PTSD), panic disorder, disorders requiring a stimulant effect, attention deficit/hyperactivity disorder (ADHD), narcolepsy, hypersomnia, substance-abuse disorders, stimulant dependence, marijuana dependence, nicotine dependence, obesity, female and male sexual dysfunction such as premature ejaculation, premenstrual syndrome, premenstrual dysphoric disorder, neuropathic pain, fibromyalgia, diabetic neuropathy, viral infection, sleep apnea, sleep disorders and migraines. The conditions may be focused on different demographic populations, such as reproductive related mood disorders, specific age population disorders and specific ethnic population disorders.

According to an aspect of the invention, there is provided a composition for administration to a subject in need of treatment for a condition. The composition comprises a pharmaceutically effective amount of a bupropion salt that is more stable than bupropion hydrochloride as defined herein. In addition, the composition is more stable than a corresponding composition comprising bupropion hydrochloride.

The present invention includes both oral and non-oral bupropion hydrobromide containing medicaments. Prior to the present invention medicaments containing bupropion hydrobromide were unavailable Particularly, the invention embraces compositions suitable for topical, injectable, inhalation and other modes of administration. Typically the medicaments of the present invention are orally administrable.

In particular the invention includes extended release formulations. In another aspect, the present invention includes delayed release formulations. Further, the present invention embraces enhanced absorption formulations.

In a particular embodiment, the inventive compositions include controlled release matrix tablet formulations.

In a more particular implementation of the invention, a bupropion medicament composition according to the invention may comprise (i) a core that includes bupropion hydrobromide, a binder and a lubricant; and (ii) a control releasing coat substantially surrounding said core; wherein said composition provides controlled release of said bupropion hydrobromide. Such composition optionally may comprise one or more additional coatings surrounding the core and/or the control releasing coat such as moisture barrier coats, enteric coats or coatings that affect the physical integrity and/or appearance of the bupropion The binder can be selected from known pharmaceutical binders such as polyvinyl alcohol. The lubricant also can be selected from known pharmaceutical lubricants such as glyceryl behenate. The control releasing coat can include a water-insoluble polymer, a water-soluble polymer, and optionally a plasticizer. The water-insoluble polymer can be selected from a range of water insoluble polymers useful in extended release pharmaceutical compositions such as ethylcellulose. The water-soluble polymer can be selected from a variety of water-soluble polymers useful in extended release pharmaceutical compositions such as polyvinylpyrrolidone. The plasticizer if present can be selected from a range of known plasticizers such as mixtures of polyethylene glycol 4000 and dibutyl sebacate. These compositions include once-daily administrable compositions that are bioequivalent to WELLBUTRIN™ or ZYBAN™/WELLBUTRIN™ SR tablets when administered once-daily to a subject in need thereof may be bioequivalent. These compositions optionally may not exhibit a food effect and/or may be resistant to dose dumping in the presence of high alcohol concentrations (i.e., 40% by weight of ethanol).

In a more particular implementation of the invention, the subject bupropion composition comprises (i) a core that includes bupropion hydrobromide, a binder and a lubricant; and (ii) a control releasing coat substantially surrounding said core; wherein said control releasing coat includes an aqueous dispersion of a neutral ester copolymer without any functional groups, a polyglycol having a melting point greater than 55° C., and one or more pharmaceutically acceptable excipients, wherein said coat is coated onto said core and cured at a temperature at least equal to or greater than the melting point of the polyglycol. Optionally, this medicament may comprise one or more additional coatings surrounding the core and/or control-release coating such as moisture barrier coats, enteric coats, coats that preclude dose dumping in specific media such as alcohol, and coatings that affect the physical stability or integrity of the medicament and/or its physical appearance.

In a particular implementation of the invention, the subject bupropion composition comprises multiparticulates.

In a particular implementation of the invention, the subject bupropion composition comprises a second drug. The second drug can be any drug which may be administered in combination with the subject bupropion salt such as other anti-depressants, SSRI's, anti-anxiety agents, etc. The invention embraces drug combinations wherein the second drug may elicit a synergistic benefit on bupropion efficacy as well as non-synergistic drug combinations. In particular the invention embraces bupropion hydrobromide compositions wherein the second drug is citalopram, escitalopram and/or venlafaxine.

According to another aspect of the invention, there is provided a method of using a composition according to any of the foregoing claims for treatment in a subject in need of such administration. This includes in particular the treatment of depression, obesity and abuse disorders such as nicotine addiction and smoking cessation. In an exemplary embodiments such treatments comprise once-daily dosage regimens.

According to another aspect of the invention, there is provided a use of bupropion hydrobromide to prepare a medicament to treat conditions which benefit from administration of bupropion, wherein said medicament has greater stability than a corresponding medicament comprising bupropion hydrochloride.

In accordance with one aspect of the present invention, there is provided a controlled release tablet, comprising (i) a core comprising an effective amount of a bupropion hydrobromide, a binder, a lubricant; and (ii) a control-releasing coat surrounding said core; and optionally (iii) a moisture barrier surrounding said control-releasing coat or the core; and; wherein the extended release tablet exhibits a dissolution profile such that after 2 hours, no more than 20% of the bupropion hydrobromide content is released, for example in certain embodiments 2% to 18%, 4% to 8%, or 5% of the bupropion hydrobromide content is released after 2 hours; after 4 hours, 15% to 45% of the bupropion hydrobromide content is released, for example in certain embodiments 21% to 37%, 28% to 34%, or 32% of the bupropion hydrobromide content is released after 4 hours; after 8 hours, 40% to 90% of the bupropion hydrobromide content is released, for example in certain embodiments 60% to 85%, 68% to 74%, or 74% of the bupropion hydrobromide content is released after 8 hours; and after 16 hours no less than 80% of the bupropion hydrobromide content is released, for example in certain embodiments not less than 93%, not less than 96%, or not less than 99% of the bupropion hydrobromide content is released after 16 hours; and wherein the bupropion hydrobromide salt contained in said extended release tablet has greater stability than a tablet having the same composition with the exception that bupropion hydrobromide is replaced with bupropion hydrochloride.

In another aspect the composition exhibits a dissolution profile such that after 2 hours not more than 40% of the bupropion hydrobromide is released, e.g., 33%, after 4 hours from 40-75%, e.g., 59% of the bupropion hydrobromide is released, after 8 hours not less than 75% of the bupropion hydrobromide is released, e.g., 91%, and after 16 hours not less than 85% of the bupropion hydrobromide is released, e.g., 97%. These medicaments will typically comprise 50-500 mg of bupropion hydrobromide. In exemplary embodiments disclosed herein the medicament contain 174 mg or 348 mg of bupropion hydrobromide.

In accordance with another aspect of the present invention, there is provided an enhanced-absorption tablet, comprising (i) a core comprising an effective amount of bupropion hydrobromide, a binder, a lubricant; and (ii) a control-releasing coat surrounding said core; and wherein the enhanced absorption tablet exhibits a dissolution profile such that after 2 hours, no more than 25% of the bupropion hydrobromide content is released, for example in certain embodiments 10% to 20% of the bupropion hydrobromide content is released after 2 hours; after 4 hours, 25% to 55% of the bupropion hydrobromide content is released, for example in certain embodiments 30% to 50%, of the bupropion hydrobromide content is released after 4 hours; after 8 hours, more than 60% of the bupropion hydrobromide content is released, for example in certain embodiments 70% to 90% of the bupropion hydrobromide content is released after 8 hours; and after 16 hours more than 70% of the bupropion hydrobromide content is released, for example in certain embodiments more than 80% of the bupropion hydrobromide content is released after 16 hours; and wherein said extended release tablet has greater stability than a tablet having the same composition with the exception that bupropion hydrobromide is replaced with bupropion hydrochloride. This composition optionally may further comprise one or more additional coats surrounding the core and/or control-release coat.

In an exemplary embodiment this composition may comprise a dissolution profile such that after 2 hours not more than 40% of bupropion hydrobromide is released therefrom, e.g., 33%; after 4 hours 40-75% of bupropion hydrobromide is released therefrom, e.g., 59%, after 8 hours not less than 75% of bupropion hydrobromide is released therefrom, e.g., 91%, and after 16 hours not less than 85% of bupropion hydrobromide is released therefrom, e.g., 97%.

In accordance with a further aspect of the invention there is provided a salt of bupropion and polymorphic forms thereof having enhanced stability wherein the salt is hydrobromide, and wherein enhanced stability refers to the reduced formation of at least one degradation product characteristic of bupropion degradation and/or the increased retention of potency as evidenced e.g., by a reduced fluctuation in the in vitro dissolution profile in at least one dissolution medium relative to an otherwise equivalent formulation containing bupropion hydrochloride when the formulations containing these bupropion salts are stored for prolonged time periods under equivalent conditions. In particular enhanced stability refers to bupropion hydrobromide compositions that are less subject to degradation than an otherwise equivalent bupropion hydrochloride composition when stored under accelerated storage conditions, i.e., 40 degrees C. at 75% relative humidity for at least 3 months, and/or for at least 6 months or longer and/or which exhibits less fluctuation or reduction in potency as evidence by a reduced fluctuation in the in vitro dissolution profile in at least one dissolution medium wherein dissolution is effected under the same conditions after the bupropion hydrobromide and bupropion hydrochloride compositions are stored for at least 3 months and/or at least 6 months at 40 degrees C. and 75% relative humidity. In the present invention, as described infra, degradation is assayed based on the amount of at least one compound characteristic of bupropion degration.

More particularly, the present invention embraces enhanced absorption tablets comprising (i) a core comprising an effective amount of bupropion HBr, a binder, a lubricant: and (ii) a control-releasing coat surrounding said core; wherein the enhanced absorption tablet exhibits a dissolution profile such that after 2 hours no more than 40% of bupropion is released, (e.g, 33%); after 4 hours 40-75% bupropion is released (e.g., 59%), after 8 hours at least 75% is released (e.g., 91%); and after 16 hours at least 85% is released (e.g, 97%)

As discussed infra, in vitro dissolution of bupropion from controlled or extended release formulations according to the invention can be determined by methods well known to those skilled in the pharmaceutical art. Suitable methods are contained in the United States Pharmacopoiea (USP) as well as European and Japanese counterparts of the USP and are exemplified infra. This includes by way of example effecting dissolution in a USP 1 apparatus (Rotating Type Basket Method) in 900 ml water, 0.1N HCl, 0.1N HCl+0.1% Cetrimide, USP Buffer pH 1.5, Acetate Buffer pH 6.5 or Phosphate Buffer pH 7.4 at 75 RPM at 37 degrees C.+/−0.5 degrees C. or by effecting dissolution using a USP3 dissolution medium such as SGF having a pH 1.2; acetate buffer having a pH of 4.5 or phosphate buffer having a pH of 6.8.

BRIEF DESCRIPTION OF THE DRAWINGS

FIGS. 51A and 50B contain bar graphs showing the % of 20U78 formed in forced degradation studies of bupropion HCl vs. bupropion HBr in the presence of excipients.

FIG. 63 contains the results of stability studies for Bupropion HBr XL 174 mg core (Lot # Bup-HBr-XL-004-5 core; Bupropion HBr XL 348 mg core (Lot # Bup-HBr-XL-009-5 core; Bupropion HCl XL 150 mg core (Lot # 05E056) and Bupropion HCl XL 300 mg core (Lot # 05D380) initially, after 10 days open and closed, and after 20 days open and closed. The % of impurities 3-CBZ, 852U77, 20U78dilu, 827U76 are shown therein.

FIG. 64 and FIGS. 65A and 65B respectively contain stability data for bupropion 348 mg HBr XL tablets (Lot #

Bup-HBr-XL-348-025-5) and Bupropion HBr EA 300 mg tablets (Lot # Bup-HBr-EA-300-001-5 initially and after 3 months, 6 months, 9 months and 12 months under accelerated storage conditions (40 degrees C. and 75% relative humidity). The assay tested for amount of impurities 3-CBA, 852U77, 20U78/diluent. 827U76, and also compared the dissolution profiles and appearance thereof.

FIGS. 66A and 66B compare the dissolution profiles and in vitro drug release of Bupropion HBr XL 348 mg tablets (final) Lot # Bup-HBr-XL-012-5, Wellbutrin XL 300 mg tablets final (Lot # 05A116), Bupropion HBr XL 348 mg tablets ECl) Lot # Bup-HBr-XL-012-5 (EC 32mg wg), and Wellbutrin XL 300 mg tablets (ECl) (Lot # 05D047) in different USP-3 media (SGF pH 1.2, Acetate Buffer pH 4.5, and Phosphate Bulter pH 6.8 over a period of 16 hours.

FIGS. 67A, 67B and 67C compare the dissolution profiles and drug release for Bupropion HBr 348 mg Lot # 05E304 in different USP-3 media (SGF pH 1.2, Acetate Buffer pH 4.5, Phosphate Buffer SIF pH6.8) over a period of 16 hours and further compares this release profile against the release profile for Bup 300 XL Target (01L238) in vivo and BUP 300XL Target (01L238) in vitro in USP-3 media.

FIGS. 68A and 68B contain comparative dissolution profiles for Bupropion HBr XL 348 mg and Wellbutrin XL (final and EC) in USP-3 media (ph 1.2 SGF, pH 4.5 acetate buffer and pH 6.8 phosphate buffer over a period of 16 hours.

FIG. 66 compares the dissolution profiles and in vitro drug release of Bupropion HBr XL 348 mg tablets (final) Lot # Bup-HBr-XL-012-5, Wellbutrin XL 300 mg tablets final (Lot # 05A 116), Bupropion HBr XL 348 mg tablets ECl) Lot # Bup-HBr-XL-012-5 (EC 32 mg wg), and Wellbutrin XL 300 mg tablets (ECl) (Lot # 05D047) in different USP-3 media (SGF pH 1.2, Acetate Buffer pH 4.5, and Phosphate Buffer pH 6.8 over a period of 16 hours.

Figure 67:
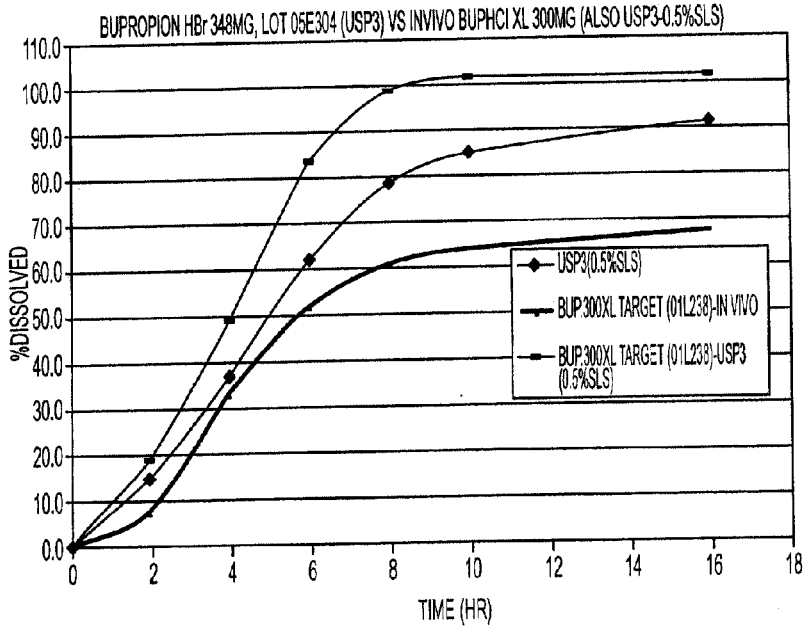

FIG. 67 compares the dissolution profiles and drug release for Bupropion HBr 348 mg Lot # 05E304 in different USP-3 media (SGF pH 1.2, Acetate Buffer pH 4.5, Phosphate Buffer SIF pH 6.8) over a period of 16 hours and further compares this release profile against the release profile for Bup 300 XL Target (01L238) in vivo and BUP 300XL Target (01L238) in vitro in USP-3 media.

Figure 68:
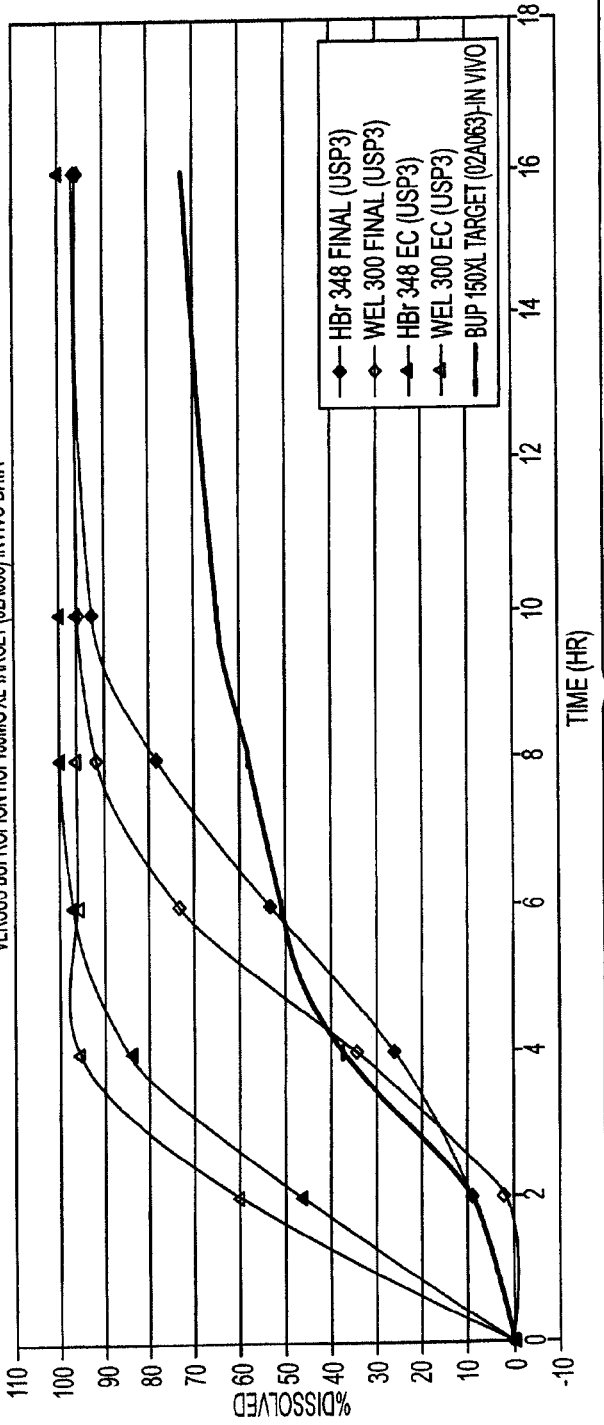

FIG. 68 contains comparative dissolution profiles for Bupropion HBr XL 348 mg and Wellbutrin XL (final and EC) in USP-3 media (pH 1.2 SGF, pH 4.5 acetate buffer and pH 6.8 phosphate buffer over a period of 16 hours.

DEFINITIONS

The term "bupropion salt" herein has its ordinary meaning and includes any salt of bupropion.

The term "bupropion salt that is more stable than bupropion hydrochloride" refers to a bupropion salt or a composition containing that is less subject to degradation than an otherwise equivalent bupropion hydrochloride salt or composition containing when stored for at least 3 months, 4 months, 5 months, and/or at least 6 months under accelerated storage conditions (40 degrees C., and 75% relative humidity), and/or when stored for at least 3, 4, 5 and/or 6 months under accelerated storage conditions (40 degrees C. and 75% relative humidity) and/or which exhibits less of a reduction or fluctuation in potency as evidenced by less fluctuation in the in vitro dissolution profile in at least one dissolution medium relative to an otherwise similar bupropion hydrochloride composition wherein dissolution is effected under the same conditions after these compositions are stored for at least 3, 4, 5, or 6 months at 40 degrees C. at 75% relative humidity. Particularly, bupropion hydrobromide salts and polymorphs thereof may result in bupropion formulations that exhibit dissolution profiles over time that are less subject to fluctuation when stored under accelerated storage conditions for prolonged time periods, i.e., at least 3, 4, 5, or 6 months at 40 degrees C. and 75% relative humidity.

The term "active", "active agent", "active pharmaceutical agent", "active drug" or "drug" as used herein means any active pharmaceutical ingredient ("API"), including its pharmaceutically acceptable salts (e.g. the hydrochloride salts, the hydrobromide salts, the hydroiodide salts, and the saccharinate salts), as well as in the anhydrous, hydrated, and solvated forms, in the form of prodrugs, and in the individually optically active enantiomers of the API as well as polymorphs of the API.

The term "dose dumping" herein refers to the rapid release of a drug from a medicament under certain conditions such as solvent conditions e.g., high (40%) ethanol.

The term "other drug" or "second drug" as used herein means a drug other than bupropion, including but not limited to anti-depression agents, other neuropsychiatric drugs, vasodilators, anti-anxiety agents, appetite modulators, sleep modulating drugs, SSRIs, anti-viral agents, anti-pain agents, anti-migraine agents, anti-inflammatories (both steroidal and non-steroidal) and marc particularly may include citalopram, escitalopram, venlafaxine, clozapine, melperone. amperozide, iloperidone, risperidone, quetiapene, olanzapine, ziprasidone, aripiprazole, reboxetine, VIAGRA®, sertraline, paroxetine, fluoxetine, gabapentin, vaiproic acid, amitriptyline, lofepramine, fluvoxamine, in,ipramine, mirtazapine, nefazodane, nortriptvline, SAM-E, combinations thereof, and their pharmaceutically acceptable salts (e.g. the hydrochloride salts, the hydrobromide salts, the hydroiodide salts, and the saceharinate salts), as well as in the anhydrous, hydrated, and solvated forms, in the form of prodrugs, and in the individually optically active enantiomers of the drug.

The term "formulation" or "composition" as used herein refers to the drug in combination with pharmaceutically acceptable carriers and additional inert ingredients. This includes orally administrable formulations as well as formulations administrable by other means.

The term "dosage form" as used herein is defined to mean a pharmaceutical preparation in which doses of active drug are included.

"Modified release dosage forms" as used herein is as defined by the United States Pharmacopoeia (USP) as those whose drug release characteristics of time course and/or location are chosen to accomplish therapeutic or convenience objectives not offered by conventional, immediate release or uncoated normal matrix dosage forms. The rate of release of the active drug from a modified release dosage form is controlled by features of the dosage form and/or in combination with physiologic or environmental conditions rather than by physiologic or environmental conditions alone. The modified release dosage forms of the invention can be contrasted to conventional, immediate release, or uncoated normal matrix dosage forms which typically produce large maximum/minimum plasma drug concentrations (Cmax/Cmin) due to rapid absorption of the drug into the body (i.e., in vivo, relative to the drug's therapeutic index; i.e., the ratio of the maximum drug concentration needed to produce and maintain a desirable pharmacological response). In conventional, immediate release or uncoated normal matrix dosage forms, the drug content is released into the gastrointestinal tract within a short period of time, and plasma drug levels peak shortly after dosing. The design of conventional, immediate release or uncoated normal matrix dosage forms is generally based on getting the fastest possible rate of drug release, and therefore absorbed, often at the risk of creating undesirable dose related side effects. The modified release dosage forms of the invention, on the other hand, improve the therapeutic value of the active drug by reducing the ratio of the maximum/minimum plasma drug concentration (Cmax/Cmin) while maintaining drug plasma levels within the therapeutic window. The modified release dosage forms of the invention attempt to deliver therapeutically effective amount of bupropion salt and combinations thereof as a once-daily dose so that the ratio Cmax/Cmin in the plasma at steady state is less than the therapeutic index, and to maintain drug levels at constant effective levels to provide a therapeutic benefit over a 24-hour period. The modified release dosage forms of the invention, therefore, avoid large peak-to-trough fluctuations normally seen with conventional or immediate release dosage forms and can provide a substantially flat serum concentration curve throughout the therapeutic period. Modified-release dosage forms can be designed to provide a quick increase in the plasma concentration of the bupropion salt which remains substantially constant within the therapeutic range of bupropion salt for at least a 24-hour period. Alternatively, modified-release dosage forms can be designed to provide a quick increase in the plasma concentration of the bupropion salt, which although may not remain constant, declines at rate such that the plasma concentration remains within the therapeutic range for at least a 12 hour and desirably at least a 24-hour period.

The modified release dosage forms of the invention can be constructed in many forms known to one of ordinary skill in the drug delivery arts and described in the prior art such as for example, "modified release matrix dosage forms", "normal release matrix dosage forms" coated with at least one "control-releasing coat", "osmotic dosage forms", "multiparticulate dosage forms", and "gastric retention dosage forms". The USP considers that the terms controlled release, prolonged release and sustained release are interchangeable. Accordingly, the terms "modified-release", controlled-release", "control-releasing", "rate-controlled release", "prolonged-release", and "sustained-release" are used interchangeably herein. For the discussion herein, the definition of the term "modified-release" encompasses the scope of the definitions for the terms "extended release", "enhanced-absorption", "controlled release", and "delayed release".

"Controlled release dosage forms" or "control-releasing dosage forms", or dosage forms which exhibit a "controlled release" of the bupropion salt as used herein is defined to mean dosage forms administered once- or twice-daily that release the bupropion salt at a controlled rate and provide plasma concentrations of the bupropion salt that remain controlled with time within the therapeutic range of the bupropion salt over a 12 or 24-hour period. "Controlled release" or "control releasing" is defined to mean release of the drug gradually or in a controlled manner per unit time. For example, the controlled rate can be a constant rate providing plasma concentrations of the bupropion salt that remain invariant with time within the therapeutic range of the bupropion salt over at least a 12 or 24-hour period.

"Sustained-release dosage forms" or dosage forms which exhibit a "sustained-release" of the bupropion salt as used herein is defined to mean dosage forms administered once-daily that provide a release of the bupropion salt sufficient to provide a therapeutic dose soon after administration, and then a gradual release over an extended period of time such that the sustained-release dosage form provides therapeutic benefit over a 12 or 24-hour period.

"Extended-or sustained-release dosage forms" or dosage forms which exhibit an "extended or sustained release" of the bupropion salt as used herein is defined to include dosage forms administered once-or twice-daily that release the bupropion salt slowly, so that plasma concentrations of the bupropion salt are maintained at a therapeutic level for an extended period of time such that the extended or sustained-release dosage form provides therapeutic benefit over a 12 or 24-hour period.

"Prolonged-release dosage forms" or dosage forms which exhibit a "prolonged release" of the bupropion salt as used herein is defined to mean dosage forms administered once daily which provide for absorption of the bupropion salt over a longer period of time than from a conventional, immediate release or uncoated normal release matrix dosage form and which provide therapeutic benefit over at least a 12 hour and more typically at least a 24-hour period.

"Delayed-release dosage forms" or dosage forms which exhibit a "delayed release" of the bupropion salt as used herein is defined to mean dosage forms administered once-daily that do not effectively release drug immediately following administration but at a later time. Delayed-release dosage forms provide a time delay prior to the commencement of drug-absorption. This time delay is referred to as "lag time" and should not be confused with "onset time" which represents latency, that is, the time required for the drug to reach minimum effective concentration.

"Enhanced absorption dosage forms" or dosage forms which exhibit an "enhanced absorption" of the bupropion salt as used herein is defined to mean dosage forms that when exposed to like conditions, will show higher release and/or more absorption of the bupropion base as compared to other dosage forms with the same or higher amount of bupropion base. The same therapeutic effect can be achieved with less bupropion base in the enhanced absorption dosage form as compared to other dosage forms.

The term "controlled release matrix" as used herein is defined to mean a dosage form in which the bupropion salt and combinations thereof is dispersed within a matrix, which matrix can be either insoluble, soluble, or a combination thereof. Controlled release matrix dosage forms of the insoluble type are also referred to as "insoluble polymer matrices", "swellable matrices", or "lipid matrices" depending on the components that make up the matrix. Controlled release matrix dosage forms of the soluble type are also referred to as "hydrophilic colloid matrices", "erodible matrices", or "reservoir systems". Controlled release matrix dosage forms of the invention refer to dosage forms comprising an insoluble matrix, a soluble matrix or a combination of insoluble and soluble matrices in which the rate of release is slower than that of an uncoated non-matrix conventional or immediate release dosage forms or uncoated "normal release matrix" dosage forms. Controlled release matrix dosage forms can be coated with a "control-releasing coat" to further slow the release of the bupropion salt from the controlled release matrix dosage form. Such coated controlled release matrix dosage forms can exhibit "modified-release", controlled-release", "sustained-release", "extended-release", "prolonged-release", "delayed-release" or combinations thereof of the bupropion salt.

The term "normal release matrix" as used herein is defined to mean dosage forms in which the bupropion salt and combinations thereof is dispersed within a matrix, which matrix can be either insoluble, soluble, or combinations thereof but constructed such that the release of the bupropion salt mimics the release rate of an uncoated non-matrix conventional or immediate release dosage form comprising the bupropion salt. The release rate from normal release matrix dosage forms can be slowed down or modified in conjunction with a "control releasing coat".

A "control releasing coat" or "controlled release coat" as used herein is defined to mean a functional coat which can for example comprise at least one pH independent polymer, pH dependent (such as for example enteric or reverse enteric types) polymer, soluble polymer, insoluble polymer, lipids, lipidic materials or combinations thereof which when applied onto a dosage form can slow (for example when applied to a normal release matrix dosage form), further slow (for example when applied to a controlled release matrix dosage form) or modify the rate of release of the bupropion salt when applied to an uncoated dosage form. For example, the control releasing coat can be designed such that when the control releasing coat is applied to a dosage form, the dosage form in conjunction with the control releasing coat can exhibit the release of the bupropion salt, such as for example, as a "modified-release", "controlled-release", "sustained-release", "extended-release", "delayed-release", "prolonged-release" or combinations thereof. The "control releasing coat" can optionally comprise additional materials that can alter the functionality of the control releasing coat.

The term "moisture barrier" as used herein is one, which impedes or retards the absorption of moisture. It is known that bupropion salts are hygroscopic and, as such, are susceptible to decomposition over time under high humidity conditions. The proportion of the components of the moisture barrier and the amount of the moisture barrier optionally applied onto the control-releasing coat or onto the core is typically such that the moisture barrier does not fall within the USP definition and requirement for an enteric coat. Suitably, the moisture barrier is comprised of an enteric and/or acrylic polymer, suitably an acrylic polymer, optionally a plasticizer, and a permeation enhancer. The permeation enhancer is a hydrophilic substance, which allows water to enter without physical disruption of the coating. The moisture barrier may additionally contain other conventional inert excipients, which may improve processing of the extended-release formulation described herein.

The term "medicament" as used herein refers to all possible oral and non-oral dosage forms, including but not limited to, all modified release dosage forms, osmosis controlled release systems, erosion controlled release systems, dissolution controlled release systems, diffusion controlled release systems, matrix tablets, enteric coated tablets, single and double coated tablets (including the extended release and enhanced absorption tablets as described herein), capsules, minitablets, caplets, coated beads, granules, spheroids, pellets, microparticles, suspensions, topicals such as transdermal and transmucoasal compositions and delivery systems (containing or not containing matrices), injectables, and inhalable compositions.

The term "enhanced stability", "greater stability", "increased stability" or "more stable" as used herein when referring to a bupropion salt (bupropion HBr) means that the bupropion salt (bupropion hydrobromide), and compositions, formulations or medicaments comprising the bupropion salt, when exposed to like conditions, i.e, when stored for at least 3 months under accelerated storage conditions (40 degrees C., 75% relative humidity) and/or when stored for at least 3, 4, 5 and/or 6 months or a year or more under accelerated storage conditions (40 degrees C., 75% relative humidity) show less degradation as determined by the formation of less of at least one degradation product than an otherwise similar composition containing bupropion HCl. Additionally enhanced stability or greater stability or increased stability of a bupropion salt (relative to bupropion HCl) includes bupropion HBr compositions which exhibit more consistent dissolution profiles and therefore potency, compared to an otherwise similar bupropion hydrochloride formulation after being stored for at least 3, 4, 5 and/or 6 months under the same accelerated storage conditions of 40 degrees C. and 75% relative humidity.

By "less degradation" it is meant any measurable decrease in the amount of at least one impurity characteristic of bupropion degradation or any measurable difference in the retention of potency relative to an otherwise similar bupropion HCl composition after being stored for at least 3, 4, 5 and/or 6 months or longer, e.g, one or two years under the afore-identified accelerated storage conditions. The "degradation products" include those listed on page 281 of the 26th edition of the USP and any other degradation products that may appear as peaks on a chromatogram during the assay that are characteristic of bupropion degradation.

As used herein "total impurities" mean all degradation products resulting from the degradation of bupropion hydrobromide. The "degradation products" include those listed on page 281 of the 26th edition of the USP and any other degradation products that may appear as peaks on a chromatogram during the assay.

The term "plasticizer" as used herein includes any compounds capable of plasticizing or softening a polymer or a binder used in the present invention. The use of plasticizers is optional, and can be included in the dosage form to modify the properties and characteristics of the polymers used in the coat(s) or core of the dosage form for convenient processing during manufacture of the coat(s) and/or the core of the dosage form. Once the coat(s) and/or core has been manufactured, certain plasticizers can function to increase the hydrophilicity of the coat(s) and/or the core of the dosage form in the environment of use. During manufacture of the coat(s) and/or core, the plasticizer can lower the melting temperature or glass transition temperature (softening point temperature) of the polymer or binder. Plasticizers can broaden the average molecular weight of a polymer in which they are included thereby lowering its glass transition temperature or softening point. Plasticizers also can reduce the viscosity of a polymer. Plasticizers can impart some particularly advantageous physical properties to the dosage forms of the invention.

The term "moiety" as used herein is defined to mean the molecule or ion, excluding those appended portions of the molecule that cause the drug to be an ester, salt (including a salt with hydrogen or coordination bonds), of the molecule, responsible for the physiological or pharmacological action of the drug substance.

The term "microparticle", as used herein refers to a drug formulation in discrete particulate form, and is interchangeable with the terms "microspheres", "spherical particles", "microcapsules", "particles", "multiparticulates", "granules", "spheroids", beads" and "pellets".

The term "core" as used here in is defined to mean any structure that is surrounded by a wall, membrane, or coating. The wall, membrane, or coating can be a functional or non-functional coating.

The term "tablet" as used herein refers to a single dosage form, i.e. the single entity containing the active pharmaceutical agent that is administered to the subject. The term "tablet" also includes a tablet that may be the combination of one or more "minitablets".

The term "osmosis" as used herein refers to the flow of a solvent through a selectively-permeable membrane from a region of high solvent potential to a region of low solvent potential. The selectively-permeable membrane must be permeable to the solvent, but not to the solute, resulting in a pressure gradient across the membrane.

The term "osmotic dosage form", "osmotic delivery device", "modified release osmotic dosage form" or "controlled release osmotic dosage form" as used herein is defined to mean dosage forms which forcibly dispense the bupropion salt all or in part by pressure created by osmosis or by a combination of osmosis and diffusion of fluid into a dosage form which forces the bupropion salt to be dispensed from the osmotic dosage form. The term "osmotic dosage form", "osmotic delivery device", "modified release osmotic dosage form", or "controlled release osmotic dosage form" also encompasses such forms that can be coated with a "control releasing coat".

The terms "osmagent", "osmotic agent", "osmotically effective solute", "osmotic enhancer" "osmotically effective compounds", "osmotic solutes", or "osmotic fluid imbibing agents" are all used interchangeably herein and define any material that increases the osmotic pressure of the core, thus, increasing the hydrostatic pressure inside the osmotic dosage form. The osmagent can be either soluble or swellable and totally or partially solubilized. The osmagent can be the bupropion salt.

The term "pharmaceutically acceptable" means compatible with the treatment of subjects, in particular, humans.

The term "subject" or "patient" as used herein means all members of the animal kingdom, in particular, humans.

The term "effective amount" as used herein means a "pharmaceutically effective amount". A "pharmaceutically effective amount" is the amount or quantity of the bupropion salt or polymorph or anantiomer thereof which is sufficient to elicit an appreciable biological response when administered to a patient. It will be appreciated that the precise therapeutic dose will depend on the age and condition of the patient and the nature of the condition to be treated and will be at the ultimate discretion of the attendant physician.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "a" or "an" as used herein means "one" or "one or more". The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Where particular values are described in the application and claims, unless otherwise stated, the term "about" means within an acceptable error range for the particular value.

Unless otherwise indicated, all numbers expressing quantities of ingredients, properties such as molecular weight, reaction conditions, and so forth used in the specification and claims are to be understood as being modified in all instances by the term "about" Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Other terms are defined as they appear in the following description and should be construed in the context with which they appear.

DETAILED DESCRIPTION

There is a need for dosage forms comprising a pharmaceutically acceptable salt of bupropion that are more stable than otherwise similar compositions containing bupropion hydrochloride. Accordingly, the present invention relates to dosage forms comprising an effective amount of bupropion hydrobromide that are more stable than bupropion hydrochloride. Also, the invention encompasses polymorphs thereof and specific purified enantiomeric forms thereof. The present invention also relates to the use of such dosage forms for the treatment of one or more conditions in a subject suitable for treatment by bupropion or pharmaceutically acceptable salts thereof such as depression, obesity, smoking cessation, and other conditions treatable with bupropion such as are disclosed herein.

Formulations

The present invention encompasses any medicament containing a pharmaceutically effective amount of a stable bupropion salt according to the invention, i.e., bupropion hydrobromide. This includes both oral and non-orally administrable medicaments such as topicals, injectables, aerosols and other inhalable medicaments. Particularly such medicament compositions include orally administrable modified release dosage form containing the bupropion salt. The dosages can be conveniently presented in unit dosage form and prepared by any of the methods well-known in the art of pharmacy.

"Dosage form" as used herein, means a pharmaceutical preparation that comprises an effective amount of a bupropion salt that is more stable than bupropion hydrochloride. In at least one embodiment the bupropion salt is bupropion hydrobromide.

A "solid dosage form" as used herein, means a dosage form that is neither liquid nor gaseous. Dosage forms include solid dosage forms, such as tablets, powders, microparticles, capsules, suppositories, sachets, troches, patches and losenges as well as liquid suspensions and elixirs. Capsule dosages contain the solid composition within a capsule that can be made of gelatin or other conventional encapsulating material.

The modified release dosage forms contemplated in the present invention can be multiparticulate or monolithic. For example, those skilled in the pharmaceutical art and the design of medicaments are aware of modified release matricies conventionally used in oral pharmaceutical compositions adopted for modified release and means for their preparation. Examples of modified release formulations are disclosed in U.S. Pat. Nos. 5,591,452 and 5,965,161.

A modified release formulation containing the bupropion salt according to the present invention can be coated with one or more functional or non-functional coatings. Examples of functional coatings include controlled release polymeric coatings (i.e. control releasing coats), moisture barrier coatings, enteric polymeric coatings, and the like. Non-functional coatings are coatings that do not affect drug release, but which affect other properties; such as the enhancement of the chemical, biological or physical stability characteristics, or the enhancement of the physical appearance of the formulation.

In at least one embodiment of the present invention the controlled release polymeric coating (or control-releasing coat) comprises an acrylic polymer. Suitable acrylic polymers include but are not limited to acrylic acid and methacrylic acid copolymers, methyl methacrylate copolymers, ethoxyethyl methacrylates, cynaoethyl methacrylate, aminoalkyl methacrylate copolymer, poly(acrylic acid), poly (methacrylic acid), methacrylic acid alkylamine copolymer, poly(methyl methacrylate), poly(methacrylic acid) (anhydride), polyacrylamide, poly(methacrylic acid anhydride), and glycidyl methacrylate copolymers.

In at least one embodiment polymerizable quaternary ammonium compounds are employed in the control releasing coat, of which non-limiting examples include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, and trimethylaminomethyl-methacrylamide methosulfate. The quaternary ammonium atom can also be part of a heterocycle, as in methacryloxyethylmethyl-morpholiniom chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, styryl-trialkyl ammonium salts, and the like. Other polymerizable quaternary ammonium compounds useful in the present invention include acryl- and methacryl-oxyethyltrimethyl-ammonium chloride and methosulfate, benzyldimethylammoniumethyl-methacrylate chloride, diethylmethylammoniumethyl-acrylate and -methacrylate methosulfate, N-trimethylammoniumpropylmethacrylamide chloride, and N-trimethylammonium-2,2-dimethylpropyl-1-methacrylate chloride.

In at least one embodiment the acrylic polymer is comprised of one or more ammonia methacrylate capolyiners. Ammonio methacrylate copolymers (such as those sold under the Trade Mark EUDRAGIT® RS and RL) are described in National Formulary (NF) XVII as fully polymerized copolymers of acrylic and methacrylic acid esters with a low content of quaternary ammonium groups. In order to obtain a desirable dissolution profile for a given therapeutically active agent, such as bupropion hydrobromide, two or more ammonia methacrylate copolymers having differing physical properties can be incorporated. For example, it is known that by changing the molar ratio of the quaternary ammoniurn groups to the neutral (meth)acrylic esters, the permeability properties of the resultant coating can be modified.

In other embodiments of the present invention, the control releasing coat further includes a polymer whose permeability is pH dependent, such as anionic polymers synthesized from methacrylic acid and methacrylic acid methyl ester. Such polymers are commercially available, e.g., from Rohm Pharma GmbH under the tradename EUDRAGIT® and EUDRAGIT® S. The ratio of free carboxyl groups to the esters is known to be 1:1 in EUDRAGIT® L and 1:2 in EUDRAGIT® S. EUDRAGIT® L is insoluble in acids and pure water, but becomes increasingly permeable above pH 5.0. EUDRAGIT® S is similar, except that it becomes increasingly permeable above pH 7. The hydrophobic acrylic polymer coatings can also include a polymer which is cationic in character based on dimethylaminoethyl methacrylate and neutral methacrylic acid esters (such as EUDRAGIT® B, commercially available from Rohm Pharma). The hydrophobic acrylic polymer coatings of the present invention can further include a neutral copolymer based on poly (meth)acrylates, such as EUDRAGIT® NE (NE=neutral ester), commercially available from Rohm Pharma. EUDRAGIT® NE 30D lacquer films are insoluble in water and digestive fluids, but permeable and swellable.

In at least one other embodiment of the invention, the control releasing coat comprises a dispersion of poly (ethylacrylate, methyl methacrylate) 2:1 (KOLLICOAT® EMM 30 D, BASF).

In at least one other embodiment of the invention, the control releasing coat comprises a polyvinyl acetate stabilized with polyvinylpyrrolidone and sodium lauryl sulfate such as KOLLICOAT® SR30D (BASF). The dissolution profile can by altered by changing the relative amounts of different acrylic resin lacquers included in the coating. Also, by changing the molar ratio of polymerizable permeability-enhancing agent (e.g., the quaternary ammoniuxu compounds) to the neutral (meth)acrylic esters, the permeability properties (and thus the dissolution profile) of the resultant coating can be modified.

In at least one embodiment of the invention the control releasing coat comprises ethylcellulose, which can be used as a dry polymer (such as ETHOCEL®, Dow Corning) solubilised in organic solvent prior to use, or as an aqueous dispersion. One suitable commercially-available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® can be intimately mixed with a suitable plasticizer prior to use. Another suitable aqueous dispersion of ethylcellulose is commercially available as SURELEASE® (Colorcon, Inc., West Point, Pa., U.S.A.). This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

Other examples of polymers that can be used in the control-releasing coat include cellulose acetate phthalate, cellulose acetate trimaletate, hydroxy propyl methylcellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of waler and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight 5 k to 5000 k). polyvinylpyrrolidone (molecular weight 10 k to 360 k), anionic and cationic hydrogcls, zein, polyamides, polyvinyl alcohol having a low acetate residual, a swellable mixture of agar and carboxymethyl cellulose, copolymers of maleic anhydride and styrene, ethylene, propylene or isobutylene, pectin (molccular weight 30 k. to 300 k), polysaceharides such as agar, acacia, karaya, tragacanth, algins and guar, polyacrylamides, POLYOX polyethylene oxides (molecular weight 100 k to 5000 k), AQUAKEEP® acrylate polymers, diesters of polyglucan, crosslinked polyvinyl alcohol and poly N-vinyl-2-pyrrolidone, hydrophilic polymers such as polysaccharides, methyl cellulose, sodium or calcium carboxyrnethyl cellulose, hydroxypropyl methyl cellulose, hydroxypropyl cellulose, hydroxyethyl cellulose, nitro cellulosc, carboxymethyl cellulose, cellulose ethers, methyl ethyl cellulose, ethyihydroxy ethylcellulose, cellulose acetate, cellulose butyrate, cellulose propionate, gelatin, starch, maltodextrin, pullulan, polyvinyl pyirrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginares, propylene glycol alginate, agar, and gums such as arabic, karaya, locust bean, tragacanth. carrageens, guar, xanthan, scicroglucan and mixtures and blends thereof.

In at least one embodiment of the invention the dosage forms are coated with polymers in order to faciliatate mucoadhsion within the gastrointestinal tract. Non-limiting examples of polymers that can be used for mucoadhesion include carboxyinethylcellu lose, polyacrylic acid, CARBOPOL™, POLYCARBOPHIL™, gelatin and other natural or synthetic polymers.

In at least one embodiment of the invention, the dosage form is an extended release tablet comprising: (i) a core that includes bupropion hydrobromide (e.g. from 40% to 99% by weight of tablet dry weight), a binder such as polyvinyl alcohol (e.g. from 0.5% to 25% by weight of tablet dry weight), and a lubricant such as glyceryl behenate (e.g. from 0.1% to 5% by weight of tablet dry weight); and (ii) a control releasing coat that includes a water-insoluble water-permeable film-forming polymer such as ethylcellulose (e.g. from 1% to 12% by weight of tablet dry weight), a water-soluble polymer such as polyvinylpyrrolidone (POVIDONE® USP), (e.g. from 1.5% to 10% by weight of tablet dry weight), optionally a plasticizer such as dibutyl sebacate, polyethylene glycol 4000 or a mixture thereof (e.g. from 0.5% to 4% by weight of tablet dry weight), and optionally a wax such as carnauba wax (e.g. from 0.01% to 0.05% by weight of tablet dry weight).

In at least one embodiment of the invention, the dosage form is a 174 mg XL tablet comprising: (i) a core that includes bupropion hydrobromide (e.g. 81% by weight of tablet dry weight), a binder such as polyvinyl alcohol (e.g. 3% by weight of tablet dry weight), and a lubricant such as glyceryl behenate (e.g. 3% by weight of tablet dry weight); and (ii) a control releasing coat that Includes a water-insoluble water-permeable film-forming polymer such as ethylcellulose (e.g. 8% by weight of tablet dry weight), a water-soluble polymer such as polyvinylpyrrolidone (POVIDONE® USP), (e.g. 5% by weight of tablet dry weight), optionally a plasticizer such as dibutyl sebacate, polyethylene glycol 4000 or a mixture thereof (e.g. 3% by weight of tablet dry weight), and optionally a wax such as carnauba wax (e.g. 0.03% by weight of tablet dry weight).

In at least one embodiment of the invention, the dosage form is a 348 mg XL tablet comprising: (i) a core that includes bupropion hydrobromide (e.g. 87% by weight of tablet dry weight), a binder such as polyvinyl alcohol (e.g. 3% by weight of tablet dry weight), and a lubricant such as glyceryl behenate (e.g. 3% by weight of tablet dry weight); and (ii) a control releasing coat that includes a water-insoluble water-permeable film-forming polymer such as ethylcellulose (e.g. 4% by weight of tablet dry weight), a water-soluble polymer such as polyvinylpyrrolidone (POVIDONE® USP), (e.g. 3% by weight of tablet dry weight), optionally a plasticizer such as diburyl sebacate, polyethylene glycol 4000 or a mixture thereof (e.g. 2% by weight of tablet dry weight), and optionally a wax such as carnauba wax (e.g. 0.01% by weight of tablet dry weight).

In addition to the modified release dosage forms described herein, other modified release technologies known to those skilled in the art can be used in order to achieve the modified release formulations of the present invention, i.e., formulations which provide a mean $T_{max}$ of the drug and/or other pharmacokinetic parameters described herein when administered e.g., orally or by other mode of administration to human patients. Such formulations can be manufactured as a modified release oral formulation in a suitable tablet or multiparticulate formulation known to those skilled in the art. In either case, the modified release dosage form can optionally include a controlled release carrier which is incorporated into a matrix along with the drug, or which is applied as a controlled release coating.

Tablets

In another specific aspect of the present invention, there is provided a modified-release tablet having a core comprising a pharmaceutically acceptable salt of bupropion and conventional excipients, wherein the bupropion salt is more stable than bupropion hydrochloride (bupropion hydrobromide). The core can be surrounded by a control-releasing coat which controls the release of the bupropion salt. In other embodiments, a moisture barrier can optionally be added to surround the control-releasing coat. This moisture barrier is optional given the enhanced stability of bupropion HBr relative to bupropion HCl and by selection of an appropriate control-releasing coats and amount thereof. If present, this moisture barrier may affect in vitro drug release as well as precluding moisture from coming into contact with the bupropion salt. Optionally, this tablet may further comprise one or more additional functional or non-functional coatings surrounding the core, moisture barrier and/or control-releasing coat.

Extended Release (XL) Tablets

In another specific aspect of the present invention, there is provided an extended-release (XL) tablet having a core comprising a pharmaceutically acceptable salt of bupropion and conventional excipients, wherein the bupropion salt is more stable than bupropion hydrochloride. In at least one embodiment the bupropion salt is bupropion hydrobromide. The core can be surrounded by a control-releasing coat, which controls the release of the bupropion salt. The tablet optionally may comprise one or more additional functional or non-functional coats surrounding the core or control-releasing coat. The extended-release tablet of the invention has unexpected enhanced stability.

The XL Core

The core of the extended-release tablet comprises an effective amount of a bupropion salt, a binder, and a lubricant and can contain other conventional inert excipients. In at least one embodiment the bupropion salt is bupropion hydrobromide. The amount of the bupropion salt present in the XL core can vary in an amount from 40% to 99% by weight of the tablet dry weight. For example, in certain embodiments bupropion hydrobromide is present in an amount from 70% to 95% by weight of the tablet dry weight. For example, in certain embodiments, the core of the dosage form of the present invention comprises bupropion hydrobromide in a proportion of 40%, 45%, 50%, 55%, 60%, 65%, 70%, 75%, 80%, 85%, 90%, 95% or 99% of the core dry weight. The tablet comprises an effective amount of bupropion salt that typically will vary from 50 mg to 450 mg. For example, in certain embodiments, the tablet comprises 174 mg of bupropion hydrobromide, and in other embodiments the tablet comprises 348 mg of bupropion hydrobromide. In at least one embodiment of a 174 mg dose tablet, the bupropion hydrobromide is present at from 75% to 85% by weight of the tablet dry weight. In at least one embodiment of a 348 mg dose tablet, the amount of bupropion hydrobromide can be present at from 80% to 90% by weight of the tablet dry weight. In certain embodiments of both the 174 mg and 348 mg dose bupropion hydrobromide extended-release tablets of the invention, the amount of bupropion hydrobromide is present from 90% to 99% by weight of the dry core for each dose.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the XL tablets is in the form of a solution binder. Non-limiting examples of binders useful for the core include hydrogenated vegetable oil, castor oil, paraffin, higher aliphatic alcohols, higher alphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. The amount of binder present can vary from 0.5% to 25% by weight of the tablet dry weight. For example, in certain embodiments the binder is present in an amount of from 0.5% to 15% by weight of the tablet dry weight; in other embodiments from 1% to 6% by weight of the tablet dry weight; and in still other embodiments at 3% by weight of the tablet dry weight. For example, in certain embodiments of both the 174 mg and 348 mg dose tablets, the binder is present in an amount of from 1% to 6% by weight of each dry core weight, and in other embodiments at 3% by weight of each dry core weight. In at least one embodiment of the invention the binder is polyvinyl alcohol.

Lubricants can be added to pharmaceutical formulations to decrease any friction that occurs between the solid and the die wall during tablet manufacturing. High friction during tabletting can cause a series of problems, including inadequate tablet quality (capping or even fragmentation of tablets during ejection, and vertical scratches on tablet edges) and may even stop production. Accordingly, lubricants are added to certain tablet formulations of the present invention including certain embodiments of the XL tablet formulation described herein. Non-limiting examples of lubricants useful for the core include glyceryl behenate, stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K), stearyl alcohol, leucine, polyethylene glycol (MW 1450, suitably 4000, and higher), magnesium stearate, glyceryl monostearate, stearic acid. polyethylene glycol, ethylene oxide polymers (for example, available under the registered trademark CARBOWAX® from Union Carbide, Inc., Danbury. Conn.), sodium lauryl sulfate, magnesium lauryl sulfate, sodium oleate, sodium stearyl fumarate, DL-leucine, colloidal silica, mixtures thereof and others as known in the art. In at least one embodiment of the present invention, the lubricant is glyceryl behenate (for example, COMPRITOL®888). The amount of lubricant present can vary from 0.1% to 6% by weight of the tablet dry weight. For example, in certain embodiments the amount of lubricant present is from 2% to 3% by weight of the tablet dry weight; and in other embodiments the amount of lubricant present is at 3% by weight of the tablet dry weight. In certain embodiments of the 174 mg and 348 mg dose XL tablets of the invention, the lubricant is present in an artiount of 3% by weight of the tablet dry weight, or from 1% to 6% by weight of the dry core weight. For example, in certain embodiments the lubricant is present in an amount of 3% by weight of the dry core weight for both the 174 mg and 348 mg dose XL tablets.

At this stage, the XL core formulation of certain embodiments of the present invention, is an uncoated immediate release formulation resulting in 100% dissolution of the bupropion salt within 1 hour. In at least one embodiment the XL core is a normal release matrix formulation. In certain embodiments the core comprises an effective pharmaceutical amount of bupropion hydrobromide, a binder (e.g. polyvinyl alcohol), and a lubricant (e.g. glyceryl behenate). Additional inert excipients consistent with the objects of the invention can also be added to the core formulation. The additional inert excipients can be added to facilitate the preparation and/or improve patient acceptability of the final extended-release dosage form as described herein. The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

In at least one embodiment of the invention, the granules to be compressed to form the core of the XL tablet of the invention described herein, are manufactured by the wet granulation process. Wet granulation involves agitation of a powder (the active drug) by convention in the presence of a liquid (the solution binder) followed by drying. For forming the granules, which are to be eventually compressed into the tablet cores, the bupropion salt is first granulated, for example, with a solution binder, in a granulator, for example using a fluidized bed granulator (e.g. a fluidized bed granulator manufactured by Glatt (Germany) or Aeromatic (Switzerland)). The binder (e.g. polyvinyl alcohol) is first dissolved or dispersed in a suitable solvent (e.g. water). The solution binder is then top sprayed onto the drug in a granulator (e.g. a fluidized bed granulator). Alternatively, granulation can also be performed in a conventional or high shear mixer. If necessary, the additional inert excipients (e.g. a filler) can be mixed with the bupropion salt prior to the granulation step.

The granules formed are subsequently dried and then sieved prior to blending the granules with the lubricant. In certain embodiments, the dried granules are sieved through a 1.4 mm mesh screen. The sieved granules are then blended with the lubricant, and if necessary, any other additional inert excipients, which can improve processing of the extended-release tablets of the invention. Blending of the granules with the lubricant, and if necessary, any additional inert excipients, such as for example a glidant, can be performed in a V-blender or any other suitable blending apparatus. Glidants can improve the flowability of the powder. This is especially important during tablet production at high production speeds and during direct compaction. However, because the requirement for adequate flow is high, a glidant is often also added to a granulation before tabletting. The blended granules are subsequently pressed into tablets and are hereinafter referred to as tablet cores. Tablet cores can be obtained by the use of standard techniques and equipment well known to the skilled artisan. For example, the XL tablet cores can be obtained by a rotary press (also referred to as a multi-station press) fitted with suitable punches.

The granules can also be manufactured by using other processes known to the skilled artisan. Examples of other granule manufacturing processes include dry granulation (e.g. slugging, roller compaction), direct compression, extrusion, spheronization, melt granulation, and rotary granulation.

An example of the granulation process for the XL cores (60 kg batch) is as follows: A Fluid Bed Processor is used for granulation in order to agglomerate the particles of the materials to obtain a uniform particle size for the final blend. The granulating solution is prepared by dissolving the binder (e.g. polyvinyl alcohol) in hot purified water while mixing. The percent solids content can be adjusted to obtain a viscosity to control the build up (agglomeration size) of the material. A lower viscosity leads to smaller particles, and a higher viscosity leads to larger particles. In addition, the application rate (e.g. from 150 gm/min to 250 gm/min; or 200 gm/min), position of Spray gun (e.g. center position) and nozzle size (e.g. from 0.5 mm to 2 mm; or 1 mm) and atomization pressure (e.g. from 20 psi to 40 psi; or 30 psi) contribute further to control particle size. The active material is fluidized and heated (e.g. from 35° C. to 45° C.; or 40° C.) prior to start of solution application. During the spray cycle, the bed temperature (e.g. from 35° C. to 45° C.; or 40° C.) is kept at a constant temperature to avoid over-wetting. Once all the required binder solution is applied, the material is further dried to the targeted LOD value (i.e. loss on drying) (e.g. below 1%) prior to unloading. The amount of binder (e.g. polyvinyl alcohol) is between 2% to 6%, and in some cases 3%; and the solution concentration is between 3% to 7%, and in some cases 4.5%. The time of agglomeration process for the 60 kg batch is between 45 minutes to 220 minutes, and in some cases 150 minutes. Once the granulate is dry, material is passed through a 1.4 and 2.00 mm screen to remove any oversized particles. The oversize particles are passed through the mill to reduce oversize particles. Oversized particles generally not to exceed 5% of total yield. The screened and milled materials are placed into a shell blender (e.g. V-Blender, Bin blender) and the lubricant (e.g. glyceryl behenate) is added. The lubricant is screened and added to the granules and blended at the predetermined number of revolutions or time (e.g. mix time of 5 min to 15 min, and in some cases 10 min). The percent lubricant is between 0.5% to 4%, and in some cases 2%. The level of lubrication is established for sufficient coverage of either larger or smaller particle size distribution. Additional characteristics include bulk density (e.g. from 0.3 gm/ml to 0.8 gm/ml, and in some cases 0.5 gm/ml), and moisture content (e.g. not more than 1%). Particle size and flow of final blend are factors in obtaining uniform fill of cavities on a rotary press. The flow and top rotation speed of the press are adjusted (dependant on the type/size of press) so as to not jeopardize the weight uniformity of individual tablets. The product blend is passed through a hopper into a feed frame to fill the die cavities passing under the feed frame. Weight adjustments are made to keep the weight within the specified range, and adjustments made to the pressure settings to obtain the required hardness. Some components monitored for the tablets are tablet thickness and friability (e.g. less than 0.5%). Suitable thickness (related to overall surface area) and lower friability help reduce core damage and loss of active during coating. Tablet samples are removed at predetermined intervals to monitor specifications.

Coatings

The tablet cores can be coated for administration to a subject. In at least one embodiment of the invention, the tablet cores are coated with an extended release control-releasing coating ("XL Control-Releasing Coat"). In at least one other embodiment, the tablet cores are coated with an aqueous control-releasing coating that comprises an aqueous dispersion of a neutral ester copolymer without any functional groups ("AQ Control-Releasing Coat").

In certain embodiments the tablet dosage form comprises an optional moisture barrier in addition to the control-releasing coat. The control-releasing coat and the moisture barrier can be applied in two stages. The control-releasing coating can be applied directly onto the surface of the tablet cores and functions to control the release of the bupropion salt. The moisture barrier can be applied directly onto the surface of the control-releasing coat to impede or retard the absorption of moisture.

Prophetic examples of control-releasing coat formulations are provided below. It should be understood that the constituents and/or proportions of the constituents in these coatings as well as the amounts thereof may be varied in order to achieve formulations possessing different release characteristics. In all instances wherein prophetic examples are provided these compositions are intended to be exemplary and it should be understood that the specific procedures, constituents, amounts thereof and the like may be varied in order to obtain a composition possessing desired properties.

In at least one embodiment the control-releasing coat is a delayed release coating formulation for a tablet core, the coating formulation to be applied to the core comprising:

| | |
|---|---|
| Eudragit L12.5 | 50% by weight of coating suspension |
| Triethyl citrate | 0.63% by weight of coating suspension |
| Talc | 1.25% by weight of coating suspension |
| Isopropyl alcohol | 48.12% by weight of coating suspension |

Solids total = 8.1%
Polymer content of suspension = 6.3%

Preparation of the delayed release coating formulation can be as follows: Talc and triethyl citrate are homogenized in the solvent by means of a homogenizer for approximately 10 minutes. The suspension is poured directly into the EUDRAGIT® L12.5 dispersion and stirred gently to avoid sedimentation. The coating is sprayed onto tablets until approximately 5 mg/cm2 of EUDRAGIT® L has been applied to the tablet core.

In at least one embodiment the control-releasing coat is a sustained release coating formulation for a tablet core, the coating formulation applied to the core comprising:

| | |
|---|---|
| Eudragit RL 12.5 | 10% by weight of coating suspension |
| Eudragit RS 12.5 | 30% by weight of coating suspension |
| Dibutyl sebacate | 0.5% by weight of coating suspension |
| Talc | 3.5 g by weight of coating suspension |
| Magnesium stearate | 1% by weight of coating suspension |
| Acetone | 27.5% by weight of coating suspension |
| Isopropyl alcohol | 27.5% by weight of coating suspension |

Solids total = 10%
Polymer content of suspension = 5%

Preparation of the sustained release coating formulation can be as follows: Dibutyl sebacate, talc and magnesium stearate are mixed and finely dispersed together with the diluents acetone and isopropyl alcohol. The suspension is then combined with the EUDRAGIT® polymer dispersions. The coating is sprayed onto the core until approximately 10 mg/cm2 of polymer has been applied to the core.

In at least one embodiment the control-releasing coat is a polymer blend coating possessing pH dependent polymer (EUDRAGIT® L 30D 55) in combination with a sustained release polymer (AQUACOAT®), the coating formulation applied to the core comprising:

| | |
|---|---|
| Aquacoat (ethylcellulose 30%) | 21% by weight of coating suspension |
| Eudragit L30 D 55 | 21% by weight of coating suspension |
| Triethyl citrate | 3% by weight of coating suspension |
| Water | 55% by weight of coating suspension |

Solids total = 15.6%
Polymer content of suspension = 12.6%

Application of the polymer blend coating can be as follows: Coating applied to a 10 mg/cm$^2$ application of polymer to the drug core.

In at least one embodiment the control-releasing coat is a drug coating (Citalopram) on top of a bupropion salt core, the coating formulation applied to the core comprising:

| | |
|---|---|
| Kollidon VA64 (Vinylpyrrolidone-vinyl acetate copolymer) | 2.5% by weight of drug coating suspension |
| KLUCEL ™ EF (Hydroxypropylcellulose) | 2.5% by weight of drug coating suspension |
| Citalopram | 2% by weight of drug coating suspension |
| Talc | 3% by weight of drug coating suspension |
| 2-propanol | 90% by weight of drug coating suspension |

Solids total = 10%
Polymer content of suspension = 5%

Application of the drug coating formulation can be as follows: Drug coating is sprayed onto tablets until the desired amount of Citalopram is applied.

A top-coat can subsequently be applied as a cosmetic coating and also to prevent tablet sticking, the top-coat formulation applied to the drug coated core comprising:

| | |
|---|---|
| Kollidon VA64 (Vinylpyrrolidone-vinyl acetate copolymer) | 2.5% by weight of top-coat suspension |
| KLUCEL ™ EF (Hydroxypropylcellulose) | 2.5% by weight of top-coat suspension |
| Talc | 2.5% by weight of top-coat suspension |
| Isopropyl alcohol | 92.5% by weight of top-coat suspension |

Solids total = 7.5%
Polymer content of suspension = 5%

Application of the top-coating formulation can be as follows: Coating is applied to a 2% weight gain (expressed as % of drug coated tablet core)

The Extended Release (XL) Control-Releasing Coat

The XL control-releasing coat is a semi-permeable coat comprising a water-insoluble, water-permeable film-forming polymer, optionally a water-soluble polymer, and optionally a plasticizer.

Non-limiting examples of water-insoluble, water-permeable film-forming polymers useful for the XL control-releasing coat include cellulose ethers, ceUulose esters, and polyvinyl alcohol. For example, the water-insoluble, water-permeable film forming polymers can be the ethyl celluloses, and can be selected from the following: ethyl cellulose grades PR100, PR45, PR20, PR10 and PR7 (ETHOCEL®, Dow), and any combination thereof. In at least one embodiment of the invention, ethyl cellulose grade PR 100 is the water-insoluble, water-permeable film-forming polymer. The amount of the water-insoluble water-permeable film-forming polymer can vary from 1% to 12% by weight of the tablet dry weight. For example, in certain embodiments the amount of the water-insoluble water-permeable film-forming polymer is present in an amount from 5% to 10%, and in other embodiments from 6% to 8% by weight of the tablet dry weight. In certain embodiments of the 174 mg dose modified-release tablets of the invention, the amount of water-insoluble water permeable film-forming polymer is from 3% to 8% by weight of the tablet dry weight, and in other embodiments from 6% to 7% by weight of the tablet dry weight. With respect to the control-releasing coat itself, the amount of water-insoluble water-permeable film-forming polymer in certain embodiments of the 174 mg dose tablet is from 35% to 60% by weight of the control-releasing coat dry weight, and in other embodiments from 40% to 50% by weight of the control-releasing coat dry weight. In certain embodiments of the 348 mg dose modified-release tablet of the invention, the amount of water-insoluable water-permeable film-forming polymer is from 2% to 5% by weight of the tablet dry weight, and in other embodiments from 3% to 4% by weight of the tablet dry weight. With respect to the control-releasing coat itself, the water-insoluble water-permeable filni-fonning polymer in certain embodiments of the 348 mg dose tablet is present in an amount of 40% by weight of the control-releasing coat dry weight.

Non-limiting examples of water-soluble polymers useful for the XL control-releasing coat include pol ywinylpyrrolidone, hydroxypropyl muethylcellulose, hydroxypropyl cellulose and mixtures thereof. In at least one embodiment the water-soluble polymer is polyvinylpyrrolidone (POVIDON® USP). The amount of water-soluble polymer can vary from 1.5% to 10% by weight of the tablet dry weight. For example, in certain embodiments the amount of water-soluable polymer is from 3% to 8%, and in other embodiments at 4% by weight of the tablet dry weight. With respect to the control-releasing coat itself, in certain embodiments the amount of water-soluble polymer present is from 25% to 55% by weight of the control-releasing coat dry weight. For certain embodiments of the 174 mg dose of the extended release tablet of the invention, the amount of water-soluble polymer is from 3% to 5% by weight of the tablet dry weight, and from 25% to 50% by weight of the control-releasing coat dry weight. For certain embodiments of the 348 mg dose of the extended release tablet of the invention, the amount of water-soluble polymer present is from 2% to 5% of the tablet dry weight and 40% to 50% by weight of the control-releasing coat dry weight.

In certain embodiments, the XL control-releasing coat further comprises a plasticizer. The use of plasticizers is optional, and they can be added to film coating formulations to modify the physical properties of a polymer to make it more usable during manufacturing. Plasticizers can be high boiling point organic solvents used to impart flexibility to otherwise hard or brittle polymeric materials. Plasticizers generally cause a reduction in the cohesive intermolecular forces along the polymer chains resulting in various changes in polymer properties including a reduction in tensile strength, and increase in elongation and a reduction in the glass transition or softening temperature of the polymer. The amount and choice of the plasticizer can affect the hardness of a tablet and can even affect its dissolution or disintegration characteristics, as well as its physical and chemical stability. Certain plasticizers can increase the elasticity and/or pliability of a coat, thereby decreasing the coat's brittleness. Once the dosage form is manufactured, certain plasticizers can function to increase the hydrophilicity of the coat(s) and/or the core of the dosage form in the environment of use (in-vitro or in-vivo). Non-limiting examples of plasticizers that can be used in the control-releasing coat described herein include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, polyols (e.g. polyethylene glycol) of various molecular weights, and mixtures thereof. It is contemplated and within the scope of the invention, that a combination of plasticizers can be used in the present formulation. In at least one embodiment of the invention, the plastizer is polyethylene glycol 4000, dibutyl sebacate or a mixture thereof. The amount of plasticizer for the control-releasing coat can vary in an amount of from 0.5% to 4% by weight of the tablet dry weight. For example, in certain embodiments the plasticizer is present in an amount of from 2% to 3% by weight of the tablet dry weight. For certain embodiments of the 174 mg dose extended-release tablet of the invention, the amount of plasticizer present in the control-releasing coat is from 1% to 4% by weight of the tablet dry weight. For certain embodiments of the 348 mg dose extended-release tablet of the invention, the amount of plasticizer present is from 0.5% to 4% by weight of the tablet dry weight. In certain embodiments of both the 174 mg and 348 mg dosage forms, the plasticizer is present in an amount of from 6% to 30% by weight of the control-releasing coat dry weight. For example, in certain embodiments the plasticizer is present in an amount of 12% by weight of the control-releasing coat dry weight.

The ratio of water-insoluble water-permeable film forming polymer:plasticizer:water-soluble polymer for the XL control releasing coat of the invention described herein can vary from 3:1:4 to 5:1:2. For example, in certain embodiments the ratio of water-insoluble water-permeable film forming polymer:plasticizer:water-soluble polymer for the XL control releasing coat is 4:1:3. For certain embodiments of the XL tablet the ratio of the water-insoluble water-impermeable film-forming polymer:plasticizer:water-soluble polymer in the XL control releasing coat is from 7:2:6 to 19:5:18. In at least one embodiment the ratio of water-insoluble water-permeable film forming polymer: plasticizer:water-soluble polymer for the XL control releasing coat is 13:4:12.

Preparation and application of the XL control-releasing coat can be as follows. The water-insoluble water-permeable film-forming polymer (e.g. ethylcellulose), and the plasticizer (e.g. polyethylene glycol 4000), are dissolved in an organic solvent (e.g. a mixture of ethyl alcohol). In the manufacture of embodiments that do not require a plasticizer, the water-insoluble water-permeable film-forming polymer can be dissolved in the organic solvent without the plasticizer. The water-soluble polymer (e.g. polyvinyl pyrrolidone) is next added until a homogenous mixture is achieved. The resulting control-releasing coat solution is then sprayed onto the tablet cores using a tablet coater, fluidized bed apparatus or any other suitable coating apparatus known in the art until the desired weight gain is achieved. The tablet cores coated with the control-releasing coat are subsequently dried. In the manufacture of embodiments that have a moisture barrier, the control-releasing coat is dried before the moisture barrier is applied.

An example of the coating process for the XL control releasing coat is as follows: The XL control releasing coat solution is prepared by dissolving the water insoluble polymer (e.g. ethylcellulose) and water soluble polymer (e.g. polyvinylpyrrolidone) and an ethyl alcohol mixture while mixing and is followed with the addition of the plasticizer(s) (e.g. polyethylene glycol 4000 and dibutyl sebacate). Once completely dissolved, the solution is homogenized to obtain a uniform mixture of appropriate viscosity. This procedure assures a complex mix of a water permeable film to control the release of the active drug. The composition of the solution can be formulated to contain various levels of the water insoluble polymer and water soluble polymer and a mix of the plasticizer(s). The release function is further controlled by the film thickness applied and measured as weight gain of solids in the coating required. Tablets are coated in a perforated coating pan with control of pan speed (e.g. from 8 rpm to 14 rpm, and in some cases 12 rpm), spray rate (e.g. from 150 gm/min to 250 gm/min, and in some cases 200 gm/min), atomization pressure (e.g. from 15 psi to 25 psi, and in some cases 20 psi), supply volume (from 800 to 1000 cubic ft/min, and in some cases 900 cubic ft/min), and air temperature (e.g. from 50° C. to 60° C., and in some cases 55° C.), monitored through a bed temperature and/or outlet temperature of from 38° C. to 42° C., and in some cases 40° C. On completion of the coating cycle, tablets are dried and unloaded into bulk containers. The printing process comprises the transfer of a print image from a print plate covered with edible black ink and transferred via a print roll or print pad onto the surface of the tablets. The printed tablets are transferred through a drying element prior to discharging into bulk containers. Samples for final testing are taken throughout the printing process.

The skilled artisan will appreciate that controlling the permeability can control the release of the bupropion salt and/or the amount of coating applied to the tablet cores. The permeability of the XL control-releasing coat, can be altered by varying the ratio of the water-insoluble, water-permeable film-forming polymer:plasticizer:water-soluble polymer and/or the quantity of coating applied to the tablet core. A more extended release can be obtained with a higher amount of water-insoluble, water-permeable film forming polymer. The addition of other excipients to the tablet core can also alter the permeability of the control-releasing coat. For example, if it is desired that the tablet core further comprise an expanding agent, the amount of plasticizer in the control-releasing coat could be increased to make the coat more pliable, as the pressure exerted on a less pliable coat by the expanding agent could rupture the coat. Further, the proportion of the water-insoluble water-permeable film forming polymer and water-soluble polymer can also be altered depending on whether a faster or slower dissolution and/or release profile is desired.

Depending on the dissolution or in-vivo release profile desired, the weight gained after coating the tablet core with the XL control-releasing coat typically will vary from 3% to 30% of the weight of the dry tablet core. For a 174 mg dose extended release tablet according to the present invention, the weight gain can typically vary from 10% to 17% of the weight of the dry tablet core. For example in certain embodiments, the weight gain is 14% of the weight of the dry tablet core. For the 348 mg dose extended release tablet of the present invention, the weight gain can vary from 7% to 10% of the weight of the dry tablet core. For example in certain embodiments, the weight gain is 9% of the weight of the dry tablet core.

AQ Control-Releasing Coat

The AQ control-releasing coat is a stable monolithic controlled release coating comprising an aqueous dispersion of a neutral ester copolymer without any functional groups, a poly glycol having a melting point greater than 55° C., and one or more pharmaceutically acceptable excipients; wherein said coating composition is coated onto the dosage form and cured at a temperature at least equal to or greater than the melting point of the poly glycol. The coating formulation is quite versatile in that it can be used to coat a variety of drug cores and can be easily manipulated to obtain the desired drug release profile.

In certain other embodiments, the AQ control-releasing coat comprises an aqueous dispersion of an ethylcellulose, a poly glycol having a melting point greater than 55° C., and one or more pharmaceutically acceptable excipients; wherein said coating composition is coated onto the dosage form and cured at a temperature at least equal to or greater than the melting point of the poly glycol. Non limiting examples of aqueous dispersions of an ethylcellulose include SURELEASE® (Colorcon, Inc., West Point, Pa., U.S.A.), and AQUACOAT® (FMC Corp., Philadelphia, Pa., U.S.A.).

Non-limiting examples of neutral ester copolymers without any functional groups that can be used in the AQ control-releasing coat include EUDRAGIT® NE30D, EUDRAGIT® NE40D (Röhm America LLC), and mixtures thereof. In at least one embodiment the polymer is Eudragit NE30D, which can be present in an amount of from 1% to 35% by weight of the control-releasing coat, depending on the controlled release profile desired. Hydrophilic agents can also be included in the AQ control-releasing coat to promote wetting of the coat when in contact with gastrointestinal fluids. Non-limiting examples of such hydrophilic agents include hydrophilic water soluble polymers such as hydroxypropyl methylcellulose (HPMC), hydroxypropyl cellulose (HPC) and combinations thereof. In at least one embodiment, HPMC is the hydrophilic water soluble polymer. If hydrophilic agents are to be included in the coat composition, the agents can be present in an amount from 0.1% to 10% by weight of the coating composition. For example, in certain embodiments the hydrophilic agents are present in an amount of from 0.1 % to 5%, and in other embodiments from 0.1% to 3% by weight of the control-releasing coat composition.

The AQ control-releasing coat formulation also comprises a poly glycol with a melting point of greater than 55° C. Non-limiting examples of the polyglycol include polyethylene glycol 6000, polyethylene glycol 8000, polyethylene glycol 10000, polyethylene glycol 20000, and mixtures thereof. In at least one embodiment, the poly glycol is polyethylene glycol 8000. The poly glycol can be present in an amount of from 0.1% to 5% by weight of the coat. Other examples of suitable polyglycol derivatives having a melting point of at least 55° C. include, but are not limited to, Poloxamer 188, Poloxamer 338, Poloxamer 407, Polyethylene Oxides, Polyoxyethylene Alkyl Ethers, and Polyoxyethylene Stearates.

In addition to the copolymers and the poly glycol, the AQ control-releasing coat formulation comprises at least one pharmaceutically acceptable excipient. The excipients can include but are not limited to anti-tacking agents, emulsifying agents, antifoaming agents, flavourants, colourants, etc. It is known in the art that depending on the intended main function, excipients can affect the properties of the coat in a series of ways, and many substances used in coat formulations can thus be described as multifunctional. A skilled worker will know, based on his technical knowledge, which pharmaceutically acceptable excipients are suitable for the desired AQ control releasing coat composition.

The tackiness of polymeric films is a factor for the coating of solid dosage forms and for the subsequent curing step (post coating thermal treatment). During coating with either cellulosic or acrylic polymers, sometimes an unwanted, and in other times irreversible agglomeration of several granules or beads or, in the worst case, of the complete batch, can occur, especially at higher product processing temperatures. Accordingly, the addition of anti-tacking agents to coating formulations can be desirable. The anti-tacking agents which can be used include but are not limited to adipic acid, magnesium stearate, calcium stearate, zinc stearate, hydrogenated vegetable oils, sterotex, glyceryl monostearate, talc, sodium benzoate, sodium lauryl sulfate, magnesium lauryl sulfate, and mixtures thereof. In at least one embodiment, talc is the anti-tacking agent. Talc can also function as a wetting agent. Mixtures of the anti-tacking agents are operable. The amount of anti-tacking agent in the control-releasing coat composition can be in the range from 1% to 15% by weight of the control-releasing coating dispersion. For example, in certain embodiments the anti-tacking agent is present in an amount of from 1% to 7% by weight of the control-releasing coating dispersion.

The anti-foaming agents, which can be included in the AQ control-releasing coat composition include silicon oil, simethicone, and mixtures thereof. In at least one embodiment, simethicone is the anti-foaming agent. The anti-foaming agent can be present in an amount of up to 0.5% by weight of the AQ control-releasing coat composition. For example, in certain embodiment the anti-foaming agent is present in an amount of from 0.1% to 0.4% by weight of the AQ control-releasing coat composition.

The emulsifying agent(s) (also called emulsifiers or emulgents) can be included to facilitate emulsification during manufacture of the AQ control-releasing coat, and also to provide emulsion stability during the shelf-life of the product. Non-limiting examples of emulsifying agents include naturally occurring materials and their semi synthetic derivatives, such as the polysaccharides, as well as glycerol esters, cellulose ethers, sorbitan esters and polysorbates. Mixtures are operable. In at least one embodiment the emulsifying agent is Polysorbate 80 (polyoxyethylene sorbitan mono-oleate)(TWEEN™ 80). The emulsifying agent(s) can be present in an amount of up to 0.5% by weight of the AQ control-releasing coat composition. For example, in certain embodiments the emulsifying agent(s) are present in an amount of from 0.1% to 0.3% by weight of the AQ control-releasing coat composition.

Colorants in the film coat formula can be water-insoluble colors (pigments). Pigments have certain advantages over water-soluble colors in that they tend to be more chemically stable towards light, provide better opacity and covering power, and optimize the impermeability of a given film to water vapor. Non-limiting examples of suitable colorants include iron oxide pigments, titanium dioxide, and aluminum Lakes. Mixtures are operable. In at least one embodiment the pigment is titanium dioxide. The pigment or colorant can be present in an amount of from 0.1% to 10% by weight of the AQ control-releasing coat composition. For example, in certain embodiments the pigment or colorant is present in an amount of from 0.1% to 5%, and in other embodiments from 0.1% to 2% by weight of the AQ control-releasing coat composition.

The AQ control-releasing coat can be applied onto a core comprising an effective amount of the bupropion salt by a process, which involves the atomization (spraying) of the coating solution or suspension onto a bed of the tablet cores. Some examples of equipment suitable for film coating include: Accela Cota (Manesty Machines, Liverpool, UK), Hi-Coater (Freund Company, Japan), Driacoater (Driam Metallprodukt GmbH, Germany), HTF/150 (GS, Italy), and IDA (Dumoulin, France). Examples of units that function on a fluidized-bed principle include: Aeromatic (Fielder, Switzerland and UK) and Glatt AG (Switzerland). In at least one embodiment, the apparatus used for film coating is the Accela Cota.

The coating fluid can be delivered to the coating apparatus from a peristaltic pump at the desired rate and sprayed onto the rotating or fluidizing tablet cores. The tablet cores are pre-warmed to 30° C. During the coating process, the product temperature range is maintained between 25° C. and 35° C. by adjusting the flow rate of the inlet and outlet air, temperature of the inlet air and spray rate. A single layer of coat is applied and once spraying is complete, the coated tablet cores are dried between 30° C. to 40° C. for 3-5 minutes at a low pan speed and low air flow. The pan is readjusted to jog speed, and drying continues for 12-15 minutes.

The coated tablet cores are placed onto a tray and cured (post coating thermal treatment) in an electrical or steam oven at a temperature above the temperature of the melting point of the polyethylene glycol or derivative thereof. The curing temperature is preferably greater than the melting point of the polyethylene glycol or derivative thereof. The curing time is preferably 2 to 7 hours. The cured coated tablets are subsequently cooled to room temperature.

The AQ control-releasing coat is quite versatile. The length and time for the delay can be controlled by rate of hydration and the thickness of the coat. The drug release rate subsequent to the delay can be determined by the thickness and permeability of the hydrated coat. Thus, it is possible to regulate the rate of hydration and permeability of the AQ control-releasing coat so that the desired controlled-release drug profile can be achieved. There is no preferred coat thickness, as this will depend on the controlled release profile desired. Other parameters in combination with the thickness of the coat include varying the concentrations of some of the ingredients of the stable coat composition of the invention described and/or varying the curing temperature and length of curing the coated tablet cores. The skilled artisan will know which parameters or combination of parameters to change for a desired controlled release profile.

The Moisture Barrier Coat

In certain embodiments, an optional moisture barrier is applied directly onto the control-releasing coat. In other embodiments a moisture barrier coat is not included in the dosage form. The moisture barrier typically comprises an enteric polymer (e.g. acrylic polymer), a permeation enhancer and optionally a plasticizer.

In certain embodiments, the enteric polymer is an acrylic polymer. For example, the acrylic polymer can be a methacrylic acid copolymer type C [poly(methacrylic acid, methyl methacrylate) 1:1] available commercially under the trade name EUDRAGIT® (e.g. Eudragit L 30 D-55). The metbacrylic acid copolymer can be present in an amOunt, which can vary from 1% to 3% of the tablet dry wcight and from 55% to 70% of the moisture barrier dry weight. For the 174 mg dose of the extended release tablet of the present invention, the methacrylic acid copolymer can vary from 2% to 3% of the tablet dry weight. For exampic in certain embodiments, the amount of the methactylic acid copolymer is present at 2.5% of the tablet dry weight. With respect to the moisture barrier itself: the amount of the methacrylic acid copolymer can be present in an amount of from 55% to 70% by weight of the moisture barrier dry weight. For example, in certain embodiments the methacrylic acid copolymer is present in an amount of 60% of the moisture barrier dry weight. For the 348 mg dose of the extended release tablet of the present invention, the amount of the methacrylic acid copolymer can vary from 1.5% to 3% of the tablet dry weight. For example, in certain embodiments, the amount of methacrylic acid copolymer is present at 2% by weight of the tablet dry weight. With respect to the coating itself, the methacrylic acid copolymer typically will be present in an amount of from 55% to 70% of the moisture barrier dry weight. For example, in certain embodiments the methacrylic acid copolymer is present in an amount of 60% of the moisture barrier dry weight.

It is known in the art that methacrylic acid copolymers can become brittle, and that coatings that contain methacrylic acid copolymers could be made more elastic and pliable by the addition of a plasticizer. In certain embodiments the moisture barrier coat comprises a plasticizer. Non-limiting examples of plasticizers useful for the moisture barrier coat described herein include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof, polyols (e.g. polyethylene glycol) of various molecular weights, and mixtures thereof. In certain embodiments, the plasticizer in the moisture barrier coat comprises a combination of triethyl citrate and polyethylene glycol 4000 (e.g. CARBOWAX® 4000). In certain of these embodiments, the ratio of triethyl citrate to polyethylene glycol 4000 is 1:2. The plasticizer can be present in an amount which can vary from 0.2% to 0.5%. For example, in certain embodiments the plasticizer is present in an amount of from 0.2% to 0.4% of the tablet dry weight. The plasticizer can be present in an amount of 0.35% of the tablet dry weight for a 174 mg tablet; and in an amount of from 0.2% to 0.4% of the tablet dry weight for a 348 mg tablet. With respect to the moisture barrier itself, the plasticizer if present typically can be present in an amount of from 1% to 30% by weight of the moisture barrier dry weight. For example, in certain embodiments the plasticizer is present in an amount of from 10% to 14% of the moisture barrier dry weight for both the 174 mg and 348 mg dose extended release tablet of the present invention. It is well known in the art that depending on the intended main function, excipients to be used in tablets are subeategorized into different groups. However, one excipient can affect the properties of a drug or the tablet as a whole in a series of ways, and many substances used in tablet formulations can therefore be described as multifunctional. Thus, the polyethylene glycol used in the plasticizer combination for the moisture barrier can serve not only to increase the hydrophilicity of the moisture barrier, but can also act as a glidant.

The moisture barrier further may comprise a permeation enhancer that can increase its hydrophilicity, and can also act as a glidant. The permeation enhancer can be a hydrophilic substance and can be selected from the following: hydrophilic polymers such as hydroxypropylmethylcellulose, cellulose ethers and protein-derived materials of these polymers, the cellulose ethers, especially hydroxyalkylcelluloses and carboxyalkylcelluloses, are preferred. Also, synthetic water-soluble polymers can be used, such as polyvinylpyrrolidone, cross-linked polyvinyl-pyrrolidone, polyethylene oxide, etc., water-soluble polydextrose, saccharides and polysacehalosides, such as pullulan, dextran, sucrose, glucose, lactose, fructose, mannitol, mannose, galactose, sorbitol and the like. In at least one embodiment of the present invention, the hydrophilic polymer comprises hydroxypropyl-methylcellulose. Other non-limiting examples of permeation enhancers include alkali metal salt.s such as aluminum oxidelithium carbonate, sodium chloride, sodium bromide, potassium chloride, potassium sulfate, potassium phosphate, sodium acetate, sodium citrate, and the like. The pore-forming solids can also be polymers which are soluble in the environment of use, such as CARBOWAXES®, CARBOPOL®, and the like. The pore-formers embrace diols, polyols, polyhydric alcohols, polyalkylene glycols, polyglycols, poiy(a-w)alkylenediols, and the like. Other permeation enhancers which can be useful in the formulations of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, etc. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers. microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophillic microporous hiomopolymers, copolymers or interpolymers having a reduced bulk density, and other similar materials, poly(urethane), cross-linked chain-extendedpoly(urethane), poly(imides), poly(benzimidazoles), collodion, regenerated proteins, semi-solid cross-linked poly(vinylpyrrolidone), silicon dioxide, colloidal silica, microcrystalline cellulose and any combination thereof. In at least one embodiment of the invention the permeation enhancer is silicon doxide (e.g. SYLOID® 244FP). The amount of permeation enhancer can very from 0.5% to 1% by weight of the tablet dry weight and from 25% to 30% by weight of the moisture barrier dry weight. For the 174 mg dose extended-release tablet of the invention, the permeation enhancer can be present in an amount of 0.5% to 2% of the tablet dry weight, and from 20% to 40% by weight of the moistuer barrier dry weight. For example, in certain embodiments of the 174 mg dose tablet, the permeation enhancer is present in an amount of from 25% to 30% by weight of the moistuer barrier dry weight. For the 348 mg dose extended release tablet of the invention, the permeation enhancer can be present in an amount which can very from 0.5% to 2% by weight of tablet dry weight, and from 20% to 40% by weight of the moisture of the barrier dry weight. For example, in certain embodiments of the 348 mg dose tablet, the permeation enhancher is present in an amount of from 25% to 30% by weight of the moisture barrier dry weight.

In at least one embodiment of the invention, the ratio of the methacrylic acid copolymer:plasticizer:permeation enhancer is 13:2:5.

The preparation and application of the moisture barrier process can be as follows. The optional plasticizer (e.g. a combination of polyethylene glycol 4000 and triethyl citrate), can be first added to water and the mixture mixed to homogeneity. The methacrylic acid co-polymer (e.g. EUDRAGIT® L 30 D-55), is next sieved and added to the plasticizer mixture and mixed to homogeneity. In a separate container the permeation enhancer (e.g. silicon dioxide) is dissolved in water until a homogeneous mixture is achieved. The plasticizer and methacrylic acid copolymer mixture is then combined with the permeation enhancer solution and mixed to homogeneity. The resulting moisture barrier solution is then sprayed onto the tabict cores coated with the control-releasing coat using a tablet coater, fluidized bed apparatus or any other suitable coating apparatus known in the art until the desired weight gain is achieved. The tablets coated with the moisture barrier are subsequently dried prior to packaging.

The moisture barrier is applied to the control-releasing coated tablet cores such that the weight gain is not more than 6% of the tablet dry weight for both the 174 mg and 348 mg extended release tablets of the present invention. In at least one embodiment the weight gain is not more than 3.5% of the tablet dry weight for both 174 mg and 348 mg extended release tablets according to the present invention. The amount of the moisture barrier applied typically does not significantly render the extended release tablet described herein more resistant to gastric fluid. However, the moisture barrier can have an impact on the drug release characteristics.

The moisture barrier as used herein if present .in the bupropion hydrobromide medicament typically does not function as an enteric coat. Even though the methacrylic acid copolymer, EUDRAGIT® L 30 D-55, is referenced and is used in enteric coating formulations in the art, its functionality is formulation dependent and on the quantity of the material applied. As is known in the art, an enteric coating is applied where a drug may be destroyed or inactivated by gastric juice or where the drug may irritate the gastric mucosa. To meet the requirements for an enteric coat, the test as described in the USP (method A or B) stipulates that after 2 hours in acidic media (0.1N HCl), no individual values of at least six experiments exceed 10% of the active drug dissolved and not less than 75% dissolved at 45 minutes in pH 6.8. The moisture barrier typically does not meet this requirement for the following reasons even though the bupropion salt (e.g. bupropion hydrobromide) is not negatively affected in acidic media nor is it irritating the gastric mucosa: (1) to obtain enteric integrity with a film containing EUDRAGIT® L 30 D-55, a weight gain of between 6% to 8% based on the dry polymer per dosage unit is recommended. The amount of EUDRAGIT® L 30 D-55 solid applied onto the cono-ol-releasing coated tablet cores is not more than 6%, and in at least one embodiment, is not more than 3%, (2) if enteric integrity would be required, the dissolution test for the finished product (i.e., the moisture barrier coated tablet cores) at the 2 hour time point would not stipulate a limit of no more than 20%, and (3) analytical tests performed on these coatings indicate that the coatings do not meet all the test requirements as an enteric coated product as defined by USP test methods.

The XL tablet of the invention provides an extended release of the bupropion salt. Generally no pore forming agent is present in the XL coating formulation. An extended release bupropion hydrobromide formulation is provided such that after 2 hours, not more than 20% of the bupropion hydrobromide content is released. For example, in certain embodiments, from 2% to 18%, from 4% to 8%, or 5% of the bupropion hydrobromide content is released after 2 hours. After 4 hours, from 15% to 45% of the bupropion hydrobromide content is released. For example, in certain embodiments from 21% to 37%, from 28% to 34%, or 32% of the bupropion hydrobromide content is released after 4 hours. After 8 hours, 40% to 90% of the bupropion hydrobromide content is released. For example, in certain embodiments from 60% to 85%, from 68% to 74%, or 74% of the bupropion hydrobromide content is released after 8 hours. After 16 hours not less than 80% of the bupropion hydrobromide content is released. For example, in certain embodiments not less than 93%, not less than 96%, or not less than 99% of the bupropion hydrobromide content is released.

Also, extended release tablets are provided wherein after 2 hours not more than 40% (e.g., 33%) of the bupropion hydrobromide is released; after 4 hours from 40-75% of the bupropion hydrobromide is released (e.g., 59%); after 8 hours at least 75% of the bupropion hydrobromide is released (e.g., 91%); and after 16 hours at least 85% of the bupropion hydrobromide is released (e.g., 97%). In all instances herein when actual or prophetic dissolution profiles are provided this means that the medicament possesses such a profile in at least one dissolution medium under prescribed conditions such as are identified herein and are well known to those skilled in the art. Such dissolution media, dissolution conditions and apparatus for use therein are disclosed in the United States Pharmacopoeia (USP) and European and Japanese counterparts thereof. Additionally, specific examples thereof are provided in this application.

Enhanced Absorption (EA) Tablets

In another aspect of the present invention, there is provided an enhanced absorption (EA) tablet having a core comprising a pharmaceutically acceptable salt of bupropion and conventional excipients, wherein the bupropion salt is more stable than bupropion hydrochloride such as bupropion hydrobromide. The core is surrounded by an EA coating, which controls the release of the bupropion salt. In certain embodiments, the EA coating consists of one coat. An advantage of the EA tablet includes the lessening of the amount of drug required in the composition, which in turn can lead to a reduction of side effects. The EA tablet of the invention has unexpected enhanced stability.

The EA Core

The core of the EA tablet comprises an effective amount of a bupropion salt, a binder and a lubricant, and can contain other conventional inert excipients. The amount of the bupropion salt present in the EA core can vary from 40% to 99% by weight of the tablet dry weight. For example, in certain embodiments bupropion hydrobromide is present in an amount of from 50% to 95%, and in other embodiments in an amount of from 70% to 90% by weight of the tablet dry weight. The tablet comprises an effective amount of bupropion salt that can vary from 50 mg to 450 mg. For example, the EA tablet can comprise 150 mg or 300 mg of bupropion hydrobromide. For a 150 mg dose tablet the bupropion hydrobromide can be present in an amount of from 76% to 84% by weight of the tablet dry weight. For a 300 mg dose, the amount of bupropion hydrobromide can be present in an amount of from 80% to 83% by weight of the tablet dry weight. For both the 150 mg and 300 mg dose bupropion hydrobromide EA tablets of the invention, the amount of bupropion hydrobromide can be present at 94% by weight of the dry core for each dose.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction, (referred to as a dry binder). Solution binders are a common way of incorporating a binder into granules. In certain embodiments, the binder used in the EA tablets is in the form of a solution binder. Non-limiting examples of binders include hydrogenated vegetable oil, castor oil, paraffin, higher aliphatic alcohols, higher alphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. The amount of binder present can vary from 0.5% to 25% by weight of the tablet dry weight. For example, in certain embodiments of the invention, the amount of binder present varies from 0.5% to 15% by weight of the tablet dry weight; in other embodiments from 1% to 6% by weight of the tablet dry weight; and in still other embodiments 3% by weight of the tablet dry weight. For both the 150 mg and 300 mg dose EA tablets, the amount of binder can be present in an amount of from 1% to 6% by weight of each dry core weight. For example, in certain embodiments the amount of binder is present in an amount of 3% by weight of each dry core weight. In at least one embodiment of the invention the binder is polyvinyl alcohol.

Lubricants can be added to pharmaceutical formulations to decrease any friction that occurs between the solid and the die wall during tablet manufacturing. High friction during tabletting can cause a series of problems, including inadequate tablet quality (capping or even fragmentation of tablets during ejection; and vertical scratches on tablet edges) and may even stop production. Accordingly, lubricants can be added to certain tabletformulations of the present invention including the EA tablet formulation described herein. Non-limiting examples of lubricants useful for the EA core include glyceryl hehenate, stearic acid, hydrogenated vegetable oils (such as hydrogenated cottonseed oil (STEROTEX®). hydrogenated soybean oil (STEROTEX® HM) and hydrogenated soybean oil & castor wax (STEROTEX® K), stearyl alcohol, leucine, polyethylene glycol (MW 1450, suitably 4000. and higher), magnesium stearate, glyceryl monostearate, stearic acid, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate. sodium stearyl fumarate, DL-leucine, colloidal silica, and others as known in the art. In at least one embodiment of the invention, the lubricant is glyceryl behenate (e.g. COMPRITOL® 888). The amount of lubricant present can vary from 0.1% to 6% by weight of the tablet dry weight. For example, in certain embodiments the amount of lubricant present is 3% by weight of the tablet dry weight. For certain embodiments of the 174 mg and 348 mg dose EA tablets of the invention the lubricant is present in an amount of 3% by weight of the tablet dry weight and from 1% to 6% by weight of the dry core weight. For example, in certain embodiments the lubricant is present in an amount of 3% by weight of the dry core weight for both the 174 mg and 348 mg dose EA tablets.

At this stage, the EA core formulation is an uncoated immediate release formulation resulting in 100% dissolution of the bupropion salt within 1 hour. In at least one embodiment the EA core is a normal release matrix formulation. In certain embodiments the core comprises an effective amount of bupropion hydrobromide, a binder (e.g. polyvinyl alcohol), and a lubricant (e.g. glyceryl behenate). However, if necessary, additional inert excipients consistent with the objects of the invention can be added to the core formulation. The additional inert excipients can be added to facilitate the preparation and/or improve patient acceptability of the final EA bupropion salt dosage form as described herein.

The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

In certain embodiments, the granules to be compressed to form the core of the EA tablet of the invention described herein are manufactured by the wet granulation process. Wet granulation involves agitation of a powder (the active drug) by convention in the presence of a liquid (the solution binder) followed by drying. For forming the granules, which are to be eventually compressed into the tablet cores, the bupropion salt is first granulated, for example with a solution binder, in a granulator, for example a fluidized bed granulator such as a fluidized bed granulator manufactured by Glatt (Germany) or Aeromatic (Switzerland). The binder (e.g. polyvinyl alcohol) is first dissolved or dispersed in a suitable solvent (e.g. water). The solution binder is then top sprayed onto the drug in a granulator (e.g. a fluidized bed granulator). Alternatively, granulation can also be performed in a conventional or high shear mixer. If necessary, the additional inert excipients (e.g. a filler) can be mixed with the bupropion salt prior to the granulation step.

The granules formed are subsequently dried and then sieved prior to blending the granules with the lubricant. In certain embodiments the dried granules are sieved through a 1.4 mm mesh screen. The sieved granules are then blended with the lubricant, and if necessary, any other additional inert excipients, which can improve processing of the EA tablets of the invention. Blending of the granules with the lubricant, and if necessary, any additional inert excipients, such as for example a glidant, can be performed in a V-blender or any other suitable blending apparatus. Glidants can improve the flowability of the powder. This is especially important during tablet production at high production speeds and during direct compaction. However, because the requirement for adequate flow is high, a glidant is often also added to a granulation before tabletting. The blended granules are subsequently pressed into tablets and are hereinafter referred to as tablet cores. Tablet cores can be obtained by the use of standard techniques and equipment well known to the skilled artisan. In certain embodiments the tablet cores are obtained by a rotary press (also referred to as a multi-station press) fitted with suitable punches.

The granules can also be manufactured by using other processes known to the skilled artisan. Examples of other granule manufacturing processes include dry granulation (e.g. slugging, roller compaction), direct compression, extrusion, spheronization, melt granulation, and rotary granulation.

An example of the granulation process for the EA cores (60 kg batch) is as follows: A Fluid Bed Processor is used for granulation in order to agglomerate the particles of the materials to obtain a uniform particle size for the final blend. The granulating solution is prepared by dissolving the binder (e.g. polyvinyl alcohol) in hot purified water while mixing. The percent solids content can be adjusted to obtain a viscosity to control the build up (agglomeration size) of the material. A lower viscosity leads to smaller particles, and a higher viscosity leads to larger particles. In addition, the application rate (e.g. from 150 gm/min to 250 gm/min; or 200 gm/min), position of Spray gun (e.g. center position) and nozzle size (e.g. from 0.5 mm to 2 mm; or 1 mm) and atomization pressure (e.g. from 20 psi to 40 psi; or 30 psi) contribute further to control particle size. The active material is fluidized and heated (e.g. from 35° C. to 45° C.; or 40° C.)

prior to start of solution application. During the spray cycle, the bed temperature (e.g. from 35° C. to 45° C.; or 40° C.) is kept at a constant temperature to avoid over-wetting. Once all the required binder solution is applied, the material is further dried to the targeted LOD value (i.e. loss on drying) (e.g. below 1%) prior to unloading. The amount of binder (e.g. polyvinyl alcohol) is between 2% to 6%, and in some cases 3%; and the solution concentration is between 3% to 7%, and in some cases 4.5%. The time of agglomeration process for the 60 kg batch is between 45 minutes to 220 minutes, and in some cases 150 minutes. Once the granulate is dry, material is passed through a 1.4 and 2.00 mm screen to remove any oversized particles. The oversize particles are passed through the mill to reduce oversize particles. Oversized particles generally not to exceed 5% of total yield. The screened and milled materials are placed into a shell blender (e.g. V-Blender, Bin blender) and the lubricant (e.g. glyceryl behenate) is added. The lubricant is screened and added to the granules and blended at the predetermined number of revolutions or time (e.g. mix time of 5 min to 15 min, and in some cases 10 min). The percent lubricant is between 0.5% to 4%, and in some cases 2%. The level of lubrication is established for sufficient coverage of either larger or smaller particle size distribution. Additional characteristics include bulk density (e.g. from 0.3 gm/ml to 0.8 gm/ml, and in some cases 0.5 gm/ml), and moisture content (e.g. not more than 1%). Particle size and flow of final blend are factors in obtaining uniform fill of cavities on a rotary press. The flow and top rotation speed of the press are adjusted (dependant on the type/size of press) so as to not jeopardize the weight uniformity of individual tablets. The product blend is passed through a hopper into a feed frame to fill the die cavities passing under the feed frame. Weight adjustments are made to keep the weight within the specified range, and adjustments made to the pressure settings to obtain the required hardness. Some components monitored for the tablets are tablet thickness and friability (e.g. less than 0.5%). Suitable thickness (related to overall surface area) and lower friability help reduce core damage and loss of active during coating. Tablet samples are removed at predetermined intervals to monitor specifications.

The EA Tablet Coating

The EA tablet cores can be coated in one stage. The EA coating is applied directly onto the surface of the tablet cores and functions to control the release of the bupropion salt.

The EA coating is a semi-permeable coat comprising a water-insoluble, water-permeable film-forming polymer, a water-soluble polymer, and optionally a plasticizer.

Non-limiting examples of water-insoluble, water-permeable film-forming polymers useful for the EA coating include cellulose ethers, cellulose esters, polyvinyl alcohol and mixtures thereof. In certain embodiments, the water-insoluble, water-permeable film forming polymers are the ethyl celluloses, and can be selected from the following: ethyl cellulose grades PR 100, PR45 PR20, PR 10 and PR7 (ETHOCEL®, Dow) and combinations thereof. In at least one embodiment ethyl cellulose grade PR 100 is the water-insoluble, water-permeable film-forming polymer. The amount of the water-insoluble water-permeable film-forming polymer can vary from 1% to 8% by weight of the tablet dry weight. For example, in certain embodiments the amount of the water-insoluble water-permeable film-forming polymer is from 2% to 6% by weight of the tablet dry weight. For certain embodiments of the 174 or 348 mg dose EA tablets of the invention, the amount of water-insoluble water permeable film-forming polymer is from 1% to 15% by weight of the tablet dry weight. For example, in certain embodiments of the 174 mg dose EA tablets, the amount of the water-insoluble water-permeable film-forming polymer is present at 10.5% by weight of the tablet dry weight. With respect to the BA coat itself, the amount of water-insoluble water-permeable film-forming polymer in certain embodiments of the 174 mg dose EA tablets is from 35% to 60% by weight of the EA coat dry weight. For example, in certain embodiments of the 174 mg dose EA tablet, the amount of water-insoluble water-permeable polymer is present at 55% by weight of the EA coat dry weight. For certain embodiments of the 348 mg dose EA tablet of the invention, the amount of water-insoluble water-permeable film-forming polymer is from 1% to 8% by weight of the tablet dry weight. For example, in certain embodiments of the 300 mg dose EA tablet, the amount of water-insoluble water-permeable film forming polymer is present at 6.3% by weight of the tablet dry weight. With respect to the EA coat itself, the water-insoluble water-permeable film-forming polymer in the 300 mg dose EA tablet can be present in an amount of 55% by weight of the EA coat dry weight.

In certain embodiments, the EA coat further comprises a plasticizer. Non-limiting examples of plasticizers that can be used in the EA coat described herein include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. polyols (e.g. polyethylene glycol) of various molecular weights, and mixtures thereof. The amount of plasticizer for the EA coat can vary in an amount from 0.5% to 4% by weight of the tablet dry weight. In a further embodiment of the invention, when a mixture of two plasticizers are used, the ratio of the two plasticizers can range from 5:95 to 95:5. In at least one embodiment of the invention, the plasticizer is polyethylene glycol 4000, dibutyl sebacate, or a mixture thereof. The ratio of polyethylene glycol 4000:dibutyl sebacate can range from 5:95 to 95:5. For certain embodiments of the 174 mg dose EA tablet of the invention, the amount of plasticizer present in the EA coat is from 0.5% to 4% by weight of the tablet dry weight. For example, in certain embodiments of the 174 mg dose EA tablet, the amount of plasticizer is present at 3.1% by weight of the tablet dry weight. For certain embodiments of the 348 mg dose EA tablet of the invention, the amount of plasticizer present is from 0.5% to 3% by weight of the tablet dry weight. For example, in certain embodiments of the 348 mg dose EA tablet, the amount of plasticizer is present at 2.0% by weight of the tablet dry weight. For certain embodiments of both the 174 mg and 348 mg dosage forms, the plasticizer is present in an amount of from 6% to 30% by weight of the EA coat dry weight. For example, in certain embodiments the amount of plasticizer is present at 17% by weight of the EA coat dry weight.

Non-limiting examples of water-soluble polymers useful for the EA coat include polyvinylpyrrolidone, hydroxypropyl methylceliulose, hydroxypropyl cellulose and mixtures thereof. In at least one embodiment of the invention, the water-soluble polymer is polyvinylpyrrolidone (e.g. POVIDONE® USP) the amount of which can vary from 1.5% to 10% by weight of the tablet dry weight. With respect to the EA coat itself, the amount of water-soluble polymer present can vary from 20% to 50% by weight of the EA coat dry weight. For certain embodiments of the 174 mg dose of the EA tablet of the invention, the amount of water-soluble polymer present is from 1.5% to 10% by weight of the tablet dry weight or from 20% to 50% by weight of the EA coat dry weight. For example, in certain embodiments of the 174 mg dose EA tablet, the water-soluble polymer is present in an amount of 28% by weight of the EA coat dry weight. For certain embodiments oF the 348 mg dose of the EA tablet of the invention, the amount of water-soluble polymer present is from 1.5% to 10% of the tablet dry weight and from 20% to 50% by weight of the EA coat dry weight. For example, in certain embodiments of the 300 mg dose EA tablet, the water-soluble polymer is present in an amount of 28% by weight of the EA coat dry weight.

The ratio of water-insoluble water-permeable film forming polymer:plasticizer:water-soluble polymer for the EA tablet coating typically will vary from 3:1:4 to 5:1:2. For example in certain embodiments the ratio of water-insoluble water-permeable film forming polymer:plasticizer:water-soluble polymer for the EA tablet coating is 4:1:3. In at least one embodiment of the EA tablet coating, the ratio of the water-insoluble water-impermeable film-forming polymer:plasticizer:water-soluble polymer is from 7:2:6 to 19:5:18, and in other embodiments is 13:4:12.

Preparation and application of the EA coat can be as follows. The water-insoluble water-permeable film-forming polymer, (e.g. ethylcellulose), and the plasticizer (e.g. polyethylene glycol 4000, dibutyl sebacate, or a mixture thereof), are dissolved in an organic solvent (e.g. ethyl alcohol). The water-soluble polymer (e.g. polyvinyl pyrrolidone) is next added until a homogenous mixture is achieved. The resulting control-releasing coat solution is then sprayed onto the tablet cores using a tablet coater, fluidized bed apparatus or any other suitable coating apparatus known in the art until the desired weight gain is achieved. The tablet cores coated with the EA coat are subsequently dried before a moisture barrier is applied.

The skilled artisan will appreciate that controlling the permeability can control the release of the bupropion salt and/or the amount of coating applied to the tablet cores. The permeability of the EA coat can be altered by varying the ratio of the water-insoluble, water-permeable film-forming polymer:plasticizer:water-soluble polymer and/or the quantity of coating applied to the tablet core. A more extended release can be obtained with a higher amount of water-insoluble, water-permeable film forming polymer. The addition of other excipients to the tablet core can also alter the permeability of the EA coat. For example, if it is desired that the tablet core further comprise an expanding agent, the amount of plasticizer in the control-releasing coat should be increased to make the coat more pliable as the pressure exerted on a less pliable coat by the expanding agent could rupture the coat. Further, the proportion of the water-insoluble water-permeable film forming polymer and water-soluble polymer may also have to be altered depending on whether a faster or slower dissolution and/or release profile is desired.

Depending on the dissolution or in-vivo release profile desired, the weight gained after coating the tablet core with the EA coat can vary from 3% to 30% of the weight of the dry tablet core. For certain embodiments of the 174 mg dose EA tablet of the invention the weight gain is from 8% to 20% of the weight of the dry tablet core. For example, in certain embodiments of the 174 mg dose EA tablet, the weight gain is 14% of the weight of the dry tablet core. For certain embodiments of the 348 mg dose EA tablet of the invention the weight gain is from 10% to 15% of the weight of the dry tablet core. For example, in certain embodiments of the 348 mg dose EA tablet, the weight gain is 13% of the weight of the dry tablet core.

The EA tablet of the invention provides an enhanced-absorption of the bupropion salt wherein typically no pore forming agent is present in the formulation. An enhanced absorption bupropion hydrobromide formulation is provided such that after 2 hours, not more than 25% of the bupropion hydrobromide content is released. For example, in certain embodiments from 10% to 20% of the bupropion hydrobromide content is released after 2 hours. After 4 hours, 25% to 55% of the bupropion hydrobromide content is released. For example, in certain embodiments from 30% to 50% of the bupropion hydrobromide content is released after 4 hours. After 8 hours, more than 60% of the bupropion hydrobromide content is released. For example, in certain embodiments from 70% to 90% of the bupropion hydrobromide content is released after 8 hours. After 16 hours more than 70% of the bupropion hydrobromide content is released. For example, in certain embodiments more than 80% of the bupropion hydrobromide content is released after 16 hours.

In addition in some embodiments the invention provides enhanced absorption formulations wherein not more than 40% is released after 2 hours (e.g, 33%); after 4 hours from 40-75% is released (e.g., 59%); after 8 hours at least 75% is released (e.g., 91%); and after 16 hours at least 85% is released (e.g., 97%).

Controlled Release Matrix

In other embodiments of the present invention, a controlled release matrix is provided from which the kinetics of drug release from the matrix core are dependent at least in part upon the diffusion and/or erosion properties of excipients within the composition. In this embodiment controlled release matrices contain an effective amount of a bupropion salt and at least one pharmaceutically acceptable excipient. The amount of the bupropion salt present in the controlled release matrix can vary in an amount of from 40% to 90% by weight of the matrix tablet dry weight. For example, in certain embodiments bupropion hydrobromide is present in an amount from 60% to 80%, and in other embodiment at 70% by weight of the matrix tablet dry weight. The controlled release matrix can be multiparticulate or uniparticulate, and can be coated with at least one functional or non-functional coating, or an immediate release coating containing a bupropion salt or other drug. Functional coatings include by way of example controlled release polymeric coatings, enteric polymeric coatings, and the like. Non-functional coatings are coatings that do not affect drug release but which affect other properties (e.g., they may enhance the chemical, biological, or the physical appearance of the controlled release formulation). Those skilled in the pharmaceutical art and the design of medicaments are well aware of controlled release matrices conventionally used in oral pharmaceutical compositions adopted for controlled release and means for their preparation. Examples of controlled release matrices are described in U.S. Pat. Nos. 6,326,027; 6,340,475; 6,905,709; 6,645,527; 6,576,260; 6,326,027; 6,254,887; 6,306,438; 6,129,933; 5,891,471; 5,849,240; 5,965,163; 6,162,467; 5,567,439; 5,552,159; 5,510,114; 5,476,528; 5,453,283; 5,443,846; 5,403,593; 5,378,462; 5,350,584; 5,283,065; 5,273,758; 5,266,331; 5,202,128; 5,183,690; 5,178,868; 5,126,145; 5,073,379; 5,023,089; 5,007,790; 4,970,075; 4,959,208; 4,59,208; 4,861,598; 4,844,909; 4,834,984; 4,828,836; 4,806,337; 4,801,460; 4,764,378; 4,421,736; 4,344,431; 4,343,789; 4,346,709; 4,230,687; 4,132,753; 5,591,452; 5,965,161; 5,958,452; 6,254,887; 6,156,342; 5,395,626; 5,474,786; and 5,919,826.

Suitable excipient materials for use in such controlled release matrices include, by way of example, release-resistant or controlled release materials such as hydrophobic polymers, hydrophilic polymers, lipophilic materials and mixtures thereof. Non-limiting examples of hydrophobic, or lipophilic components include glyceryl monostearate, mixtures of glyceryl monostearate and glyceryl monopalmitate (Myvaplex, Eastman Fine Chemical Company), glycerylmonooleate, a mixture of mono, di and tri-glycerides (ATMUL 84S), glycerylmonolaurate, paraffin, white wax, long chain carboxylic acids, long chain carboxylic acid esters, long chain carboxylic acid alcohols, and mixtures thereof. The long chain carboxylic acids can contain from 6 to 30 carbon atoms; in certain embodiments at least 12 carbon atoms, and in other embodiments from 12 to 22 carbon atoms. In some embodiments this carbon chain is fully saturated and unbranched, while others contain one or more double bonds. In at least one embodiment the long chain carboxylic acids contain 3-carbon rings or hydroxyl groups. Non-limiting examples of saturated straight chain acids include n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Non-limiting examples of these include oleic acid, gadoleic acid and erucic acid. Also useful are unsaturated (polyolefinic) straight chain monocaboxyic acids. Non-limiting examples of these include linoleic acid, linolenic acid, arachidonic acid and behenolic acid. Useful branched acids include, for example, diacetyl tartaric acid. Non-limiting examples of long chain carboxylic acid esters include glyceryl monostearates; glyceryl monopalmitates; mixtures of glyceryl monostearate and glyceryl monopalmitate (Myvaplex 600, Eastman Fine Chemical Company); glyceryl monolinoleate; glyceryl monooleate; mixtures of glyceryl monopalmitate, glyceryl monostearate glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters, distilled monoglycerides, sodium stearoyl lactylate and silicon dioxide (Myvatex TL, Eastman Fine Chemical Company) d-alpha tocopherol polyethylene glycol 1000 succinate (Vitamin E TPGS, Eastman Chemical Company); mixtures of mono- and diglyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; cetearyl octanoate; C10-C30 cholesterol/lavosterol esters; sucrose long chain carboxylic acid esters; and mixtures thereof.

The alcohols useful as excipient materials for controlled release matrices can include the hydroxyl forms of the carboxylic acids exemplified above and also cetearyl alcohol.

In addition, waxes can be useful alone or in combination with the materials listed above, as excipient materials for the controlled release matrix embodiments of the present invention. Non-limiting examples of these include white wax, paraffin, microcrystalline wax, carnauba wax, and mixtures thereof.

The lipophilic agent can be present in an amount of from 5% to 90% by weight of the controlled release matrix dosage form. For example, in certain embodiments the lipophilic agent is present in an amount of from 10% to 85%, and in other embodiments from 30% to 60% by weight of the controlled release matrix dosage form.

Non-limiting examples of hydrophilie polymers that can be used in certain embodiments of the controlled release matrix dosage form include hydroxypropylmethylcel lulose (HPMC), hydroxypropylcellulose (HPC), hydroxyethylcefluluse (HEC), carboxymethylcellulose (CMC) or other cellulosc ethers, polyoxyethylene, alginic acid, acrylic acid derivatives such as polyacmylic acid, Carbopol (B. F. Goodrich, Cleveland, Ohio). polymethacrylate polymer such as EUDRAGIT® RL, RS, R. S, NE and E (Rhome Pharma, Darmstadt, Germany), acrylic acid polymer, methacrylic acid polymer, hydroyethyl methacrylic acid (HEMA) polymer, hydroxymethyl methacrylic acid (HMMA) potymer, polyvinyl alcohols.

The hydrophilic polymer can be present in an amount of from 10% to 90% by weight of the controlled release matrix dosage form. For example, in certain embodiments the hydrophilic polymer is present in an amount of from 20% to 75%, and in other embodiments from 30% to 60% by weight of the controlled release matrix dosage form.

In at least one embodiment, the controlled release matrix dosage form comprises hydroxypropylmethylcellulose (HPMC). HPMC is an anhydroglucose in which some of the hydroxyl groups are substituted with methyl groups to form methyl ether moieties, and others are substituted with hydroxypropyl groups or with methoxypropyl groups to form hydroxypropyl ether or methoxypropyl ether moieties. Non-limiting examples of hydroxypropyl methylcelluloses that are commercially available include METHOCEL® E (USP type 2910), METHOCEL® F (USP type 2906). METHOCEL® J (USP type 1828), METHOCEL® K (USP type 2201), and METHOCEL® 310 Series, products of The Dow Chemical Company, Midland, Mich., USA. The average degree of methoxyl substitution in these products can range from 1.3 to 1.9 (of the three positions on each unit of the cellulose polymer that are available for substitution) while the average degree of hydroxypropyl substitution per unit expressed in molar terms can range from 0.13 to 0.82. The dosage form can comprise the different HPMC grades having different viscosities. The size of a HPMC polymer is expressed not as molecular weight but instead in terms of its viscosity as a 2% solution by weight in water. Different HPMC grades can be combined to achieve the desired viscosity characteristics. For example, the at least one pharmaceutically acceptable polymer can comprise two HPMC polymers such as for example METHOCEL® K3 LV (which has a viscosity of 3 cps) and METHOCEL® K100M CR (which has a viscosity of 100,000 cps). In addition, the polymer can comprise two hydroxypropylcellulose forms such as KLUCEL® LF and KLUCEL® EF. In addition, the at least one polymer can comprise a mixture of a KLUCEL® and a METHOCEL®.

In at least one embodiment the controlled release matrix dosage form comprises a polyethylene oxide (PEO). PEO is a linear polymer of unsubstituted ethylene oxide. In certain embodiments poly(ethylene oxide) polymers having viscosity-average molecular weights of 100,000 daltons and higher are used. Non-limiting examples of poly(ethylene oxide)s that are commercially available include: POLYOX® NF, grade WSR Coagulant, molecular weight 5 million; POLYOX® grade WSR 301, molecular weight 4 million; POLYOX® grade WSR 303, molecular weight 7 million; POLYOX® grade WSR N-60 K, molecular weight 2 million; and mixtures thereof. These particular polymers are products of Dow Chemical Company, Midland, Mich., USA. Other examples of polyethylene oxides exist and can likewise be used. The required molecular weight for the PEO can be obtained by mixing PEO of differing molecular weights that are available commercially.

In at least one embodiment of the controlled release matrix dosage form, PEO and HPMC are combined within the same controlled release matrix. In certain embodiments, the poly(ethylene oxide)s have molecular weights ranging from 2,000,000 to 10,000,000 Da. For example, in at least one embodiment the polyethylene oxides have molecular weights ranging from 4,000,000 to 7,000,000 Da. In certain embodiments the HPMC polymers have a viscosity within the range of 4,000 centipoise to 200,000 centipoise. For example, in at least one embodiment the HPMC polymers have a viscosity of from 50,000 centipoise to 200,000 centipoise, and in other embodiments from 80,000 centipoise to 120,000 centipoise. The relative amounts of PEO and HPMC within the controlled release matrix can vary within the scope of the invention. In at least one embodiment the PEO:HPMC weight ratio is from 1:3 to 3:1. For example, in certain embodiments the PEO:HPMC weight ratio is from 1:2 to 2:1. As for the total amount of polymer relative to the entire matrix, this can vary as well and can depend on the desired drug loading. In at least one embodiment the total amount of polymer in the matrix can constitute from 15% to 90% by weight of the matrix dosage form. For example, in certain embodiments the total amount of polymer in the matrix is from 20% to 75%, in other embodiments from 30% to 60%, and in still other embodiments from 10% to 20% by weight of the matrix dosage form.

In at least one embodiment of the invention the controlled release matrix dosage form comprises a hydrophobic polymer such as ethylcellulose. The viscosity of ethylcellulose can be selected in order to influence of rate the drug release. In certain embodiments the ethylcellulose has a viscosity from 7 to 100 cP (when measured as a 5% solution at 25° C. in an Ubbelohde viscometer, using a 80:20 toluene:ethanol solvent.) In certain embodiments the hydrophobic polymer can constitute from 10% to 90% by weight of the matrix dosage form. For example, in at least one embodiment the hydrophobic polymer constitutes from 20% to 75%, and in other embodiments from 30% to 60% by weight of the matrix dosage form.

In at least one embodiment of the invention the controlled release matrix dosage form comprises at least one lubricant. Non-limiting examples of lubricants include stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K)) stearyl alcohol, leucine, polyethylene glycol (MW 1450, suitably 4000, and higher), magnesium stearate, glyceryl monostearate, stearic acid, glycerylbehenate, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, and mixtures thereof. The lubricant can be present in an amount of from 0 to 4% by weight of the compressed uncoated matrix. For example, in certain embodiments the lubricant is present in an amount of from 0 to 2.5% by weight of the compressed, uncoated matrix.

In at least one embodiment of the invention the controlled release matrix dosage form comprises a plasticizer. Non-limiting examples of plasticizers include dibutyl sebacate, diethyl phthalate, triethyl citrate, tributyl citrate, triacetin, citric acid esters such as triethyl citrate NF XVI, tributyl citrate, dibutyl phthalate, 1,2-propylene glycol, polyethylene glycols, propylene glycol, diethyl phthalate, castor oil, acetylated monoglycerides, phthalate esters, and mixtures thereof. In at least one embodiment, the plasticizer can be present in an amount of from 1% to 70% by weight of the controlled release polymer in the matrix dosage form. For example, in certain embodiments the plasticizer is present in an amount of from 5% to 50%, and in other embodiments from 10% to 40% by weight of the controlled release polymer in the matrix dosage form.

In at least one embodiment of the invention the controlled release matrix dosage form comprises at least one diluent, non-limiting examples of which include dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol, sucralfate, calcium hydroxyl-apatite, calcium phosphates and fatty acid salts such as magnesium stearate. In certain embodiments the diluent can be added in an amount so that the combination of the diluent and the active substance comprises up to 60%, and in other embodiments up to 50%, by weight of the composition.

In at least one embodiment of the invention the controlled release matrix dosage form comprises a solubilizer. The solubilizer can act to increase the instantaneous solubility of the bupropion salt. The solubilizer can be selected from hydrophilic surfactants or lipophilic surfactants or mixtures thereof. The suifactants can be anionic, nonionic, cationic, and zwitterioriic surfactants. The hydrophilic non-ionic surfactants can be selected from the group comprised of, but not limited to: polyethylene glycol sorbitan fatty acid esters and hydrophilic transesterification products of a polyol with at least one member of the group from triglycerides, vegetable oils, and hydrogenated vegetable oils such as glycerol, ethylene glycol, polyethylene glycol, sorbitol, propylene glycol, pentaerythritol, or a saccharide, d-α-iocopheryl polyethylene glycol 1000 succinate. The ionic surfactants can be selected from the group comprised of, but not limited to: alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkyisulfates; fatty acid salts; sodium docusate; acyl lactylates; mono- and di-acetylated tartaric acid esters of mono- and di- glycericles; succinylated mono-and di-glycerides; citric acid esters of mono-and di- glycerides; and mixtures thereof. The lipophilic surfactants can be selected from the group comprised of, but not limited to: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives: polyoxyethylated sterols and sterol derivatives; polyethylene glycol alkyl ethers; sugar esters; sugar ethers; lactic acid derivatives of mono-and di-glycerides; hydrophobic transesterification products of a polyol with at least one member of the group from glycerides, vegetable oils, hydrogenated vegetable oils, fatty acids and sterols; oil-soluble vitamins/vitamin derivatives; PEG sorbitan fatty acid esters, PEG glycerol fatty acid esters, polyglycerized fatty acid, polyoxycihylene-polyoxypropylene block copolymers, sorbi tan fatty acid esters; and mixtures thereof. In at least one embodiment the solubilizer can be selected from: PEG-20-glyceryl stearate (CAPMUL® by Abitec), PEG-40 hydrogenated castor oil (CREMOPHOR RH 40® by BASF), PEG 6 corn oil (LABRAFIL® by Gattefosse), lauryl macrogol-32 glyceride (GELUCIRE44/14® by Gattefosse) stearoyl macrogol glyceride (GELUCIRE50/13® by Gattefosse), polyglyceryl-10 mono dioleate (CAPROL® PEG860 by Abitec). propylene glycol olcate (LUTROL® by BASE), Propylene glycol dioctanoate (CAPTEX® by Abitec), Propylene glycol caprylate/caprate (LABRAFAC® by Gattefosse), Glyceryl monooleate (PECEOL® by Gattefrosse), Glycerol monolinoleate (MAISINE® by Gattefrosse), Glycerol monostearate (CAPMUL® by Abitec), PEG-20 sorbitan monolaurate (TWEEN20® by ICI), PEG-4 lauryl ether (BRIJ30® by ICI), Sucrose distearate (SUCROESTER7® by Gattetosse), Sucrose monopalmitate (SUCROESTER15® by Gattefosse), polyoxyethylene-polyoxypropylene block copolyrner (LUTROL® series BASF), polyethylene glycol 660 hydroxystearate, (SOLUTOL® by BASE), Sodium lauryl sulfate, Sodium dodecyl sulphate, Dioctyl suphosuccinate, L-hydroxypropyl cellulose, hydroxylethylcellulose, hydroxyl propylcellulose, Propylene glycol alginate, sodium taurochol ate, sodium glycocholate, sodium deoxycholate, betains, polyethylene glycol (CARBOWAX® by DOW), d-a-tocopheryl polyethylene glycol 1000 succinate, (VITAMIN E TPGS® by Eastman), and mixtures thereof. In at least one other embodiment the solubilizer can be selected from PEG-40 hydrogenated castor oil (CREMOPHOR RH 40® by BASF), lauryl macrogol-32 glyceride (GELUCIRE44/14® by GaUefosse) stearoyl macrogol glyceride (GELUCIRE 50/13® by Gattefosse), PEG-20 sorbitan monolaurate (TWEEN 20® by Id), PEG-4 lauryl ether (BRIJ30® by ICI), polyoxyethylene- polyoxypropylene block copolymer (LUTROL® series BASF), Sodium lauryl sulphate, Sodium dodecyl sulphate, polyethylene glycol (CARBOWAX® by DOW), and mixtures thereof.

In at least one embodiment of the invention the controlled release matrix dosage form comprises a swelling enhancer. Swelling enhancers are members of a special category of excipients that swell rapidly to a large extent resulting in an increase in the size of the tablet. At lower concentrations, these excipients can be used as superdisintegrants; however at concentrations above 5% w/w these agents can function as swelling enhancers and help increase the size of the matrix dosage form. According to certain embodiments of the matrix dosage forms of the invention, examples of swelling enhancers include but are not limited to: low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinised starch, sodium carboxymethyl starch and mixtures thereof. In at least one embodiment of the matrix dosage forms, the swelling enhancer is cross-linked polyvinyl pyrrolidone. The content of the swelling enhancer can be from 5% to 90% by weight of the matrix dosage form. For example, in certain embodiments the swelling enhancer is present in an amount of from 10% to 70%, and in other embodiments from 15% to 50% by weight of the matrix dosage form.

In at least one embodiment of the invention the controlled release matrix dosage form comprises additives for allowing water to penetrate into the core of the preparation (hereinafter referred to as "hydrophilic base"). In certain embodiments, the amount of water required to dissolve 1 g of the hydrophilic base is not more than 5 ml, and in other embodiments is not more than 4 ml at the temperature of 20° C.±5° C. The higher the solubility of the hydrophilic base in water, the more effective is the base in allowing water into the core of the preparation. The hydrophilic base includes, inter alia, hydrophilic polymers such as polyethylene glycol (PEG); (e.g. PEG400, PEG1500, PEG4000, PEG6000 and PEG20000, produced by Nippon Oils and Fats Co.) and polyvinylpyrrolidone (PVP); (e.g. PVP K30, of BASF), sugar alcohols such as D-sorbitol, xylitol, or the like, sugars such as sucrose, anhydrous maltose, D-fructose, dextran (e.g. dextran 40), glucose or the like, surfactants such as polyoxyethylene-hydrogenated castor oil (HCO; e.g. Cremophor RH40 produced by BASF, HCO-40 and HCO-60 produced by Nikko Chemicals Co.), polyoxyethylene-polyoxypropylene glycol (e.g. Pluronic F68 produced by Asahi Denka Kogyo K.K.), polyoxyethylene-sorbitan high molecular fatty acid ester (Tween; e.g. Tween 80 produced by Kanto Kagaku K.K.), or the like; salts such as sodium chloride, magnesium chloride, or the like; organic acids such as citric acid, tartaric acid, or the like; amino acids such as glycine, .beta.-alanine, lysine hydrochloride, or the like; and amino sugars such as meglumine. In at least one embodiment the hydrophilic base is PEG6000, PVP, D-sorbitol, or mixtures thereof.

In another embodiment of the invention the controlled release matrix dosage form comprises at least one disintegrant. Non-limiting examples of disintegrants for use in the matrix dosage form include croscarmellose sodium, crospovidone, alginic acid, sodium alginate, methacrylic acid DVB, cross-Linked PVP, microcrystalline cellulose, polacrilin potassium, sodium starch glycolatc, starch, pregelatinized starch and the like. In at least one embodiment the disintegrant is selected from cross-linked polyvinylpyrrolidone (e.g. KOLLIDON® CL), cross-linked sodium carboxyinethylcellulose (e.g. Ac-Di-Sol), starch or starch derivatives such as sodium starch glycolate (e.g. EXPLOTAB®), or combinations with starch (e.g. PRIMOJEL™), swellable ion-exchange resins, such as Ainberlite JRP 88, formaldehyd-casein (e.g. ESNIA SPRENG™), and mixtures thereof. In at least one embodiment the disintegrant is sodium starch glycolate. The disintegrant can be present in an amount of from 0 to 20% of the total weight of the matrix.

The controlled release matrices of the present invention can further contain one or more pharmaceutically acceptable excipients such as, granulating aids or agents, colorants, flavorants, pH adjusters, anti-adherents, glidants and like excipients conventionally used in pharmaceutical compositions.

In at least one embodiment of the invention comprising water swellable polymers formulated into the matrix, the release kinetics of the bupropion salt from the matrix are dependent upon the relative magnitude of the rate of polymer swelling at the moving rubbery/glassy front and the rate of polymer erosion at the swollen polymer/dissolution medium front. The release kinetics for the release of the bupropion salt from the matrix can be approximated by the following equation:

$$M_t/M_T = kt^n$$

where t is time,
$M_t$ is the amount of the pharmaceutical agent which has been released at time t,
$M_T$ is the total amount of the pharmaceutical agent contained in the matrix,
k is a constant, and
n is the release kinetics exponent This equation is valid so long as n remains nearly constant. When n is equal to one, the release of the pharmaceutical agent from the matrix has zero-order kinetics. The amount of pharmaceutical agent released is then directly proportional to the time.

Where the swelling process of the polymer chosen for the excipient is the primary process controlling the drug release (compared to erosion of the swollen polymer), non-zero order release kinetics can result. Generally, these release kinetics dictate a value of n approaching 0.5, leading to square-root Fickian-type release kinetics.

In at least one embodiment of the invention, polymers are selected for inclusion into the formulation to achieve zero order kinetics. The release kinetics of the matrix can also be dictated by the pharmaceutical agent itself. A drug which is highly soluble can tend to be released faster than drugs which have low solubility. Where a drug has high solubility, polymer swelling and erosion must take place rapidly to maintain zero order release kinetics. If the swelling and erosion take place too slowly, the swelling process of the polymer is the primary process controlling the drug release (since the drug will diffuse from the swollen polymer before the polymer erodes). In this situation, non-zero order release kinetics can result. As a result, the administration of a highly soluble pharmaceutical agent requires a relatively rapidly swelling and eroding excipient. To use such a material to produce a matrix which will last for 24 hours can require a large matrix. To overcome this difficulty, a doughnut-shaped matrix with a hole though the middle can be used with a less rapidly swelling and eroding polymer. With such a matrix, the surface area of the matrix increases as the matrix erodes. This exposes more polymer, resulting in more polymer swelling and erosion as the matrix shrinks in size. This type of matrix can also be used with very highly soluble pharmaceutical agents to maintain zero order release kinetics.

In at least one other embodiment of the invention, zero order drug release kinetics can be achieved by controlling the surface area of the matrix dosage form that is exposed to erosion. When water is allowed to diffuse into a polymer matrix composition zero order release is obtained when the release rate is governed or controlled by erosion of a constant surface area per time unit. In order to ensure that the erosion of the polymer matrix composition is the predominant release mechanism, it is helpful to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents in the polymer matrix composition a zero order release mechanism can be achieved. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period. Accordingly, these embodiments provide a method for controlling the release of a bupropion salt into an aqueous medium by erosion of at least one surface of a pharmaceutical composition comprising (i) a matrix composition comprising (a) a polymer or a mixture of polymers, (b) a bupropion salt and, optionally, (c) one or more pharmaceutically acceptable excipients, and (ii) a coating having at least one opening exposing at the one surface of said matrix, the coating comprising: (a) a first cellulose derivative which has thermoplastic properties and which is substantially insoluble in the aqueous medium in which the composition is to be used, and at least one of (b) a second cellulose derivative which is soluble or dispersible in water, (c) optionally a plasticizer, and (d) a filler, the method comprising adjusting the concentration and/or the nature of the ingredients making up the matrix composition in such a manner that the diffusion rate of the aqueous medium into the matrix composition corresponds to 100%±30% such as, for example 100%±25%, 100%±20%, 100%±15% or 100%±10%, or 100% of the dissolution rate of the matrix composition so as to obtain a zero order release of at least 60% w/w such as, for example at least 65% w/w, at least 70% w/w, at least 75% w/w, at least 80% w/w, at least 85% w/w, at least 90% w/w, at least 95% w/w or at least 97% to 98% w/w of the bupropion salt from the pharmaceutical composition when subject to an in vitro dissolution test.

In at least one other embodiment of the invention, zero order drug release is approached through the use of: (a) a deposit-core comprising the bupropion salt and having defined geometric form, (b) a support-platform applied to said deposit-core, and is characterised in that said deposit-core contains, mixed with the bupropion salt, a polymeric material having a high degree of swelling on contact with water or aqueous liquids, a gellable polymeric material, said polymeric materials being replaceable by a single polymeric material having both swelling and gelling properties, and other adjuvants able to provide the mixture with suitable characteristics for its compression and for its intake of water, said support-platform comprising a polymeric material insoluble in aqueous liquids and partially coating said deposit-core.

These and further characteristics and advantages of the system according to certain embodiments of the matrix dosage form will be more apparent from the detailed description of preferred embodiments of the invention given hereinafter by way of non-limiting example. The deposit-core can generally be obtained by compressing the mixture containing the bupropion salt to a pressure of between 1000 and 4000 kg/cm$^2$, to thus assume a defined geometric form. Polymeric materials having a high degree of swelling can generally be cross-linked insoluble polymers, whereas gellable polymeric materials are soluble, and can control the intake of water.

The coating platform comprises a polymeric material insoluble in water and optionally insoluble in biodegradable biological liquids, and able to maintain its impermeability characteristics at least until the complete transfer of the buprosion salt contained in the deposit-core. It is applied to a part of the external deposit-core surface chosen such as to suitably direct and quantitatively regulate the release of the bupropion salt. In this respect, as the support-platform is impermeable to water, the polymeric material of the deposit-core in certain embodiments can swell only in that portion of the deposit not coated with the platform.

The support-platform can be obtained by compressing prechosen polymeric materials onto the deposit-core, by immersing the deposit-core in a solution of said polymeric materials in normal organic solvents, or by spraying said solutions. Polymeric materials usable for preparing the support-platform can be chosen from the class comprising acrylates, celluloses and derivatives such as ethylcellulose, cellulose acetate-propionate, polyethylenes and methacrylates and copolymers of acrylic acid, polyvinylalcohols etc. This platform can have a thickness of between 2 mm if applied by compression and 10 microns if applied by spraying or immersion, and comprises from 10% to 90% of the total surface of the system.

A factor in controlling the release of the bupropion salt is the intensity and duration of the swelling force developed by the swellable polymeric materials contained in the deposit-core on contact with aqueous fluids. In this respect, the energy for activating, executing and regulating the release of the bupropion salt can be determined by the swelling force developed in the deposit-core when this comes into contact with water or with biological liquids. Said force has an intensity and duration which can vary in relation to the type and quantity of the polymeric materials used in formulating the deposit, and it lies between limits having a maximum value which occurs in the case of a deposit mainly containing the swellable polymer, and a minimum value which occurs in the case of a deposit mainly containing the gellable polymer. Said swellable polymer can be present to the extent of between 5% and 80% by weight, and said gellable polymer to the extent of between 10% and 90% by weight, with respect to the mixture forming the deposit-core.

A further control factor is the geometry of the support-platform, which limits the swelling of the deposit and directs the emission of material from it. Within the scope of these embodiments it is possible to conceive many systems for the controlled release of bupropion salt, which base their operation on the swelling force and differ from each other by the type of support-platform used.

In at least one other embodiment of the invention designed to achieve zero order release of the bupropion salt, the kinetics of drug release from a controlled release matrix is governed by a combination of different polymers with different swelling characteristics. More specifically, the bupropion salt is first granulated with or encapsulated in a less swellable polymer, such as a gum, to form a granule. This granule is disposed in a matrix of a more swellable, erodible polymer. The more swellable erodible polymer has a diffusion rate coefficient which is greater than the diffusion rate coefficient of the relatively less swellable polymer. Averaged over the entire period of drug release, the diffusion rate for the more swellable polymer is greater than the diffusion rate for the less swellable polymer. It is this general difference in rates of diffusion between the first and second polymers which controls the rate of drug release and allows the system to approach zero order drug delivery over the drug release period. In at least one embodiment, pectin and HPMC are present as the more swellable polymers in ratios of is between 2:7 and 4:5, and gelatin is present as the less swellable polymer.

In at least one other embodiment of the invention there is provided a controlled release matrix composition comprising bupropion hydrobromide incorporated within a homogeneous matrix including effective amounts of at least two polymers having opposing wettability characteristics, wherein at least one polymer is selected which demonstrates a stronger tendency towards hydrophobicity and the other polymer(s) is selected which demonstrates a stronger tendency towards hydrophilicity. In at least one embodiment the polymer demonstrating a stronger tendency towards hydrophobicity is ethylcellulose (EC) whereas the polymer demonstrating a stronger tendency towards hydrophilicity is hydroxyethylcellulose (HEC) and/or hydroxypropyl methylcellulose (HPMC). The composition and device of the present invention can be provided as a matrix and can be optionally encased in a coating material which prevents the burst and/or food effect associated with orally ingested medicaments and imparts gastrointestinal "stealth" characteristics. In accordance with at least one embodiment is a method for preparing a device for the controlled release of the bupropion salt, the method comprising blending bupropion hydrobromide with 5% to 25% by weight of hydrophillic polymer, and 1% to 25% by weight of hydrophobic polymer, adding suitable pharmaceutical excipients, surface active agents and lubricants, granulating the mixture with solvents such as isopropyl alcohol, drying the granular mixture, milling the dried mixture, adding from 5% to 70% by weight of ethylcellulose, adding a lubricant and optionally a glidant and compressing the granules into matrices. The matrices are optionally encased in a gastrointestinal encasement or a pharmaceutically acceptable film coat.

In another embodiment of the present invention, a swellable matrix dosage form is provided in which the bupropion salt is dispersed in a polymeric matrix that is water-swellable rather than merely hydrophilic, that has an erosion rate that is substantially slower than its swelling rate, and that releases the bupropion salt primarily by diffusion. The rate of diffusion of the bupropion salt out of the swellable matrix can be slowed by increasing the drug particle size, by the choice of polymer used in the matrix, and/or by the choice of molecular weight of the polymer. The swellable matrix is comprised of a relatively high molecular weight polymer that swells upon ingestion. In at least one embodiment the swellable matrix swells upon ingestion to a size that is at least twice its unswelled volume, and that promotes gastric retention during the fed mode. Upon swelling, the swellable matrix can also convert over a prolonged period of time from a glassy polymer to a polymer that is rubbery in consistency, or from a crystalline polymer to a rubbery one. The penetrating fluid then causes release of the bupropion salt in a gradual and prolonged manner by the process of solution diffusion, i.e., dissolution of the bupropion salt in the penetrating fluid and diffusion of the dissolved bupropion salt back out of the swellable matrix. The swellable matrix itself is solid prior to administration and, once administered, remains undissolved in (i.e., is not eroded by) the gastric fluid for a period of time sufficient to permit the majority of the bupropion salt to be released by the solution diffusion process during the fed mode. The rate-limiting factor in the release of the bupropion salt from the swellable matrix is therefore controlled diffusion of the bupropion salt from the swellable matrix rather than erosion, dissolving or chemical decomposition of the swellable matrix.

As such, the swelling of the polymeric matrix can achieve at least the following objectives: (i) renders the matrix sufficiently large to cause retention in the stomach during the fed mode; (ii) localizes the release of the drug to the stomach and small intestine so that the drug will have its full effect without colonic degradation, inactivation, or loss of bioavailability; (iii) retards the rate of diffusion of the drug long enough to provide multi-hour, controlled delivery of the drug into the stomach.

The bupropion salt in the swellable matrix can be present in an effective amount of from 0.1% to 99% by weight of the matrix. For example, in certain embodiments bupropion hydrobromide is present in the swellable matrix in an amount of from 0.1% to 90%, in other embodiments from 5% to 90%, in still other embodiments from 10% to 80%, and in even still other embodiments from 25% to 80% by weight of the swellable matrix.

The water-swellable polymer forming the swellable matrix in accordance with these embodiments of the present invention can be any polymer that is non-toxic, that swells in a dimensionally unrestricted manner upon imbibition of water, and that provides for a modified release of the bupropion salt. Non-limiting examples of polymers suitable for use in the swellable matrix include cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly (2-ethyl-2-oxazoline), poly(ethyleneimine), polyurethane hydrogels, and crosslinked polyacrylic acids and their derivatives, and mixtures thereof. Further examples include copolymers of the polymers listed in the preceding sentence, including block copolymers and grafted polymers. Specific examples of copolymers include PLURONIC® and TECTONIC®, which are polyethylene oxide-polypropylene oxide block copolymers available from BASF Corporation, Chemicals Div., Wyandotte, Mich., USA.

The terms "cellulose" and "cellulosic", as used within this section regarding the swellable matrix embodiments of the present invention, can denote a linear polymer of anhydroglucose. Non-limiting examples of cellulosic polymers include alkyl-substituted cellulosic polymers that ultimately dissolve in the gastrointestinal (GI) tract in a predictably delayed manner. In certain embodiments the alkyl-substituted cellulose derivatives are those substituted with alkyl groups of 1 to 3 carbon atoms each. Non-limiting examples include methylcellulose, hydroxymethylcellulose, hydroxyethylcellulose, hydroxypropylcellulose, hydroxypropylmethylcellulose, carboxymethylcellulose, and mixtures thereof. In terms of their viscosities, one class of alkyl-substituted celluloses includes those whose viscosity is within the range of 100 to 110,000 centipoise as a 2% aqueous solution at 20° C. Another class includes those whose viscosity is within the range of 1,000 to 4,000 centipoise as a 1% aqueous solution at 20° C. In certain embodiments the alkyl-substituted celluloses are hydroxyethylcellulose and hydroxypropylmethylcellulose. In at least one embodiment the hydroxyethylcellulose is NATRASOL® 250HX NF (National Formulary), available from Aqualon Company, Wilmington, Del., USA.

Polyalkylene oxides that can be used in certain embodiments of the swellable matrices include those having the properties described above for alkyl-substituted cellulose polymers. In at least one embodiment the polyalkylene oxide is poly(ethylene oxide), which term is used herein to denote a linear polymer of unsubstituted ethylene oxide. In at least one embodiment the poly(ethylene oxide) polymers have molecular weights of 4,000,000 and higher. For example, in certain embodiment the poly(ethylene oxide) polymers have molecular weights within the range of 4,500,000 to 10,000,000, and in other embodiments have molecular weights within the range of 5,000,000 to 8,000,000. In certain embodiments the poly(ethylene oxide)s are those with a weight-average molecular weight within the range of $1 \times 10^5$ to $1 \times 10^7$, and in other embodiments within the range of $9 \times 10^5$ to $8 \times 10^6$. Poly(ethylene oxide)s are often characterized by their viscosity in solution. For example, in certain embodiments the poly(ethylene oxide)s have a viscosity range of 50 to 2,000,000 centipoise for a 2% aqueous solution at 20° C. In at least one embodiment the poly(ethylene oxide) is one or more of POLYOX® NF, grade WSR Coagulant, molecular weight 5 million, and grade WSR 303, molecular weight 7 million, both products of Union Carbide Chemicals and Plastics Company Inc. of Danbury, Conn., USA. Mixtures thereof are operable.

Polysaccharide gums, both natural and modified (semi-synthetic) can be used in the swellable matrix embodiments of the present invention. Non-limiting examples include dextran, xanthan gum, gellan gum, welan gum, rhamsan gum, and mixtures thereof. In at least one embodiment the polysaccharide gum is xanthan gum.

Crosslinked polyacrylic acids that can be used in the swellable matrices of the present invention include those whose properties are the same as those described above for alkyl-substituted cellulose and polyalkylene oxide polymers. In certain embodiments the crosslinked polyacrylic acids are those with a viscosity ranging from 4,000 to 40,000 centipoise for a 1% aqueous solution at 25° C. Non-limiting examples of suitable crosslinked polyacrylic acids include CARBOPOL® NF grades 971P, 974P and 934P (BFGoodrich Co., Specialty Polymers and Chemicals Div., Cleveland, Ohio, USA). Further examples of suitable crosslinked polyacrylic acids include polymers known as WATER LOCK®, which are starch/acrylates/acrylamide copolymers available from Grain Processing Corporation, Muscatine, Iowa, USA.

The hydrophilicity and water swellability of these polymers can cause the drug-containing swellable matrices to swell in size in the gastric cavity due to ingress of water in order to achieve a size that can be retained in the stomach when introduced during the fed mode. These qualities also cause the swellable matrices to become slippery, which provides resistance to peristalsis and further promotes their retention in the stomach. The release rate of drug from the swellable matrix is primarily dependent upon the rate of water imbibition and the rate at which the drug dissolves and diffuses from the swollen polymer, which in turn is related to the drug concentration in the swellable matrix. Also, because these polymers dissolve very slowly in gastric fluid, the swellable matrix maintains its physical integrity over at least a substantial period of time, for example in many cases at least 90% and preferably over 100% of the dosing period.

The particles will then slowly dissolve or decompose. Complete dissolution or decomposition may not occur until 24 hours or more after the intended dosing period ceases, although in most cases, complete dissolution or decomposition will occur within 10 to 24 hours after the dosing period.

The amount of polymer relative to the drug can vary, depending on the drug release rate desired and on the polymer, its molecular weight, and excipients that may be present in the formulation. The amount of polymer will typically be sufficient to retain at least 40% of the drug within the swellable matrix one hour after ingestion (or immersion in the gastric fluid). In certain embodiments, the amount of polymer is such that at least 50% of the drug remains in the matrix one hour after ingestion; in other embodiments at least 60%, and in still other embodiments at least 80%, of the drug remains in the swellable matrix one hour after ingestion. In certain embodiments the drug will be substantially all released from the swellable matrix within ten hours; and in other embodiments within eight hours, after ingestion, and the polymeric matrix will remain substantially intact until all of the drug is released. In other embodiments the amount of polymer will be such that after 2 hours no more than 40% is released; after 4 hours 40-75% is released; after 8 hours at least 75% is released and after 16 hours at least 85% is released. The term "substantially intact" is used herein to denote a polymeric matrix in which the polymer portion substantially retains its size and shape without deterioration due to becoming solubilized in the gastric fluid or due to breakage into fragments or small particles.

In other exemplary embodiments the swellable matrix after 2 hours will release no more than 40% of the bupropion HBr, after 4 hours from 40-75%, after 8 hours at least 75% and after 16 hours at least 85%.

The water-swellable polymers of the swellable matrices can be used individually or in combination. Certain combinations will often provide a more controlled release of the drug than their components when used individually. Examples include cellulose-based polymers combined with gums, such as hydroxyethyl cellulose or hydroxypropyl cellulose combined with xanthan gum. Another example is poly(ethylene oxide) combined with xanthan gum.

The benefits of this invention can be achieved over a wide range of drug loadings and polymer levels, with the weight ratio of drug to polymer ranging in general from 0.01:99.99 to 80:20. For example, in certain embodiments the drug loadings (expressed in terms of the weight percent of drug relative to total of drug and polymer) are within the range of 15% to 80%; in other embodiments within the range of 30% to 80%; and in still other embodiments within the range of 30% to 70%. In at least one embodiment the drug loading is within the range of 0.01% to 80%, and in at least one other embodiment from 15% to 80%. In at least one embodiment the weight ratio of bupropion hydrobromide to polymer in the swellable matrix is from 15:85 to 80:20.

The formulations of the swellable matrices of the present invention can assume the form of microparticles, tablets, or microparticles retained in capsules. In at least one embodiment the formulation comprises microparticles consolidated into a packed mass for ingestion, even though the packed mass will separate into individual particles after ingestion. Conventional methods can be used for consolidating the microparticles in this manner. For example, the microparticles can be placed in gelatin capsules known in the art as "hard-filled" capsules and "soft-elastic" capsules. The compositions of these capsules and procedures for filling them are known among those skilled in drug formulations and manufacture. The encapsulating material should be highly soluble so that the particles are freed and rapidly dispersed in the stomach after the capsule is ingested.

In certain embodiments of the swellable matrices of the present invention, the formulation contains an additional amount of bupropion salt or other drug applied as a quickly dissolving coating on the outside of the microparticle or tablet. This coating is referred to as a "loading dose" and it is included for immediate release into the recipient's bloodstream upon ingestion of the formulation without first undergoing the diffusion process that the remainder of the drug in the formulation must pass before it is released. The "loading dose" can be high enough to quickly raise the blood concentration of the drug but not high enough to produce the transient overdosing that is characteristic of immediate release dosage forms that are not formulated in accordance with this invention.

In at least one embodiment of the swellable matrices of the present invention, the dosage form is a size 0 gelatin capsule containing either two or three pellets of drug-impregnated polymer. For two-pellet capsules, the pellets are cylindrically shaped, 6.6 or 6.7 mm (or more generally, 6.5 to 7 mm) in diameter and 9.5 or 10.25 mm (or more generally, 9 to 12 mm) in length. For three-pellet capsules, the pellets are again cylindrically shaped, 6.6 mm in diameter and 7 mm in length. For a size 00 gelatin capsule with two pellets, the pellets are cylindrical, 7.5 mm in diameter and 11.25 mm in length. For a size 00 gelatin capsule with three pellets, the pellets are cylindrical, 7.5 mm in diameter and 7.5 mm in length. In at least one other embodiment, the dosage form is a single, elongated tablet, with dimensions of 18 to 22 mm in length, 6.5 to 10 mm in width, and 5 to 7.5 mm in height. In at least one other embodiment, the dosage form is a single, elongated tablet, with dimensions of 18 to 22 mm in length, 6.5 to 7.8 mm in width, and 6.2 to 7.5 mm in height. In at least one embodiment the dimensions are 20 mm in length, 6.7 mm in width, and 6.4 mm in height. These are merely examples; the shapes and sizes can be varied considerably.

The particulate drug/polymer mixture or drug-impregnated swellable polymer matrix can be prepared by various conventional mixing, comminution and fabrication techniques readily apparent to those skilled in the chemistry of drug formulations. Examples of such techniques include: (1) Direct compression, using appropriate punches and dies, such as those available from Elizabeth Carbide Die Company, Inc., McKeesport, Pa., USA; the punches and dies are fitted to a suitable rotary tableting press, such as the Elizabeth-Hata single-sided Hata Auto Press machine, with either 15, 18 or 22 stations, and available from Elizabeth-Hata International, Inc., North Huntington, Pa., USA; (2) Injection or compression molding using suitable molds fitted to a compression unit, such as those available from Cincinnati Milacron, Plastics Machinery Division, Batavia, Ohio, USA.; (3) Granulation followed by compression; and (4) Extrusion in the form of a paste, into a mold or to an extrudate to be cut into lengths.

In regards to the swellable matrices of the present invention, when microparticles are made by direct compression, the addition of lubricants can be helpful and sometimes important to promote powder flow and to prevent capping of the microparticle (breaking off of a portion of the particle) when the pressure is relieved. Non-limiting examples of suitable lubricants include magnesium stearate (in a concentration of from 0.25% to 3% by weight, and in certain embodiments less than 1% by weight, in the powder mix), and hydrogenated vegetable oil (in certain embodiments hydrogenated and refined triglycerides of stearic and palmitic acids at 1% to 5% by weight, for example in at least one embodiment at 2% by weight). Additional excipients can be added to enhance powder flowability and reduce adherence.

Certain embodiments of the swellable matrices of the present invention can find utility when administered to a subject who is in the digestive state (also referred to as the postprandial or "fed" mode). The postprandial mode is distinguishable from the interdigestive (or "fasting") mode by their distinct patterns of gastroduodenal motor activity, which determine the gastric retention or gastric transit time of the stomach contents.

The controlled release matrices of the present invention can be manufactured by methods known in the art such as those described in the patents listed above (e.g. U.S. Pat. No. 5,965,161). An example of a method of manufacturing controlled release matrices is melt-extrusion of a mixture containing the bupropion salt, hydrophobic polymer(s), hydrophilic polymer(s), and optionally a binder, plasticizer, and other excipient(s) as described above. Other examples of methods of manufacturing controlled release matrices include wet granulation, dry granulation (e.g. slugging, roller compaction), direct compression, melt granulation, and rotary granulation.

Additionally, controlled release particles which can be compressed or placed in capsules can be produced by combining the bupropion salt and a hydrophobic fusible component and/or a diluent, optionally with a release modifying agent including a water soluble fusible material or a particulate soluble or insoluble organic or inorganic material. Examples of potential hydrophobic fusible components include hydrophobic materials such as natural or synthetic waxes or oils (e.g., hydrogenated vegetable oil, hydrogenated castor oil, microcrystalline wax, Beeswax, carnauba wax and glyceyl monostearate). In at least one embodiment the hydrophobic fusible component has a melting point from 35° C. to 140° C. Examples of release modifying agents include polyethylene glycol and particulate materials such as dicalcium phosphate and lactose.

In certain embodiments, controlled release matrices can be produced by mechanically working a mixture of bupropion salt, a hydrophobic fusible component, and optionally a release component including a water soluble fusible material or a particulate soluble or insoluble organic or inorganic material under mixing conditions that yield aglomerates, breaking down the agglomerates to produce controlled release seeds having desired release properties; and optionally adding more carrier or diluent and repeating the mixing steps until controlled release seeds having desired release properties are obtained. These particles also can be size separated (e.g. by sieving and encapsulated in capsules or compressed into a matrix).

The amount of the hydrophobic fusible material used in the foregoing methods can range from 10% to 90% by weight. Mixers useful in such methods are known and include conventional high-speed mixers with stainless steel interiors. For example, a mixture can be processed until a bed temperature of 40° C. or higher is realized, and the mixture achieves a cohesive granular texture comprising desired particle sizes.

As noted if the mixture contains agglomerates, they can be broken down using conventional methods to produce a mixture of powder and particles of the desired size which, can be size-separated using a sieve, screen or mesh of the appropriate size. This material can be returned to a high-speed mixer and further processed as desired until the hydrophobic fusible materials begin to soften/melt, and optionally additional hydrophobic material can be added and mixing continued until particles having a desired size range are obtained. Still further, particles containing bupropion salt can be produced by melt processing as known in the art and combined into capsules or compressed into matrices.

These particles can be combined with one or more excipients such as diluents, lubricants, binding agents, flow aids, disentegrating agents, surface acting agents, water soluble materials, colorants, and the like.

In addition, the controlled release matrices can optionally be coated with one or more functional or non-functional coatings using well-known coating methods. Examples of coatings can include the XL control-releasing coat and the EA matrix coating described herein, which can further control the release of the bupropion salt and/or other drug.

In at least one embodiment, the controlled release matrices can each be coated with at least one taste-masking coating. The taste-masking coating can mask the taste of the bupropion salt in the matrices. In at least one embodiment the taste-masking coating formulations contain polymeric ingredients. It is contemplated that other excipients consistent with the objects of the present invention can also be used in the taste-masking coating.

In at least one embodiment of the matrix dosage form, the taste-masking coating comprises a polymer such as ethylcellulose, which can be used as a dry polymer (such as ETHOCEL®, Dow Corning) solubilised in organic solvent prior to use, or as an aqueous dispersion. One commercially-available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to foi-m a pseudolatex. The plasticizer is not incorporated in the pseudolatex during the manufacturing phase. Thus, prior to using the same as a coating, the Aquacoat is intimately mixed with a suitable plasticizer prior to use. Another aqueous dispersion of ethylcellulose is commercially available as SURELEASE® (Colorcon, Inc., West Point, Pa., U.S.A.). This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

In other embodiments of the matrix dosage form, polymethacrylate acrylic polymers can be employed as taste masking polymers. in at least one embodiment, the taste masking coating is an acrylic resin lacquer used in the form of an aqueous dispersion, such as that which is commercially available from Rohm Pharma under the tradename EUDRAGIT® or from BASF under the tradename KOLLICOAT®. In further preferred embodiments, the acrylic coating comprises a mixture of two acrylic resin lacquers commercially available from Robm Pharma under the tradenames EUDRAGIT® RL and EUDRAGIT® RS, respectively. EUDRAGIT® RL and EUDRAGIT® RS are copolymers of acrylic and inethacrylic esters with a low content of quaternary ammonium groups, the molar ratio of ammonium groups to the remaining neutral (meth)acrylic esters being 1:20 in EUDRAGEIT® RL and 1:40 in EUDRAGIT® RS. The mean molecular weight is 150,000. The code designations RL (high permeability) and RS (low permeability) refer to the permeability properties of these agents. EUDRAGIT® RL/RS mixtures are insoluble in water and in digestive fluids. However, coatings formed from the same are swellable and permeable in aqueous solutions and digestive fluids. EUDRAGIT® RL/RS dispersions or solutions of the present invention can be mixed together in any desired ratio in order to ultimately obtain a taste masking coating having a desirable drug dissolution profile. Desirable controlled release formulations can be obtained, for example, from a retardant coating derived from 100% EUDRAGIT® RL; 50% EUDRAGIT® RL with 50% EUDRAGIT® RS; and 10% EUDRAGIT® RL with 90% EUDRAGIT® RS.

In other embodiments of the matrix dosage form, the taste masking polymer can be an acrylic polymer which is cationic in character based on dimethylaminoethyl methacrylate and neutral methacrylic acid esters (such as EUDRAGIT® E, commercially available from Rohm Pharma). The hydrophobic acrylic polymer coatings of the present invention can further include a neutral copolymer based on poly (meth)acrylates, such as EUDRAGIT® NE (NE=neutral ester), commercially available from Rohm Pharma. EUDRAGIT® NE 30D lacquer films are insoluble in water and digestive fluids, but permeable and swellable.

In other embodiments of the matrix dosage form, the taste masking polymer is a dispersion of poly (ethylacrylate, methyl methacrylate) 2:1 (KOLLICOAT® EMM 30 D, BASF).

In other embodiments of the matrix dosage form, the taste masking polymer can be a polyvinyl acetate stabilized with polyvinylpyrrolidone and sodium lauryl sulfate such as KOLLICOAT® SR30D (BASF).

Other taste masking polymers used in the matrix dosage forms include hydroxypropylcellulose (HPC); hydroxypropylmethylcellulose (HPMC); hydroxyethylcellulose; gelatin; gelatin/acacia; gelatin/acacia/vinylmethylether maleic anhydride; gelatin/acacia/ethylenemaleic anhydride; carboxymethyl cellulose; polyvinylalcohol; nitrocellulose; polyvinylalcohol-polyethylene glycol graft-copolymers; shellac; wax and mixtures thereof.

The taste-masking coatings can be applied to the matrices from one or more organic or aqueous solvent solutions or suspensions. In at least one embodiment of the matrix dosage forms the organic solvents that can be used to apply the taste-masking coatings include one or more of acetone, lower alcohols such as ethanol, isopropanol and alcohol/water mixtures, chlorinated hydrocarbons, and the like. Devices used to coat the matrices of the invention with a taste-masking coating include those conventionally used in pharmaceutical processing, such as fluidized bed coating devices. The control-releasing coatings applied to the matrices can contain ingredients other than the cellulosic polymers. One or more colorants, flavorants, sweeteners, can also be used in the taste-masking coating.

In some embodiments of the matrix dosage forms a pore former can be included into the taste masking coat in order to influence the rate of release of bupropion hydrobromide from the matrix. In other embodiments, a pore former is not included in the taste masking coat. The pore formers can be inorganic or organic, and may be particulate in nature and include materials that can be dissolved, extracted or leached from the coating in the environment of use. Upon exposure to fluids in the environment of use, the pore-formers can for example be dissolved, and channels and pores are formed that fill with the environmental fluid.

For example, the pore-formers of certain embodiments of the matrix dosage forms can comprise one or more water-soluble hydrophilic polymers in order to modify the release characteristics of the formulation. Examples of suitable hydrophilic polymers used as pore-formers include hydroxypropylmetlhylcellulose, cellulose ethers and protein-derived materials of these polymers, the cellulose ethers, especially hydroxyalkylcelluloses and carboxyalkylcelluloses. Also, synthetic water-soluble polymers can be used, examples of which include polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, and sorbitol. In at least one embodiment, the hydrophilic polymer comprises hydroxypropyl-methylcellulose.

Other non-limiting examples of pore-formers include alkali metal salts such as lithium carbonate, sodium chloride, sodium bromide, potassium chloride, potassium sulfate, potassium phosphate, sodium acetate, and sodium citrate. The pore-forming solids can also be polymers which are soluble in the environment of use, such as Carbowaxes, and Carbopol. In addition, the pore-formers embrace diols, polyols, polyhydric alcohols, polyalkylene glycols, polyglycols, and poly(a-w)alkylenediols. Other pore-formers which can be useful in the formulations of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, etc. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous hiomopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly (vinylpyrrolidone), and mixtures thereof.

In general, the amount of pore-former included in the taste masking coatings of certain embodiments of the matrix dosage forms can be from 0.1% to 80%, by weight, relative to the combined weight of polymer and pore-former. The percentage of pore former as it relates to the dry weight of the taste-masking polymer, can have an influence on the drug release properties of the coated matrix. In at least one embodiment that uses water soluble pore formers such as hydroxypropylmethylcellulose, a taste masking polymer: pore former dry weight ratio of between 10:1 and 1:1 can be present. In certain embodiments the taste masking polymer: pore former dry weight ratio is from 8:1 to 1.5:1; and in other embodiments from 6:1 to 2:1. In at least one embodiment using EUDRAGIT® NE30D as the taste masking polymer and a hydroxypropylmethylcellulose (approx Scps viscosity (in a 2% aqueous solution)) such as METHO- CEL® E5, Pharmacoat 606G as the water soluble pore former, a taste masking polymer: pore former dry weight ratio ratio of 2:1 is present.

Colorants that can be used in the taste-masking coating of certain embodiments of the matrix dosage forms include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Flavorants that can be used in the taste-masking coating of certain embodiments of the matrix dosage forms include natural and synthetic flavoring liquids. An illustrative list of such flavorants includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such as lemon, orange, grape, lime and grapefruit, and fruit essences, including apple, pear, peach, grape, strawberry, raspberry, cherry, plum, pineapple, apricot, or other fruit flavors. Other useful flavorants include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodenal (citrus mandarin); mixtures thereof and the like.

Sweeteners that can be used in the taste-masking coating of certain embodiments of the matrix dosage forms include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; Steva Rebaudiana (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The matrix taste masking coat can also include one or more pharmaceutically acceptable excipients such as lubricants, emulsifiers, anti-foaming agents, plasticisers, solvents and the like.

Lubricants can be included to help reduce friction of coated matrices during manufacturing. The lubricants that can be used in the taste masking coat of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium beazoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™, MYVATEX™ TL and mixtures thereof. In at least one embodiment, the lubricant is selected from magnesium stearate and talc. Combinations of these lubricants are operable. The lubricant can each be present in an amount of from 1% to 100% by weight of the polymer dry weight in the taste masking coat. For example, in certain embodiments wherein the taste masking polymer is EUDRAGIT® NE30D or EUDRAGIT® NE40D (Rohm America LLC) together with a hydrophilic pore former, the lubricant is present in an amount of from 1% to 30% by weight of the polymer dry weight; in other embodiments from 2% to 20%; and in still other embodiments at 10% by weight of the matrix taste masking coat dry weight. In another embodiment where the taste masking polynier is erhylceliulose (ETHOCEL™ PR100, PR45, PR20, PR 10 or PR7 polymer, or a mixture thereof), the lubricant can be present in an amount of from 10% to 100% by weight of the matrix taste-masking coat dry weight; in another embodiment from 20% to 80%; and in still another embodiments at 50% by weight of the matrix taste masking coat dry weight. In other embodiments, the taste masking coat does not include a pore former.

Emulsifying agent(s) (also called emulsifiers or emulgents) can be included in the matrix taste masking coat to facilitate actual emulsification during manufacture of the coat, and also to ensure emulsion stability during the shelf-life of the product. Emulsifying agents useful for the matrix taste masking coat composition include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from 0.01% to 5% by weight of the matrix taste masking polymer dry weight. For example, in certain embodiments the emulsifying agent is present in an amount of from 0.05% to 3%; in other embodiments from 0.08% to 1.5%, and in still other embodiments at 0.1% by weight of the matrix taste masking polymer dry weight.

Anti-foaming agent(s) can be included in the matrix taste masking coat to reduce frothing or foaming during manufacture of the coat. Anti-foaming agents useful for the coat composition include, but are not limited to simethicone, polyglycol, silicon oil, and mixtures thereof. In at least one embodiment the anti-foaming agent is Simethicone C. The anti-foaming agent can be present in an amount of from 0.1% to 10% of the matrix taste masking coat weight. For example, in certain embodiments the anti-foaming agent is present in an amount of from 0.2% to 5%; in other embodiments from 0.3% to 1%, and in still other embodiments at 0.6% by weight of the matrix taste masking polymer dry weight.

Plasticizer(s) can be included in the matrix taste masking coat to provide increased flexibility and durability during manufacturing. Plasticisers that can be used in the matrix taste masking coat include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from 1% to 80% of the taste masking polymer dry weight. For example, in certain embodiments the plasticizer is present in an amount of from 5% to 50%, in other embodiments from 10% to 40%, and in still other embodiments at 20% of the taste masking polymer dry weight.

The taste-masking coating can be present in an amount of from 1% to 90% by weight of the matrix, depending upon the choice of polymer, the ratio of polymer:pore former, and the total surface area of the matrix formulation. Since a certain thickness of taste masking coating has to be achieved in order to achieve effective taste masking, the amount of taste masking polymer coating used during manufacture is related to the total surface area of the batch of uncoated matrices that requires a coating. For example, the taste masking polymer surface area coverage can range from 0.5 mg/cm2 to 20 mg/cm2. For example, in certain embodiments the surface area coverage of the taste masking polymer is from 0.6 mg/cm2 to 10 mg/cm2, and in other embodiments is from 1 mg/cm2 to 5 mg/cm2. In at least one embodiment of the invention, EUDRAGIT® E is employed as the taste masking polymer at a surface area coverage of 4 mg/cm2.

In the absence of an accurate determination of total surface area of a matrix, the amount of taste masking polymer to be applied can be expressed as a percentage of the uncoated matrix. For example, in certain embodiments the taste-masking coating is present in an amount of from 5% to 60%; in other embodiments from 10% to 40%; and in still other embodiments from 15% to 35% by weight of the matrix. In at least one embodiment the taste-masking coating is present in an amount of 30% by weight of the matrix.

Prophetic examples of matrix tablet formulations are described below. It should be understood that these examples are intended to be exemplary and that the specific constituents, amounts thereof, and formulation methods may be varied therefrom in order to achieve different release characteristics:

In at least one embodiment, the controlled matrices comprise:

| | |
|---|---|
| Bupropion HBr | 30.0% by weight of the matrix |
| Hydroxypropylmethylcellulose E50 | 10.0% by weight of the matrix |
| Hydroxypropylmethylcellulose K15M | 30.0% by weight of the matrix |
| Calcium phosphate dehydrate | 9.5% by weight of the matrix |
| ATMUL ® 84S (mono/di/tri glycerides) | 20.0% by weight of the matrix |
| Magnesium stearate | 0.5% by weight of the matrix |

Preparation of the matrix formulation can be as follows: Combine the drug, a portion of each HPMC, calcium phosphate and Atmul 84S in a planetary mixer and dry mix for 15 minutes. Add a solution of the remainder of the HPMC in water to the mixer while mixing, until a wet mass is obtained. Pass the wet material through a screen to make the resultant granules of uniform size (to achieve uniform drying) and dry in an oven at 40° C. for 24 hours. Mill the dried granules through a Fitzpatrick Mill, knives forward, and collect the material in a mixer. Add the magnesium stearate and mix for 5 minutes. The resultant mixture is tableted on a suitable tablet press.

In at least one embodiment, the controlled release matrices comprise a deposit-core and support-platform. Preparation of the deposit-core can be as follows: Deposit-cores can be prepared using the following materials in the stated quantities:

| | |
|---|---|
| Bupropion HBr | 45.0 g |
| hydroxypropylmethylcellulose (methocel K 100M-Colorcon) | 35.0 g |
| mannitol | 10.0 g |
| ethylcellulose (high viscosity-BDH) | 3.75 g |
| 3.75 g magnesium stearate | 1.0 g |
| 5:1 ethanol-chloroform mixture | 75.0 ml |

The bupropion HBr is mixed intimately with the mannitol and hydroxypropylmethylcellulose in a suitable mixer. The solution of ethylcellulose in ethanol-chloroform is prepared separately, and is used for wetting the previously obtained powder mixture. The resultant homogeneous mass is forced through an 800 micron screen and then dried to obtain a granulate which is passed through a 420 micron screen. The homogeneous granulate obtained is mixed with the magnesium stearate and then compressed using concave punches of diameter 7 mm (radius of curvature 9 mm) using a pressure of 3000 kg/cm2 to obtain cylindrical deposit-cores with convex bases.

Application of the support-platform can be as follows: The support-platform can be applied by coating one or both the convex bases of the deposit-core with a solution of 15 g low-permeability acrylic-methacrylic copolymer (Eudragit RS Rohm Pharma) in methylene chloride of a quantity to make up to 100 ml. Thereafter 0.3 ml of said solution is applied to each base to be covered, taking care to protect the lateral core surface. The system is then dried with tepid air. The quantity of polymeric material deposited is sufficient to keep the structure intact during transfer.

In at least one embodiment, the matrix formulation is a PEO based tablet matrix formulation comprising:

| | |
|---|---|
| Bupropion HBr | 50% |
| PEO WSR Coagulant (polyethylene oxide) | 15% |
| Methocel K100M (hydroxypropylmethyl cellulose) | 15% |
| Avicel PH101 (microcrystalline cellulose) | 19% |
| Magnesium Stearate | 1% |

Preparation of the PEO based tablet matrix formulation can be as follows: Excipients dry blended in an appropriate mixer and compressed into tablets using conventional apparatus.

Multiparticulates

Microparticles

In certain embodiments of the present invention, a multiparticulate system is provided which contains multiple microparticles each containing an effective amount of a bupropion salt and at least one pharmaceutically acceptable excipient. In at least one embodiment the bupropion salt is bupropion hydrobromide. The multiparticulates can be contained within a capsule, or can be compressed into a matrix or tablet, that upon ingestion dissolves into multiple units (e.g. pellets), wherein the sub-units or pellets possess the desired controlled release properties of the dosage form. The multiparticulates or the multiple unit dosage forms can be surrounded by one or more coatings. Examples of such coatings include polymeric controlled release coatings, delayed release coatings, enteric coatings, immediate release coatings, taste-masking coatings, extended release coatings, and non-functional coatings.

The bupropion salt in the microparticles can be present in an effective amount of from 0.1% to 99% by weight of the microparticles. For example, in certain embodiments bupropion hydrobromide is present in the microparticles in an amount of from 0.1% to 90%, in other embodiments from 5% to 90%, in still other embodiments from 10% to 80%, and in even still other embodiments from 25% to 80% by weight of the microparticle. In certain embodiments wherein the microparticles are manufactured using a spheronization process, the bupropion hydrobromide can be present in the microparticles in an amount of from 0.1% to 60%; in other such embodiments from 5% to 50%; and in still other such embodiments from 10% to 40% by weight of the microparticle. In at least one embodiment wherein the microparticles are manufactured using a spheronization process, the bupropion hydrobromide is present in the microparticle in an amount of 30% by weight of the microparticle.

In addition to the bupropion salt, the microparticles of the present invention also include at least one pharmaceutically acceptable excipient. Excipients can be added to facilitate in the preparation, patient acceptability and functioning of the dosage form as a drug delivery system. Excipients include spheronization aids, solubility enhancers, disintegrating agents, diluents, lubricants, binders, fillers, glidants, suspending agents, emulsifying agents, anti-foaming agents, flavouring agents, colouring agents, chemical stabilizers, pH modifiers, etc. Depending on the intended main function, excipients to be used in formulating compositions are sub-categorized into different groups. However, one excipient can affect the properties of a composition in a series of ways, and many excipients used in compositions can thus be described as being multifunctional.

The microparticles of the present invention can be manufactured using standard techniques known to one of skill in the art. Useful microparticles include drug-layered microparticles and drug-containing microparticles.

Drug-Containing Microparticles

Microparticles containing drug in the core can be prepared by a number of different procedures. For example: In a spray drying process, an aqueous solution of core material and hot solution of polymer is atomized into hot air, the water then evaporates, and the dry solid is separated in the form of pellets, for example by air suspension. A spray-drying process can produce hollow pellets when the liquid evaporates at a rate that is faster than the diffusion of the dissolved substances back into the droplet interior, or if due to capillary action the dissolved substance migrates out with the liquid to the droplet surface, leaving behind a void. Another example is a spray congealing process, where a slurry of drug material that is insoluble in a molten mass is spray congealed to obtain discrete particles of the insoluble materials coated with the congealed substance. A further example is a fluidized bed based granulation/pelletization process, where a dry drug is suspended in a stream of hot air to form a constantly agitated fluidized bed. An amount of binder or granulating liquid is then introduced in a finely dispersed form to cause pelletization.

The drug-containing microparticles of the present invention can also be made by, for example, a spheronization process. One method of manufacturing the drug-containing microparticles is the applicant's proprietary CEFORM™ (Centrifugally Extruded & Formed Microspheres/Microparticles) technology, which is the simultaneous use of flash heat and centrifugal force, using proprietary designed equipment, to convert dry powder systems into microparticles of uniform size and shape. The production of microparticles containing an active drug using this CEFORM™ technology is described in U.S. Pat. No. 5,683,720. This patent deals with the use of LIQUIFLASH® processing to spheronize compositions containing one or more active drugs to form LIQUIFLASH® microparticles.

With the CEFORM™ technology, the processing of the drug-containing microparticles of the present invention is carried out in a continuous fashion, whereby a pre-blend of drug and excipients is fed into a spinning "microsphere head", also termed as a "spheronizing head". The microsphere head, which is a multi-aperture production unit, spins on its axis and is heated by electrical power. The drug and excipient(s) pre-blend is fed into the center of the head with an automated feeder. The material moves, via centrifugal force, to the outer rim where the heaters, located in the rim of the head, heat the material. Microparticles are formed when the molten material exits the head, which are then cooled by convection as they fall to the bottom of the Microparticle Chamber. The product is then collected and stored in suitable product containers. Careful selection of the types and levels of excipient(s) control microparticle properties such as sphericity, surface morphology, and dissolution rate. One advantage of such a process is that the microparticles are produced and collected from a dry feedstock without the use of any solvents.

There are at least two approaches that can be used to produce drug-containing microparticles using the CEFORM process: (i) the encapsulation approach and (ii) the co-melt approach. In the encapsulation approach, the process is conducted below the melting point of the drug. Therefore, the excipients are designed to melt and entrain the drug particles on passing through the apertures to form microparticles. The resulting microparticles contain the drug, in its native state, essentially enveloped by or as an intimate matrix with the resolidified excipients. In the co-melt approach, the process is conducted above the melting point of the drug. In this case, the drug and the excipients melt or become fluid simultaneously upon exposure to the heat. The molten mixture exits the head and forms microparticles, which cool as they fall to the bottom of the collection bin where they are collected.

In at least one embodiment the microparticles are manufactured using the encapsulation approach. In the encapsulation approach the excipient(s) which are chosen have a lower melting point than the drug with which they will be combined. Therefore the spheronizing process can be performed at lower temperatures, than the melting point of the drug. As a result, this can reduce the risk of polymeric interconversion, which can occur when using processing temperatures close to the melting point.

In a prophetic example of certain embodiments of the present invention, the manufacturing process for the microparticles can hypothetically be as follows: Spheronization aid is screened through a 425 micron (μm) screen. In at least one embodiment, the spheronization aid is distilled glyceryl monostearate (i.e. DMG-03VF). 50% of the spheronization aid is added to a bowl in a high shear mixer. In at least one embodiment, the bowl is a 6 litre bowl and the high shear mixer is a Diosna P1-6 high speed mixer granulator. The active drug is then added to the bowl of the mixer, and then the remainder of the spheronization aid is added. The material is then blended in the mixer for a time from 1 minute to 30 minutes; preferably from 3 minutes to 10 minutes; and more preferably 6 minutes. The mixer motor speed is from 50 rpm to 2000 rpm; preferably from 200 rpm to 500 rpm; and more preferably 300 rpm. The chopper motor speed is from 50 rpm to 2000 rpm; preferably from 200 rpm to 500 rpm; and more preferably 400 rpm. The blended material is then spheronized in a CEFORM™ spheronizing head. The spheronizing head speed is from 5 Hz to 60 Hz; preferably from 10 Hz to 30 Hz; and more preferably 15 Hz. In at least one embodiment the CEFORM™ spheronizing head is a 5 inch head. The spheronizing head temperature is maintained at a temperature from 70° C. to 130° C.; preferably from 90° C. to 110° C.; and more preferably 100° C. The microparticles obtained from the spinning process are then screened through a screen that is from 150 μm to 800 μm.

For microparticles manufactured using a spheronization process such as the CEFORM™ process, the inicroparticles include, in addition to the bupropion salt, at least one spheronization aid. Spheronization aids can assist the drug-containing mix to form robust durable spherical particles. Some examples of materials useful as spheronization aids include, but are not limited to glyceryl monostearate, glyceryl behenate, glyceryl dibehenate, glyceryl palmitostearate, hydrogenated oils such as hydrogenated castor oil marketed under the name CUTINA™ HR. fatty acid salts such as magnesium or calcium stearate, polyols such as mannitol, sorbitol, xylitol, stearic acid, palmitic acid, sodium lauryl sulfate, polyoxyethylene ethers, esterified polyoxyethylenes such as PEG-32 distearate, PEG-150 distearate, cetostearyl alcohol, waxes (e.g. carnauba wax, white wax, paraffin wax) anti wax-like materials. Certain thermo-plastic or thermo-softening polymers can also function as spheronization aids. Some non-limiting examples of such thermo-plastic or thermno-softening polymers include Povidone, cellulose ethers and polyvinylalcohols. Combinations of spheronization aids can be used. In at least one embodiment, the spheronization aid is glyceryl monostearate (i.e. DMG-03VF). The spheronization aid can be present in an amount of from 0.1% to 99% by weight of the microparticle. For example, in certain embodiments the spheronization aid is present in an amount of 5% to 90%; in other embodiments from 10% to 80%; in still other embodiments from 20% to 70%; and in even still other embodiments from 30% to 60% by weight of the microparticle. In at least one embodiment the spheronization aid is present in an amount of 50% by weight of the microparticle. In at least one other embodiment, the microparticles include 50% (w/w) of bupropion hydrobromide and 50% (w/w) of the spheronization aid.

In certain embodiments, each microparticle can also include at least one solubility enhancer. Solubility enhancers can be surfactants. Certain embodiments of the invention include a solubility enhancer that is a hydrophilic surfactant. Hydrophilic surfactants can be used to provide any of several advantageous characteristics to the compositions, including: increased solubility of the bupropion salt in the microparticle; improved dissolution of the bupropion salt; improved solubilization of the bupropion salt upon dissolution; enhanced absorption and/or bioavailability of the bupropion salt. The hydrophilic surfactant can be a single hydrophilic surfactant or a mixture of hydrophilic surfactants, and can be ionic or non-ionic.

Likewise, various other embodiments of the invention include a lipophilic component, which can be a lipophilic surfactant, including a mixture of lipophilic surfactants, a triglyceride, or a mixture thereof. The lipophilic surfactant can provide any of the advantageous characteristics listed above for hydrophilic surfactants, as well as further enhancing the function of the surfactants. These various embodiments are described in more detail below.

As is well known in the art, the terms "hydrophilic" and "lipophilic" are relative terms. To function as a surfactant, a compound includes polar or charged hydrophilic moieties as well as non-polar hydrophobic (lipophilic) moieties; i.e., a surfactant compound is amphiphilic. An empirical parameter commonly used to characterize the relative hydrophilicity and lipophilicity of non-ionic amphiphilic compounds is the hydrophilic-lipophilic balance (the "HLB" value). Surfactants with lower HLB values are more lipophilic, and have greater solubility in oils, whereas surfactants with higher HLB values are more hydrophilic, and have greater solubility in aqueous solutions.

Using HLB values as a rough guide, hydrophilic surfactants can generally be considered to be those compounds having an HLB value greater than 10, as well as anionic, cationic, or zwitterionic compounds for which the HLB scale is not generally applicable. Similarly, lipophilic surfactants can be compounds having an HLB value less than 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as 8 HLB units, depending upon the empirical method chosen to determine the HLB value (Schott, J. Pharm. Sciences, 79(1), 87-88 (1990)). Likewise, for certain polypropylene oxide containing block copolymers (poloxamers, available commercially as PLURONIC® surfactants, BASF Corp.), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or lipophilicity for use in the present invention, as described herein.

Solubility enhancers can be any surfactant suitable for use in pharmaceutical compositions. Suitable surfactants can be anionic, cationic, zwitterionic or non-ionic. Such surfactants can be grouped into the following general chemical classes detailed in Tables 81-98 herein. The HLB values given in Tables 81-98 below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

It should be emphasized that the invention is not limited to the surfactants in Tables 81-98, which show representative, but not exclusive, lists of available surfactants. In addition, refined, distilled or fractionated surfactants, purified fractions thereof, or re-esterified fractions, are also within the scope of the invention, although not specifically listed in the Tables.

Although polyethylene glycol (PEG) itself does not function as a surfactant, a variety of PEG-fatty acid esters have useful surfactant properties. Examples of polyethoxylated fatty acid monoester surfactants commercially available are shown in Table 81.

Polyethylene glycol (PEG) fatty acid diesters are also suitable for use as surfactants in the compositions of the present invention. Representative PEG-fatty acid diesters are shown in Table 82.

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 83.

Suitable PEG glycerol fatty acid esters are shown in Table 84.

A large number of surfactants of different degrees of lipophilicity or hydrophilicity can be prepared by reaction of alcohols or polyalcohols with a variety of natural and/or hydrogenated oils. In certain embodiments, the oils used are castor oil or hydrogenated castor oil or an edible vegetable oil such as corn oil, olive oil, peanut oil, palm kernel oil, apricot kernel oil, or almond oil. Examples of alcohols include glycerol, propylene glycol, ethylene glycol, polyethylene glycol, sorbitol, and pentaerythritol. Representative surfactants of this class suitable for use in the present invention are shown in Table 85.

Polyglycerol esters of fatty acids are also suitable surfactants for the present invention. Examples of suitable polyglyceryl esters are shown in Table 86.

Esters of propylene glycol and fatty acids are suitable surfactants for use in the present invention. Examples of surfactants of this class are given in Table 87.

In general, mixtures of surfactants are also suitable for use in the present invention. In particular, mixtures of propylene glycol fatty acid esters and glycerol fatty acid esters are suitable and are commercially available. Examples of these surfactants are shown in Table 88.

Another class of surfactants is the class of mono- and diglycerides. These surfactants are generally lipophilic. Examples of these surfactants are given in Table 89.

Sterols and derivatives of sterols are suitable surfactants for use in the present invention. These surfactants can be hydrophilic or lipophilic. Examples of surfactants of this class are shown in Table 90.

A variety of PEG-sorbitan fatty acid esters are available and are suitable for use as surfactants in the present invention. In general, these surfactants are hydrophilic, although several lipophilic surfactants of this class can be used. Examples of these surfactants are shown in Table 91.

Ethers of polyethylene glycol and alkyl alcohols are suitable surfactants for use in the present invention. Examples of these surfactants are shown in Table 92.

Esters of sugars are suitable surfactants for use in the present invention. Examples of such surfactants are shown in Table 93.

Several hydrophilic PEG-alkyl phenol surfactants are available, and are suitable for use in the present invention. Examples of these surfactants are shown in Table 94.

The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are availabic under various trade names, including SYNPERONIC™ PE series (ICI); PLURONIC® series (BASF), EMKALYX™, LUTROL™ (BASF), SUPRONIC™ MONOLAN™, PLURACARE™, and PLURODAC®. The generic term for these polymers is "poloxamer" (CAS 9003-11-6). These polymers have the formula:

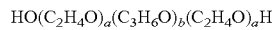

where "a" and "b" denote the number of polyoxyethylene and polyoxypropylene units, respectively. Examples of suitable surfactants of this class are shown in Table 95.

Sorbitan esters of fatty acids are suitable surfactants for use in the present invention. Examples of these surfactants are shown in Table 96.

Esters of lower alcohols (C2 to C4) and fatty acids (C8 to C18) are suitable surfactants for use in the present invention. Examples of these surfactants are shown in Table 97.

Ionic surfactants, including cationic, anionic and zwitterionic surfactants, are suitable hydrophilic surfactants for use in the present invention. In certain embodiments, the surfactant is an anionic surfactant such as a fatty acid salt, a bile salt, or a combination thereof. In other embodiments the surfactant is a cationic surfactant such as a carnitine. Examples of ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown in Table 98.

Ionizable surfactants, when present in their unionized (neutral, non-salt) form, are lipophilic surfactants suitable for use in the compositions of the present invention. Particular examples of such surfactants include free fatty acids, particularly C6-C22 fatty acids, and bile acids. More specifically, suitable unionized ionizable surfactants include the free fatty acid and bile acid forms of any of the fatty acid salts and bile salts shown in Table 98.

Derivatives of oil-soluble vitamins, such as vitamins A, D, E, K, etc., are also useful surfactants for the compositions of the present invention. An example of such a derivative is tocopheryl PEG-1000 succinate (TPGS, available from Eastman).

In certain embodiments, surfactants or mixtures of surfactants that solidify at ambient room temperature are used. In other embodiments, surfactants or mixtures of surfactants that solidify at ambient room temperature in combination with particular lipophilic components, such as triglycerides, or with addition of appropriate additives, such as viscosity modifiers, binders, thickeners, and the like, are used.

Examples of non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; polyethoxylated fat-soluble vitamins or derivatives; and mixtures thereof.

In certain embodiments, the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. The glyceride can be a monoglyceride, diglyceride, triglyceride, or a mixture thereof.

In certain other embodiments, the surfactants used are non-ionic hydrophilic surfactants that are reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol can be glycerol, ethylene glycol, polyethylene glycol, sorbitol, propylene glycol, pentaerythritol, a saccharide, or a mixture thereof.

The hydrophilic surfactant can also be, or include as a component, an ionic surfactant. Examples of ionic surfactants include alkyl ammonium salts; bile acids and salts, analogues, and derivatives thereof; fusidic acid and derivatives thereof; fatty acid derivatives of amino acids, oligopeptides, and polypeptides; glyceride derivatives of amino acids, oligopeptides, and polypeptides; acyl lactylates; mono-,diacetylated tartaric acid esters of mono-,diglycerides; succinylated monoglycerides; citric acid esters of mono-,diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

In certain embodiments the ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono-,diacetylated tartaric acid esters of mono-,diglycerides; succinylated monoglycerides; citric acid esters of mono-diglycerides; carnitines; and mixtures thereof.

Examples of ionic surfactants include lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

In certain embodiments, ionic surfactants used include lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof. In at least one embodiment, the ionic surfactant is selected from lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

Examples of lipophilic surfactants include alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; and mixtures thereof.

As with the hydrophilic surfactants, lipophilic surfactants can be reaction mixtures of polyols and fatty acids, glycerides, vegetable oils, hydrogenated vegetable oils, and sterols.

In certain embodiments, the lipophilic surfactants include one or more selected from the group consisting of fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, sterols, and mixtures thereof.

In certain other embodiments, the lipophilic surfactants include one or more selected from the group consisting of lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof. Among the glycerol fatty acid esters, the esters can be mono- or diglycerides, or mixtures of mono- and diglycerides, where the fatty acid moiety is a C6 to C22 fatty acid.

Other embodiments include lipophilic surfactants which are the reaction mixture of polyols and fatty acids, glycerides, vegetable oils, hydrogenated vegetable oils, and sterols. Examples of polyols are polyethylene glycol, sorbitol, propylene glycol, pentaerythritol, and mixtures thereof.

Combinations of solubility enhancers (i.e. surfactants) can be used. Examples of macrogol fatty acid esters useful as solubility enhancers include GELUCIRE 50/13 ® and GELUCIRE 44/14®. In at least one embodiment the solubility enhancer is GELUCIRE 50/13®. The solubility enhancer can be present in an amount of from 0.1% to 70% by weight of the microparticle. For example, in certain embodiments, the solubility enhancer is present in an amount of from 1to 50%; in other embodiments from 10% to 30%; in still other embodiments from 15% to 25% by weight of the microparticle. In at least one embodiment the solubility enhancer is present in an amount of 20% by weight of the microparticle.

It is contemplated that in some embodiments, one or more other pharmaceutically acceptable excipients consistent with the objects of the present invention can be used in the microparticles, such as a lubricant, a binder, a pH modifier, a filler and/or a glidant.

The process for manufacturing the drug-containing microparticles of the present invention by spheronization are not limited to the CEFORM™ technology, and any other technology resulting in the formation of the microparticles consistent with the objects of the present invention can also be used. For example, microparticles of the invention can also be manufactured by extrusion/spheronization, granulation or pelletization.

Extrusion/spheronization is a multi-step process used to make uniformly sized spherical particles. The technique offers the ability to incorporate high levels of active ingredients without producing excessively large particles. The main steps in the process are:
(i) Dry-mixing of ingredients to achieve a homogenous powder dispersion;
(ii) Wet massing using for example a high-shear wet granulator to form rod shaped particles of uniform diameter;
(iii) Extrusion to form rod-shaped particles of uniform diameter;
(iv) Spheronization to round off the rods into spherical particles;
(v) Screening to achieve the desired narrow particle size distribution.

The mixing vessel used for dry-mixing can be of any size and shape compatible with the size of the formulation to be produced. For example, commercially available mixing devices such as planetary mixers, high shear mixers, or twin cone blenders can be used. If relatively small quantities of formulation are to be prepared, a simple mortar and pestle can be sufficient to mix the ingredients. The type of mixing vessel would be apparent to one skilled in the pharmaceutical art. The moistened mass formed by wet-massing in conventional granulation equipment is extruded through a perforated mesh in order to produce cylindrical filaments. The port of the meshes can determine the diameter of the filaments. A port ranging from 0.2 mm to 3 mm can be used in this process. In at least one embodiment utilizing this process, the port ranges from 0.4 mm to 2 mm. The extrusion can be carried out using screw, double screw, "sieve and basket" kind, "roll extruder", "ram extruder" extruders or any other pharmaceutically acceptable means to produce cylindrical filaments. In certain embodiments utilizing this extrusion/spheronization process, a double screw coaxial extruder is used. The spheronization device comprises a hollow cylinder with a horizontal rotating plate. The filaments are broken in short segments which are transformed in spherical or quasi-spherical particles on the upper surface of the rotating plate at a velocity ranging from 200 rpm to 2,000 rpm. The particles can be dried in any pharmaceutically acceptable way, such as for example by air drying in a static condition. The particles are used as they are or they are coated to obtain granules to use in tablets, capsules, packets or other pharmaceutical formulations.

A prophetic example of an extrusi.on/spheronization formulation comprising bupropion hydrobromide can be as follows: In this example, the bupropion hydrobromide can be present in an amount of from 1% to 80% w/w. In certain embodiments within this example, the bupropion hydrobromide is present in an amount of from 1% to 50% w/w; in other embodiments from 10% to 30%; and in still other embodiments 10% wlw. In this example, the filler can be present in an amount of from 0% to 80% w/w. In certain embodiments of this example, the filler is present in an amount of from 10% to 60%; and in other embodiments at 40% w/w. In this example, the microcrystalline cellulose can be present in an amount of from 10% to 90% w/w. In certain embodiments of this example, the microciystalline cellulose is present in an amount of from 10% to 70%; and in other embodiments from 20% to 50% w/w. In this example, thc binder can be present in an amount of from 0% to 10% w/w. In certain embodiments of this example, the binder is present in an amount of from 1% to 8%; and in other embodiments from 2% to 4% w/w. in this example, water can be present in an amount of from 10% to 80% w/w. In certain embodiments of thi.s example, water is present in an amount of from 15% to 70%; and in other embodiments from 20% to 50% w/w. Suitable fillers in this example include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, mahodextrins, lactose, and fructose. Suitable lubricants in this example include but are not limited to metal stearates (such as calcium, magnesium on zinc stearates), stearic acid, hydrogenated vegetable oils, talc, starch, light mineral oil, sodium benzoate, sodium chloride, sodium lauryl sulfate, magnesium Jauryl sulfate, sodium stearyl fumarate, glyceryl behenate and polyethylene glycol (such as CAROWAX™ 4000 and 6000). Suitable antiadherents in this example include but axe not limited to colloidal silicon dioxide. Suitable binders in this example include but are not limited to ethyl cellulose, a polymethacrylate polymer. polyvinylalcohol, polyvinyl pyrrol idone, polyvinylpyrrolidone-vinylacetate copolymer (e.g. Kollidon VA64) hydroxyethylcellulose, low molecular weight hydroxypropylmethylcellulose (e.g. viscosity of 1-50 cps at 20oC; 2-12 eps at 20oC; or 4-6 cps at 20oC), hydroxypropylcellulose polymethactylates, and mixtures thereof.

The drug-containing microparticles formed by extrusionlspheronization in this prophetic example can be produced using cross-linked amphiphilic polymers by the following steps: (a) the mixing of one or more cross-linked amphiphilic polymers with bupropion hydrobromide and optionally other pharmaceutical cxcipicnts in order to obtain a uniform mixture in the form of dry powder to which a suitable amount of liquid is added to obtain a pasty consistency; (b) the extrusion of the mixture obtained from step (a) through a perforated mesh in order to obtain cylindrical filaments having desired length and diameter; (c) the spheronization of the filaments in order to obtain a product in the form of spherical multiparticulates; (d) the drying of the product; and (c) the optional depositing of a drug on the surface of the microparticles. "Cross-linked amphiphilic polymer" refers in this example to polymers showing characteristics of swellability in the whole pH range of aqueous solutions and also in solvents or solvent mixtures having different polarity characteristics. The polymers can be cross-linked either physically through the interpenetration of the macromolecular meshes, or chemically, thus showing points of link among the macromolecular chains. Non-limiting examples of such polymers include cross-linked polyvinyl pyrrolidone, sodium carboxymethylcellulose, sodium glycolate starch and dextrans. OPtional excipients include dispersing, emulsifying, wetting agents and colouring agents. The expression "uniform mixture" in this example means that the components of the mixture are uniformly dispersed in the formulation by a mixing process which assures the uniform distribution of each component. A reasonable mixing time can range from 1 to 60 minutes using one of the mixing equipments conventionally used for the dry mixing of the powders (e.g. "V", fixed body, rotating body, sigma mixers). The term "liquid" in this example means any liquid substance or mix (solution or emulsion) of liquids of normal pharmaceutical use able to moisten the powder mix, as for example water, aqueous solutions having different pH, organic solvents of normal pharmaceutical use (e.g. alcohols, chlorinated solvents), and oils. Among the oils and surfactants which can be used in this example are: natural oils, either saturated or unsaturated (olive, peanut, soybean, corn, coconut, palm, sesame and similar oils); semisynthetic and synthetic mono-, di- and triglycerides containing saturated and/or unsaturated fatty acids and their polyhydroxyethylated derivatives (caprico-caprilic triglycerides [MYGLIOL™, CAPTEX™, LABRAIFAC™, Lipo], saturated or unsaturated polyhydroxylated triglycerides of various kind [LABRAFIL™, LABRAFAC™ Hydro, GELUCiRE™]); liquid waxes (isopropyl myristate, isopropyl-caprinate, -caprylate, -laurate, -palmitate, -stearate); fatty acids esters (ethyl oleate, oleyl oleate); silicone oils; polyethylene glycols (PEG 200, PEG 400, PEG 600, PEG 1000, and so on); polyglycolic glycerides (for example LABRASOL™); polyglycols (propylene glycol, tetraglycol, and ethoxydiglycol (TRANSCUTOL™), sorbitan-esters of fatty acids (for example SPAN, ARLACEL, BRU), polyoxyethylenesorbitan esters of fatty acids (for example TWEEN, CAPMUL, LIPOSORB), polypropylene oxide-polyethylene oxide (Poloxamer) copolymers, polyethylene glycol esters (PEG)-glycerol (LABRASOL®, LABRAFIL®), PEG esters and long chain aliphatic acids or alcohols (for example CREMOPHOR®), polyglycerid esters (PLUROL), saccharide and fatty acid esters (sucro-esters). Moreover, anionic surfactants (for example sodium lauryl sulfate, sodium stearate, sodium oleate) or cationic surfactants (for example tricetol), can be used as well as lecithins, phospholipids and their semi-synthetic or synthetic derivatives. Also bupropion hydrobromide and/or excipients can be dissolved, dispersed and/or emulsified in such liquids.

In a particular embodiment formed by an extrusion/spheronization process from the prophetic example described above, the moistening liquid comprises an oill-surfactant system wherein the bupropion hydrobromide optionally emulsitied with an aqueous phase is dissolved or dispersed. The amount of liquid with respect to the solid used in the preparation of the mixture can range from 1% to 80% by weight. As a prophetic example of this embodiment, a mixture of bupropion hydrobromide and KOLLIDON™ CL in a ratio equal to 1/3 by weight is co-milled obtaining the mixture in the form of powder having the 100% of granulometry lower than 50 microns. The mixture is moistened using a Jiquid demineralized water containing KOLLIDON™ 25 (polyvinyl pyrrolidone, BASF) in a solution 3% w/w. The extrusion is carried out forcing the moistened mass through a threader having diameter of the holes equal to 1 mm. The operative parameters in this prophetic example can be as follows: powder flow rate: 4.5 kg/h; liquid flow rate: 4.1 kg/h; torsional stress: 27%; head temperature: 460° C.; and screw rotation velocity: 140 rpm. The extrusion filaments are then processed in a spheronizator adjusted at a velocity equal to 1,000 rpm for 2 minutes. The obtained microparticles are then dried in a fluid bed for 2 hours to a maximum temperature equal to 59° C. At the end of the drying the product is discharged and is mechanically screened separating the fraction ranging from 0.7 mm to 1.2 mm.

Another prophetic example of a drug-containing microparticle embodiment of the invention formed by an extrusion/spheronization process, uses a charged resin, the steps of which can comprise: (a) adding the charged resin, bupropion hydrobromide and other excipients, to a mixing vessel; (b) mixing the ingredients to obtain a uniform mixture; (c) adding a granulating solution—a liquid capable of wetting the dry mixture. Liquids resulting in conversion of the dry powder mixture into a wet granulation that supports subsequent extrusion and spheronization (marumerization) are included. Typically, water or aqueous solutions are employed. Alcohols, typically ethanol or isopropanol, can be included with the granulating water to enhance the workability of the granulation. In another embodiment of this invention, one or more of the components of the formulation is first dissolved in water and this solution is used to produce the wet granulation. An active ingredient or an excipient which is present at very low concentration can initially be dissolved or suspended in the granulating solvent to assure more uniform distribution throughout the formulation. (d) granulating the mixture until a uniform granulation results; (e) extruding the wet granulation through a screen to produce strands of granulation; (f) spheronizing the strands of granulation to produce spherical multiparticulates; and (g) collecting and drying the spherical multiparticulates. By "charged resin" is meant in this example to mean a polymer with ionizable functional groups that becomes useful in the embodiment of this invention. This broadly encompasses any polymer that upon ionization, is capable of producing cationic or anionic polymeric chains and which support spheronization. Typically from 10% to 70% by weight of the spherical multiparticulate is charged resin. Non limiting examples of these charged resins include sodium polystyrene sulfonate which is sold under the trade name AMBERLITE IRP-69™ by Rohm and Haas, Co., Philadelphia, Pa.; the chloride salt of cholestyramine resin USP, sold as AMBERLITE IRP-276™ by Rohm and Haas, Co., Philadelphia, Pa.; the acid form of methacrylic acid-divinyl benzene, sold as AMBERLITE IRP-64™ by Rohm and Haas Co., Philadelphia, Pa.; carboxypolymethylenes sold under the trade names CARBOPOL™ 974P and CARBOPOL™ 934P by B. F. Goodrich, Inc., Brecksville, Ohio, and sodium polyacrylate, sold under the trade name AQUAKEEP® J-550 by Seitetsu Kagaku, Japan. In order for the resin to maintain the desired degree of ionization, agents which produce an acidic or basic environment during granulation and spheronization can be included within the formulation. Among the groups of compounds that can exert this effect are acids, bases, and the salts of acids and bases such as adipic acid, citric acid, fumaric acid, tartaric acid, succinic acid, sodium carbonate, sodium bicarbonate, sodium citrate, sodium acetate, sodium phosphates, potassium phosphates, ammonium phosphate, magnesium oxide, magnesium hydroxide, sodium tartrate, and tromethamine. Certain compounds can be added to the granulation to provide the proper degree of hydration of the charged resin, medicament and excipients. These hydrating agents include sugars such as lactose, sucrose, mannitol, sorbitol, pentaerythritol, glucose and dextrose. Polymers such as polyethylene glycol as well as surfactants and other organic and inorganic salts can also be used to modulate polymer hydration.

In another prophetic example, multiparticulates containing bupropion hydrobromide can be obtained as follows:

| Component | Percent w/w |
| --- | --- |
| Bupropion HBr | 8.7 |
| Disodium Phosphate | 7.0 |
| Monosodium phosphate | 1.7 |
| Sodium dodecyl sulfate | 21.7 |
| Sodium Chloride | 17.4 |

-continued

| Component | Percent w/w |
| --- | --- |
| Povidone 29-32K | 8.7 |
| AMBERLITE IRP-69 | 34.8 |
| Butylated Hydroxyanisol | 0.0002 |

In this prophetic example, approximately 5.75 kg of the above formulation is mixed in a planetary mixer for 15 minutes. The butylated hydroxyanisol is dissolved in 60 cc of ethanol and water is added to bring the final solution to a volume of 133 cc. This solution is added to the planetary mixer over a two (2) minute period. The mixer is then granulated with seven aliquots of 250 cc of water added over a fifteen minute period. The granulation thus formed is extruded through a 1.0 mm screen and aliquots spheronized by marumerization at approximately 1200 rpm for approximately 10 minutes each. The spherical multiparticulates formed are then dried at 50° C. for 24 hours.

Another embodiment of this invention involves the production of drug containing microparticles in the form of 'pearls'. Pearls can be manufactured by mixing bupropion hydrobromide with one or more pharmaceutical excipients in molten form; the melt is forced to pass through a nozzle which is subjected to a vibration; the pearls formed are allowed to fall in a tower countercurrentwise to a gas; and the solid pearls are collected in the bottom of the tower. In this example, the quantity of bupropion hydrobromide can vary from 5% to 95% by weight; and in certain embodiments from 40% to 60% by weight. The additives which enable the crystallization of the supercooled product to be induced in this example can be chosen from the following: fatty alcohols such as: cetyl alcohol, stearyl alcohol, fatty acids such as: stearic acid, palmitic acid, glycerol esters such as: glycerol palmitostearate, the glycerol stearate marketed under the mark PRECIROL™, the glycerol behenate marketed under the mark COMPRITOL™, hydrogenated oils such as: hydrogenated castor oil marketed under the mark CUTINA™ HR, fatty acid salts such as: magnesium or calcium stearate, polyols such as: mannitol, sorbitol, xylitol, waxes such as: white wax, carnauba wax, paraffin wax, polyoxyethylene glycols of high molecular weight, and esterified polyoxyethylenes such as: PEG-32 distearate, and PEG-150 distearate. To these crystallization additives it can be desirable in this example to add polymers which are soluble or dispersible in the melt, and which provide a controlled and adjustable dissolution of the pearls when they are used, examples of which include: cellulose derivatives (hydroxypropyl cellulose, hydroxypropyl methyl cellulose, hydroxyethyl cellulose, ethyl cellulose, carboxymethyl cellulose), acrylic resins (marketed under the mark EUDRAGIT®), polyvinyl acetates (marketed under the mark RHODOPAS®), polyalkylene (ethylene propylene), polylactic, maleic anhydride and silicone resins. In addition, inorganic additives can be added to accelerate the solidification of the active substances, examples of which include: silicas, inorganic oxides such as titanium or iron oxide, phosphates, carbonates, clays, and talc. In addition, a surface-active agent can be added to improve the dispersion of the active substance in the crystallization additive, examples of which include: sorbitol esters, the polyoxyethylene polysorbates marketed under the mark TWEEN®, and glycols such as glycerine or propylene glycol. The process for the preparation of pearls comprise preparing a melt of the bupropion hydrobromide with one or more excipients. This melt can be prepared by separately melting the various constituents and then mixing them or by melting the mixture of the constituents, possible insoluble compounds being added at the end of the melting so as to obtain a homogeneous mass. The nature of the constituents of the melt is chosen by the person skilled in the art, which is considered as a function of the compatibility of the constituents, the viscosity of the mixture of constituents, the nozzle diameter, the hydrophilicity of the active substance, the surface tension of the active substance, the particle size of the insoluble additives, the flow rate of the nozzle, the temperature of the tower, its height and, above all, the size of the desired pearls, the proportion of bupropion hydrobromide to be included therein and the desired release time of the active substance.

Alternative procedures other than extrusion or spheronization for manufacturing drug-containing microparticles can include wet granulation, solvent granulation and melt granulation. All of these techniques involve the addition of an inactive binder to aggregate smaller particles into larger granules. For example, wet granulation and solvent granulation involve the addition of a liquid binder which aggregates the active materials and excipients into granules. After granulation, the liquid can be removed by a separate drying step. Melt granulation is similar to wet granulation, but uses a low melting point solid material as a binder. The solid binder in melt granulation is melted and acts as a liquid binder thereby aggregating the powdered active material and excipients into granules. The binder thereby, can be incorporated into the granules when the granules cool.

Certain embodiments of the present invention include microparticles manufactured by a process for producing granules by rotomelt granulation that comprises mixing bupropion hydrobromide and a powdered excipient material that has a higher melting point than bupropion hydrobromide in a zone wherein both powdered materials are maintained in a fluidized state by a rising stream of gas in an apparatus having a rapidly rotating horizontal-disk located within a vertical vessel having a bottom surface; wherein said rapidly rotating disk is located on the bottom surface of the vertical vessel wherein said gas is at a temperature sufficient to cause the bupropion hydrobromide to at least partially melt thereby causing said powdered materials to aggregate and form granules. Other embodiments of the present invention include microparticles manufactured by a process for producing granules by rotomelt granulation comprising mixing powdered binder material and bupropion hydrobromide wherein the bupropion hydrobromide has a higher melting point than the powdered binder material in a zone wherein both powdered materials are maintained in a fluidized state by a rising stream of gas in an apparatus having a rapidly rotating horizontal-disk located within a vertical vessel having a bottom surface; and wherein said rapidly rotating disk is located on the bottom surface of the vertical vessel wherein said gas is at a temperature sufficient to cause the powdered binder material to at least partially melt thereby causing said powdered materials to aggregate and form granules.

In rotomelt granulation, one of the feed powders must have a lower melting point than the other powder in order to serve as a binder. The feed powders are introduced into a vertical vessel with rotatable horizontal-disk located in the bottom of the vessel. The powder is maintained in fluidized state by at least one stream of filtered air being circulated from the bottom of the vertical vessel through one or more inlets. The rotatable horizontal disk is then rotated while the air supplied to fluidize the powder is maintained at a temperature sufficient to soften or melt the lower melting point powder. The temperature to which the binder must be heated to soften can be empirically determined by observing the formation of granules at various temperatures for various binders. It is presently believed that temperatures from 3° C. to 5° C. below the melting point or melting range provides sufficient softening to result in granule formation. The lower melting point powder then acts as a binding agent to promote the aggregation of powder particles into granules. Suitable powders for use in rotomelt granulation have a diameter size in the range of from 5 microns to 150 microns; and in certain embodiments have a diameter size in the range of 35 microns to 80 microns. The temperature which the components will be exposed to depends on the binder employed to aggregate the powders. Generally, the melting point of the binder is above 30° C.; and in certain embodiments is below 100° C.

The powders used in these microparticles manufactured by rotomelt granulation can be formed into granules by at least two alternative granulation mechanisms. The first mechanism for granule formation utilizes a larger particulate binder and a smaller particulate powder. The temperature during the rotomelt granulation is then elevated only to the point where the external surface of the binder particles become tacky. As the second powdered material of a smaller size is contacted with the tacky surface it forms a microlayer on the surface of the binder particle. This granulation mechanism results in granules which have size distribution similar to the original binder particles employed. Alternatively, the rotomelt granulation can be conducted at a temperature at which the binder acts as a cement bridging the gaps between the unmelted particles (this is referred to as agglomeration). This mechanism results in the formation of granules where the components are intermingled. For each binder used the mechanism can be controlled primarily by the temperature at which the rotomelt granulation is performed. Those skilled in the art will appreciate that the granules formed can be observed by electron microscopy to determine the type of granulation process occurring. If one particular type of granule is desired, the process conditions or starting materials can be varied to produce the desired granules.

In at least one embodiment of the present invention, bupropion hydrobromide is melted to act as a binding agent in the rotomelt granulation process. Examples of suitable excipients include those selected from the following: fillers, lubricants, glidants and antiadherents. Suitable fillers include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, maltodextrins, lactose, and fructose. The amount of binder added to aggregate the particles into granules can be in the range of from 10% w/w to 80% w/w; and in certain embodiments is in the range of from 30% w/w to 70% w/w of the powdered materials in the rotomelt granulation. The remaining weight percentage to provide a total of 100% w/w can be one or more suitable powdered pharmaceutical actives. Optionally the rotomelt granulation can also contain from 0% to 60% w/w of one or more powdered excipients wherein the total weight of all the powdered materials equals 100% w/w. The binder used in these embodiment of the invention can be a pharmaceutically acceptable dry powder having a particle size in the range of from 5 μm to 150 μm; and in certain embodiments in the range of from 35 μm to 80 μm. Suitable binders for rotomelt granulation are low melting point powdered binders, examples of which include: polyethylene glycol 4000, polyethylene glycol 6000, stearic acid, and low melting point waxes. Suitable low melting point waxes include but are not limited to glyceryl monostearate, hydrogenated tallow, myristyl alcohol, myristic acid, stearyl alcohol, substituted monoglycerides, substituted diglycerides, substituted triglycerides, white beeswax, carnauba wax, castor wax, japan wax, acetylate monoglycerides and combinations thereof. The binders can have a melting point of from 30° C. to 100° C.; and in certain embodiments from 40° C. to 85° C.

As a prophetic example of these embodiments that are manufactured by a rotomelt granulation process, 320 g of bupropion hydrobromide and 80 g PEG 8000 is dry blended and poured into a Glatt 1.1 chamber set-up as a rotary granulator with a longitudinal plate. Inlet air temperature is set to 60° C. and the product chamber heated to approximately 50° C. The blend is fluidized at approximately 120 m3/hr and the frictional plate set to 900 rpm. The product chamber temperature is raised to 60° C. and then gradually reduced to 20° C. over a period of approximately 20 minutes, during which spheronization is achieved.

Other embodiments of the invention involve the formation of a microparticle that has a core which includes bupropion hydrobromide and a compound which is sweet in taste and which has a negative heat of solution. Examples of compounds falling into this category include mannitol and sorbitol. Sugars or artificial sweeteners to which, for example, menthol have been added can also work as well. A binder and/or other excipient can also be disposed within the core. The amount of sweetening compound used can depend on a number of factors including the size of the resulting microparticles, the size or volume of the resulting tablet, the sturdiness of the microparticle-coated microparticulant, the speed at which the tablet will disintegrate in the mouth, the degree of sweetness imparted by the particular sweetener used, either in the microparticle or in the tablet, or both, the amount of drug used, and the like. For example, particularly rugged microparticles can be less likely to break during chewing and/or compression. Therefore, the amount of material provided to protect against the release of objectionably flavored material can be lessened. In other cases a greater relative amount of sweetening compound can be used. Generally, the amount of sweetening material used will range from greater than zero to 80% of the weight of the resulting microparticles. The sweetener and bupropion hydrobromide can be combined in any number of known ways, such as for example by wet granulation, dry granulation, agglomeration, or spray coating. For example, the sweetener can be used as an adsorbent for the active agent. Alternatively, particles of each can also be simply mixed together. One or more binders, or other adjuvants can also be used in the formulation of a tablet as well. Binders in these embodiments include, for example: starch (for example, in an amount of from 5% to 10% as an aqueous paste); pregelatinized starch (for example, in an amount of 5% to 10% added dry to powder); gelatin (for example, in an amount of from 2% to 10% as an aqueous solution, or 2% in starch paste); polyvinylpyrrolidone (for example, in an amount of from 2% to 20% in an aqueous or alcoholic solution); methylcellulose (for example, in an amount of from 2% to 10% as an aqueous solution); sodium carboxy methylcellulose (for example, in an amount of from 2% to 10% as an aqueous solution); ethylcellulose (for example, in an amount of from 5% to 10% as an alcohol or hydroalcoholic solution); polyacrylamides (Polymer JR) (for example, in an amount of from 2% to 8% as an aqueous solution); polyvinyloxoazolidone (Devlex) (for example, in an amount of from 5% to 10% as an aqueous or hydroalcoholic solution); and polyvinyl alcohols (for example, in an amount of from 5% to 20% in aqueous solutions). Other adjuvants can also be used in forming the core of the microparticles of the present embodiments of the invention, non-limiting examples of which include: calcium sulfate NF, Dibasic Calcium phosphate NF, Tribasic calcium sulfate NF, starch, calcium carbonate, microcrystalline cellulose, modified starches, lactose, sucrose and the like, STA-RX™, AVICEL™, SOLKA-FLOC™ BW40, alginic acid, EXPLOTAB™, AUTOTAB™, guar gum, kaolin VECGUM™, and bentonite. These adjuvants can be used in up to 20% w/w; and in certain embodiments are present in an amount of from 3% to 5% w/w.

As a prophetic example of these embodiments that have a core comprising bupropion hydrobromide and a compound which is sweet in taste, bupropion hydrobromide can be granulated using the following procedure: Polyvinylpyrrolidone K-30 USP (240.0 gm) is dissolved into distilled water (1,890.0 gm) with agitation. Mannitol powder USP (11,160 gm) and bupropion hydrobromide (600.0 gm) are placed in a Zanchetta 50-liter granulator/processor. After an initial two-minute dry mix of the powders with the chopper on and the propeller adjusted to 200 rpm, the polyvinylpyrrolidone K-30 solution is slowly sprayed into the mixing powder bed using an air-driven spray system. The total time of granulation including the time of solution addition is approximately eight minutes. The granulation end-point is determined visually and by the consistency of the resulting material. The material is then discharged onto trays and dried at 80° C. utilizing supplied dry air for a period of six hours to a moisture content of not more than 0.08 percent. The dried material is then passed through a hammermill (knives forward) equipped with a U.S. #40 (420 micron) screen.

Other embodiments of this invention involve the combined granulation and coating of bupropion hydrobromide into microparticles in which the drug is at least partly located within the microparticle core but capable of immediate release. To do this, the bupropion hydrobromide and a granular disintegrant are first dry-mixed; the powder obtained is then granulated, in the presence of a mixture of excipients comprising at least one binder capable of binding the particles together to give grains; the grains thus formed are then coated by spraying with a suspension comprising at least one coating agent and a membrane disintegrant; and then the coated granules obtained are dried. The distinction between the actual granulation and coating steps is relatively theoretical, insofar as, even though the primary function of the binder used in the granulation step is to bind together the particles, it nevertheless already partially coats the grains formed. Similarly, even though the primary function of the coating agent used in the actual coating step is to complete the final coating of each of the grains, it may, however, arbitrarily bind other coated grains by a mechanism of granular agglomeration. The binder and the coating agent are chosen from the group comprising cellulose polymers and acrylic polymers. However, even though the binder and the coating agent are chosen from the same group of compounds, they nevertheless differ from each other in their function as previously mentioned. Among the cellulose polymers that can be advantageously chosen are ethylcellulose, hydroxypropylcellulose (HPC), carboxymethylcellulose (CMC) and hydroxypropylmethylcellulose (HPMC), or mixtures thereof. Among the acrylic polymers that can be advantageously chosen are the ammonio-methacrylate copolymer (EUGRAGIT® RL or RS), the polyacrylate (EUGRAGIT® NE) and the methacrylic acid copolymer (EUGRAGIT® L or S), EUGRAGIT® being a registered trademark of Rohm. In at least one embodiment, the binder is of the same nature as the coating agent. To further accelerate the release of the bupropion hydrobromide, the coating suspension also comprises a permeabilizer which, on account of its intrinsic solubility properties, causes perforation of the membrane coating, thus allowing the bupropion hydrobromide to be released. Non-limiting examples of permeabilizers include povidone and its derivatives, polyethylene glycol, silica, polyols and low-viscosity cellulose polymers. Polymers of the type such as hypromellose, whose viscosity is equal to 6 centipoises, are used, for example, as low-viscosity cellulose polymer. In at least one embodiment, the dry-mixing of initial powder and the granulation, coating and drying steps are performed in a fluidized bed. In this case, the initial powder mixture is first fluidized before being granulated by spraying said powder with the excipient mixture comprising at least the binder, the grains obtained then being coated by spraying with the coating suspension, the coated granules formed finally being dried in the fluidized bed. In at least one embodiment, the mixture of excipients used during the granulation step and the coating suspension used during the coating step form a single mixture. In this case, the granulation step can be distinguished from the spraying step by varying different parameters, such as the rate of spraying of the mixture and the atomization pressure of said mixture. Thus, only some of the mixture of excipients is used during the granulation step, while the other portion can be used during the coating step. Thus, the rate of spraying of the coating suspension is higher during the granulation step than during the coating step, whereas the atomization pressure of the coating suspension is lower during the granulation step than during the coating step. In practice, at the laboratory scale in a fluidized-bed device, for example of the type such as Glatt GPCG1, during the granulation step, the rate of spraying of the coating suspension is between 10 grams/minute and 25 grams/minute, and the atomization pressure is between 1 bar and 1.8 bar. During the coating step, the rate of spraying of the coating suspension is between 5 grams/minute and 15 grams/minute, while the atomization pressure is between 1.5 bar and 2.5 bar. In at least one embodiment, between 10% and 20% of the mixture of excipients is sprayed during the granulation step, the remainder being sprayed during the coating step.

As a prophetic example of these embodiments that involve the combined granulation and coating of bupropion hydrobromide into microparticles in which the drug is at least partly located within the microparticle core but capable of immediate release, the microparticles can be manufactured according to the following process: A granulation solution is first prepared by dissolving 48 g of ethylcellulose in 273 g of ethyl alcohol. A coating suspension is then prepared by mixing 97 g of ethylcellulose, 28.5 g of polyethylene glycol 6000, 26 g of sodium croscarmellose, 10 g of precipitated silica and 27.5 g of aspartam in 1900 g of ethyl alcohol, until a homogeneous suspension is obtained. The powder mixture consisting of 700 grams of bupropion hydrobromide and 35 grams of Acdisol is then fluidized. The granulation is then started by spraying the granulation solution for 15 to 20 minutes at a spraying rate of 25 grams/minute and a suspension atomization pressure of 0.8 bar. The actual coating is then performed by spraying the coating suspension for 1 hour 30 minutes at a spraying rate of 15 to 20 grams/minute and a suspension spraying pressure of 1.5 bar.

Other embodiments of the invention involve coating the bupropion hydrobromide material, thereby forming a drug-containing microparticle. One such process for achieving this involves:
(i) Blending and fluidizing a powder mix of active principle and an adjuvant in order to obtain individual grains,
(ii) Separately liquefying under warm conditions a lipid matrix agent comprising either an ester of behenic acid and alcohol or an ester of palmitic/stearic acid and alcohol,
(iii) Coating the fluidized powder mix under warm conditions by spraying the lipid matrix agent over the individual grains,
(iv) Lowering the temperature of the combined product in order to allow the lipid matrix agent to solidify.

This process does not require an evaporation phase or a drying phase, since it does not require a wet-route or solvent-route granulation step, thus making it possible to be freed from any risk due to the presence of toxic residues in the final product. Furthermore, it is not necessary to carry out the quantitative determination of the traces of solvents, an analysis that can be very expensive. According to the process of this embodiment of the invention, the spraying conditions and thus the coating characteristics can be modified, in order to vary the release profile of bupropion hydrobromide, by varying several parameters, the adjustment characteristics of which remain simple. Thus, the spraying air pressure can be increased in order to promote the formation of a homogeneous film of lipid matrix agent around the grains. Advantageously, the rate of spraying of the lipid matrix agent can simultaneously be decreased. In this case, the bupropion hydrobromide release profile, that is to say a percentage of dissolution as a function of the time, is obtained which can be low, corresponding to a slow release of the drug. Conversely, the spraying air pressure can be decreased in order to promote the agglomeration of the grains with one another. Advantageously, the rate of spraying of the lipid matrix agent can simultaneously be increased. In this case, a release profile of the grains obtained can be obtained which is high, corresponding to a rapid release of bupropion hydrobromide. In practice and according to the mass of powder employed, the value of the rate of spraying of the lipid matrix agent can be from two to four times higher when it is desired to promote the agglomeration of the grains with one another than when it is desired to promote the formation of a homogeneous film around the grains. On the other hand, the value of the spraying air pressure can be from one to two times lower when it is desired to promote the agglomeration of the grains with one another than when it is desired to promote the formation of a homogeneous film around the grains. According to the process for manufacturing these embodiments, it is possible, after having determined a given drug release profile, to vary the values of spraying air pressure and of spraying rate throughout the coating stage, making it possible to promote the formation of a homogeneous film around the grains or to promote the agglomeration of the grains. Once the sequence of the duration of the spraying air pressure and of the spraying rate has been determined, the coating operation can be carried out continuously and automatically. According to another characteristic of the process of manufacturing these embodiments, the temperature of the mixture of liquefied matrix agent and of spraying air is greater by 35° C. to 60° C. than the melting temperature of the lipid matrix agent. Likewise, the temperature of the fluidization air and that of the powder is approximately equal to the melting temperature of the lipid matrix agent, plus or minus 10° C. Furthermore, in order to obtain a mixture of individual grains, an air-operated fluidized bed device or a turbine device can be used. Furthermore, the lipid matrix agent can be sprayed by the air spray technique, that is to say liquid spraying under pressure in the presence of compressed air. According to at least one embodiment, use is made of a powder comprising the drug and the adjuvant. In other words, after mixing and fluidizing the combined constituents of the powder, the lipid matrix agent is sprayed over the individual grains obtained. In order to avoid adhesion of the coated grains obtained, whether in the case where all the grains are treated or whether in the case where only a portion of the grains is treated, a stage of lubrication of the grains is inserted between the coating stage and the stage of putting into a pharmaceutical form. Furthermore, in order to obtain greater stability of the pharmaceutical composition, that is to say in order to minimize modifications relating to the release of the bupropion hydrobromide over time, the granules or tablets obtained in certain embodiments of this example can be subjected to a maturing stage in an oven, for at least 8 hours, at a temperature of between 45° C. and 60° C.; and in certain embodiments at 55° C.

As a prophetic example of these drug-containing microparticle embodiments that are formed by coating the bupropion hydrobromide material, the drug-containing microparticles can be manufactured according to the following process: A mixture of powder is prepared comprising: bupropion hydrobromide; dicalcium phosphate dehydrate; and polyvinylpyrrolidone. Batches of granules are prepared by a process comprising the following stages: the mixture of powder obtained is sieved; the said powder is mixed, heating while by means of an air-operated fluidized bed, in order to obtain individual grains; the lipid matrix agent (glyceryl behenate, sold under the trade name COMPRITOL® 880 ATO) is liquefied separately at 120° C.; the lipid matrix agent is sprayed over the heated powder mixture, and, finally, the temperature is lowered in order to allow the lipid matrix agent to solidify. These stages are carried out while varying various parameters, either in order to promote the formation of a homogeneous film around the grains or in order to promote the agglomeration of the grains, in accordance with the following table:

| Parameters | Batch 1 | Batch 2 | Batch 3 | Batch 4 |
|---|---|---|---|---|
| % by weight of lipid matrix agent (COMPRITOL ® 888 ATO) | 5 | 4 | 4 | 5 |
| Fluidization air flow rate (m$^3$/h) | 80 | 110 | 80 | 80 |
| Agglomeration | | | | |
| Atomization air pressure (bar) | 2 | | 1.5 | 1.5 |
| Temperature of the powder bed (° C.) | 70 | | 70 | 74 |
| Spraying rate for COMPRITOL ® (g/min) | 42 | | 40 | 40 |
| Coating | | | | |
| Atomization air pressure (bar) | 2.5 | 3.5 | 2 | 2 |
| Temperature of the powder bed (° C.) | 70 | 66 | 71 | 70 |
| Spraying rate for COMPRITOL ® (g/min) | 41 | 20 | 40 | 40 |

Another embodiment of the invention for coating the bupropion hydrobromide material, thereby forming a drug-containing microparticle, involves the formation of coated microcrystals that can subsequently be incorporated into a tablet. Through selection of the appropriate polymer the microcrystals can possess diversified features such as gastroresistance and controlled release due to the fact that the said coated or non-coated microcrystals and microgranules preserve, after having been shaped in the form of a multiparticulate tablet, their initial properties amongst which are included masking of taste, gastroresistance and controlled release of the bupropion hydrobromide. In certain embodiments of this example, the following non-limiting list of polymers can be selected for coating of the bupropion hydrobromide in conventional fluidized based coating equipment: ethylcellulose (EC); hydroxypropylcellulose (HPC); hydroxypropylmethylcellulose (HPMC); gelatin; gelatin/acacia; gelatin/acacia/vinylmethylether maleic anhydride; gelatin/acacia/ethylenemaleic anhydride; carboxymethyl cellulose; polyvinylalcohol; cellulose acetate phthalate; nitrocellulose; shellac; wax; polymethacrylate polymers such as EUGRAGIT® RS; EUGRAGIT® RL or combinations of both, EUGRAGIT® E and Eudragit NE30D; KOLLICOAT™ SR30D; and mixtures thereof.

The drug-layered microparticles can be made by coating an inert particle or core, such as a non-pareil sphere (e.g. sugar sphere), with the bupropion salt and a polymeric binder. In certain embodiments of the drug-layered microparticles, the inert cores include water-insoluble materials such as cellulose spheres or silicon dioxide. In other embodiments, the inert cores include water-soluble materials such as starch, salt or sugar spheres. The inert cores can have a diameter ranging from 100 microns to 2000 microns. For example, in certain embodiments the diameter of the inert cores range from 150 microns to 1500 microns. In at least one embodiment, the inert cores are sugar spheres NF, containing not less than 62.5% and not more than 91.5% of sucrose. In at least one embodiment the inert cores have substantially consistent bulk density, low friability, and low dust generation properties. In at least one embodiment, the inert cores are coated with an osmotic sub-coat comprising an osmotic agent and a polymeric binding agent. Further, the inert cores can initially be coated with a seal-coat to provide a more consistent core surface and to minimize any osmotic effects. The seal-coat layer can be applied to the core prior to the application of the drug, polymeric binder, and any polymeric film layers. In at least one embodiment, the seal-coat layer does not substantially modify the release of the bupropion salt. Examples of suitable sealants that can be used in the seal-coat include permeable or soluble agents such as hydroxypropyl methylcellulose, hydroxypropyl cellulose, ethylcellulose, a polymethacrylate polymer, hydroxypropyl ethylcellulose, xanthan gum, and mixtures thereof. In at least one embodiment the sealant used in the seal-coat is hydroxypropyl methylcellulose. Other agents can be added to improve the processability of the sealant. Examples of such agents include talc, colloidal silica, polyvinyl alcohol, titanium dioxide, micronised silica, fumed silica, glycerol monostearate, magnesium trisilicate, magnesium stearate, and mixtures thereof. The seal-coat layer can be applied from solution (e.g. aqueous) or suspension using a fluidised bed coater (e.g. Wurster coating), or in a pan coating system. Examples of such seal-coats coatings are commercially available such as those sold under the Trade Marks OPADRY® White Y-1-7000 and OPADRY® OY/B/28920 White, each of which is available from Colorcon Limited, England.

The binding agent of these drug-layered embodiments is used to adhere the bupropion salt layer to the inert core or seal-coat of the core. In certain embodiments, the binding agent is water soluble, possesses sufficiently high adhesivity in order to adhere the bupropion salt layer to the inert core, and possesses an appropriate viscosity to provide substantial adhesion between the inert core and the bupropion salt. In other embodiments the binding agent is water-insoluble. In at least one embodiment the binding agent is ethyl cellulose, a polymethacrylate polymer, polyvinylalcohol, polyvinyl pyrrolidone, polyvinylpyrrolidone-vinylacetate copolymer (such as Kollidon VA64), hydroxyethylcellulose, low molecular weight hydroxypropylmethylcellulose (e.g. viscosity of 1-50 cps at 20° C.; 2-12 cps at 20° C.; or 4-6 cps at 20° C.), hydroxypropylcellulose polymethacrylates, or mixtures thereof. For example, in certain embodiments the composition of the binder for bupropion hydrobromide is from 1% to 25% w/w; in other embodiments from 2% to 10% w/w; and in still other embodiments from 3% to 5% w/w, expressed as a percentage of the total weight of the core.

Solvents can be used to apply the bupropion salt to the inert core, examples of which include lower alcohols such as ethanol, isopropanol and alcohol/water mixtures, acetone and chlorinated hydrocarbons.

The drug-layered microparticles can be prepared by forming a suspension or solution of the binder and the bupropion salt and then layering the suspension or solution on to the inert or sub-coated core using any of the layering techniques known in the art, such as fluidized bed coating or pan coating. This can be effected in a single coating or the process can be carried out in multiple layers, optionally with intervening drying/evaporation steps. This process can be conducted so as to produce microparticles containing a desired amount of bupropion salt and achieve the desired dosage and release thereof upon in vivo administration.

In certain embodiments, the drug-layered microparticles can be manufactured using for example, the procedure in the following hypothetical experiment: Bupropion hydrobromide (2.8 kg) and hydroxypropyl methylcellulose (METHOCEL® E5) (0.40 kg) is dissolved in a mixture of water and isopropyl alcohol. The active drug solution can then be sprayed onto sugar spheres 30/35 (1.06 kg) in a fluidized bed processor with a Wurster insert. The active core microparticles can then be dried in a fluidized bed processor until the loss on drying is below 1%. The bupropion microparticles can then be passed through a 16 mesh screen and a 30 mesh screen and microparticles can be collected that are smaller than 16 mesh and larger than 30 mesh.

Microparticle Taste-Masking Coatings

The microparticles of the present invention can each be coated with at least one taste-masking coating. The taste-masking coating can mask the taste of the active drug in the microparticles. In at least one embodiment the taste-masking coating formulations contain polymeric ingredients. It is contemplated that other excipients consistent with the objects of the present invention can also be used in the taste-masking coating.

In at least one embodiment, the taste-masking coating comprises a polymer such as ethylcellulose, which can be used as a dry polymer (such as ETHOCEL®, Dow Corning) solubilised in organic solvent prior to use, or as an aqueous dispersion. One commercially-available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the Aquacoat is intimately mixed with a suitable plasticizer prior to use. Another aqueous dispersion of ethylcellulose is commercially available as SURELEASE® (Colorcon, Inc., West Point, Pa., U.S.A.). This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

In other embodiments, polymethacrylate acrylic polymers can be employed as taste masking polymers. In at least one embodiment, the taste masking coating is an acrylic resin lacquer used in the form of an aqueous dispersion, such as that which is commercially available from Rohm Pharma under the tradename EUGRAGIT® or from BASF under the tradename KOLLICOAT®. In further preferred embodiments, the acrylic coating comprises a mixture of two acrylic resin lacquers commercially available from Rohm Pharma under the tradenames EUGRAGIT® RL and EUGRAGIT® RS, respectively.

EUGRAGIT® RL and EUGRAGIT® RS are copolymers of acrylic and methacrylic esters with a low content of quaternary ammonium groups, the molar ratio of ammonium groups to the remaining neutral (meth)acrylic esters being 1:20 in EUGRAGIT® RL and 1:40 in EUGRAGIT® RS. The mean molecular weight is 150,000. The code designations RL (high permeability) and RS (low permeability) refer to the permeability properties of these agents. EUGRAGIT® RL/RS mixtures are insoluble in water and in digestive fluids. However, coatings formed from the same are swellable and permeable in aqueous solutions and digestive fluids. EUGRAGIT® RL/RS dispersions or solutions of the present invention can be mixed together in any desired ratio in order to ultimately obtain a taste masking coating having a desirable drug dissolution profile. Desirable formulations can be obtained, for example, from a coating derived from 100% EUGRAGIT® RL; 50% EUGRAGIT® RL with 50% EUGRAGIT® RS; and 10% EUGRAGIT® RL with 90% EUGRAGIT® RS.

In other embodiments, the taste masking polymer can be an acrylic polymer which is cationic in character based on dimethylaminoethyl methacrylate and neutral methacrylic acid esters (such as EUGRAGIT® E, commercially available from Rohm Pharma). The hydrophobic acrylic polymer coatings of the present invention can further include a neutral copolymer based on poly (meth)acrylates, such as EUGRAGIT® NE (NE=neutral ester), commercially available from Rohm Pharma. EUGRAGIT® NE 30D lacquer films are insoluble in water and digestive fluids, but permeable and swellable.

In other embodiments, the taste masking polymer is a dispersion of poly (ethylacrylate, methyl methacrylate) 2:1 (KOLLICOAT® EMM 30 D, BASF).

In other embodiments, the taste masking polymer can be a polyvinyl acetate stabilized with polyvinylpyrrolidone and sodium lauryl sulfate such as KOLLICOAT® SR30D (BASF).

Other taste masking polymers include hydroxypropylcellulose (HPC); hydroxypropylmethylcellulose (HPMC); hydroxyethylcellulose; gelatin; gelatin/acacia; gelatin/acacia/vinylmethylether maleic anhydride; gelatin/acacia/ethylenemaleic anhydride; carboxymethyl cellulose; polyvinylalcohol; nitrocellulose; polyvinylalcohol-polyethylene glycol graft-copolymers; shellac; wax and mixtures thereof.

The taste-masking coatings can be applied to the microparticles from one or more organic or aqueous solvent solutions or suspensions. In at least one embodiment the organic solvents that can be used to apply the taste-masking coatings include one or more of acetone, lower alcohols such as ethanol, isopropanol and alcohol/water mixtures, chlorinated hydrocarbons, and the like. Devices used to coat the microparticles of the invention with a taste-masking coating include those conventionally used in pharmaceutical processing, such as fluidized bed coating devices. The coatings applied to the microparticles can contain ingredients other than the functional polymers. One or more colorants, flavorants, sweeteners, can also be used in the taste-masking coating.

In some embodiments a pore former can be included into the taste masking coat in order to influence the rate of release of bupropion hydrobromide from the microparticle. In other embodiments, a pore former is not included in the taste masking coat. The pore formers can be inorganic or organic, and include materials such as particulate materials that can be dissolved, extracted or leached from the coating in the environment of use. Upon exposure to fluids in the environment of use, the pore-formers can for example be dissolved, and channels and pores are formed that fill with the environmental fluid.

For example, the pore-formers of certain embodiments can comprise one or more water-soluble hydrophilic polymers in order to modify the release characteristics of the formulation. Examples of suitable hydrophilic polymers used as pore-formers include hydroxypropylmetlhylcellulose, cellulose ethers and protein-derived materials of these polymers, the cellulose ethers, especially hydroxyalkylcelluloses and carboxyalkylcelluloses. Also, synthetic water-soluble polymers can be used, examples of which include polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, and sorbitol. In at least one embodiment, the hydrophilic polymer comprises hydroxypropyl-methylcellulose.

Other non-limiting examples of pore-formers include alkali metal salts such as lithium carbonate, sodium chloride, sodium bromide, potassium chloride, potassium sulfate, potassium phosphate, sodium acetate, and sodium citrate. The pore-forming solids can also be polymers which are soluble in the environment of use, such as CARBOWAXES™, and CARBOPOL™. In addition, the pore-formers embrace diols, polyols, polyhydric alcohols, polyalkylene glycols, polyglycols, and poly(a-w)alkylenediols. Other pore-formers which can be useful in the formulations of the present invention include starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambdacarrageenan, gum karaya, biosynthetic gum, etc. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous hiomopolymers, copolymers or interpolymers having a reduced bulk density, and other similar materials, poly (urethane), cross-linked chain-extended poly(urethane), poly(imides), poly(benzimidazoles), collodion, regenerated proteins, semi-solid cross-linked poly(vinylpyrrolidone), and mixtures thereof.

In general, the amount of pore-former included in the taste masking coatings of certain embodiments of the present invention can be from 0.1% to 80%, by weight, relative to the combined weight of polymer and pore-former. The percentage of pore former as it relates to the dry weight of the taste-masking polymer, can have an influence on the drug release properties of the coated microparticle. In at least one embodiment that uses water soluble pore formers such as hydroxypropylmethylcellulose, a taste masking polymer: pore former dry weight ratio of between 10:1 and 1:1 can be present. In certain embodiments the taste masking polymer: pore former dry weight ratio is from 8:1 to 1.5:1; and in other embodiments from 6:1 to 2:1. In at least one embodiment using EUGRAGIT® NE30D as the taste masking polymer and a hydroxypropylmethylcellulose (approx 5 cps viscosity (in a 2% aqueous solution)) such as METHO-CEL® E5, Pharmacoat 606G as the water soluble pore former, a taste masking polymer:pore former dry weight ratio of 2:1 is present.

Colorants that can be used in the taste-masking coating include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Flavorants that can be used in the taste-masking coating include natural and synthetic flavoring liquids. An illustrative list of such flavorants includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such as lemon, orange, grape, lime and grapefruit, and fruit essences, including apple, pear, peach, grape, strawberry, raspberry, cherry, plum, pineapple, apricot, or other fruit flavors. Other useful flavorants include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodenal (citrus mandarin); mixtures thereof and the like.

Sweeteners that can be used in the taste-masking coating include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; Steva Rebaudiana (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The microparticle taste masking coat can also include one or more pharmaceutically acceptable excipients such as lubricants, emulsifiers, anti-foaming agents, plasticisers, solvents and the like.

Lubricants can be included to help reduce friction of coated microparticles during manufacturing. The lubricants that can be used in the taste masking coat of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™, MYVATEX™ TL and mixtures thereof. In at least one embodiment, the lubricant is selected from magnesium stearate and talc. Combinations of these lubricants are operable. The lubricant can each be present in an amount of from 1% to 100% by weight of the polymer dry weight in the taste masking coat. For example, in certain embodiments wherein the taste masking polymer is EUGRAGIT® NE30D or EUGRAGIT® NE40D (Rohm America LLC) together with a hydrophilic pore former, the lubricant is present in an amount of from 1% to 30% by weight of the polymer dry weight; in other embodiments from 2% to 20%; and in still other embodiments at 10% by weight of the microparticle taste masking coat dry weight. In another embodiment where the taste masking polymer is ethylcellulose (ETHOCEL™ PR100, PR45, PR20, PR10 or PR7 polymer, or a mixture thereof), the lubricant can be present in an amount of from 10% to 100% by weight of the microparticle taste masking coat dry weight; in another embodiment from 20% to 80%; and in still another embodiments at 50% by weight of the microparticle taste masking coat dry weight. In other embodiments, the taste masking coat does not include a pore former.

Emulsifying agent(s) (also called emulsifiers or emulgents) can be included in the microparticle taste masking coat to facilitate actual emulsification during manufacture of the coat, and also to ensure emulsion stability during the shelf-life of the product. Emulsifying agents useful for the microparticle taste masking coat composition include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from 0.01% to 5% by weight of the microparticle taste masking polymer dry weight. For example, in certain embodiments the emulsifying agent is present in an amount of from 0.05% to 3%; in other embodiments from 0.08% to 1.5%, and in still other embodiments at 0.1% by weight of the microparticle taste masking polymer dry weight.

Anti-foaming agent(s) can be included in the microparticle taste masking coat to reduce frothing or foaming during manufacture of the coat. Anti-foaming agents useful for the coat composition include, but are not limited to simethicone, polyglycol, silicon oil, and mixtures thereof. In at least one embodiment the anti-foaming agent is Simethicone C. The anti-foaming agent can be present in an amount of from 0.1% to 10% of the microparticle taste masking coat weight. For example, in certain embodiments the anti-foaming agent is present in an amount of from 0.2% to 5%; in other embodiments from 0.3% to 1%, and in still other embodiments at 0.6% by weight of the microparticle taste masking polymer dry weight.

Plasticizer(s) can be included in the microparticle taste masking coat to provide increased flexibility and durability during manufacturing. Plasticisers that can be used in the microparticle taste masking coat include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from 1% to 80% of the taste masking polymer dry weight. For example, in certain embodiments the plasticizer is present in an amount of from 5% to 50%, in other embodiments from 10% to 40%, and in still other embodiments at 20% of the taste masking polymer dry weight.

The taste-masking coating can be present in an amount of from 1% to 90% by weight of the microparticle, depending upon the choice of polymer, the ratio of polymer:pore former, and the total surface area of the microparticle formulation. Since a certain thickness of taste masking coating has to be achieved in order to achieve effective taste masking, the amount of taste masking polymer coating used during manufacture is related to the total surface area of the batch of uncoated microparticles that requires a coating. The taste masking polymer surface area coverage can range from 0.5 mg/cm2 to 20 mg/cm2. For example, in certain embodiments the surface area coverage of the taste masking polymer is from 0.6 mg/cm2 to 10 mg/cm2, and in other embodiments is from 1 mg/cm2 to 5 mg/cm2. In at least one embodiment of the invention, EUGRAGIT® E is employed as the taste masking polymer at a surface area coverage of 4 mg/cm2. One approach in estimating the total surface area of a multiparticulate batch is the permeability method according to Blaine (ASTM Des. C 205-55), which is based upon the mathematical model of laminar flow through capillaries arranged in parallel.

In the absence of an accurate determination of total surface area of a microparticle, the amount of taste masking polymer to be applied can be expressed as a percentage of the uncoated microparticle. For example, in certain embodiments the taste-masking coating is present in an amount of from 5% to 60%; in other embodiments from 10% to 40%; and in still other embodiments from 15% to 35% by weight of the microparticle. In at least one embodiment the taste-masking coating is present in an amount of 30% by weight of the microparticle.

In certain embodiments, the diameter of the microparticles (with or without the taste-masking coating) range from 50 μm to 800 μm. For example, in certain embodiments the diameter of the microparticles range from 100 μm to 600 μm, and in other embodiments from 150 μm to 450 μm.

Microparticle Control-Releasing Coat

The microparticles of the present invention can each be coated with at least one control-releasing coat. As used herein, the term "microparticle control-releasing coat" refers to the control-releasing coat that substantially surrounds each microparticle. The microparticle control-releasing coat is designed to achieve a controlled release of the bupropion salt from the microparticle. For example, the microparticle control-releasing coat can be an enteric coat with low solubility at a gastric pH to reduce or minimize the drug release in the lumen of the stomach, whilst possessing pH dependent solubility to facilitate drug release in the duodenum. In another embodiment, the control releasing coat can be a delayed release coating that provides a delayed release of the bupropion salt with a predetermined lagtime that is independent of, or alternatively dependent on, the pH of the dissolution medium. For example, by increasing the thickness of the microparticle control-releasing coat using a pH independent diffusion polymer, lagtimes of 1 hour, 2 hours, 3 hours, 4 hours, 5 hours, 6 hours, 7 hours, 8 hours, 9 hours, 10 hours, 11 hours, or 12 hours can be achieved. Alternatively, controlled release polymers can be selected that become soluble above a certain pH. Drug release from such a system is reduced or minimized until the critical pH for the polymer of choice is exceeded. With either approach, following the predetermined lag, drug is released, for example within 1 hour for an immediate release pulse, or alternatively over a prolonged period of time, for example from 3 to 24 hours. In other embodiments, the microparticle control-releasing coat can provide a diffusion barrier that is independent of pH, thus facilitating a sustained release profile, with substantially full release of the bupropion salt occurring in from 3 to 24 hours following administration. In at least one embodiment, the microparticle control-releasing coat provides a delayed and sustained release of the bupropion salt from the microparticle with substantially full release in 24 hours following administration.

In certain embodiments, the microparticle control-releasing coat can provide substantially full release of the bupropion salt from the microparticle without requiring the use of any pore formers. Unnecessary pore formers that are not required in the microparticle control-releasing coat include hydrophilic polymers such as hydroxypropyl methylcellulose.

The microparticle control-releasing coat includes at least one polymer in an amount sufficient to achieve a controlled release of the bupropion salt. In at least one embodiment of the invention the control releasing polymer is an acrylic polymer. Suitable acrylic polymers include but are not limited to acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid, methacrylic acid alkylamine copolymer, poly(methyl methacrylate), poly(methacrylic acid) (anhydride), glycidyl methacrylate copolymers, and mixtures thereof.

In at least one embodiment the control-releasing coat comprises polymerizable quaternary ammonium compounds, of which non-limiting examples include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, and trimethylaminomethyl-methacrylamide methosulfate. The quaternary ammonium atom can also be part of a heterocycle, as in methacryloxy-ethylmethyl-morpholiniom chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, and styryltrialkyl ammonium salts. Other polymerizable quaternary ammonium compounds useful in the present invention include acryl- and methacryl-oxyethyltrimethyl-ammonium chloride and methosulfate, benzyldimethylammoniumethyl-methacrylate chloride, diethylmethylammoniumethyl-acrylate and -methacrylate methosulfate, N-trimethylammoniumpropyl-methacrylamide chloride, and N-trimethylammonium-2,2-dimethylpropyl-1-methacrylate chloride.

In at least one embodiment, the polymer of the control-releasing coat is an acrylic polymer comprised of one or more ammonio methacrylate copolymers. Ammonio methacrylate copolymers (such as those sold under the Trade Mark EUGRAGIT® RS and RL) are described in NF XVII as fully polymerized copolymers of acrylic and methacrylic acid esters with a low content of quaternary ammonium groups. In order to obtain a desirable dissolution profile for a given therapeutically active agent such as bupropion hydrobromide, it may be necessary in some embodiments to incorporate two or more ammonio methacrylate copolymers having differing physical properties. For example, it is known that by changing the molar ratio of the quaternary ammonium groups to the neutral (meth)acrylic esters, the permeability properties of the resultant control-releasing coat can be modified.

In other embodiments of the present invention, the acrylic polymer coating further includes a polymer whose permeability is pH dependent, such as anionic polymers synthesized from methacrylic acid and methacrylic acid methyl ester. Such polymers are commercially available, e.g., from Rohm Pharma GmbH under the tradename EUGRAGIT® L and EUGRAGIT® S, and the ratio of free carboxyl groups to the esters is said to be 1:1 in EUGRAGIT® L and 1:2 in EUGRAGIT® S. EUGRAGIT® L is insoluble in acids and pure water, but becomes increasingly permeable above pH 5.0. EUGRAGIT® S is similar, except that it becomes increasingly permeable above pH 7. The hydrophobic acrylic polymer coatings can also include a polymer which is cationic in character based on dimethylaminoethyl methacrylate and neutral methacrylic acid esters (such as EUGRAGIT® E, commercially available from Rohm Pharma). The hydrophobic acrylic polymer coatings of certain embodiments can further include a neutral copolymer based on poly (meth)acrylates, such as EUGRAGIT® NE (NE=neutral ester), commercially available from Rohm Pharma. EUGRAGIT® NE 30D lacquer films are insoluble in water and digestive fluids, but permeable and swellable.

In other embodiments of the invention the control-releasing polymer is a dispersion of poly (ethylacrylate, methyl methacrylate) 2:1 (KOLLICOAT® EMM 30 D, BASF). In other embodiments the control releasing polymer can be a polyvinyl acetate stabilized with polyvinylpyrrolidone and sodium lauryl sulfate such as KOLLICOAT® SR30D (BASF). The dissolution profile can be altered by changing the relative amounts of different acrylic resin lacquers included in the coating. Also, by changing the molar ratio of polymerizable permeability-enhancing agent (e.g., the quaternary ammonium compounds) in certain embodiments to the neutral (meth)acrylic esters, the permeability properties (and thus the dissolution profile) of the resultant coating can be modified.

In at least one embodiment the control releasing polymer is ethylcellulose, which can be used as a dry polmer (such as ETHOCEL®, Dow Corning) solubilised in organic solvent prior to use, or as an aqueous dispersion. One commercially available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® is intimately mixed with a suitable plasticizer prior to use. Another aqueous dispersion of ethylcellulose is commercially available as SURELEASE® (Colorcon, Inc., West Point, Pa., U.S.A.). This product can be prepared by incorporating a plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

Other examples of polymers that can be used in the microparticle control-releasing coat include cellulose acetate phthalate, cellulose acetate trimaletate, hydroxy propyl methylcellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight 5 k to 5000 k), polyvinylpyrrolidone (molecular weight 10 k to 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight 30 k to 300 k), polysaccharides such as agar, acacia, karaya, tragacanth, algins and guar, polyacrylamides, POLYOX® polyethylene oxides (molecular weight 100 k to 5000 k), AQUAKEEP® acrylate polymers, diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof.

In at least one embodiment the control-releasing coat of the microparticles comprises polymers that can faciliatate mucoadhsion within the gastrointestinal tract. Non-limiting examples of polymers that can be used for mucoadhesion include carboxymethylcellulose, polyacrylic acid, CARBOPOL™, POLYCARBOPHIL™, gelatin and other natural or synthetic polymers.

In at least one embodiment the microparticles are coated with a control-releasing coat comprised of:
(i) at least one film-forming polymer which is insoluble in the liquids of the digestive tract, present in an amount of from 50% to 90% (e.g. from 50% to 80%) by weight of dry matter of the control-releasing coat composition, and including at least one non-hydrosoluble cellulose derivate, (e.g. ethylcellulose, cellulose acetate, or mixtures thereof);
(ii) at least one nitrogen-containing polymer, present in an amount of from 2% to 25% (e.g. from 5% to 15%) by weight of dry matter of the control-releasing coat composition, and including at least one polyacrylamide, poly-N-vinylaride, poly-N-vinyl-lactame, polyvinylpyrrolidone, or mixtures thereof;
(iii) optionally at least one plasticizer present in an amount of from 2% to 20% (e.g. from 4% to 15%) by weight of dry matter of the control-releasing coat composition, and including at least one of the following compounds: glycerol esters, phtalates, citrates, sebacates, cetylalcohol esters, castor oil, cutin, or mixtures thereof;
(iv) at least one surface-active and/or lubricating agent, present in an amount of from 2% to 20% (e.g. from 4% to 15%) by weight of dry matter of the control-releasing coat composition, and chosen from anionic surfactants such as the alkali metal and alkakine-earth metal salts of fatty acids, (e.g. stearic acid, oleic acid, and mixtures thereof), and/or from nonionic surfactants such as polyoxyethylenated esters of sorbitan, polyoxyethylenated esters of sorbitan, polyoxyethylenated derivatives of castor oil, and/or from lubricants such as stearates (e.g. calcium, magnesium, aluminium, zinc stearate and mixtures thereof), stearylfumarates (e.g. sodium stearylfumarate, glyceryl behenate and mixtures thereof); and mixtures thereof;

wherein the coated microparticles are designed so as to be able to remain in the small intestine for a period of at least 5 hours; in certain embodiments at least 7 hours; and in certain other embodiments for a period of between 8 hours and 24 hours; so as to allow absorption of the bupropion hydrobromide during at least part of its time in the small intestine.

In a prophetic example of this embodiment of the invention, the microparticles are coated in a fluidized bead coater with the following coating solution:

| Ethylcellulose | 44.7 g |
| PVP | 4.8 g |
| Castor oil | 4.8 g |
| Magnesium Stearate | 6.1 g |
| Acetone | 479 g |
| Isopranol | 53 g |

In other embodiments of the present invention, the release of the bupropion hydrobromide from a controlled release formulation can be further influenced, i.e., adjusted to a desired rate, by the addition of one or more pore-formers to the control-releasing coat, where the pore-formers can be inorganic or organic, and can include materials that can be dissolved, extracted or leached from the control-releasing coat in the environment of use. Upon exposure to fluids in the environment of use, the pore-formers are, for example, dissolved, and channels and pores are formed that fill with the environmental fluid. For example, the pore-formers can include one or more water-soluble hydrophilic polymers in order to modify the release characteristics of the formulation. Non-limiting examples of suitable hydrophilic polymers include hydroxypropylmetlhylcellulose, cellulose ethers and protein-derived materials of these polymers, the cellulose ethers, (e.g. hydroxyalkylcelluloses and carboxyalkylcelluloses), and mixtures thereof. Also, synthetic water-soluble polymers can be used, such as polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol, and mixtures thereof. In at least one embodiment the hydrophilic polymer(s) include hydroxypropyl-methylcellulose. Other examples of pore-formers include alkali metal salts such as lithium carbonate, sodium chloride, sodium bromide, potassium chloride, potassium sulfate, potassium phosphate, sodium acetate, sodium citrate, and mixtures thereof. The pore-forming solids can also be polymers which are soluble in the environment of use, such as CARBOWAXES®, CARBOPOL®, and the like. The possible pore-formers embrace diols, polyols, polyhydric alcohols, polyalkylene glycols, polyglycols, poly(a-w)alkylenediols, and mixtures thereof. Other pore-formers which can be useful in the formulations of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous hiomopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), and mixtures thereof.

In other embodiments a surfactant or an effervescent base can be included in the control-releasing coat, which can reduce and in certain embodiments overcome surface tension effects. In addition, the control-releasing coat of certain embodiments can include one or more osmagents (i.e., which can osmotically deliver the active agent from the device by providing an osmotic pressure gradient against the external fluid), swelling agents (i.e., which can include, but are not limited to hydrophilic pharmaceutically acceptable compounds with various swelling rates in water), or other pharmaceutically acceptable agents (i.e., provided in an amount sufficient to facilitate the entry of the environmental fluid without causing the disruption of the impermeable coating). The surfactants that can be used in the control-releasing coat of certain embodiments can be anionic, cationic, nonionic, or amphoteric. Non-limiting examples of such surfactants include sodium lauryl sulfate, sodium dodecyl sulfate, sorbitan esters, polysorbates, pluronics, potassium laurate, and mixtures thereof. Non-limiting examples of effervescent bases that can be used in the control-releasing coat of certain embodiments include sodium glycine carbonate, sodium carbonate, potassium carbonate, sodium bicarbonate, potassium bicarbonate, calcium bicarbonate, and mixtures thereof. Non-limiting examples of osmagents that can be used in the control-releasing coat of certain embodiments include sodium chloride, calcium chloride, calcium lactate, sodium sulfate, lactose, glucose, sucrose, mannitol, urea, other organic and inorganic compounds known in the art, and mixtures thereof. The swelling agent can include, but is not limited to at least one pharmaceutically acceptable hydrophilic compound, having a swelling rate or swelling amount in water at 25° C. that is: greater than or equal to at least 10% by weight (wt/wt), greater than or equal to at least 15% by weight (wt/wt), or greater than or equal to at least 20% by weight (wt/wt). Non-limiting examples of swelling agents that can be used in the control-releasing coat of certain embodiments of the present invention include crosslinked polyvinylpyrrolidones (e.g. polyplasdone, crospovidone and mixtures thereof), crosslinked carboxyalkylcelluloses, crosslinked carboxymethylcellulose (e.g. crosslinked sodium croscarmellose), hydrophilic polymers of high molar mass (i.e., which can be, but are not limited to being greater than or equal to 100,000 Daltons) which can include, but are not limited to: polyvinylpyrrolidone(s), polyalkylene oxides (e.g. polyethylene oxide, polypropylene oxide, and mixtures thereof), hydroxyalkylcelluloses (e.g. hydroxypropylcellulose, hydroxypropylmethylcellulose and mixtures thereof), carboxyalkylcellulose (e.g. carboxymethylcellulose), modified starch (e.g. sodium glycolate), starch or natural starch (e.g. corn, wheat, rice, potato and mixtures thereof), cellulose (i.e. which can be, but is not limited to being in powder form or microcrystalline form), sodium alginate, potassium polacriline, and corresponding blends or mixtures thereof. In other embodiments, non-limiting examples of the swelling agent include the following sub-set of compounds: crosslinked polyvinylpyrrolidone (e.g. polyplasdone, crospovidone or mixtures thereof), crosslinked carboxyalkylcelluloses (e.g. crosslinked carboxymethylcelluloses such as crosslinked sodium croscarmellose), and mixtures thereof. In other embodiments, the swelling agent can be a nitrogen containing polymer, non-limiting examples of which can include polyvinylpyrrolidone, crosslinked polyvinylpyrrolidone and mixtures thereof. The concentration of the swelling agent in the control-releasing coat of certain embodiments of the present invention can be from 3% to 40% by weight of the microparticle. For example, in certain embodiments the concentration of the swelling agent in the control-releasing coat is from 4% to 30%, and in other embodiments from 5% to 25% by weight of the microparticle.

In certain embodiments one or more pharmaceutically acceptable excipients consistent with the objects of the present invention can be used in the control-releasing coat, such as a lubricant, an emulsifying agent, an anti-foaming agent, and/or a plasticizer.

Lubricants can be included in the control-releasing coat to help reduce friction of coated microparticles during manufacturing. The lubricants that can be used in the control-releasing coat of certain embodiments of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (e.g. COMPRITOL™), STEAR-O-WET™ and MYVATEX™ TL. In at least one embodiment, the lubricant is selected from magnesium stearate, talc and mixtures thereof. Combinations of these lubricants are operable. The lubricant can each be present in an amount of from 1% to 100% by weight of the control releasing coat dry weight. For example, in certain embodiments wherein the control release polymer is EUGRAGIT® NE30D or EUGRAGIT® NE40D (Rohm America LLC) together with a hydrophilic pore former, the lubricant is present in an amount of from 1% to 30% by weight of the control-releasing coat dry weight; in other embodiments from 2% to 20%; and in still other embodiments at 10% by weight of the microparticle control-releasing coat dry weight. In another embodiments where the control-release polymer is ethylcellulose (ETHOCEL™ PR100, PR45, PR20, PR10 or PR7 polymer, or a mixture thereof), the lubricant can be present in an amount of from 10% to 100% by weight of the microparticle control-releasing coat dry weight; in another embodiment from 20% to 80%; and in still another embodiments at 50% by weight of the microparticle control-releasing coat dry weight.

Emulsifying agent(s) (also called emulsifiers or emulgents) can be included in the microparticle control-releasing coat to facilitate actual emulsification during manufacture of the coat, and also to ensure emulsion stability during the shelf-life of the product. Emulsifying agents useful for the microparticle control-releasing coat composition include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from 0.01% to 5% by weight of the microparticle control releasing coat dry weight. For example, in certain embodiments the emulsifying agent is present in an amount of from 0.05% to 3%; in other embodiments from 0.08% to 1.5%, and in still other embodiments at 0.1% by weight of the microparticle control-releasing coat dry weight.

Anti-foaming agent(s) can be included in the microparticle control-releasing coat to reduce frothing or foaming during manufacture of the coat. Anti-foaming agents useful for the coat composition include, but are not limited to simethicone, polyglycol and silicon oil. In at least one embodiment the anti-foaming agent is Simethicone C. The anti-foaming agent can be present in an amount of from 0.1% to 10% of the microparticle control-releasing coat weight. For example, in certain embodiments the anti-foaming agent is present in an amount of from 0.2% to 5%; in other embodiments from 0.3% to 1%, and in still other embodiments at 0.6% by weight of the microparticle control-releasing coat dry weight.

Plasticizer(s) can be included in the microparticle control-releasing coat to modify the properties and characteristics of the polymers used in the coat for convenient processing during manufacturing (e.g. provide increased flexibility and durability during manufacturing). As used herein, the term "plasticizer" includes any compounds capable of plasticizing or softening a polymer or binder used in the present invention. Once the coat has been manufactured, certain plasticizers can function to increase the hydrophilicity of the coat in the environment of use. During manufacture of the coat, the plasticizer can lower the melting temperature or glass transition temperature (softening point temperature) of the polymer or binder. The addition of a plasticizer, such as low molecular weight PEG, generally broadens the average molecular weight of a polymer in which they are included thereby lowering its glass transition temperature or softening point. Plasticizers can also generally reduce the viscosity of a polymer. Non-limiting examples of plasticisers that can be used in the microparticle control-releasing coat include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from 1% to 80% of the control-releasing coat dry weight. For example, in certain embodiments the plasticizer is present in an amount of from 5% to 50%, in other embodiments from 10% to 40%, and in still other embodiments at 20% of the control-releasing coat dry weight.

The control releasing coat can be present in an amount of from 1% to 100% by weight of the microparticle, depending upon the choice of polymer, the ratio of polymer:pore former, and the total surface area of the microparticle formulation. Since a certain thickness of control release coating has to be achieved in order to achieve the desired dissolution profile, the amount of polymer coating required during manufacture is related to the total surface area of the batch of uncoated microparticles that requires a coating. The control releasing polymer surface area coverage can range from 0.5 mg/cm2 to 30 mg/cm2. For example in certain embodiments the surface area coverage of the control-releasing polymer is from 0.6 mg/cm2 to 20 mg/cm2, and in other embodiments from 1 mg/cm2 to 5 mg/cm2. In at least one embodiment of the invention, EUGRAGIT® NE30D is used as the control releasing polymer at a surface area coverage of 10 mg/cm2. One approach to estimate the total surface area of a multiparticulate batch is the permeability method according to Blaine (ASTM Des. C 205-55), which is based upon the mathematical model of laminar flow through capillaries arranged in parallel. In the absence of an accurate determination of total surface area of a microparticle, the amount of control releasing polymer to be applied can be expressed as a percentage of the uncoated microparticle.

The control-releasing polymer can be present in an amount of from 1% to 99% by weight of the coated microparticle, depending on the controlled release profile desired. For example, in certain embodiments the polymer is present in an amount of from 5% to 80%, and in other embodiments from 10% to 50% by weight of the coated microparticle. In at least one embodiment wherein the control-releasing polymer is EUGRAGIT® NE30D, EUGRAGIT® NE40D (Rohm America LLC), KOLLICOAT® SR 30D, or a mixture thereof, the polymer is present in an amount of from 1% to 50%; in other embodiments from 5% to 30%; and in still other embodiments is 15% by weight of the coated microparticle. In at least one embodiment wherein the control-releasing polymer is ethylcellulose, the polymer is present in an amount of from 1% to 99% by weight of the coated microparticle; in other embodiments from 5% to 50%; and in still other embodiments at 20% by weight of the coated microparticle. In at least one embodiment wherein the control-releasing polymer is ETHOCEL™, an ethyl cellulose grade PR100, PR45, PR20, PR10, PR7 polymer, or a mixture thereof, the polymer is present in an amount of from 5% to 30% by weight of the coated microparticle; in other embodiments from 10% to 25%; and in still other embodiments at 20% by weight of the coated microparticle In certain embodiments, the diameter of the microparticles (with or without the control releasing coat) can range from 50 µm to 800 µm. For example, in certain embodiments the diameter of the microparticles range from 100 µm to 600 µm, and in other embodiments from 150 µm to 450 µm.

It is contemplated that in alternative embodiments, other excipients consistent with the objects of the present invention can also be used in the microparticle control-releasing coat.

In at least one embodiment, the microparticle control-releasing coat includes 96% EUGRAGIT® NE30D, 1.9% Magnesium stearate, 1.9% Talc, 0.04% Tween 80, and 0.19% Simethicone C, when expressed as percentage by weight of the dry control-releasing coat composition. In another embodiment, the microparticle control-releasing coat includes 68% ethylcellulose, 17% glyceryl monostearate and 15% acetyl tributylcitrate when expressed as percentage by weight of the dry control-releasing coat composition.

The manufacturing process for the microparticle control-releasing coat can be as follows. Water is split into two portions of 15% and 85%. The anti-foaming agent and the emulsifying agent are then added to the 15% water portion, and mixed at 300 rpm to form portion A. In at least one embodiment, the anti-foaming agent is Simethicone C, and the emulsifying agent is TWEEN™ 80. A first lubricant is then added to the 85% water portion and mixed at 9500 rpm to form portion B. In at least one embodiment, the first lubricant is talc. Then portion A is mixed with portion B, a second lubricant is slowly added, and mixed at 700 rpm overnight. In at least one embodiment, the second lubricant is magnesium stearate. Finally, an aqueous dispersion of a neutral ester copolymer is added and mixed for 30 minutes at 500 rpm. In at least one embodiment, the aqueous dispersion of a neutral ester copolymer is EUGRAGIT® NE30D. The resultant control-releasing coat solution can then be used to coat the microparticles to a 35% weight gain with the following parameters: An inlet temperature of from 10° C. to 60° C., preferably from 20° C. to 40° C., and more preferably from 25° C. to 35° C.; an outlet temperature of from 10° C. to 60° C., preferably from 20° C. to 40° C., and more preferably from 25° C. to 35° C.; a product temperature of from 10° C. to 60° C., preferably from 15° C. to 35° C., and more preferably from 22° C. to 27° C.; an air flow of from 10 c.m/h to 180 c.m/h, preferably from 40 c.m/h to 120 c.m/h, and more preferably from 60 c.m/h to 80 c.m/h;

and an atomizing pressure of from 0.5 bar to 4.5 bar, preferably from 1 bar to 3 bar, and more preferably 2 bar. The resultant control-releasing coated microparticles can then be discharged from the coating chamber and ovencured with the following parameters: A curing temperature of from 20° C. to 65° C., preferably from 30° C. to 55° C., and more preferably 40° C.; and a curing time of from 2 hours to 120 hours, preferably from 10 hours to 40 hours, and more preferably 24 hours. Any other technology resulting in the formulation of the microparticle control-releasing coat consistent with the objects of the invention can also be used.

3.2.4 Microparticle Dosage Forms

Highly useful dosage forms result when microparticles made from compositions containing a bupropion salt, spheronization aids, and other excipient(s) are coated with control-releasing polymer(s). The control-releasing coated microparticles can then be combined with an excipient mass and/or other pharmaceutical excipients, and compressed into tablets. Conventional tablets can be manufactured by compressing the coated microparticles with suitable excipients using known compression techniques. The dissolution profile of the control-releasing coated multiparticles is not substantially affected by the compression of the microparticles into a tablet. The resultant dosage forms enjoy the processing ease associated with the use of excipient masses and the release properties associated with control-releasing coated microparticles. Alternatively, the coated microparticles can be filled into capsules.

The forms of administration according to the invention are suitable for oral administration. In certain embodiments the forms of administration are tablets and capsules. However, the composition of the invention can also take the form of pellets, beads or microtablets, which can then be packaged into capsules or compressed into a unitary solid dosage form. Other solid oral dosage forms as disclosed herein can be prepared by the skilled artisan, despite the fact that such other solid oral dosage forms may be more difficult to commercially manufacture.

The present invention also contemplates combinations of differently coated microparticles into a dosage form to provide a variety of different release profiles. For example, in certain embodiments, microparticles with a delayed release profile can be combined with other microparticles having a sustained release profile to provide a multiple component controlled release bupropion formulation. In addition, other embodiments can include one or more further components of immediate release bupropion. The immediate release bupropion component can take the form of uncoated bupropion microparticles or powders; bupropion microparticles coated with a highly soluble immediate release coating, such as an OPADRY® type coating, as are known to those skilled in the art, or a combination of any of the foregoing. The multiple components can then be blended together in the desired ratio and placed in a capsule, or formed into a tablet. Examples of multiple component controlled release bupropion formulations are described in U.S. Pat. No. 6,905,708.

3.2.5 Dose Sipping Technology

The present invention also contemplates an oral delivery system for delivering microparticles containing bupropion hydrobromide in admixture with a fluid. For example, an oral delivery system is provided which comprises a hollow drug formulation chamber. In at least one embodiment, the chamber has a first end and a second end and contains a formulation in the form of microparticles. In at least one embodiment, the drug formulation comprises bupropion hydrobromide. The system further comprises a fluid passing drug formulation retainer in the first end of the chamber. The retainer prevents release of the microparticles from the first end while permitting fluid entry into the chamber. In other embodiments, the microparticles contained within the chamber comprise bupropion hydrobromide and at least one other drug.

The present invention further provides a method for orally delivering microparticles containing bupropion hydrobromide formulation in admixture with a fluid. The method involves inserting microparticles of bupropion hydrobromide formulation into a hollow drug delivery chamber of a drug delivery device. The chamber has a first end and a second end. The first end of the chamber has a fluid passing drug formulation retainer. The drug delivery device has a first and second end. The first end of the drug delivering device is inserted into a fluid and the second end is inserted into the mouth of a patient. The patient then applies suction to the second end of the device to cause delivery of the fluid and microparticles of bupropion hydrobromide formulation into the patient's mouth.

The term "drug formulation retainer" as used herein, refers to a valve, plug or restriction, or the like that prevents passage of the drug formulation from the device. By "fluid passing drug formulation retainer" is intended a valve, plug or restriction or the like that allows for passage of fluids but does not allow for passage of other ingredients such as the drug formulation that is contained in the delivery device.

The dispensing device of this embodiment of the invention finds use where it is inconvenient or unsafe to use solid oral dosage forms such as capsules or tablets. The devices can be particularly useful in geriatric or pediatric patient populations but they can also be useful for those who have difficulty swallowing capsules or tablets. A single delivery device or several devices can be administered to a patient during a therapeutic program.

Generally the device is in prepared form prior to placement in a fluid. In at least one embodiment the dispensing device comprises a hollow drug formulation chamber with a first end and a second end. Contained within the chamber are drug formulation and fluid passing drug formulation retainers. The fluid passing drug formulation retainer comprises a restriction and a one-way plug. The diameter of the opening is smaller than the plug. In at least one embodiment the restriction is made by crimping an end of the chamber. The second end of the chamber has a drug formulation retainer for preventing release of the plug. In at least one embodiment the retainer is prepared by crimping the end of the chamber. Microparticles of bupropion hydrobromide are then placed in the chamber. An end-cap is placed over the second end of the chamber prior to use to prevent release of the drug formulation. In prepared form, the plug substantially seals the first end of the chamber, thereby preventing loss of the drug formulation from the first end.

The device can be formed from any suitable material that is physically and/or chemically compatible with both the active drug and the liquid diluent to be mixed therein. In certain embodiments, representative materials for forming devices including the drug formulation chamber, the elongated tubular member, the end caps and tabs, include, without limitation, paper, plastic such as propylene/styrene copolymers, polyproylene, high density polyethylene, low density polyethylene and the like. The devices can have an inner diameter of between 3 mm and 8 mm and a wall thickness of between 0.1 mm and 0.4 mm. The devices can be between 10 cm and 30 cm in length.

The fluid passing drug formulation retainer permits the free flow of liquid medium but prohibits passage of the drug formulation from the device prior to delivery. Where the retainer comprises a one-way plug or valve, the plug or valve will seal the straw at atmospheric pressure. When suction is applied, fluid will be drawn around the plug and into the drug formulation chamber. Further, the plug has a density of less than one so that it will ascend to the top as the drug formulation is delivered into the oral cavity. When suction is no longer applied, the plug will remain in the highest position it reached during sipping. The plug can be prepared from closed cell polyethylene foam such as ETHAFOAM®. Other forms of one way plugs can be a balloon of elastomeric material, a one-way mechanical ball valve and the like.

Examples of fluid that can be used for suspending the drug formulation by sipping through the drug formulation chamber include any palatable liquid such as water, juice, milk, soda, coffee, tea etc. Care must be taken to ensure compatibility of the fluid with the drug formulation.

In at least one embodiment, a dose sipping delivery device according to the present invention can be prepared as follows. Jumbo size straws with an inside diameter of 0.21 inches and a length of 8 inches are heat sealed at one end. The seal is partially cut off so that the "one-way" plug cannot escape. The partially sealed end is enclosed by half of a size 1 hard gelatin capsule. Microparticles are then placed inside the open end of the straw. A "one-way" plug made of closed cell polyethylene foam, MICROFOAM® (DuPont) is trimmed to snugly fit inside the straw. The plug is then placed inside the straw, on top of the microparticles. During operation, the plug end of the straw is placed into a glass of water and the protective gelatin capsule on the top of the straw is removed. By slowly applying suction through the partially sealed end of the straw, the microparticles are sucked into the mouth and easily swallowed.

Osmotic Dosage Forms

Osmotic dosage forms, osmotic delivery devices, modified release osmotic dosage forms, or osmosis-controlled extended-release systems are terms used interchangeably herein and are defined to mean dosage forms which forcibly dispense the bupropion salt by pressure created by osmosis or by osmosis and diffusion of fluid into a material which expands and forces the bupropion salt to be dispensed from the osmotic dosage form. Osmosis can be defined as the flow of solvent from a compartment with a low concentration of solute to a compartment with a high concentration of solute. The two compartments are separated by a membrane, wall, or coat, which allows flow of solvent (a liquid, aqueous media, or biological fluids) but not the solute. Examples of such membranes can for example be, a semipermeable membrane, microporous, asymmetric membrane, which asymmetric membrane can be permeable, semipermeable, perforated, or unperforated and can deliver the bupropion salt by osmotic pumping, diffusion or the combined mechanisms of diffusion and osmotic pumping. Thus, in principle, osmosis controlled release of the bupropion salt involves osmotic transport of an aqueous media into the osmotic dosage form followed by dissolution of the bupropion salt and the subsequent transport of the saturated solution of the bupropion salt by osmotic pumping of the solution through at least one passageway in the semipermeable membrane or by a combination of osmosis and diffusion through the semipermeable membrane.

It is well known to one of ordinary skill in the art that the desired in-vitro release rate and the in-vivo pharmacokinetic parameters can be influenced by several factors, such as for example, the amount of the bupropion salt used to form the core, the amount of pharmaceutically acceptable excipient used to form the core, the type of pharmaceutically acceptable excipient used to form the core, the amount or type of any other materials used to form the core such as, for example, osmagents (the term osmagent, osmotically effective solutes, osmotically effective compound and osmotic agents are used interchangeably herein) osmopolymers, and any combination thereof. The release profile can also be influenced by the material used to form the semipermeable membrane covering the core or by the material used to form any coating, such as a control-releasing coating (e.g. a release slowing-coat) on the semipermeable membrane. With these factors in mind, an osmotic device can therefore be designed to exhibit an in-vitro release rate such that in certain embodiments, after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released, when measured for example by using a USP Type 1 apparatus (Rotating Basket Method) in 900 ml water, 0.1N HCl, 0.1N HCl+0.1% Cetrimide, USP Buffer pH 1.5, Acetate Buffer pH 4.5, Phosphate Buffer, pH 6.5 or Phosphate Buffer pH 7.4 at 75 rpm at 37° C.±0.5° C. Alternatively dissolution may be effected in USP-3 media such as SGF pH 1.2, Acetate Buffer at pH 4.5 or phosphate buffer at pH 6.8.

Osmotic devices also may be designed to achieve an in vitro release of no more than 40% after 2 hours, 40-75% release after 4 hours, at least 75% after 8 hours, and at least 85% after 16 hours when assayed using a dissolution medium such as identified above or known in the art.

In certain embodiments of the present invention, an osmotic dosage form is provided having a core comprising the bupropion salt and one or more excipients. In at least one embodiment the osmotic dosage form comprises an osmagent. The osmotic delivery system for example, can be in the form of a tablet or capsule containing microparticles.

In certain embodiments, the core of the osmotic dosage form comprises a water swellable polymer, non-limiting examples of which include hydroxypropyl cellulose, alkylcellulose, hydroxyalkylcellulose, polyalkylene oxide, polyethylene oxide, and mixtures thereof. A binder can be included in the core of certain embodiments of the osmotic dosage form to increase the core's mechanical strength. Non-limiting examples of binders include polyvinyl pyrollidine, carboxyvinyl polymer, methylcellulose, hydroxyethylcellulose, hydroxypropylcellulose, hydroxypropylmethylcellulose, a low molecular weight polyethylene oxide polymer, hydroxypropylmethylcellulose, dextrin, maltodextrin, gelatin, polyvinyl alcohol, xanthan gum, carbomers, caragheen, starch derivatives, and mixtures thereof. Lubricants can be included in certain embodiments of the osmotic dosage form to provide decreased friction between the solid and die wall during tablet manufacturing. Non-limiting examples of lubricants include stearic acid, magnesium stearate, glyceryl behenate, talc, mineral oil, sodium stearyl fumarate, hydrogenated vegetable oil, sodium benzoate, calcium stearate, and mixtures thereof. In other embodiments, additional inert excipients consistent with the objects of the invention can also be included in the core of the osmotic dosage form to facilitate the preparation and/or improve patient acceptability of the final osmotic dosage form as described herein. Suitable inert excipients are well known to the skilled artisan and can be found in the relevant literature, for example in the Handbook of Pharmaceutical Excipients (Rowe et. al., 4th Ed., Pharmaceutical Press, 2003).

In at least one embodiment, the present invention comprises a modified release osmotic dosage form comprising bupropion hydrobromide present in a therapeutically effective amount which releases the bupropion hydrobromide by forcibly dispensing the bupropion hydrobromide from a core via a semipermeable membrane by diffusion and/or at least one passageway in the membrane by osmotic pumping (i) all or in part by pressure created in the core by osmosis i.e., positive hydrostatic pressure of a liquid, solvent, biological fluid or aqueous media and/or all or in part by the expansion of a swellable material which forces the bupropion hydrobromide to be dispensed from the core of the dosage form, and (ii) is formulated such that the dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released.

In at least one embodiment, the modified release dosage form comprises an osmotic delivery device comprising a homogenous solid core comprising substantially the bupropion salt present in a therapeutically effective amount with at least one pharmaceutically acceptable excipient, said core surrounded by a semipermeable membrane which permits entry of an aqueous liquid into the core and delivery of the bupropion salt from the core to the exterior of the dosage form through at least one passageway or by a combination of osmosis and diffusion such that the dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released, or after 2 hours no more than 40% is released, after 4 hours 40-75% is released, after 8 hours at least 75% is released and after 16 hours at least 85% is released.

In at least one embodiment, the modified release dosage form comprises a multiparticulate dosage form, each microparticle comprising an osmotic delivery device, each microparticle comprising a homogenous solid core comprising substantially the bupropion salt with at least one pharmaceutically acceptable excipient, said core of each microparticle surrounded by a semipermeable membrane which permits entry of an aqueous liquid into the core and delivery of the bupropion salt from the core to the exterior of the dosage form through a plurality of pores formed in the semipermeable membrane by inclusion of a pore forming agent in the membrane or by a combination of osmosis and diffusion so as to allow communication of the core with the outside of the device for delivery of the bupropion salt and is formulated such that the dosage form comprises a therapeutically effective amount of the bupropion salt and exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or after 2 hours no more than 40% is released, after 4 hours from 40-75% is released, after 8 hours at least 75% is released and after 16 hours at least 85% is released.

In at least one embodiment, the modified release dosage form comprises a multiparticulate dosage form, each microparticle comprising an osmotic delivery device, each microparticle comprising a homogenous solid core comprising substantially the bupropion salt in admixture with at least one pharmaceutically acceptable excipient, an osmagent and/or an osmopolymer, said core of each microparticle surrounded by a semipermeable membrane which permits entry of an aqueous liquid into the core and delivery of the bupropion salt from the core to the exterior of the dosage form through a plurality of pores formed in the semipermeable membrane by inclusion of a pore forming agent in the membrane or by a combination of osmosis and by diffusion so as to allow communication of the core with the outside of the device for delivery of the bupropion salt and is formulated such that the dosage form comprises a therapeutically effective amount of the bupropion salt and exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or after 2 hours no more than 40% is released, after 4 hours from 40-75% is released, after 8 hours at least 75% is released and after 16 hours at least 85% is released.

In at least one embodiment, the modified release dosage form comprises a multiparticulate dosage form, each microparticle comprising a homogenous solid core comprising substantially the bupropion salt with at least one pharmaceutically acceptable excipient in admixture with an osmagent, and/or an osmopolymer, and/or an absorption enhancer, said microparticles compressed into a tablet together with at least one pharmaceutically acceptable excipient, said tablet surrounded by a semipermeable membrane which permits entry of an aqueous liquid into the core and delivery of the bupropion salt from the tablet interior to the exterior of the dosage form through at least one passageway in the semipermeable membrane and/or by diffusion through the semipermeable membrane so as to allow communication of the tablet interior with the exterior of the tablet for delivery of the bupropion salt and is formulated such that the dosage form comprises a therapeutically effective amount of the bupropion salt and exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or after 2 hours no more than 40% is released, after 4 hours from 40-75% is released, after 8 hours at least 75% is released and after 16 hours at least 85% is released.

In at least one embodiment, the modified release dosage form comprises a multiparticulate dosage form, each microparticle comprising a sugar sphere or nonpareil bead coated with at least one layer comprising substantially the bupropion salt with at least one pharmaceutically acceptable excipient, said at least one layer surrounded by a semipermeable membrane which permits entry of an aqueous liquid into the layer and delivery of the bupropion salt from the layer to the exterior of the dosage form through a plurality of pores formed in the semipermeable membrane by inclusion of a pore forming agent in the membrane and/or by diffusion so as to allow communication of the core with the outside of the device for delivery of the bupropion salt and is formulated such that the dosage form comprises a therapeutically effective amount of the bupropion salt and exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or after 2 hours no more than 40% is released, after 4 hours from 40-75% is released, after 8 hours at least 75% is released and after 16 hours at least 85% is released.

In at least one embodiment, the modified release dosage form comprises a multiparticulate dosage form, each microparticle comprising a sugar sphere or nonpareil bead coated with at least one layer comprising substantially the bupropion salt in admixture with at least one pharmaceutically acceptable excipient, an osmagent and/or an osmopolymer, said at least one layer surrounded by a semipermeable membrane which permits entry of an aqueous liquid into the layer and delivery of the bupropion salt from the layer to the exterior of the dosage form through a plurality of pores formed in the semipermeable membrane by inclusion of a pore forming agent in the membrane and/or by diffusion so as to allow communication of the core with the outside of the device for delivery of the bupropion salt and is formulated such that the dosage form comprises a therapeutically effective amount of the bupropion salt and exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or after 2 hours no more than 40% is released, after 4 hours from 40-75% is released, after 8 hours at least 75% is released and after 16 hours at least 85% is released.

In at least one embodiment, the modified release dosage form comprises a modified release osmotic dosage form comprising a homogenous core comprising a therapeutically effective amount of the bupropion salt in admixture with an osmagent, and/or an osmopolymer, and/or and absorption enhancer, said core surrounded by a nontoxic wall, membrane or coat, such as for example a semipermeable membrane which permits entry of an aqueous liquid into the core and delivery of the bupropion salt from the core to the exterior of the dosage form through at least one passageway in the semipermeable membrane and/or by diffusion through the membrane so as to allow communication of the core with the outside of the dosage form for delivery of the bupropion salt and is formulated such that the dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or after 2 hours no more than 40% is released, after 4 hours from 40-75% is released, after 8 hours at least 75% is released and after 16 hours at least 85% is released.

In at least one embodiment the modified release dosage form comprises an osmotic delivery device comprising the bupropion salt present in a therapeutically effective amount in a layered, contacting arrangement with a swellable material composition to yield a solid core with two or more layers, which core is surrounded by a nontoxic wall, membrane or coat, such as for example a semipermeable membrane which permits entry of an aqueous liquid into the core and delivery of the bupropion salt from the core to the exterior of the dosage form through at least one passageway in the semipermeable membrane or by osmosis and diffusion through the membrane so as to allow communication of the core with the outside of the dosage form for delivery of the bupropion salt and is formulated such that the dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released; or a device wherein after 2 hours no more than 40% is released, after 4 hours 40-75% is released, after 8 hours at least 75% is released and after 16 hours at least 85% is released.

In at least one embodiment, the modified release dosage form comprises an osmotic delivery device comprising a core and a membrane surrounding said core, said core comprising a therapeutically effective amount of the bupropion salt, and optionally at least one means for forcibly dispensing the bupropion salt from the device, said membrane comprising at least one means for the exit of the bupropion salt from the device, said device formulated such that when the device is in an aqueous medium, the bupropion salt, and optionally the at least one means for forcibly dispensing the bupropion salt from the device and the at least one means for the exit of the bupropion salt from the device cooperatively function to exhibit an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released; or a device wherein after 2 hours no more than 40% is released, after 4 hours from 40-75% is released, after 8 hours at least 75% is released and after 16 hours at least 85% is released.

In at least one embodiment, the modified release dosage form comprises an osmotic delivery device comprising a core and a membrane surrounding said core, said core comprising a therapeutically effective amount of the bupropion salt, at least one means for increasing the hydrostatic pressure inside the membrane and optionally at least one means for forcibly dispensing the bupropion salt from the device, said membrane comprising at least one means for the exit of the bupropion salt from the device, said device formulated such that when the device is in an aqueous medium, the at least one means for increasing the hydrostatic pressure inside the membrane, and optionally the at least one means for forcibly dispensing the bupropion salt from the device and the at least one means for the exit of the bupropion salt cooperatively function to exhibit an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released; or a device wherein after 2 hours no more than 40% is released, after 4 hours from 40-75% is released, after 8 hours at least 75% is released and after 16 hours at least 85% is released.

In at least one embodiment the invention is directed to once-a-day bupropion hydrobromide sustained release formulations that is bioequivalent according to FDA guidelines to WELLBUTRIN™ ER or ZYBAN™/WELLBUTRIN™ SR when administered once-daily to a subject in need thereof and wherein the bupropion salt contained is more stable than the bupropion hydrochloride salt contained in Wellbutrin ER or Zyban when stored at 40 degrees C. and 75% relative humidity for at least 3, 4 5 and/or at least 6 months. Particularly, the invention encompasses bioequivalent 150 mg, 174 mg, 300 mg or 348 mg bupropion HBr containing formulations.

In at least one embodiment the invention is directed to topical formulations containing bupropion hydrobromide that may be administered topically, e.g., transmucosally or transdermally. Particularly, the invention embraces topically administrable gels and patch type delivery devices which potentially may comprise another active agent such as nicotine.

In at least one embodiment the invention is directed to inhalable pulmonary deliverable compositions containing bupropion hydrobromide that may be administered via pulmonary delivery to a subject in need thereof. Preferably, these compositions are produced according to the aerosol technology disclosed in U.S. Pat. Nos. 6,682,716; 6,716,415; 6,716,417; 6,783,753; 7,029,658; and 7,033,575 and others assigned to Alexza Corporation. These patents in particular disclose the use of such methods in producing aerosols containing anti-depressants for pulmonary delivery.

In at least one embodiment the invention is directed to injectable compositions comprising an effective amount of bupropion hydrobromide and a pharmaceutically acceptable carrier or excipient.

In at least one embodiment, the invention is directed to a method of treating a condition comprising administering any one of the above described osmotic dosage forms to a patient in need of such administration once-daily.

The invention, in at least one embodiment, is directed to a method for administering a bupropion salt to the gastrointestinal tract of a human for the treatment or management of a condition, wherein the method comprises: (a) admitting orally into the human a modified release dosage form comprising a bupropion salt, the modified release dosage form comprising an osmotic dosage form; and (b) administering the bupropion salt from the osmotic dosage form in a therapeutically responsive dose to produce the treatment or management of the condition such that the osmotic dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released; or a dosage form wherein after 2 hours no more than 40% is released, after 4 hours from 40-75% is released, after 8 hours at least 75% is released and after 16 hours at least 85% is released.

The invention, in at least one embodiment, is directed to a method for administering a bupropion salt to the gastrointestinal tract of a human for the treatment or management of a condition, wherein the method comprises: (a) admitting orally into the human a modified release dosage form comprising a core and a membrane surrounding said core, said core comprising the bupropion salt and optionally a means for forcibly dispensing the bupropion salt from the device, said membrane comprising at least one means for the exit of the bupropion salt from the dosage form, and (b) administering the bupropion salt from the dosage form which is formulated such that when the dosage form is in an aqueous medium, the bupropion salt and optionally the means for forcibly dispensing the bupropion salt and the at least one means for the exit of the bupropion salt cooperatively function to exhibit an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released; or a medicament wherein after 2 hours no more than 40% is released, after 4 hours from 40-75% is released, after 8 hours at least 75% is released and after 16 hours at least 85% is released.

The invention, in at least one embodiment, is directed to a method for administering a bupropion salt to the gastrointestinal tract of a human for the treatment or management of a condition, wherein the method comprises: (a) admitting orally into the human a modified release dosage form comprising a core and a membrane surrounding said core, said core comprising the bupropion salt, a means for increasing the hydrostatic pressure within the core and optionally a means for forcibly dispensing the bupropion salt from the device, said membrane comprising at least one means for the exit of the bupropion salt from the dosage form, and (b) administering the bupropion salt from the dosage form which is formulated such that when the dosage form is in an aqueous medium, the bupropion salt, the means for increasing the hydrostatic pressure within the core and optionally the means for forcibly dispensing the bupropion salt and the at least one means for the exit of the bupropion salt cooperatively function to exhibit an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released, or a device wherein after 2 hours no more than 40% is released, after 4 hours from 40-75% is released, after 8 hours at least 75% is released and after 16 hours at least 85% is released.

In at least one other embodiment, the osmotic dosage form further comprises an immediate release coat for the immediate release of the bupropion salt from the immediate release coat. In embodiments comprising the immediate release coat, the osmotic dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or a dosage form wherein after 2 hours no more than 40% is released, after 4 hours from 40-75% is released, after 8 hours at least 75% is released or after 16 hours at least 85% is released.

In at least one other embodiment, the osmotic dosage forms further comprise an inert water-soluble coat covering the semipermeable membrane or coat. This inert water-soluble coat can be impermeable in a first external fluid, while being soluble in a second external fluid. In embodiments comprising the inert water-soluble coat, the osmotic dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or a dosage form wherein after 2 hours no more than 40% is released, after 4 hours from 40-75% is released, after 8 hours at least 75% is released and after 16 hours at least 85% is released.

In at least one other embodiment, the osmotic dosage forms further comprise an osmotic subcoat. In embodiments comprising the osmotic subcoat, the osmotic dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or a dosage form wherein after 2 hours no more than 40% is released, after 4 hours from 40-75% is released, after 8 hours at least 75% is released and after 16 hours at least 85% is released.

In at least one other embodiment, the osmotic dosage forms further comprise a control-releasing coat. The control-releasing coat of the osmotic dosage form can, for example, control, extend, and/or delay the release of the bupropion salt. In embodiments comprising the control-releasing coat, the osmotic dosage form exhibits an in-vitro release rate such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released or a dosage form wherein after 2 hours no more than 40% is released, after 4 hours from 40-75% is released, after 8 hours at least 75% is released and after 16 hours at least 85% is released.

In at least one other embodiment, the control-releasing coat of the osmotic dosage form comprises a material that is soluble or erodible in intestinal juices, substantially pH neutral or basic fluids of fluids having a pH higher than gastric fluid, but for the most part insoluble in gastric juices or acidic fluids.

In at least one embodiment, the control-releasing coat of the osmotic dosage form comprises at least one water-insoluble water-permeable film-forming polymer and at least one water-soluble polymer.

In at least one embodiment, the control-releasing coat of the osmotic dosage form comprises at least one water-insoluble water-permeable film-forming polymer and at least one water-soluble polymer and optionally at least one plasticizer.

In at least one embodiment, the control-releasing coat of the osmotic dosage form comprises at least one water-insoluble water-permeable film-forming polymer, at least one water-soluble polymer and at least one means for the exit of the bupropion salt from the core of the osmotic dosage form.

In at least one embodiment, the control-releasing coat of the osmotic dosage form comprises at least one water-insoluble water-permeable film-forming polymer, at least one water-soluble polymer and at least one passageway.

In at least one embodiment, the control-releasing coat of the osmotic dosage form comprises at least one water-insoluble water-permeable film-forming polymer, at least one water-soluble polymer and at least one plasticizer.

In at least one embodiment, the control-releasing coat of the osmotic dosage form comprises at least one water-insoluble water-permeable film-forming polymer, at least one water-soluble polymer, optionally at least one plasticizer, and at least one means for the exit of the bupropion salt from the core of the osmotic dosage form.

In at least one embodiment, the control-releasing coat of the osmotic dosage form comprises at least one water-insoluble water-permeable film-forming polymer, at least one water-soluble polymer, optionally at least one plasticizer, and at least one passageway.

In at least one embodiment, the control-releasing coat of the osmotic dosage form comprises an aqueous dispersion of a neutral ester copolymer without any functional groups; a poly glycol having a melting point greater than 55° C., one or more pharmaceutically acceptable excipients, and optionally at least one means for the exit of the bupropion salt form the core of the osmotic dosage form. This control-releasing coat is cured at a temperature at least equal to or greater than the melting point of the polyglycol.

In at least one other embodiment, the control-releasing coat of the osmotic dosage form comprises at least one enteric polymer.

The membrane or wall is permeable to the passage of aqueous media but not to the passage of the bupropion salt present in the core. The membrane can be, for example, a semipermeable membrane or an asymmetric membrane, which can be permeable, semipermeable, perforated, or unperforated and can deliver the bupropion salt by osmotic pumping, or the combined mechanisms of diffusion and osmotic pumping. The structural integrity of such membranes should remain substantially intact during the period of delivery of the bupropion salt. By "substantially intact" it is meant that the semipermeable property of the membrane is not compromised during the period of delivery of the bupropion salt.

The semipermeable membrane of the osmotic dosage form comprises at least one pharmaceutically acceptable excipient, at least one polymer, wax, or combination thereof, although appropriately treated inorganic materials such as ceramics, metals or glasses can be used. When the semipermeable membrane comprises at least one polymer, the molecular weight of the at least one polymer or combination of polymers should be such that the polymer or combination of polymers is solid at the temperature of use i.e., both in-vitro and in-vivo.

In certain embodiments, the at least one polymer included in the semipermeable membrane of the osmotic dosage form can be a cellulose ester, such as for example, cellulose acetate, cellulose acetate acetoacetate, cellulose acetate benzoate, cellulose acetate butylsulfonate, cellulose acetate butyrate, cellulose acetate butyrate sulfate, cellulose acetate butyrate valerate. cellulose acetate caprate, cellulose acetate caproate, cellulose acetate caprylate, cellulose acetate carboxymethoxypropionate, cellulose acetate chloroacetate, cellulose acetate dimethaminoacetate, cellulose acetate dimethylaminoacetate, cellulose acetate dimethylsulfamate, cellulose acetate dipalmitate, cellulose acetate dipropylsulfamate, cellulose acetate ethoxyacetate, cellulose acetate ethyl carbamate, cellulose acetate ethyl carbonate, cellulose acetate ethyl oxalate. cellulose acetate furoate, cellulose acetate heptanoate, cellulose acetate heptylate, cellulose acetate isobutyrate, cellulose acetate laurate, cellulose acetate methacrylate, cellulose acetate methoxyacetate, cellulose acetate methylcarbamate, cellulose acetate methylsulfonate, cellulose acetate myristate, cellulose acetate octanoate, cellulose acetate palmitate, cellulose acetate phthalate, cellulose acetate propionate, cellulose acetate propionate sulfate, cellulose acetate propionate valerate, cellulose acetate p-toluene sulfonate, cellulose acetate succinate, cellulose acetate sulfate, cellulose acetate trimellitate, cellulose acetate tripropionate, cellulose acetate valerate, cellulose benzoate, cellulose butyrate napthylate, cellulose butyrate, cellulose chlorobenzoate, cellulose cyanoacetates, cellulose dicaprylate, cellulose dioctanoate, cellulose dipentanate, cellulose dipentanlate, cellulose formate, cellulose methacrylates, cellulose methoxybenzoate, cellulose nitrate, cellulose nitrobenzoate, cellulose phosphate (sodium salt), cellulose phosphinates, cellulose phosphites, cellulose phosphonates, cellulose propionate, cellulose propionate crotonate, cellulose propionate isobutyrate, cellulose propionate succinate, cellulose stearate, cellulose sulfate (sodium salt), cellulose triacetate, cellulose tricaprylate, cellulose triformate, cellulose triheptanoate, cellulose triheptylate, cellulose trilaurate, cellulose trimyristate, cellulose trinitrate, cellulose trioctanoate, cellulose tripalmitate, cellulose tripropionate, cellulose trisuccinate, cellulose trivalerate, cellulose valerate palmitate; a cellulose ether, such as for example, 2-cyanoethyl cellulose, 2-hydroxybutyl methyl cellulose, 2-hydroxyethyl cellulose, 2-hydroxyethyl ethyl cellulose, 2-hydroxyethyl methyl cellulose, 2-hydroxypropyl cellulose, 2-hydroxypropyl methyl cellulose, dimethoxyethyl cellulose acetate, ethyl 2-hydroxylethyl cellulose, ethyl cellulose, ethyl cellulose sulfate, ethylcellulose dimethylsulfamate, methyl cellulose, methyl cellulose acetate, methylcyanoethyl cellulose, sodium carboxymethyl 2-hydroxyethyl cellulose, sodium carboxymethyl cellulose; a polysulfone, such as for example, polyethersulfones; a polycarbonate; a polyurethane; a polyvinyl acetate; a polyvinyl alcohol; a polyester; a polyalkene such as polyethylene, ethylene vinyl alcohol copolymer, polypropylene, poly (1,2-dimethyl-1-butenylene), poly(1-bromo-1-butenylene), poly(1, butene), poly(1-chloro-1-butenylene), poly(1-decyl-1-butenylene), poly(1-hexane), poly(1-isopropyl-1-butenylene), poly(1-pentene), poly(3-vinylpyrene), poly(4-methoxyl 1-butenylene), poly(ethylene-co-methyl styrene), poly vinyl-chloride, poly(ethylene-co-tetrafluoroethylene), poly(ethylene-terephthalate), poly(dodecafluorobutoxylethylene), poly(hexafluoroprolylene), poly(hexyloxyethylene), poly(isobutene), poly(isobutene-co-isoprene), poly(isoprene), poly-butadiene, poly[(pentafluoroethyl)ethylene], poly[2-ethylhexyloxy)ethylene], poly(butylethylene), poly (tertbutylethylene), poly(cylclohexylethylene), poly[(cyclohexylmethyl)ethylene], poly(cyclopentylethylene), poly(decylethylene), poly-(dodecy-lethylene), poly (neopentylethylene), poly(propylethylene); a polystyrene, such as for example, poly(2,4-dimethyl styrene), poly(3-methyl styrene), poly(4-methoxystyrene), poly(4-methoxystyrene-stat-styrene), poly(4-methyl styrene), poly(isopentyl styrene), poly(isopropyl styrene), polyvinyl esters or polyvinyl ethers, such as form example, poly(benzoylethylene), poly(butoxyethylene), poly(chloroprene), poly(cyclohexloxyethylene), poly(decyloxyethylene), poly(dichloroethylene), poly(difluoroethylene), poly(vinyl acetate), poly(vinyltrimethyllstyrene); a polysiloxane, such as for example, poly(dimethylsiloxane); a polyacrylic acid derivative, such as for example, polyacrylates, polymethyl methacrylate, poly(acrylic acid) higher alkyl esters, poly(ethylmethacrylate), poly(hexadecyl methacrylate-co-methylmethacrylate), poly-(methylacrylate-co-styrene), poly(n-butyl methacrylate), poly(n-butyl-acrylate), poly (cyclododecyl acrylate), poly(benzyl acrylate), poly(butylacrylate), poly(secbutylacrylate), poly(hexyl acrylate), poly(octyl acrylate), poly (decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins; a polyamide, such as for example, poly(iminoadipoyliminododecamethylene), poly(iminoadipoyliminohexamethylene), polyethers, such as for example, poly(octyloxyethylene), poly(oxyphenylethylene), poly(oxypropylene), poly (pentyloxyethylene), poly(phenoxy styrene), poly (secbutroxylethylene), poly(tert-butoxyethylene); and combinations thereof.

In at least one embodiment, the at least one wax included in the semipermeable membrane of the osmotic dosage form can be, for example, insect and animal waxes, such as for example, chinese insect wax, beeswax, spermaceti, fats and wool wax; vegetable waxes, such as for example, bamboo leaf wax, candelilla wax, carnauba wax, Japan wax, ouricury wax, Jojoba wax, bayberry wax, Douglas-Fir wax, cotton wax, cranberry wax, cape berry wax, rice-bran wax, castor wax, indian corn wax, hydrogenated vegetable oils (e.g., castor, palm, cottonseed, soybean), sorghum grain wax, Spanish moss wax, sugarcane wax, caranda wax, bleached wax, Esparto wax, flax wax, Madagascar wax, orange peel wax, shellac wax, sisal hemp wax and rice wax; mineral waxes, such as for example, Montan wax, peat waxes, petroleum wax, petroleum ceresin, ozokerite wax, microcrystalline wax and paraffins; synthetic waxes, such as for example, polyethylene wax, Fischer-Tropsch wax, chemically modified hydrocarbon waxes, cetyl esters wax; and combinations thereof.

In at least one embodiment, the semipermeable membrane of the osmotic dosage form can comprise a combination of at least one polymer, wax, or combinations thereof and optionally at least one excipient. The total weight percent of all components comprising the semipermeable membrane is 100%.

In embodiments where the bupropion salt is released through the membrane or wall in a controlled manner by the combined mechanisms of diffusion and osmotic pumping, the membrane or wall can comprise at least one of the above described polymers and/or waxes or a combination of polymers, such as for example, cellulose esters, copolymers of methacrylate salts and optionally a plasticizer.

The poly(methacrylate) copolymer salts used in the manufacturing of the membrane for the osmotic dosage form can be, for example, insoluble in water and in digestive fluids, but are permeable to different degrees. Examples of such copolymers are poly(ammonium methacrylate) copolymer RL (EUDRAGIT®RL), poly(ammonium methacrylate) copolymer (type A-USP/NF), poly(aminoalkyl methacrylate) copolymer RL-JSP I), and (ethyl acrylate)-(methyl methacrylate) -[(trimethylammonium)-ethyl methacrylate] (1:2:0.2) copolymer, MW 150,000. Other examples of such copolymers include those available from Rohm Pharma, Weiterstadt, such as for example, EUDRAGIT®RS 100: solid polymer. EUDRAGIT®RL 12.5:12.5% solution in solvent, EUDRAGIT®RL 30 D: 30% aqueous dispersion, and other equivalent products. The following poly (ammonium methacrylate) copolymers can also be used: ammonium methacrylate copolymer RS (EUDRAGIT®RS), poly (ammonium methacrylate) copolymer (type B-USP/NF), poly(aminoalkyl methacrylate) copolymer (RSL-JSP I), (ethyl acrylate)-(methyl methacrylate)-[(trimethylammonium)-ethyl methacrylate] (1:2:0.1) copolymer, PM 150, 000. Specific polymers include (Rohm Pharma, Weiterstadt): EUDRAGIT®RS 100: solid polymer, EUDRAGIT®RS 12.5: 12.5% solution in solvent, EUDRAGIT®RS 30 D: 30% aqueous dispersion and other equivalent products. RL is readily water permeable while EUDRAGIT®RS is hardly water permeable. By employing mixtures of both EUDRAGIT®RL and EUDRAGIT®RS, membranes having the desired degree of permeability to achieve the in-vitro dissolution rates and in-vivo pharmacokinetic parameters can be prepared.

The use of plasticizers is optional but can be included in the osmotic dosage forms to modify the properties and characteristics of the polymers used in the coats or core of the osmotic dosage forms for convenient processing during manufacture of the coats and/or the core of the osmotic dosage forms if necessary. As used herein, the term "plasticizer" includes any compounds capable of plasticizing or softening a polymer or binder used in invention. Once the coat or membrane has been manufactured, certain plasticizers can function to increase the hydrophilicity of the coat(s) and/or the core of the osmotic dosage form in the environment of use. During manufacture of the coat, the plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also can reduce the viscosity of a polymer. The plasticizer can impart some particularly advantageous physical properties to the osmotic device of the invention.

Plasticizers useful in the osmotic dosage form of the invention can include, for example, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol, glycerin, ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers can be used in the present formulation. The PEG based plasticizers are available commercially or can be made by a variety of methods, such as disclosed in Poly(ethylene glycol) Chemistry: Biotechnical and Biomedical Applications (J. M. Harris, Ed.; Plenum Press, NY). Once the osmotic dosage form is manufactured, certain plasticizers can function to increase the hydrophilicity of the coat(s) and/or the core of the osmotic dosage form in the environment of use may it be in-vitro or in-vivo. Accordingly, certain plasticizers can function as flux enhancers.

The ratio of cellulose esters:copolymers of methacrylate salts:plasticizer of the osmotic dosage forms can be, for example, from 1-99% of the cellulose ester by weight: 84-0.5% of the copolymers of methacrylate salt by weight: 15-0.5% of the plasticizer by weight. The total weight percent of all components comprising the wall is 100%.

Aside from the semipermeable membranes of the osmotic dosage form described above, asymmetric membranes can also be used to surround the core of an osmotic dosage form for the controlled release of the bupropion salt to provide the in-vitro release rates described above and the therapeutically beneficial in-vivo pharmacokinetic parameters for the treatment or management of a condition. Such asymmetric membranes can be permeable, semipermeable, perforated, or unperforated and can deliver the bupropion salt by osmotic pumping, diffusion or the combined mechanisms of diffusion and osmotic pumping. The reader is referred to U.S. Pat. No. 5,612,059 for the manufacture and use thereof of asymmetric membranes for the controlled-release of an active through one or more asymmetric membranes by osmosis or by a combination of diffusion osmotic pumping.

In certain embodiments of the osmotic dosage form, the semipermeable membrane can further comprise a flux enhancing, or channeling agent.

"Flux enhancing agents" or "channeling agents" are any materials which function to increase the volume of fluid imbibed into the core to enable the osmotic dosage form to dispense substantially all of the bupropion salt through at least one passageway in the semipermeable membrane by osmosis or by osmosis and by diffusion through the semipermeable membrane. The flux enhancing agent dissolves to form paths in the semipermeable membrane for the fluid to enter the core and dissolve the bupropion salt in the core together with the osmagent, if one is present, but does not allow exist of the bupropion salt. The flux enhancing agent can be any water soluble material or an enteric material which allows an increase in the volume of liquid imbibed into the core but does not allow for the exit of the bupropion salt. Such materials can be, for example, sodium chloride, potassium chloride, sucrose, sorbitol, mannitol, polyethylene glycol, propylene glycol, hydroxypropyl cellulose, hydroxypropyl methylcellulose, hydroxypropyl methylcellulose phthalate, cellulose acetate phthalate, polyvinyl alcohols, methacrylic copolymers, and combinations thereof. Some plasticizers can also function as flux enhancers by increasing the hydrophilicity of the semipermeable membrane and/or the core of the osmotic dosage form. Flux enhancers or channeling agents can also function as a means for the exit of the bupropion salt from the core if the flux enhancing or channeling agent is used in a sufficient amount.

The expression "passageway" as used herein comprises means and methods suitable for the metered release of the bupropion salt from the core of the osmotic dosage form. The means for the exit of the bupropion salt comprises at least one passageway, including orifice, bore, aperture, pore, porous element, hollow fiber, capillary tube, porous overlay, or porous element that provides for the osmotic controlled release of the bupropion salt. The means for the exit can be linear or tortuous. The means for the exit includes a weakened area of the semipermeable membrane or a material that erodes or is leached from the wall in a fluid environment of use to produce at least one dimensioned passageway. The means for the exit of the bupropion salt can comprise any leachable material, which when leaches out of the semipermeable membrane forms a passageway suitable for the exit of the bupropion salt from the core of the osmotic dosage form. Such leachable materials can comprise, for example, a leachable poly(glycolic) acid or poly(lactic) acid polymer in the semipermeable membrane, a gelatinous filament, poly(vinyl alcohol), leachable polysaccharides, salts, oxides, sorbitol, or sucrose. The means for exit can also comprise a flux enhancer or channeling agent if present in a sufficient amount. The means for the exit possesses controlled-release dimensions, such as round, triangular, square and elliptical, for the metered release of the bupropion salt from the dosage form. The dimensions of the means of the exit for the bupropion salt is sized such so as to allow the bupropion salt to pass through the means for the exit. The dosage form can be constructed with one or more means for the exit in spaced apart relationship on a single surface or on more than one surface of the wall.

The expression "fluid environment" denotes an aqueous or biological fluid as in a human patient, including the gastrointestinal tract. The means for the exit can be pre-formed e.g., by mechanical means after the semipermeable membrane is applied to the core of the osmotic dosage form, such as for example by mechanical perforation, laser perforation, or by using a properly sized projection on the interior of a tablet punch to form the means for the exit of the bupropion salt, such as for example a cylindrical or frustoconical pin which is integral with the inside surface of the upper punch of a punch used to form the osmotic dosage form. Alternatively, the means for the exit of the bupropion salt can be formed by incorporating a leachable material or pore forming agent into the semipermeable composition before the semipermeable membrane is applied to the core of the osmotic dosage form. The means for the exit of the bupropion salt can comprise a combination of the different exit means described above. The osmotic dosage form can comprise more than one means for the exit of the bupropion salt including two, three, four, five, six seven, eight, nine ten or more exit means and can be formed in any place of the osmotic dosage form. The various positions of the means for the exit are disclosed, for example, in U.S. Pat. No. 6,491, 949. The type, number, and dimension(s) of the means for the exit of the bupropion salt is such that the dosage form exhibits the desired in-vitro release rates described herein and can be determined by routine experimentation by those skilled in the pharmaceutical delivery arts. The means for the exit and equipment for forming the means for the exit are disclosed for example in U.S. Pat. Nos. 3,845,770; 3,916, 899; 4,034,758; 4,063,064; 4,077,407, 4,088,864; 4,200, 098; 4,285,987; 4,783,337; 4,816,263; and 5,071,607.

The osmotic device can further comprise a control-releasing coat surrounding the semipermeable membrane comprising an enteric or delayed release coat that is soluble or erodible in intestinal juices, substantially pH neutral or basic fluids of fluids having a pH higher than gastric fluid, but for the most part insoluble in gastric juices or acidic fluids. A wide variety of other polymeric materials arc known to possess these various solubility properties. Such other polymeric materials include, for example, cellulose acetate phthalate (CAP), cellulose acetate trimelletate (CAT), poly (vinyl acetate) phthalate (PVAP), hydroxypropyl methylcellulose phthalate (HP), poly(methacrylate ethylacrylate) (1:1) copolymer (MA-EA). poly(methacrylate methylmethacrylate) (1:1) copolymer (MA-MMA), poly(methacrylate methylmethacrylate) (1:2) copolymer, EUDRAGIT® L-30-D (MA-EA, 1:1), EUDRAGIT® L-100-55 (MA-EA, 1:1), hyciroxypropyl methylcellulose acetate succinate (HPMCAS). COATERIC® (PVAP), AQUATERIC® (CAP), AQUACOAT® (HPMCAS) and combinations thereof. The enteric coat can also comprise dissolution aids, stability modifiers, and bioabsorption enhancers.

When the control-releasing coat of osmotic dosage forms of the present invention is intended to be dissolved, eroded or become detached from the osmotic dosage form, materials such as hydroxypropylcellulose, microcrystalline cellulose (MCC, AVICEL™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis(methacryloyloxyethyloxycarbonylamino)-azobeuzene, azopolymers, enteric coated timed release system (TIME CLOCK® from Pharmaceutical Profiles, Ltd., UK) and calcium pectinate can be used.

Polymers for use in the control-releasing coat of osmotic dosage forms of the present invention can be, for example, enteric materials that resist the action of gastric fluid avoiding permeation through the semipermeable wall while one or more of the materials in the core of the dosage form arc solubilized in the intestinal tract thereby allowing delivery of the bupropion salt in the core by osmotic pumping in the osmotic dosage form to begin. A material that adapts to this kind of requirement can be, for example, a poly(vinylpyrrolidone)-vinyl acetate copolymer, such as the material supplied by BASF under its KOLLIDON® VA64 trademark, mixed with magnesium stearate and other similar excipients. The enteric coat can also comprise povidone, which is supplied by BASF under its KOLLIDON® K 30 trademark, and hydroxypropyl methylcellulose, which is supplied by Dow under its METHOCEL® E-15 trademark. The materials can be prepared in solutions having different concentrations of polymer according to the desired solution viscosity. For example, a 10% P/V aqueous solution of KOLLIDON® K 30 has a viscosity of 5.5-8.5 cps at 20° C., and a 2% P/V aqueous solution of METHOCEL® E-15 has a viscosity of 13-18 cps at 20° C.

The control-releasing coat of osmotic dosage forms of the present invention can comprise one or more materials that do not dissolve, disintegrate, or change their structural integrity in the stomach and during the period of time that the tablet resides in the stomach, such as for example a member chosen from the group (a) keratin, keratin saridarac-tolu, salol (phenyl salicylate), salol beta-naphthylbenzoate and acetotannin, salol with balsam of Peru, salol with tolu, salol with gum mastic, salol and stearic acid, and salol and shellac; (b) a member chosen from the group of formalized protein, formalized gelatin, and formalized cross-linked gelatin and exchange resins; (c) a member chosen from the group of myristic acid-hydrogenated castor oil-cholesterol, stearic acid-mutton tallow, stearic acid-balsam of tolu, and stearic acid-castor oil; (d) a member chosen from the group of shellac, ammoniated shellac, ammoniated shellac-salol, shellac-wool fat, shellac-acetyl alcohol, shellac-stearic acid-balsam of tolu, and shellac n-butyl stearate; (e) a member chosen from the group of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition chosen from the group of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

Accordingly, in at least one other embodiment, the control-releasing coat of osmotic dosage forms of the present invention comprises a water-insoluble water-permeable film-forming polymer, water-soluble polymer, and optionally a plasticizer and/or a pore-forming agent. The water-insoluble, water-permeable film-forming polymers useful for the manufacture of the control-releasing coat can be cellulose ethers, such as for example, ethyl celluloses chosen from the group of ethyl cellulose grade PR100, ethyl cellulose grade PR20 and any combination thereof; cellulose esters, and polyvinyl alcohol. The water-soluble polymers useful for the control-releasing coat can be, for example, polyvinylpyrrolidone, hydroxypropyl methylcellulose and hydroxypropyl cellulose.

The skilled artisan will appreciate that the desired in-vitro release rates described herein for the bupropion salt can be achieved by controlling the permeability and/or the amount of coating applied to the core of the osmotic dosage form. The permeability of the control-releasing coat, can be altered by varying the ratio of the water-insoluble, water-permeable film-forming polymer:water-soluble polymer:optionally the plasticizer and/or the quantity of coating applied to the core of the osmotic dosage form. A more extended release is generally obtained with a higher amount of water-insoluble, water-permeable film forming polymer. The addition of other excipients to the core of the osmotic dosage form can also alter the permeability of the control-releasing coat. For example, if the core of the osmotic dosage form comprises a swellable polymer, the amount of plasticizer in the control-releasing coat can be increased to make the coat more pliable as the pressure exerted on a less pliable coat by the swellable polymer could rupture the coat. Further, the proportion of the water-insoluble water-permeable film forming polymer and water-soluble polymer may also be altered depending on whether a faster or slower in-vitro dissolution is desired.

In at least one other embodiment, the control-releasing coat of the osmotic dosage form comprises an aqueous dispersion of a neutral ester copolymer without any functional groups; a poly glycol having a melting point greater than 55° C., and one or more pharmaceutically acceptable excipients and cured at a temperature at least equal to or greater than the melting point of the poly glycol. The manufacture and use of such coating formulations are described in detail in US published patent application 20040037883A1, published on Feb. 26, 2004. In brief, examples of neutral ester copolymers without any functional groups comprising the coat can be EUDRAGIT® NE30D, EUDRAGIT® NE40D (Röhm America LLC), or mixtures thereof. This coal can comprise hydrophilic agents to promote wetting of the coat when in contact with gastrointestinal fluids. Such hydrophilic agents include, for example, hydrophilic water-soluble polymers such as hydroxypropyl methylcellulose (HPMG), hydroxypropyl cellulose (HPC) and combinations thereof. The poly glycol can be, for example, chosen from the group of polyethylene glycol 6000, polyethylene glycol 8000, polyethylene glycol 10000, polyethylene glycol 20000, Poloxamer 188, Poloxamer 338, Poloxamer 407, Polyethylene Oxides, Polyoxyethylene Alkyl Ethers, and Polyoxyethylene Stearates, and combinations thereof. This control-releasing coat of the osmotic dosage form can further comprise a pore-forming agent. The pore former, however, must be sufficiently insoluble in the aqueous dispersion, but must be sufficiently soluble in the environment of use. One method for producing such coats is detailed in European patent EP 1267842B1.

The control-releasing coat of certain embodiments of the osmotic dosage form of certain embodiments of the present invention includes at least one polymer in an amount sufficient to achieve a controlled release of the bupropion salt. Examples of polymers that can be used in the control-releasing coat of these embodiments include cellulose acetate phthalate, cellulose acetate trimaletate, hydroxy propyl methylcellulose phthalate, polyvinyl acetate phthalate, ammonio methacrylate copolymers such as those sold under the Trade Mark EUDRAGIT® RS and RL, poly acrylic acid and poly acrylate and methacrylate copolymers such as those sold under the trademark EUDRAGIT® S and L, polyvinyl acetaldiethylalmino acetate, hydroxypropyl methylcellulose acetate succinate, shellac; hydrogel and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers in which the degree of crosslinking is low so as to facilitate adsorption of Water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (EUDRAGIT® RS-PM, Rohm & Haas), pullulan, collagen, casein, agar, gum arabic, sodium carboxymethyl cellulose, (swellable hydrophilic polymers) poly(hydroxyalkyl methacrylate) (molecular weight 5K-5000K), polyvinylpyrrolidone (molecular weight 10K-360K), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (molecular weight 30K-300K), polysaccharides such as agar, acacia, karaya, tragacanth, algins and guar, polyacrylamides, POLYOX® polyethylene oxides (molecular weight 100K-5000K), AQUAKEEP® acrylate polymers, diesters of polyglucan, crosslinked polyvinyl alcohol and poly N-vinyl-2-pyrrolidone, sodium starch glycolate(e.g. EXPLOTAB®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. POLYOX®, Union Carbide), methyl ethyl cellulose, ethylhydroxy ethylcellulose, cellulose acetate; cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. EUDRAGIT®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, seleroglucan and mixtures and blends thereof. In at least one embodiment of the osmotic dosage form of the present invention, the polymer is an acrylate dispersion such as EUDRAGIT® NE30D, EUDRAGIT® NE40D (Rohm America LLC), KOLLICOAT® SR 30D, SURELEASE®, or a mixture thereof. The polymer can be present in an amount of from 20% to 90% by weight of the control-releasing coat, depending on the controlled release profile desired. For example, in certain embodiments of the osmotic dosage form, the polymer is present in an amount of from 50% to 95%, in other embodiments from 60% to 90%, and in still other embodiments 75% of the control-releasing coat weight.

The control-releasing coat of certain embodiments of the osmotic dosage form of the present invention can also include one or more pharmaceutically acceptable excipients such as lubricants, emulsifiers, anti-foaming agents, plasticisers, solvents and the like.

Lubricants can be included in the control-releasing coat of certain embodiments of the osmotic dosage form of the present invention to help reduce friction of coated microparticles during manufacturing. The lubricants that can be used in the control-releasing coat include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. Compritol™), Stear-O-Wet™ and Myvatex™ TL. In at least one embodiment, the lubricant is selected from magnesium stearate and talc. Combinations of these lubricants are operable. The lubricant(s) can each be present in an amount of from 0.1% to 80% of the control-releasing coat weight. For example, in certain embodiments the lubricant is present in an amount of from 0.5% to 20%, in other embodiments from 0.8% to 10%, and in still other embodiments 1.5% of the control-releasing coat weight.

Emulsifying agent(s) (also called emulsifiers or emulgents) can be included in the control-releasing coat of the osmotic dosage forms of certain embodiments of the present invention to facilitate actual emulsification during manufacture of the coat, and also to increase or ensure emulsion stability during the shelf-life of the product. Emulsifying agents useful for the control-releasing coat composition of the osmotic dosage form include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. The emulsifying agent(s) can be present in an amount of from 0.01% to 0.25% of the control-releasing coat weight. For example, in certain embodiments the emulsifying agent is present in an amount of from 0.01% to 0.15%, in other embodiments from 0.01% to 0.07%, and in still other embodiments 0.03% of the control-releasing coat weight.

Anti-foaming agent(s) can be included in the control-releasing coat of the osmotic dosage form of certain embodiments of the present invention to reduce frothing or foaming during manufacture of the coat. Anti-foaming agents useful for the control-releasing coat composition of the osmotic dosage form include, but are not limited to simethicone, polyglycol and silicon oil. In at least one embodiment the anti-foaming agent is Simethicone C. The anti-foaming agent can be present in an amount of from 0.01% to 10% of the control-releasing coat weight. For example, in certain embodiments the anti-foaming agent is present in an amount of from 0.05% to 1%, in other embodiments from 0.1% to 0.3%, and in still other embodiments 0.15% of the control-releasing coat weight.

It is contemplated that in certain embodiments, other excipients consistent with the objects of the present invention can also be used in the control-releasing coat of the osmotic dosage form.

In at least one embodiment, the control-releasing coat of the osmotic dosage form includes 75% EUDRAGIT® NE30D, 1.5% Magnesium stearate, 1.5%. Talc, 0.03% TWEEN™ 80, 0.15% Simethicone C, and 21.82% water, by weight of the control-releasing coat composition.

In a prophetic example of certain embodiments of osmotic dosage forms of the present invention, the manufacturing process for the control-releasing coat of the osmotic dosage form can hypothetically be as follows: Water is split into two portions of 15% and 85%. The anti-foaming agent and the emulsifying agent are then added to the 15% water portion, and mixed at 300 rpm to form portion A. In at least one embodiment, the anti-foaming agent is Simethicone C, and the emulsifying agent is TWEEN™ 80. A first lubricant is then added to the 85% water portion and mixed at 9500 rpm to form portion B. In at least one embodiment, the first lubricant is talc. Then portion A is mixed with portion B, a second lubricant is slowly added, and mixed at 700 rpm overnight. In at least one embodiment, the second lubricant is magnesium stearate. Finally, an aqueous dispersion of a neutral ester copolymer is added and mixed for 30 minutes at 500 rpm. In at least one embodiment, the aqueous dispersion of a neutral ester copolymer is EUDRAGIT® NE30D. The resultant coat solution can then be used to coat the osmotic subcoated microparticles to a 35% weight gain with the following parameters: An inlet temperature of from 10° C. to 60° C., preferably from 20° C. to 40° C., and more preferably from 25° to 35° C.; an outlet temperature of from 10° C. to 60° C., preferably from 20° C. to 40° C., and more preferably from 25° C. to 35° C.; a product temperature of from 10° C. to 60° C., preferably from 15° C. to 35° C., and more preferably from 22° C. to 27° C.; an air flow of from 10 c.m/h to 180 c.m/h, preferably from 40 c.m/h to 1.20 c.m/h, and more preferably from 60 c.m/h to 80 c.m/h; and an atomizing pressure of from 0.5 bar to 4.5 bar, preferably from 1 bar to 3 bar, and more preferably 2 bar. The resultant coated microparticles can then be discharged from the coating chamber and overcured with the following parameters: A curing temperature of from 20° C. to 65° C., preferably from 30° C. to 55° C., and more preferably 40° C.; and a curing time of from 2 hours to 120 hours, preferably from 10 hours to 40 hours, and more preferably 24 hours. Any other technology resulting in the coating formulation of the control-releasing coat of the osmotic dosage form that is consistent with the objects of the invention can also be used.

In at least one other embodiment, the osmotic dosage forms comprise a water-soluble or rapidly dissolving coat between the semipermeable membrane and the control-releasing coat. The rapidly dissolving coat can be soluble in the buccal cavity and/or upper GI tract, such as the stomach, duodenum, jejunum or upper small intestines. Materials suitable for the manufacture of the water-soluble coat are disclosed in U.S. Pat. Nos. 4,576,604 and 4,673,405, and the text Pharmaceutical Dosage Forms: Tablets Volume I, Second Edition. A. Lieberman. ed. 1989, Marcel Dekker, Inc. In certain embodiments, the rapidly dissolving coat can be soluble in saliva, gastric juices, or acidic fluids. Materials which are suitable for making the water soluble coat or layer can comprise, for example, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as, for example, hydroxymethylcellulose, hydroxyethylcellulose, and hydroxypropylcellulose; synthetic water-soluble cellulose-based lamina formers such as, for example, methyl cellulose and its hydroxyalkyl methylcellulose cellulose derivatives such as a member chosen from the group of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other lamina forming materials that can be used for this purpose include, for example, poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer. The water soluble coating can comprise other pharmaceutical excipients that do or do not alter the way in which the water soluble coating behaves. The artisan of ordinary skill will recognize that the above-noted materials include film-forming polymers. The inert water-soluble coat covering the semipermeable wall and blocking the passageway of osmotic dosage forms of the present invention, is made of synthetic or natural material which, through selective dissolution or erosion can allow the passageway to be unblocked thus allowing the process of osmotic delivery to start. This water-soluble coat can be impermeable to a first external fluid, while being soluble in a second external fluid. This property can help to achieve a controlled and selective release of the bupropion salt from the osmotic dosage form so as to achieve the desired in-vitro release rates.

In embodiments where the core of the osmotic dosage form does not comprise an osmagent, the osmotic dosage forms can comprise an osmotic subcoat, which can surround the core of the osmotic dosage form. The osmotic subcoat comprises at least one osmotic agent and at least one hydrophilic polymer. The osmotic subcoat of this embodiment provides for the substantial separation of the bupropion salt from the osmotic agent into substantially separate compartments/layers. This separation can increase the stability of the bupropion salt by reducing possible unfavorable interactions between the bupropion salt and the osmagent, and/or between the bupropion salt and the components of the control-releasing coat. For example, the osmagent can be hygroscopic in nature, and can attract water that can lead to the degradation of the bupropion salt. Since the osmotic agent of these embodiments can be substantially separated from the bupropion salt, the bupropion salt can be less prone to degradation from the water drawn in by the osmagent. The control-releasing coat comprises a control-releasing polymer and optionally a plasticizer. The coated cores of the osmotic dosage form can be filled into capsules, or alternatively can be compressed into tablets using suitable excipients. In these embodiments the multiparticulate osmotic dosage form can utilize both diffusion and osmosis to control drug release, and can be incorporated into sustained release and/or delayed release dosage forms. In addition, in certain embodiments the osmotic pressure gradient and rate of release of the bupropion salt can be controlled by varying the level of the osmotic agent and/or the level of the hydrophilic polymer in the osmotic subcoat, without the need for a seal coat around the osmotic subcoat.

The hydrophilic polymer used in an osmotic subcoat of certain embodiments of the present invention functions as a carrier for the osmotic agent. In certain embodiments the hydrophilic polymer in the osmotic subcoat does not substantially affect the drug release. In at least one embodiment, the hydrophilic polymer used in the osmotic subcoat does not act as a diffusion barrier to the release of the bupropion salt. In at least one embodiment the release profile of the osmotic agent is substantially the same as the release profile of the bupropion salt. Such hydrophilic polymers useful in an osmotic subcoat of the present invention include by way of example, polyvinyl pyrrolidone, hydroxyethyl cellulose, hydroxypropyl cellulose, low molecular weight hydroxypropyl methylcellulose (HPMC), polymethacrylate, ethyl cellulose, and mixtures thereof. In at least one embodiment, the hydrophilic polymer of the osmotic subcoat is a low molecular weight and a low viscosity hydrophilic polymer. A wide variety of low molecular weight and low viscosity hydrophilic polymers can be used in the osmotic subcoat. Examples of HPMC polymers that can be used in the osmotic subcoat include PHARMACOAT® 606, PHARMACOAT® 606G. PHARMACOAT® 603, METHOCEL® E3, METHOCEL® E5, METHOCEL® E6, and mixtures thereof. The hydrophilic polymer of the osmotic subcoat can be present in an amount of from 1% to 30% by weight of the osmotic subcoat composition. For example, in certain embodiments the hydrophilic polymer is present in an amount of from 1% to 20%, in other embodiments from 3% to 10%, and in still other embodiments 7% by weight of the osmotic subcoat composition.

In at least one embodiment, the osmotic subcoat comprises 7% PHARMACOAT® 606, 1% sodium chloride, and 92% water, by weight of the osmotic subcoat composition.

One method for producing the osmotic subcoat can be as follows. The at least one osmotic agent, for example sodium chloride, is dissolved in water. The solution of osmotic agent and water is then heated to 60° C. The hydrophilic polymer is then added gradually to the solution. A magnetic stirrer can be used to aid in the mixing of the hydrophilic polymer to the solution of osmotic agent and water. The resultant osmotic subcoating solution can then be used to coat the core of the osmotic dosage form in a fluidized bed granulator, such as a granulator manufactured by Glatt (Germany) or Aeromatic (Switzerland) to the desired weight gain. An inlet temperature of from 10° C. to 70° C., preferably from 30° C. to 55° C., and more preferably from 40° C. to 45° C.; an outlet temperature of from 10° C. to 70° C., preferably from 20° C. to 45° C., and more preferably from 30° C. to 35° C.; a product temperature of from 10° C. to 70° C., preferably from 20° C. to 45° C., and more preferably from 30° C. to 35° C.; an air flow of from 10 c.m/h to 180 c.m/h; preferably from 40 c.m/h to 120 c.m/h; and more preferably from 60 c.m/h to 80 c.m/h; an atomizing pressure of from 0.5 bar to 4.5 bar, preferably from 1 bar to 3 bar, and more preferably 2 bar; a curing temperature of from 10° C. to 70° C., preferably from 20° C. to 50° C., and more preferably from 30° C. to 40° C.; and a curing time of from 5 minutes to 720 minutes; preferably from 10 minutes to 120 minutes, and more preferably 30 minutes. Any other technology resulting in the coating formulation of the osmotic subcoat consistent with the objects of the invention can also be used.

The ratio of the components in the core, semipermeable membrane and/or water-soluble membrane and/or at least one control-releasing coat and/or osmotic subcoat as well as the amount of the various membranes or coats applied can be varied to control delivery of the bupropion salt either predominantly by diffusion across the surface of the semipermeable membrane to predominantly by osmotic pumping through the at least one passageway in the semipermeable membrane, and combinations thereof such that the dosage form can exhibit a modified-release, controlled-release, sustained-release, extended-release, prolonged-release, bi-phasic release, delayed-release profile or a combination of release profiles whereby the in-vitro release rates of the bupropion salt is such that after 2 hours from 0 to 20% by weight of the bupropion salt is released, after 4 hours from 15% to 45% by weight of the bupropion salt is released, after 8 hours, from 40% to 90% by weight of the bupropion salt is released, and after 16 hours, more than 80% by weight of the bupropion salt is released. In embodiments where the mode of exit of the bupropion salt comprises a plurality of pores, the amount of pore forming agent employed to achieve the desired in-vitro dissolution rates can be readily determined by those skilled in the drug delivery art.

In at least one embodiment, the core of the osmotic dosage form comprises bupropion hydrobromide. The proportion of the bupropion hydrobromide in the core can be from 40% to 99%, such as for example, 40%, 45%, 50%, 55%, 60%, 65%, 70%, 75%, 80%, 85%, 90%, 95 or 99% of the core dry weight.

In certain embodiments, the core of the osmotic dosage form comprises at least one means for increasing the hydrostatic pressure inside the membrane or coat. The membrane or coat can be a semipermeable membrane, a control-releasing coat, a water-soluble coat, an osmotic subcoat, or any combination thereof. The core of the osmotic dosage form has an effective osmotic pressure greater than that of the surrounding fluid in the environment of use so that there is a net driving force for water to enter the core. The at least one means for increasing the hydrostatic pressure inside the membrane or coat can be any material that increases the osmotic pressure of the core of the osmotic dosage form. The at least one means for increasing the hydrostatic pressure inside the membrane or coat can be, for example, the bupropion salt, an osmagent, any material which can interact with water and/or an aqueous biological fluid, swell and retain water within their structure, such as for example an osmopolymer, and any combination thereof. The osmagent can be soluble or swellable. Examples of osmotically effective solutes are inorganic and organic salts and sugars. The bupropion salt can itself be an osmagent or can be combined with one or more other osmagents, such as for example, magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, water soluble acids, alcohols, surfactants, and carbohydrates such as raffinose, sucrose, glucose, lactose, fructose, algin, sodium alginate, potassium alginate, carrageenan, fucoridan, furcellaran, laminaran, hypnea, gum arabic, gum ghatti, gum karaya, locust bean gum, pectin, starch and mixtures thereof. In certain embodiments the amount of osmagent can range from, for example, 15, 20, 25, 30, 35, 40, 45, 50, 55, 60, 65, 70, 75, 80, 85, 90, or 95% of the core dry weight.

The osmagent useful in certain embodiments of the present invention can be any agent that can generate an osmotic pressure gradient for the transport of water from the external environment of use into the osmotic dosage form. Osmagents are also known as osmotically effective compounds, osmotic solutes, and osmotic fluid imbibing agents. Osmagents useful in certain embodiments of the present invention are soluble in aqueous and biological fluids, such as ionizing compounds, inherently polar compounds, inorganic acids, organic acids, bases and salts. In at least one embodiment the osmagent is a solid and dissolves to form a solution with fluids imbibed into the osmotic dosage form. A wide variety of osmagents can be used to provide the osmotic pressure gradient used to drive the bupropion salt from the core of the osmotic dosage form. Examples of inorganic salts useful as osmagents include lithium chloride, lithium sulfate, lithium phosphate, magnesium chloride, magnesium sulfate, potassium chloride, potassium sulfate, potassium phosphate, potassium acid phosphate, sodium chloride, sodium sulfate, sodium phosphate, sodium sulfite, sodium nitrate, sodium nitrite, and mixtures thereof. Examples of salts of organic acids useful as osmagents include sodium citrate, potassium acid tartrate, potassium bitartrate, sodium bitartrate, and mixtures thereof. Examples of ionizable solid acids useful as osmagents include tartaric, citric, maleic, malic, fumaric, tartronic, itaconic, adipic, succinic, mesaconic acid, and mixtures thereof. Examples of other compounds useful as osmagents include potassium carbonate, sodium carbonate, ammonium carbonate, calcium lactate, mannitol, urea, inositol, magnesium succinate, sorbitol, and carbohydrates such as raffinose, sucrose, glucose, lactose, lactose monohydrate, a blend of fructose glucose and mixtures thereof. In at least one embodiment the osmagent is selected from sodium chloride, sodium bromide, sodium bisulfate, potassium acid tartrate, citric acid, mannitol, sucrose and mixtures thereof. Combinations of these osmagents is permissible. The osmagent can be present in an amount of from 0.1% to 50% of the dosage form weight. For example, in certain embodiments the osmagent is present in an amount of from 1% to 40%, and in other embodiments from 1% to 20% of the dosage form weight.

In certain embodiments, the a least one means for increasing the hydrostatic pressure can comprise, in addition to an osmagent, any material which can interact with water and/or an aqueous biological fluid, swell and retain Water within their structure. In certain embodiments where the at least one means for increasing the hydrostatic pressure is an osmopolymer, which can be slightly cross-linked or uncross-linked. The uncross-linked polymers to be used as osmopolymers, when in contact with water and/or aqueous biological fluid, should not dissolve in water, hence maintaining their physical integrity. Such polymers can be, for example, chosen from the group of polyacrylic acid derivatives (e.g., polyacrylates, poly-methyl methacrylate, poly (acrylic acid) higher alkyl esters, poly(ethylmethacrylate), poly(hexadecyl methacrylate-co-methylmethacrylate), poly (methylacrylate-co-styrene), poly(n-butyl methacrylate), poly(n-butyl-acrylate), poly(cyclododecyl acrylate), poly (benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins), polyacrylamides, poly(hydroxy ethyl methacrylate), poly (vinyl alcohol), poly(ethylene oxide), poly N-vinyl-2-pyrrolidone, naturally occurring resins such as polysaccharides (e.g., dextrans, water-soluble gums, starches, chemically modified starches), cellulose derivatives (e.g., cellulose esters, cellulose ethers, chemically modified cellulose, microcrystalline cellulose, sodium carboxymethylcellulose and methylcellulose), starches, CARBOPOL™, acidic carboxy polymer, CYANAMER™, polyacrylamides, cross-linked water-swellable indene-maleic anhydride polymers, GOOD-RITE™, polyacrylic acid, polyphenyleneoxide, starch graft copolymers, AQUA-KEEPS™, acrylate polymer, diester cross-linked polyglucan, and any combination thereof.

In certain embodiments, the core of the osmotic dosage form further comprises a means for forcibly dispensing the bupropion salt from the core to the exterior of the dosage form. The at least one means for forcibly dispensing the bupropion salt can be any material which can swell in water and/or aqueous biological fluid and retain a significant fraction of water within its structure, and will not dissolve in water and/or aqueous biological fluid, a means for generating a gas, an osmotically effective solute or any combination thereof which can optionally be surrounded by a membrane or coat depending on the particular means used. The membrane or coat can be, for example, a membrane or coat that is essentially impermeable to the passage of the bupropion salt, gas and compounds, and is permeable to the passage of water and/or aqueous biological fluids. Such a coat or membrane comprises, for example, a semipermeable membrane, microporous membrane, asymmetric membrane, which asymmetric membrane can be permeable, semipermeable, perforated, or unperforated. In at least one embodiment, the at least one means for forcibly dispensing the bupropion salt from the core of the osmotic dosage form comprises a means for generating gas, which means for generating gas is surrounded by, for example, a semipermeable membrane. In operation, when the gas generating means imbibes water and/or aqueous biological fluids, the means for generating gas reacts and generates gas, thereby enlarging and expanding the at least one means for forcibly dispensing the bupropion salt unidirectionally or multidirectionally. The means for generating a gas comprises any compound or compounds, which can produce effervescence, such as for example, at least one solid acid compound and at least one solid basic compound, which in the presence of a fluid can react to form a gas, such as for example, carbon dioxide. Examples of acid compounds include, organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. The basic compounds include, for example, metal carbonates and bicarbonates salts, such as alkali metal carbonates and bicarbonates. The acid and base materials can be used in any convenient proportion between 1 to 200 parts of the at least one acid compound to the at least one basic compound or 1 to 200 parts of the at least one basic compound to the at least one acid compound. The means for generating gas is described, for example in U.S. Pat. No. 4,235,236.

In at least one embodiment, the at least one means for forcibly dispensing the bupropion salt form the core of the osmotic dosage form comprises any material which can swell in water and/or aqueous biological fluid and retain a significant fraction of water within its structure, and will not dissolve in water and/or aqueous biological fluid, such as for example, a hydrogel. Hydrogels include, for example, lightly cross-linked hydrophilic polymers, which swell in the presence of fluid to a high degree without dissolution, usually exhibiting a 5-fold to a 50-fold volume increase. Examples of hydrogels include poly(hydroxyalkyl methacrylates), poly(acrylamide), poly(methacrylamide), poly(N-vinyl-2-pyrrolidone), anionic and cationic hydrogels, polyelectrolyte complexes, a water-insoluble, water-swellable copolymer produced by forming a dispersion of finely divided copolymers of maleic anhydride with styrene, ethylene, propylene butylene or isobutylene cross-linked with from 0.001 to 0.5 moles of a polyunsaturated cross-linking agent per mole of maleic anhydride in the copolymer as disclosed in U.S. Pat. No. 3,989,586, the water-swellable polymers or N-vinyl lactams as disclosed in U.S. Pat. No. 3,992,652, semi-solid cross-linked poly(vinyl pyrrolidone), diester cross-linked polyglucan hydrogels as described in U.S. Pat. No. 4,002,173, the anionic hydrogels of heterocyclic N-vinyl monomers as disclosed in U.S. Pat. No. 4,036,788, the ionogenic hydrophilic gels as described in J. Biomedical Mater, Res., Vol. 7, pages 123 to 126, 1973, and the like. Some of the osmopolymers and hydrogels are interchangeable Such means can optionally be covered by a membrane or coat impermeable to the passage of the bupropion salt, and compounds, and is permeable to the passage of water and/or aqueous biological fluids. Such a coat or membrane comprises, for example, a semipermeable membrane, microporous membrane, asymmetric membrane, which asymmetric membrane can be permeable, semipermeable, perforated, or unperforated.

In at least one other embodiment, the at least one means for forcibly dispensing the bupropion salt from the core of the osmotic dosage form comprises at least one osmotically effective solute surrounded by a membrane or coat impermeable to the passage of the bupropion salt, and compounds, and is permeable to the passage of water and/or aqueous biological fluids such that the osmotically effective solute exhibits an osmotic pressure gradient across a membrane or coat. Such coat or membrane comprises, for example, a semipermeable membrane, microporous membrane, asymmetric membrane, which asymmetric membrane can be permeable, semipermeable, perforated, or unperforated. The osmotically effective solutes include, for example, the osmagents described above.

In embodiments of the osmotic dosage form where the means for forcibly dispensing the bupropion salt is surrounded by a membrane or coat, at least one plasticizer can be added to the membrane composition to impart flexibility and stretchability to the membrane or coat. In embodiments where the means for forcibly dispensing the bupropion salt comprises a means for generating a gas, the membrane or coat should be stretchable so as to prevent rupturing of the membrane or coat during the period of delivery of the bupropion salt. U.S. Pat. No. 4,235,236 describes the manufacture of such a membrane or coat. Plasticizers, which can be used in these embodiments include, for example, cyclic and acyclic plasticizers, phthalates, phosphates, citrates, adipates, tartrates, sebacates, succinates, glycolates, glycerolates, benzoates, myristates, sulfonamides halogenated phenyls, poly(alkylene glycols), poly(alkylenediols), polyesters of alkylene glycols, dialkyl phthalates, dicycloalkyl phthalates, diaryl phthalates and mixed alkyl-aryl phthalates, such as for example, dimethyl phthalate, dipropyl phthalate, di(2-ethylhexyl)phthalate, di-isopropyl phthalate, diamyl phthalate and dicapryl phthalate; alkyl and aryl phosphates, such as for example, tributyl phosphate, trioctyl phosphate, tricresyl phosphate, trioctyl phosphate, tricresyl phosphate and triphenyl phosphate; alkyl citrate and citrates esters such as tributyl citrate, triethyl citrate, and acetyl triethyl citrate; alkyl adipates, such as for example, dioctyl adipate, diethyl adipate and di(2-methoxyethyl)adipate; dialkyl tartrates, such as for example, diethyl tartrates and dibutyl tartrate; alkyl sebacates, such as for example, diethyl sebacate, dipropyl sebacate and dinonyl sebacate; alkyl succinates, such as for example, diethyl succinate and dibutyl succinate; alkyl glycolates, alkyl glycerolates, glycol esters and glycerol esters, such as for example, glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate, triethylene glycol dipropionate and mixtures thereof. Other plasticizers include camphor, N-ethyl (o- and p-toulene) sulfonamide, chlorinated biphenyl, benzophenone, N-cyclohexyl-p-toluene sulfonamide, substituted epoxides and mixtures thereof.

The at least one means for forcibly dispensing the bupropion salt from the core of certain embodiments of the osmotic dosage form can be located such that it is approximately centrally located within the core of the osmotic dosage form and is surrounded by a layer comprising the bupropion salt. Such a configuration is disclosed in U.S. Pat. No. 6,352,721. Alternatively, the core of the osmotic dosage form comprises at least two layers in which the first layer comprises the bupropion salt, osmagent and/or osmopolymer and optionally at least one pharmaceutically acceptable excipient adjacent to a second layer comprising the means for forcibly dispensing the bupropion salt. Alternatively, the core of the osmotic dosage form comprises a multilayered structure in which the layer comprising the bupropion salt is sandwiched between two layers of the means for forcibly dispensing the bupropion salt from the osmotic dosage form.

Combinations

The present invention also contemplates combinations of the bupropion salt with at least one other drug. For example, a composition is provided which comprises a first component of bupropion hydrobromide, and a second component of at least one other drug, wherein the two components are present in an amount effective in the treatment of a condition. The present invention further provides a method for treating a condition, comprising administering to a patient an effective amount of a first component of bupropion hydrobromide in combination with an effective amount of at least one other drug. The skilled artisan will know or can determine by known methods which drug combinations are acceptable. Types of drugs that may be selected as the second drug include by way of example other depressants, anti-anxiety agents, steroidal and non-steroidal inflammatories, SSRIs, anti-migraine agents, anti-pain agents, anti-emetics, drugs for treating abuse such as nicotine, appetite modulators, anti-virals, vasodilators, anti-pain agents, et al. For example, the other drug can be an antidepressant selected from: monoamine oxidase (MAO) inhibitor, tricyclic antidepressant, serotonin reuptake inhibitor, selective norepinephrine reuptake inhibitors (SNRIs), aminoketones, serotonin antagonists, dopamine reuptake inhibitors, dual reuptake inhibitors, norepinephrine enhancers, serotonin activity enhancers, dopamine activity enhancers, and combinations thereof. Examples of other drugs that can be combined with bupropion hydrobromide include citalopram, escitalopram, venlafaxine, clozapine, melperone, amperozide, iloperidone, risperidone, quetiapene, olanzapine, ziprasidone, aripiprazolc, reboxetine, VIAGRA®, sertrahne, paroxetine, fluoxetine, gabapentin, valproic acid, amitriptyline, lofepramine, fluvoxamine, imipramine, mirtazapine, nefazodone. nortriptyline, SAM-E and combinations thereof. In at least one embodiment, a combination of bupropion hydrobromide and citalopram is provided. In at least one other embodiment, a combination of bupropion hydrobromide and escitalopram is provided. In at least one other embodiment a combination of bupropion hydrobromide and venlafaxine is provided.

In certain embodiments, combination products can be made by providing an overcoat to substantially surround the control-releasing coat of each microparticle. In certain embodiments, a pulsatile release of at least one other drug is achieved from the coated microparticles. This overcoat can be an immediate release overcoat that includes at least one other drug and at least one low viscosity hydrophilic polymer. The low-viscosity polymer provides for the immediate release of the other drug from the overcoat. In at least one embodiment, the low-viscosity polymer used in the overcoat is hydroxypropyl methylcellulose (HPMC). The overcoat can also include a lubricant such as talc. As such, this embodiment can provide an immediate release of at least one other drug from the overcoat in a first phase of drug release, and then a subsequent controlled release of the bupropion hydrobromide from the control-releasing coated microparticle in a second phase of drug release.

In addition, combinations of microparticles of the invention each with a different functional coating can be combined together in a dosage form. For example, by combining a first group of uncoated, taste-masked or enteric coated microparticles with a second group of delayed or sustained release coated microparticles, a pulsatile drug release profile or chronotherapeutic profile can be achieved. (e.g. see U.S. Pat. Nos. 5,260,068, 6,270,805, 6,926,909, US2002/0098232, US2004/0197405, U.S. Pat. Nos. 6,635,284, or 6,228,398).

In other embodiments, the combination may comprise at least 2 different microparticles one of which contain bupropion hydrobromide and the other the second drug which are comprised in a capsule formulation.

While only specific combinations of the various features and components of the present invention have been discussed herein, it will be apparent to those of skill in the art that desired subsets of the disclosed features and components and/or alternative combinations of these features and components can be utilized as desired.

As will be seen from the non-limiting examples described below, the coatings of the invention are quite versatile. For example, the length and time for the lagtime can be controlled by the rate of hydration and the thickness of the control-releasing coat. It is possible to regulate the rate of hydration and permeability of the control-releasing coat so that the desired controlled-release profile can be achieved. There is no general preferred control-releasing coat thickness, as this will depend on the controlled release profile desired. Other parameters in combination with the thickness of the control-releasing coat include varying the concentrations of one or more of the ingredients of the control-releasing coat composition, varying the curing temperature and length of time for curing the coated tablet microparticles, and in certain embodiments, varying the level of osmotic agent. The skilled artisan will know which parameters or combination of parameters to change for a desired controlled release profile.

4. Stability Studies

The enhanced stability of the bupropion hydrobromide, in particular compared to bupropion HCl, is clearly evident from degradation studies performed on the active pharmaceutical ingredient (API), alone, in the presence of excipients and in the form of XL tablets. The results are described in greater detail in the examples below.

The term "enhanced stability", "greater stability", "increased stability" or "more stable" as used herein means that the bupropion salt (bupropion hydrobromide), and compositions, formulations or medicaments comprising the bupropion salt, when exposed to like conditions, i.e., storage for at least 3, 4, 5 and/or at least 6 months under accelerated torage conditions, i.e., 40 degrees C. at 75% relative humidity show less degradation as determined by the formation of at least one degradation product characteristic of bupropion degradation and/or the retention of potency, compared to otherwise similar compositions containing bupropion hydrochloride. This includes in particular compositions containing bupropion hydrobromide that show less degradation based on a reduced amount of at least one compound characteristic of bupropion degradation relative to an otherwise similar bupropion hydrochloride composition stored under similar accelerated storage conditions i.e., 40 degrees C. at 75% humidity for at least 3 months, 4 months, 5 months and/or at least 6 months. Additionally another indicator of enhanced stability is that the bupropion HBr composition exhibits less fluctuation is an in vitro dissolution profile which shows less fluctuation relative to an otherwise similar bupropion HCl composition after prolonged storage under similar conditions and wherein disolution is assayed under similar conditions (media and time) particularly after being stored for at least 3 months, 4 months, 5 months and/or at least 6 months at 40 degrees C. and 75% relative humidity.

By "less degradation" it is meant any measurable decrease in the amount of at least one impurity or degradation product characteristic of bupropion degradation or any measurable difference (enhancement or reduced fluctuation) in potency relative to an otherwise similar bupropion HCl composition after the compositions are stored for prolonged time, i.e., at least 3 months, 4 months, 5 months and/or at least 6 months at 40 degrees C. at 75% relative humidity. The "degradation products" include those listed on page 281 of the 26th edition of the USP and any other degradation products that may appear as peaks on a chromatogram during the assay. One indicator of enhanced potency is a bupropion HBr composition that exhibits less fluctuation in dissolution profile after prolonged storage, i.e at least 3, 4, 5 or 6 months at 40 degrees C. and 75% relative humidity relative to an otherwise similar bupropion HCl composition assayed under similar dissolution conditions.

A comparison of the stability of several bupropion salts, including the HBr, HCl, maleate, tosylate, fumarate, succinate, tartrate and citrate salts, was performed by placing these salts in both open and closed vials in a stability chamber kept at 40 degrees C. and 75% relative humidity for various periods of time. The stability of the salts was evaluated based on the formation of the main degradation products (see below) as determined by HPLC analysis and the % potency (or assay) of the API, after specific time periods in the stability chamber. The effect of the addition of solvents, such as water, ethanol and isopropyl alcohol, was also studied.

The results unequivocally show that after at least 3 months or after at least 6 months the HBr salt of bupropion, on average, showed the least amount of degradation products and retained the highest activity of all of the salts tested. Accordingly the HBr salt possesses the greatest stability. These results are unexpected and would be in no way predictable by a person skilled in the art since none of the other salts that were tested showed this enhanced stability.

Further stability tests were performed by directly comparing bupropion HBr and bupropion HCl salts in forced degradation studies. These studies were performed in closed bottles in a stability chamber kept at 40 degrees C. and 75% relative humidity. At specified times, the material in the bottles was analyzed for the presence of degradation products and % potency (% assay). It was unexpectedly found that the amount of impurities was consistently lower and the % potency was consistently higher for the HBr salt compared to the HCl salt.

Forced degradation studies were also performed on bupropion HBr and bupropion HCl API's in the presence of standard excipients used in pharmaceutical formulations. The amount of the main degradation products was observed at 24 and 48 hours after treatment at 55° C., at 55° C. and 100% relative humidity and at 105 degrees C. Once again, it was unexpectedly found that the HBr salt showed the lowest amount of degradation (as determined by the formation of impurities) under these conditions.

The stability of the tablet formulations of bupropion HCl and HBr salts was also compared. With both salts, a tablet having the first control-releasing (EC) coat as well as a double coated tablet (with a control-releasing and moisture barrier coat) were evaluated. The tablets were placed individually on an open dish, and exposed to the accelerated conditions of 40° C. and 75% relative humidity in a stability chamber. After 13 and 20 days, the samples were assayed and impurity analysis was performed.

For the single coated bupropion HCl tablets, the main degradation impurities 3-CBZ and 852U77 were 0.12% and 0.38% respectively, whereas, for the bupropion HBr tablets, these values were 0.07% and 0.49% respectively. The other degradation impurities and the total unknowns were very similar for both products; however, the assay value for the HBr product was higher than the HCl. The difference in the assay and the impurity levels were more significant in the double coated tablets products. For the same period of the study the assay of the Bupropion HCl was lower (95.5% compared to 98.6 for bupropion HBr) and the level of the degradation and total unknowns were higher (3-CBZ: 0.28%, 852U77: 1.23%, 827U76: 0.10% and total 1.73%) than the Bupropion HBr (3-CBZ: 0.12%, 852U77: 0.41%, 827U76: 0.05% and total 0.75%).

The stability studies performed herein have clearly demonstrated the unexpected enhanced stability of bupropion HBr, in particular compared to bupropion HCl, which is used in all pharmaceutical forms currently available. This enhanced stability is seen with the API form alone, the API form plus excipients and the extended release and enhanced absorption tablets. Therefore pharmaceutical formulations comprising bupropion HBr are not only new, but also inventive due to their unexpected and beneficial enhanced stability properties. Pharmaceutical formulations comprising bupropion HBr will show enhanced shelf life and will withstand storage at higher temperatures and humidity levels compared with the currently used bupropion HCl formulations.

5. Polymorphic Forms

It is well known that organic molecules can crystallize into solid forms. Moreover the same organic compound may assume different crystalline arrangements in solid form, depending on the conditions under which the crystal product is formed. This phenomenon is commonly known as polymorphism. A study was undertaken to explore the polymorphic forms of bupropion hydrobromide. The crystal forms of the products obtained in this study were determined by powder X-ray diffraction (PXRD). A RIGAKU miniflex instrument (Radiation Cu K$\alpha$, generator 30 KV, filter Ni) was used to obtain the PXRD data.

Figure 54:
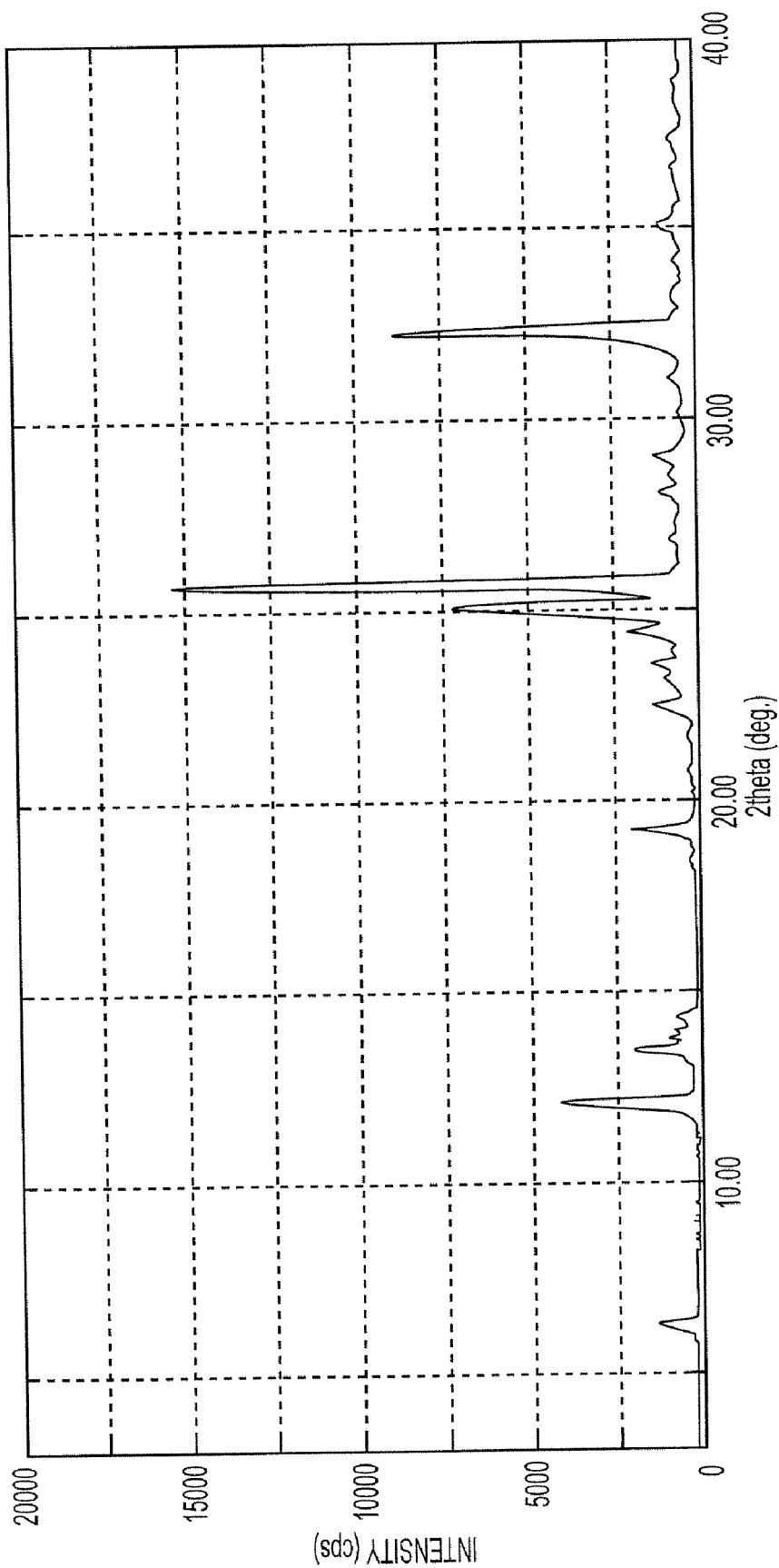
FIG. 54 is a graph showing the relative powder X-ray diffraction (PXRD) for bupropion hydrobromide polymorphic form I.
Figure 55:
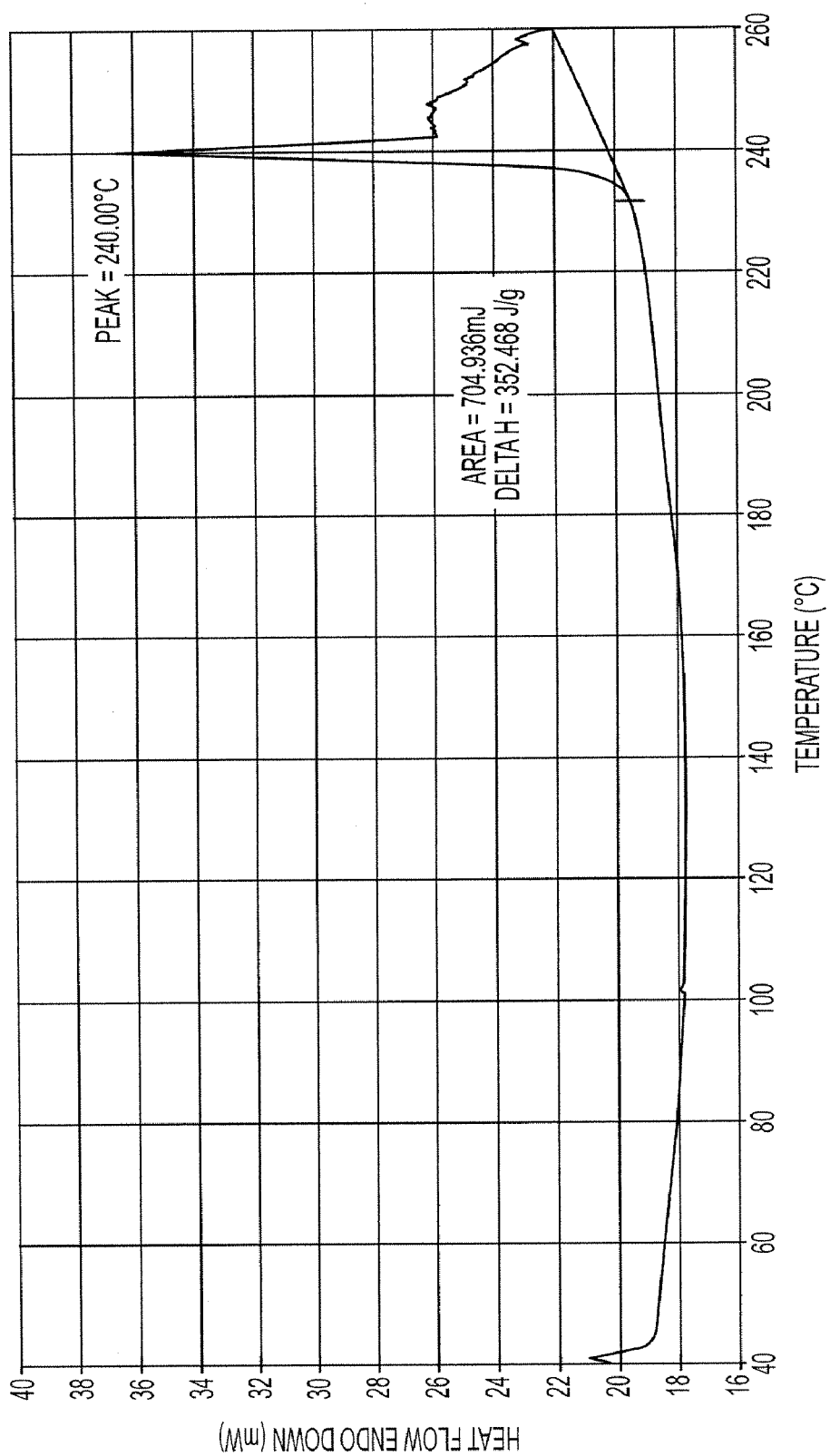
FIG. 55 is a graph showing the differential scanning calorimetry (DSC) profile of bupropion hydrobromide polymorphic form I.

A standard procedure was established to generate bupropion hydrobromide, this standard procedure produces a first polymorphic form which has been termed polymorphic form I. The relative PXRD for form I is shown in FIG. 54 and the differential scanning calorimetry (DSC) profile is shown in FIG. 55.

Figure 56:
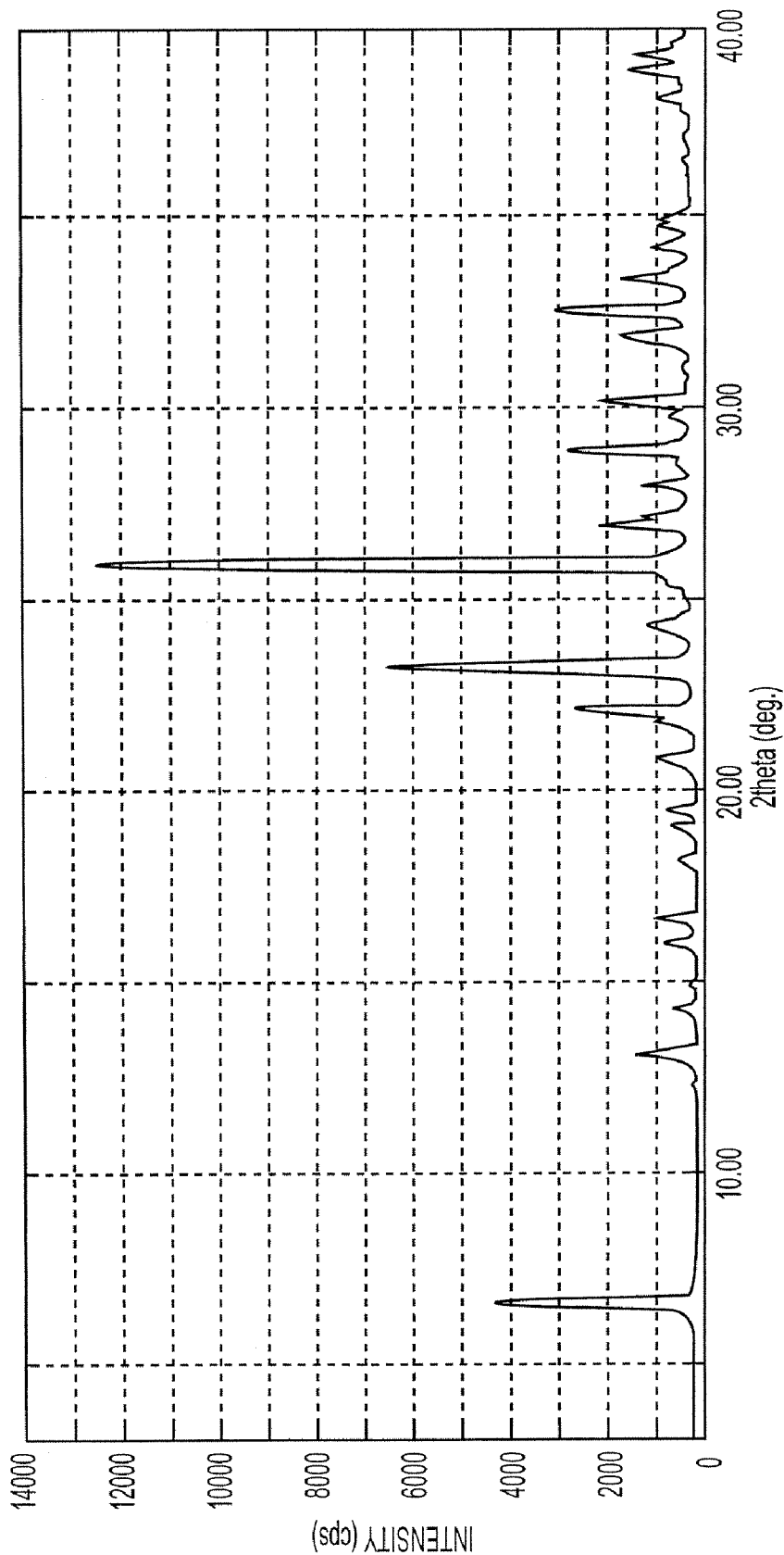
FIG. 56 is a graph showing the relative PXRD for bupropion hydrobromide polymorphic form II.
Figure 57:
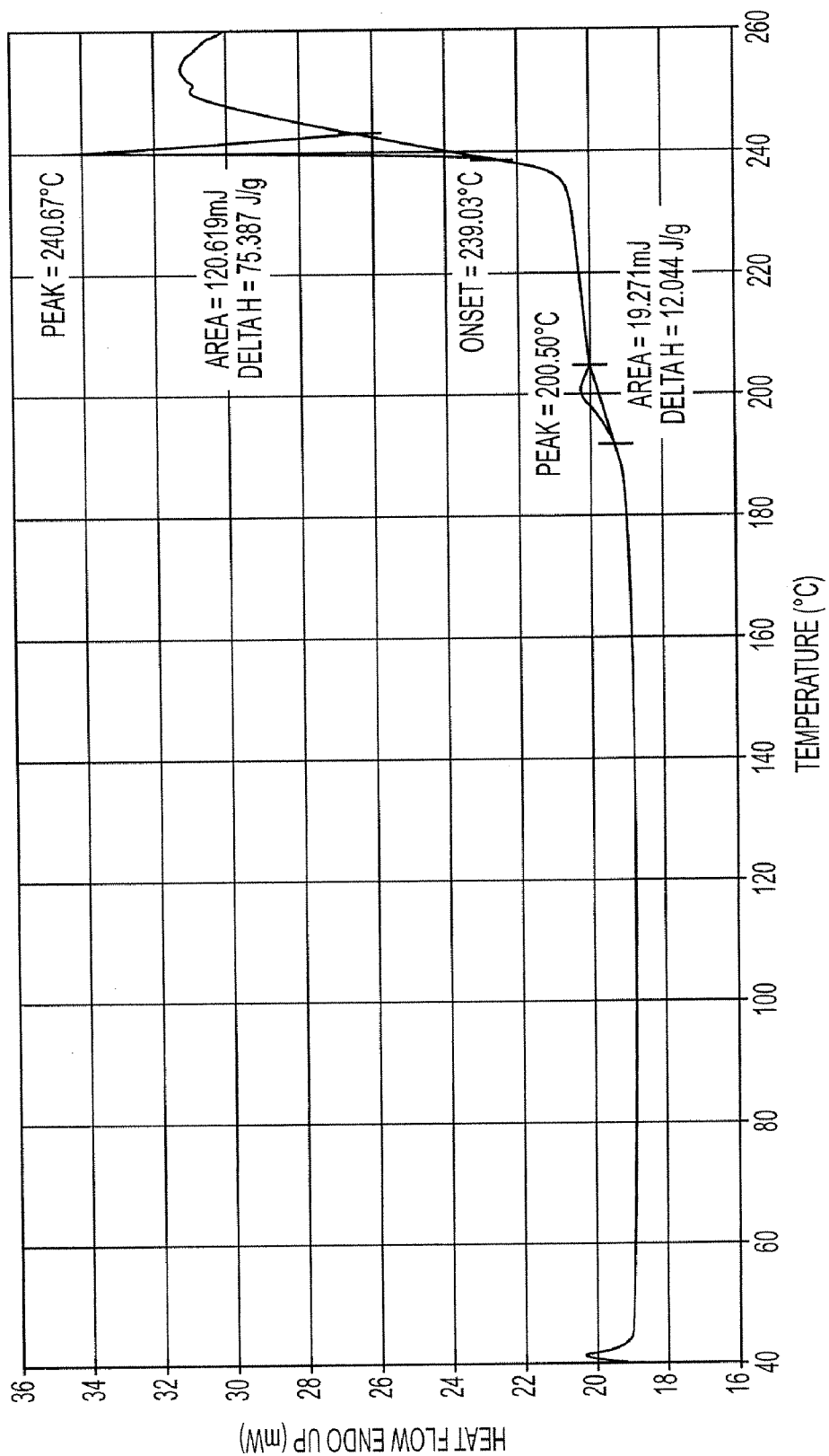
FIG. 57 is a graph showing the DSC profile of bupropion hydrobromide polymorphic form II.
Figure 58:
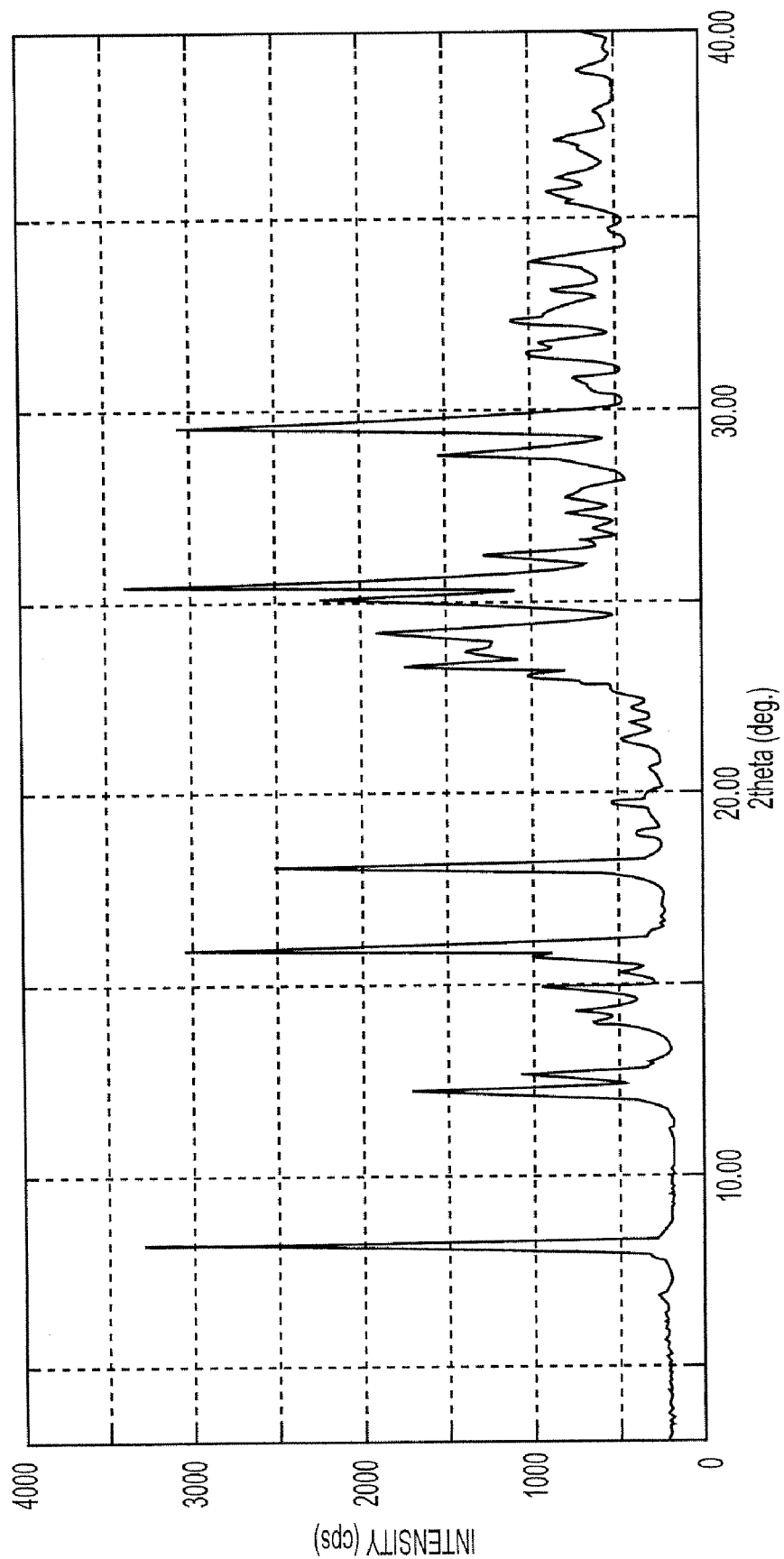
FIG. 58 is a graph showing the relative PXRD for bupropion hydrobromide polymorphic form II.
Figure 59:
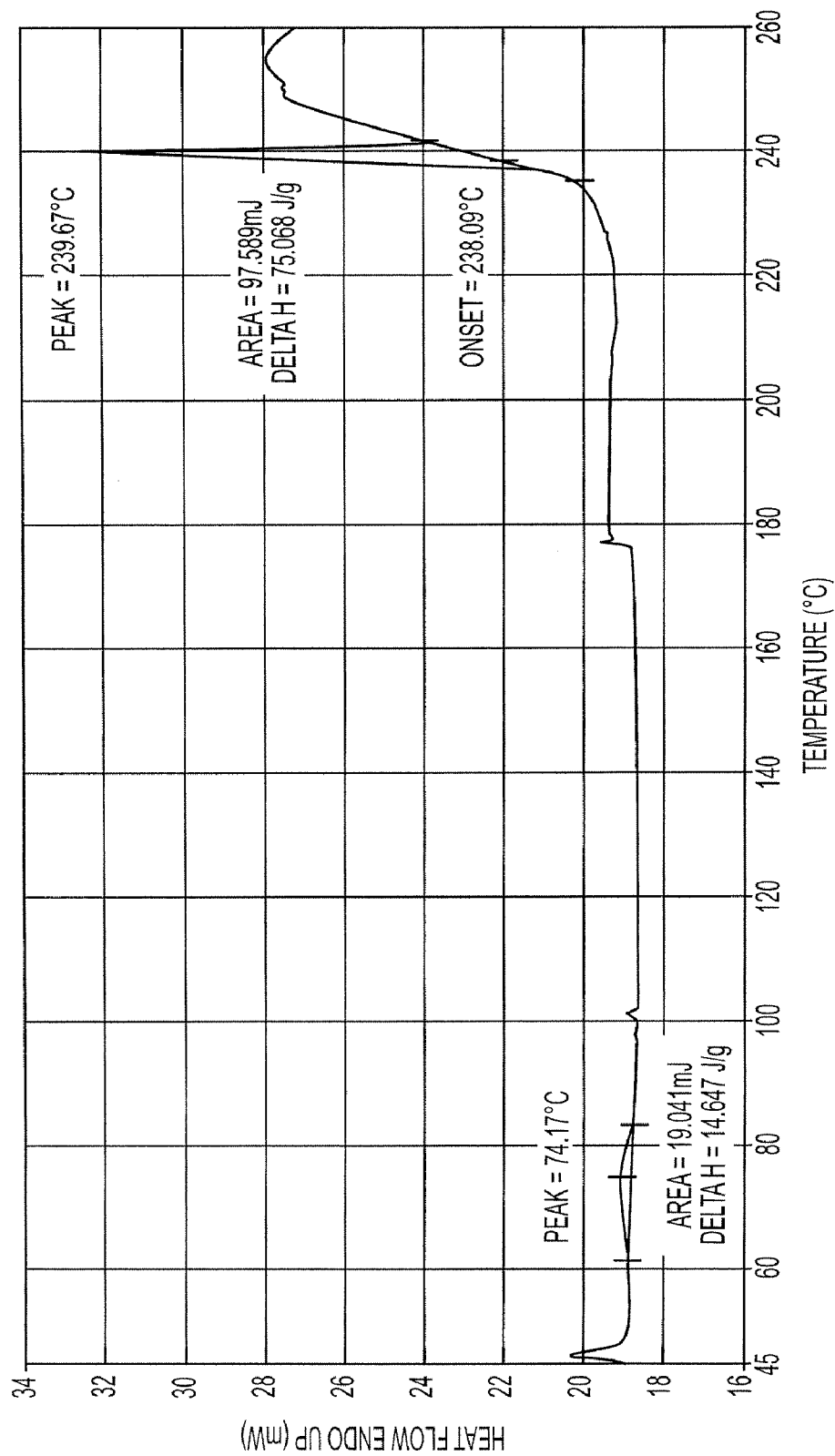
FIG. 59 is a graph showing the DSC profile of bupropion hydrobromide polymorphic form III.

Bupropion HBr of form I has been used as the starting material in experiments to identify other polymorphic forms. Two additional polymorphic forms were identified and have been named form II and form III. FIGS. 56 and 57 show the PXRD data and DSC profile respectively of polymorphic form II. FIGS. 58 and 59 shown the PXRD data and DSC profile respectively of form III.

Polymorphic form II was obtained by recrystalization of form 1 from solvents or mixtures of solvents such as acetone-water, methanol, dichloromethane, toluene-methanol and dimethylcarbonate-methanol. Polymorphic form III was obtained by recrystalization of polymorphic form I in methanol. Table 80 provides a list of recrystalization conditions and the polymorphic form obtained under each set of conditions.

The three polymorphic forms were subjected to stability testing. Samples of the polymorphic forms were subjected to ICH conditions (40° C., 75% R.H.) and PXRD data was obtained at 3 months and 6 months. All of the samples had the same PXRD profile indicating that this polymorphic form is stable at these conditions and is not changing or degrading. Samples of the polymorphic forms II and III were tested after 1 month under the same accelerated stability conditions. Polymorphic form II showed no change in the PXRD profile at that time while the PXRD profile of form III showed conversion to form II. This data suggests that polymorphic forms I and II are quite stable while polymorphic form III is not as stable as forms I and II under the test conditions.

Tables 99-104 contain exemplary 348 and 174 Bupropion HBr XL tablets according to the invention. Table 105 contains stability data for exemplary bupropion HBr formulations under accelerated conditions for different batches over different time periods.

As will be seen from the non-limiting examples described below, the coatings used in the present invention are quite versatile. For example, the length and time for the lagtime can be controlled by the rate of hydration and the thickness of the modified release overcoat. Other parameters in combination with the thickness of the coatings include varying the concentrations of some of the ingredients of the coating compositions of the invention described and/or varying the curing temperature and length of curing the coated tablet cores. The skilled artisan will know which parameters or combination of parameters to change for a desired controlled release profile.

The following examples illustrate the present invention and are not intended to limit the scope of the present invention.

EXAMPLES

Example 1

Preparation of Buproprion HBR Salt

Buproprion HBr salt was prepared according to the method shown in Scheme 1:

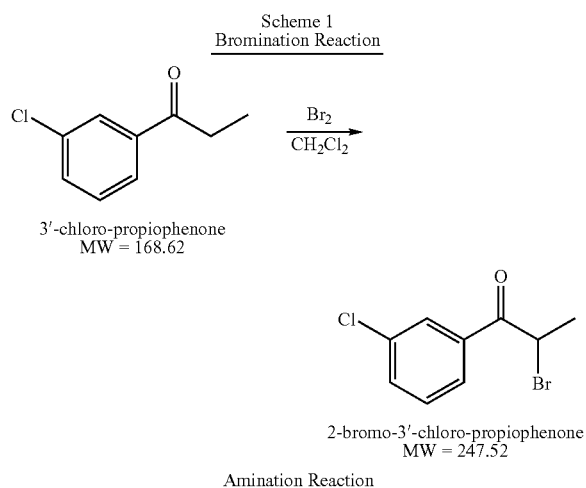

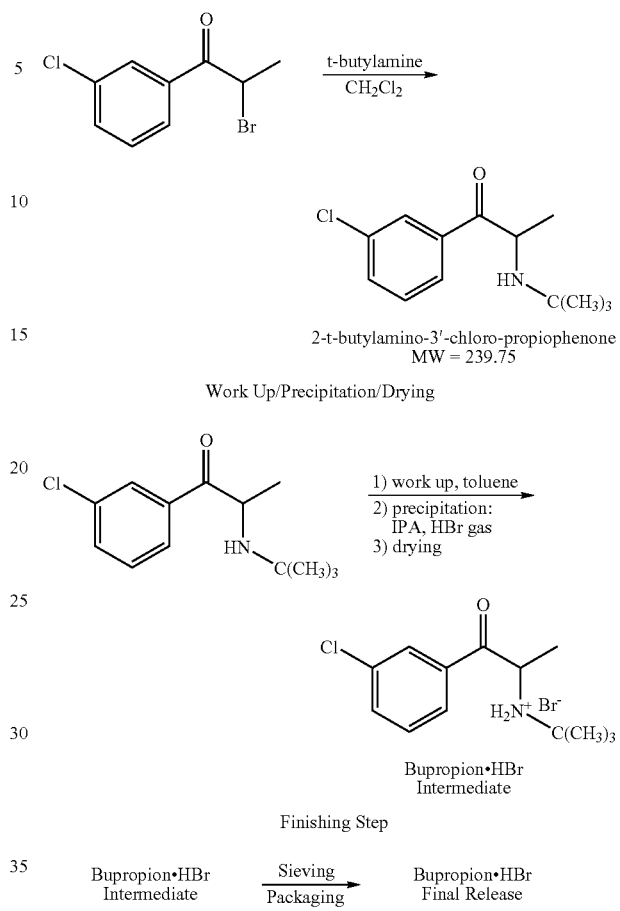

(a) Bromination and Condensation Reactions

3-Chloro-propiophenone starting material was brominated in methylene chloride by dropping bromine under controlled conditions. On reaction completion the mother liquor was worked up and then the second reaction was executed by transferring the bromoderivative solution onto the tert-butylamine. The second substitution reaction (the tert-butylamine amino-group substitutes the bromine atom) forms the final bupropion molecule. After work up of the mother liquor, a bupropion toluene solution was obtained. The solvent was evaporated and bupropion was dissolved in isopropanol. From the isopropanol solution, the hydrobromide was precipitated with hydrogen bromide gas. On precipitation completion, the product was centrifuged, washed with isopropanol and dried under vacuum. On dryer discharge approval it was discharged in Kraft drums within double polyethylene bags.

In the last finishing step, the above intermediate was sieved to obtain the Final Release which was packed in Kraft drums within double polyethylene bags.

Elemental analysis of the bupropion HBr was carried out using a Fisons Elemental Analyser EA 1108. The results were consistent with the molecular formula of bupropion HBr.

Example 2

Physiochemical Characterization of Bupropion Salts

The following bupropion salts were characterized against the HCl salt:

| Product ID | Lot # | Quantity | Potency (HPLC) determined by R&D |
|---|---|---|---|
| Bupropion maleate | 030/018 | 100 g | 99.7% |
| Bupropion tosylate | 030/011/A | 50 g | 97.4% |
| Bupropion Fumarate | 031/1 | 10 g | 89.8% |
| Bupropion HBr | 031/2 | 10 g | 99.7% |
| Bupropion succinate | 031/3 | 10 g | 97.6% |
| Bupropion tartrate acid | 031/5 | 10 g | 84.9% |
| Bupropion tartrate neutral | 031/5B | 10 g | 51.7%* |
| Bupropion citrate | 031/8 | 10 g | 85.0% |

*uncorrected for potency

Thermal Analysis (DSC) Samples:

2-5 mg of each salt was placed in an aluminium pan and covered with its lid. DSC was run for each sample at the rate of 10° C./min (for HBr salt, different rates were used to investigate for polymorphs) from 30° C. to 400° C. TGA was also used for each of the HBr, HCl, maleate and tosylate salts.

Results and Discussion:

Physicochemical Data:

The eight salts were first evaluated by HPLC, KF, pH and DSC for purity, water content, aqueous pH and possible polymorphs. As shown in the Table 1, only the maleate, tosylate, HBr and succinate salts were sufficiently pure, the assay of others ranged between 51.7%% to 89.8%.

The salts were analysed by DSC (at 10oC/min from 30oC up to 400oC) and the pH (aq. 0.5%), and the moisture content by KF were also measured. The TGA was performed on the HCl, maleate, tosylate and HBr salts.

Maleate: DSC showed a melting endothermic peak at the onset temperature 199.1oC and a smaller sharp peak at 205oC The moisture content was 0.10% and the pH of the aqueous solution of 0.5% was 4.29.

By re-crystallization in isopropyl alcohol (IPA)/EtOAc, the smaller peak almost disappeared. The TGA showed that this product was thermally stable to at least 150oC as 1.3% weight lost between room temperature and 100oC was observed. Like Bupropion HCl, no glass transition was observed when a heat-cool-heat experiment was done by TA instrument.

Fumarate: DSC showed multiple endothermic peaks at different onset temperatures (172.3, 182.3, 202 and 217oC). The moisture content was 0.09% and the pH of the aqueous solution of 0.5% was 3.84.

Tosylate: DSC showed a melting endothermic peak at the onset temperature 150oC, a smaller peak at 90oC and multiple peaks at higher temperature (>200oC, probably decomposition). The peak at 90oC was probably due to the solvent isopropyl acetate. The moisture content was 1.71% and the pH of the aqueous solution of 0.5% was 5.56.

By re-crystallization in acetonitrile/hexane or acetonitrile/EtOAc, the small peak at 90oC disappeared, the moisture content dropped to 0.23%, and the pH changed to 5.88. After two months, the re-crystallized sample was retested for moisture content and found to be 0.18%. Therefore, there was a difference between the original and the re-crystallized salt in terms of purity and moisture content (originally thought to be hydrated and/or hygroscopic).

The TGA showed that this product was not thermally stable as 1.3% weight lost was observed between room temperature and 100oC Also the sample gave a residue of 10.3% at 400oC as compared to minimal residues for bupropion HCl and maleate. The Heat-Cool-Heat experiment was done by TA instrument showed a glass transition (Tg) at 45C. The Tg indicates that the morphology is amorphous rather than crystalline.

HBr: DSC showed melting endothermic peak at temperature 224oC, with a shoulder peak. The sample was run at different temperature rates, 1, 10, 15 & 20oC/min to seek for possible polymorphs. No significant differences were observed for the endothermic peak shape at different temperature rates. By-crystallization of the HBr salt in different solvents or by internal synthesis starting from 3-chloropropiophenone, no improvements in the shape of the endothermic peak melting at ~224oC was observed (i.e, still the same shoulder at 10oC or higher rates). A Heat-Cool-Heat experiment was done by TA instrument showed a glass transition (Tg) at 23oC.

The moisture content was 0.00% and the pH of the aqueous solution of 0.5% was 5.92.

Other salts: The DSC results of other salts show multiple melting endothermic peaks. The pH, and the water content of all of the salts are shown in Table 2.

A comparison of the solubility & other physical properties of bupropion HBr vs bupropion HCl is presented in Table 3.

Hygroscopicity of Bupropion HBr

Figure 1:
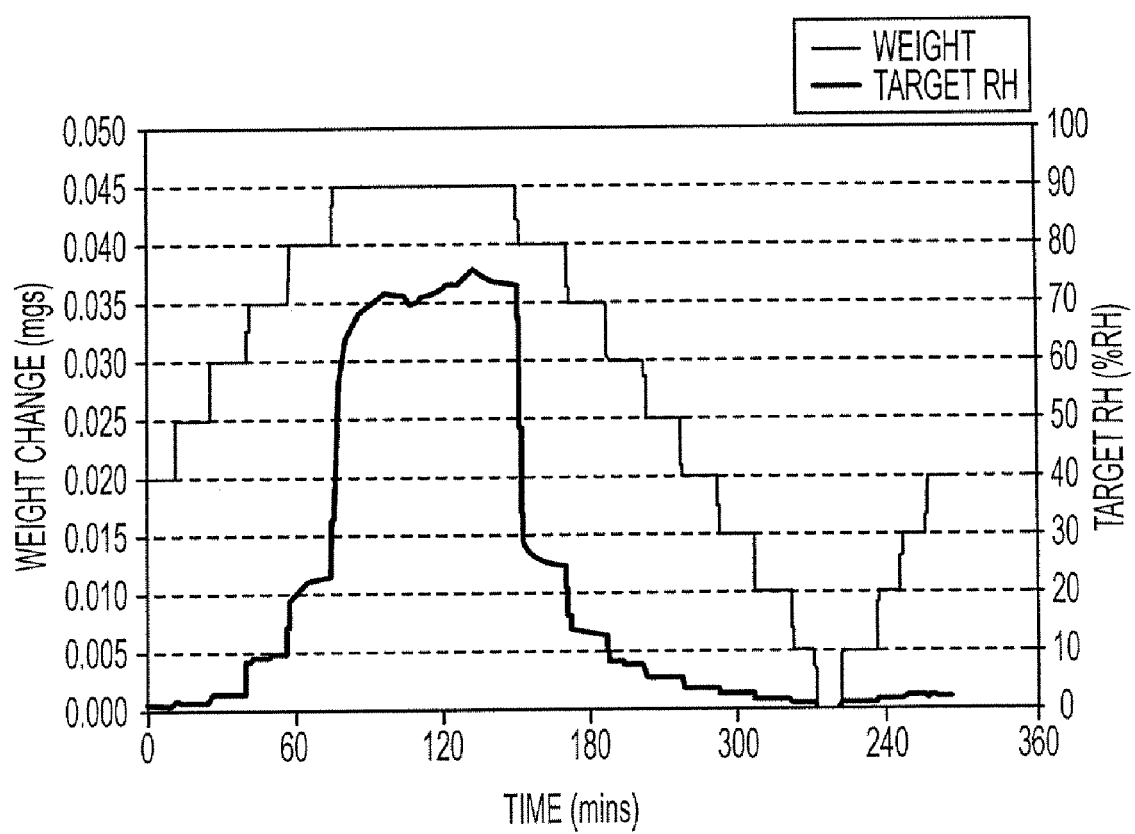
FIG. 1 shows a DVS profile for bupropion hydrobromide (HBr).
Figure 2:
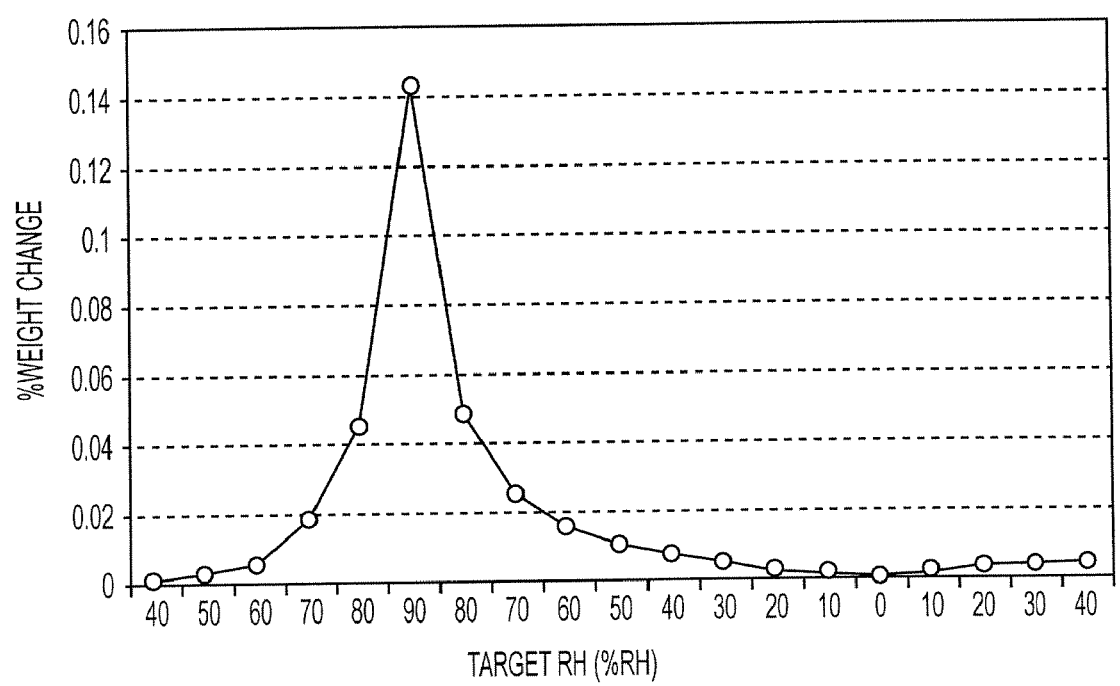
FIG. 2 shows DVS isotherm data for bupropion HBr.

The Dynamic Vapour Sorption (DVS) analysis of bupropion HBr suggests that the sample is a crystalline anhydrate and has very little water uptake capacity (i.e. non-hygroscopic). The sample of bupropion HBr shows no significant water uptake over the range 0% RH-90% RH. The maximum water uptake was measured at 0.14% weight at 90% RH. A DVS profile for bupropion HBr is shown in FIG. 1 and DVS isotherm data for bupropion HBr is shown in FIG. 2.

Example 3

Forced Degradation Stability Study

The samples of each salt and the spiked salts with the bupropion HCl XL were prepared under the conditions mentioned in Table 4. The samples were placed in the stability chamber at 40° C./75% RH, pulled out at 10, 20 and 32 days and analysed by HPLC for assay and impurities. The stability of the bupropion salts were evaluated based on the formation of the main degradation product 3-chlorobenzoic acid (3-CBZ) and the intermediate degradation products diketone 827U76 and the ketohydroxyl derivatives (20U78 and 852U77) (Scheme 2). The 3-chlorobenzoic acid is formed as a result of the oxidation/hydrolysis of the parent compound bupropion salts.

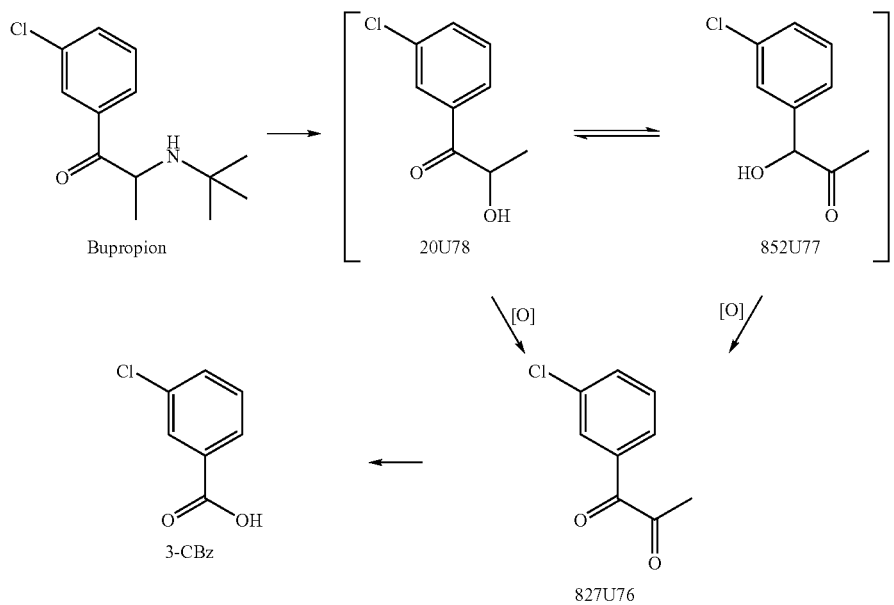

Scheme 2

As mentioned above, the stability samples were prepared in 2 mL vials and used directly for assay and impurity analysis by HPLC without further sample preparations to minimize errors.

The 10 days forced degradation studies on these salts showed that the succinate, tartrate and citrate (with or without mixing with excipients in closed vials) were not stable under the conditions mentioned in Table 4. The assay substantially dropped down, the level of known and unknown impurities increased and the colours of these salts changed from the original white powders to yellow semi liquid products. Therefore, further study on these salts was not continued.

Figure 4:
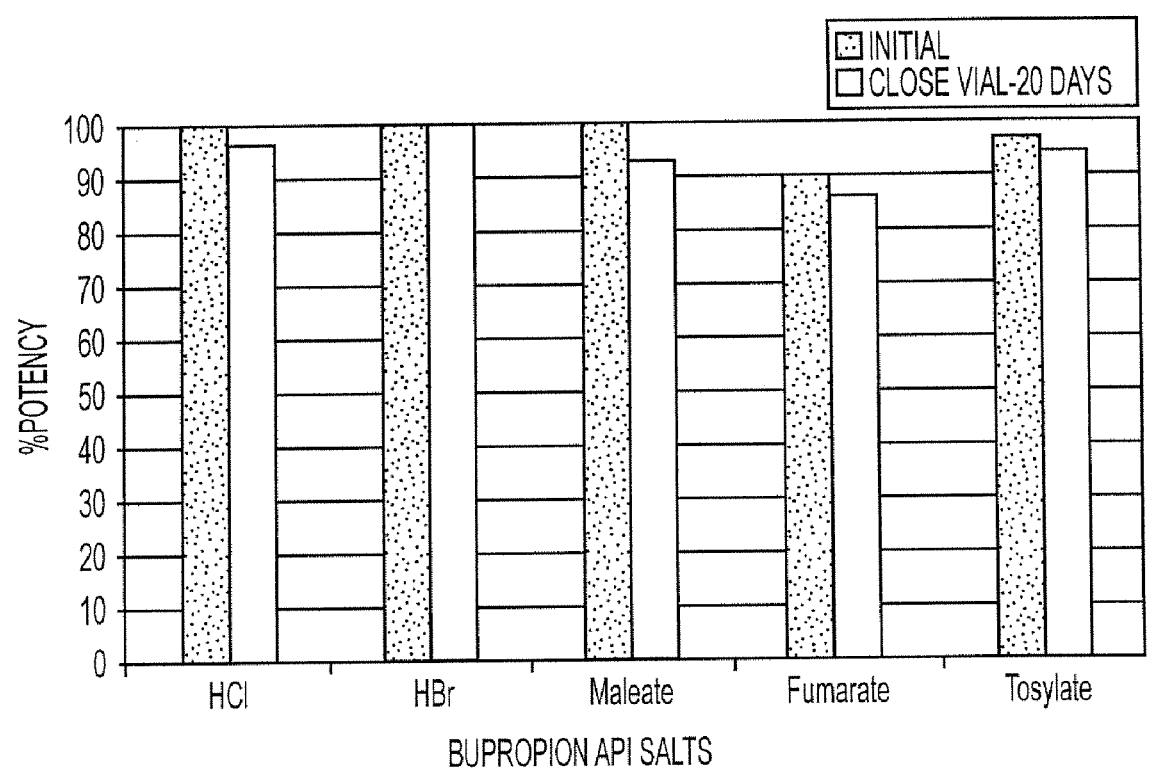
FIG. 4 is a bar graph showing the potency of the bupropion salts mixed with excipients after storage in closed vials over 20 days at 40° C./75% RH compared to their initial potency.
Figure 5:
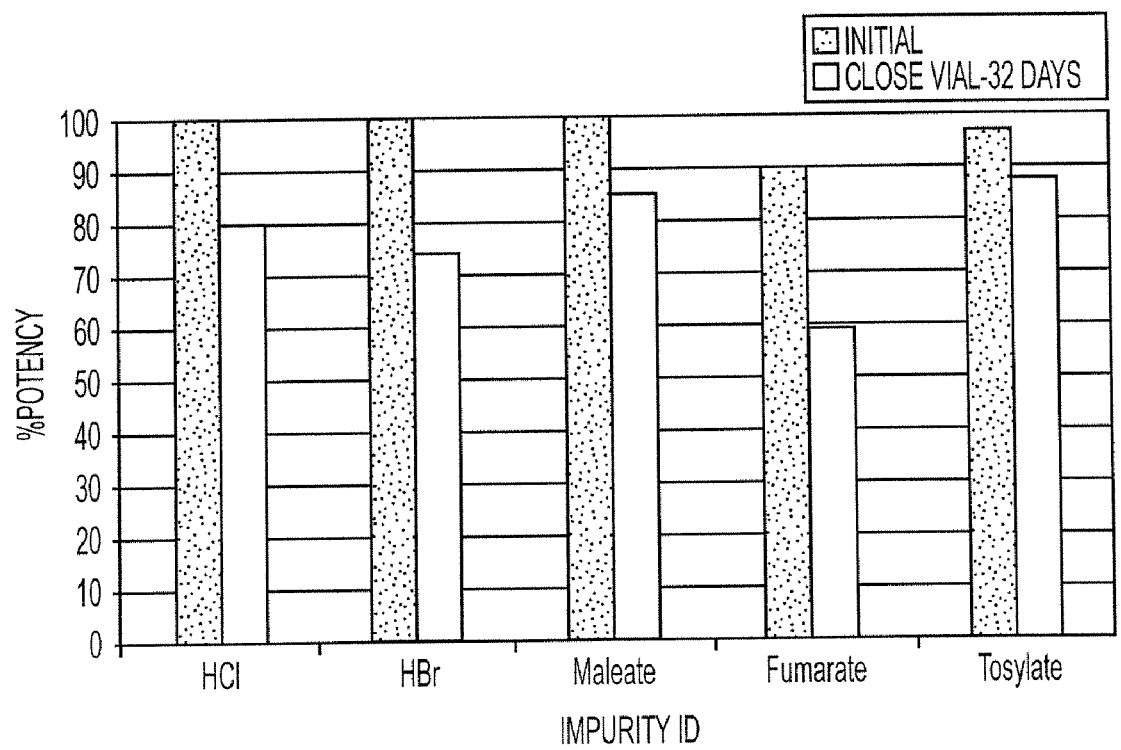
FIG. 5 is a bar graph showing the potency of the bupropion salts mixed with excipients and water after storage in closed vials over 32 days at 40° C. compared to their initial potency.
Figure 6:
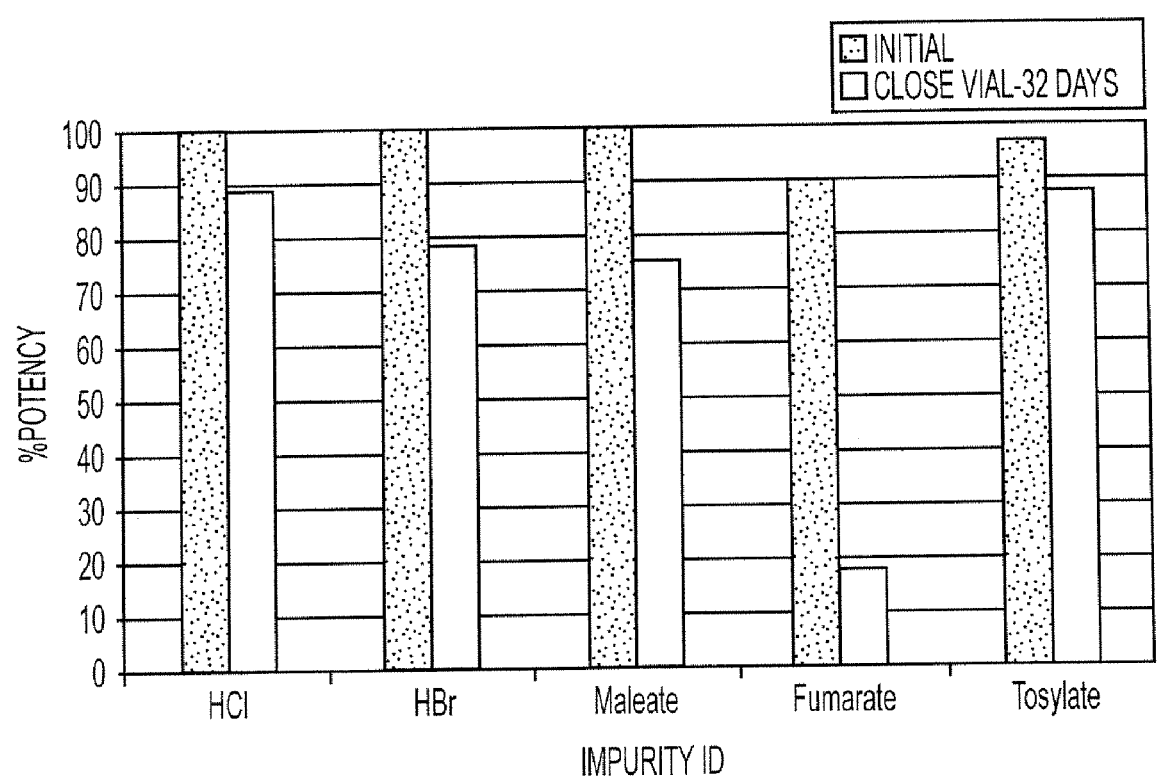
FIG. 6 is a bar graph showing the potency of the bupropion salts mixed with excipients, water, isopropyl alcohol and ethanol after storage in closed vials over 32 days at 40° C. compared to their initial potency.
Figure 7:
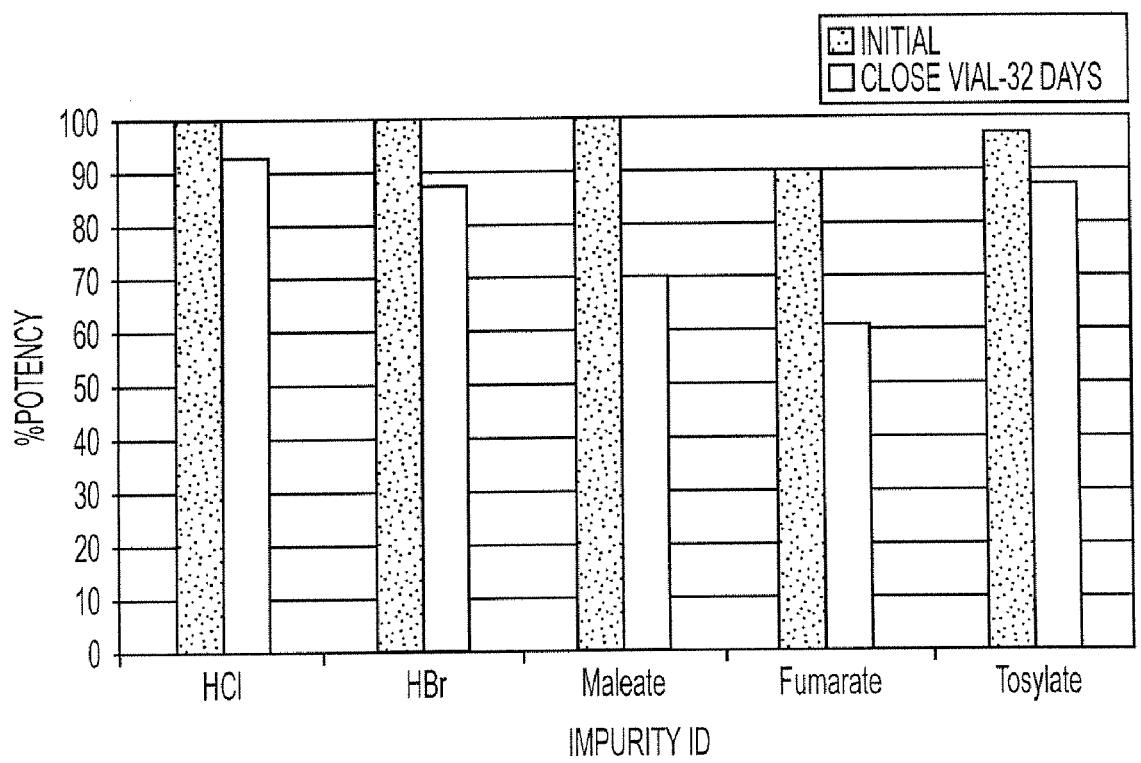
FIG. 7 is a bar graph showing the potency of the bupropion salts mixed with excipients, isopropyl alcohol and ethanol after storage in closed vials over 32 days at 40° C. compared to their initial potency.
Figure 8:
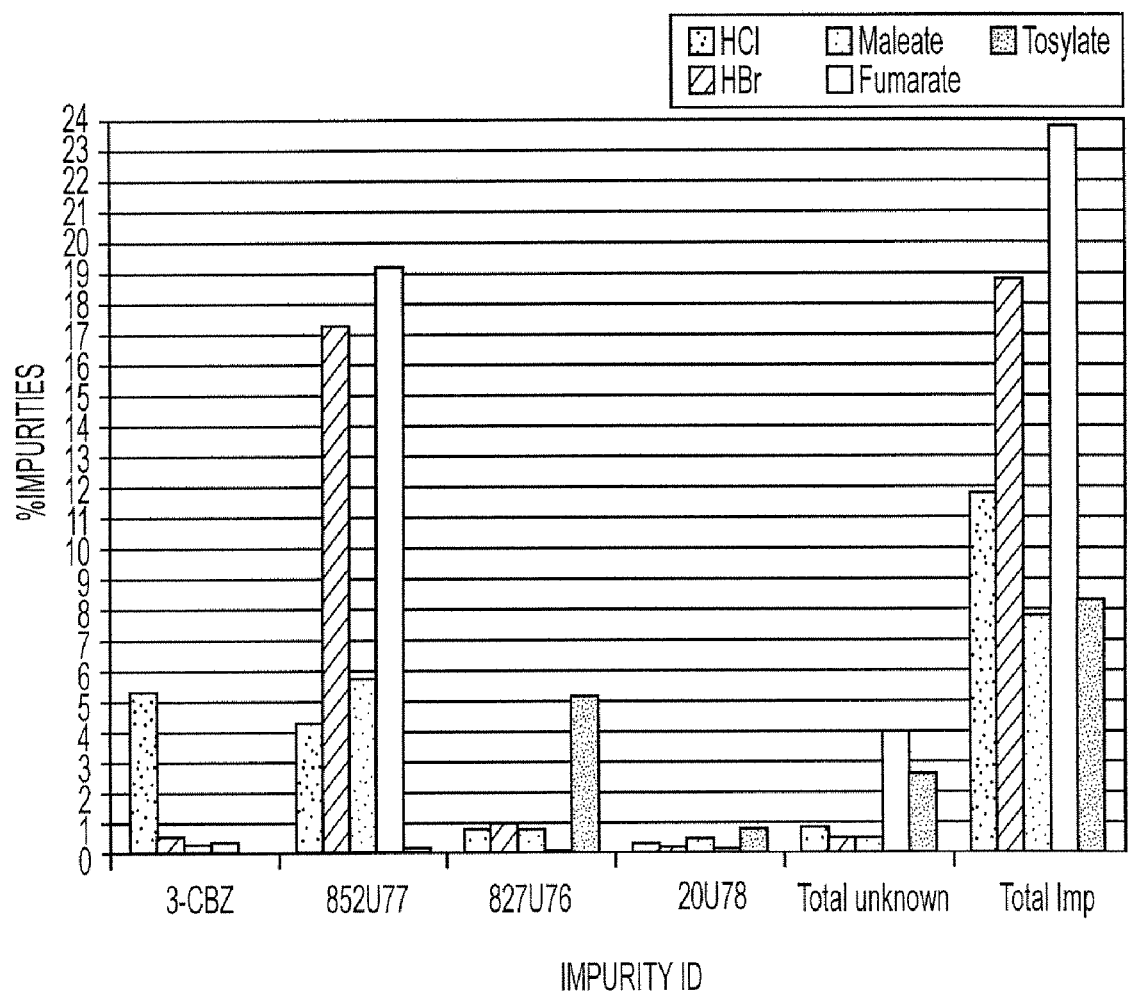
FIG. 8 is a bar graph showing the % impurities for the bupropion salts mixed with excipients and treated for 32 days in closed vials and spiked with water.
Figure 9:
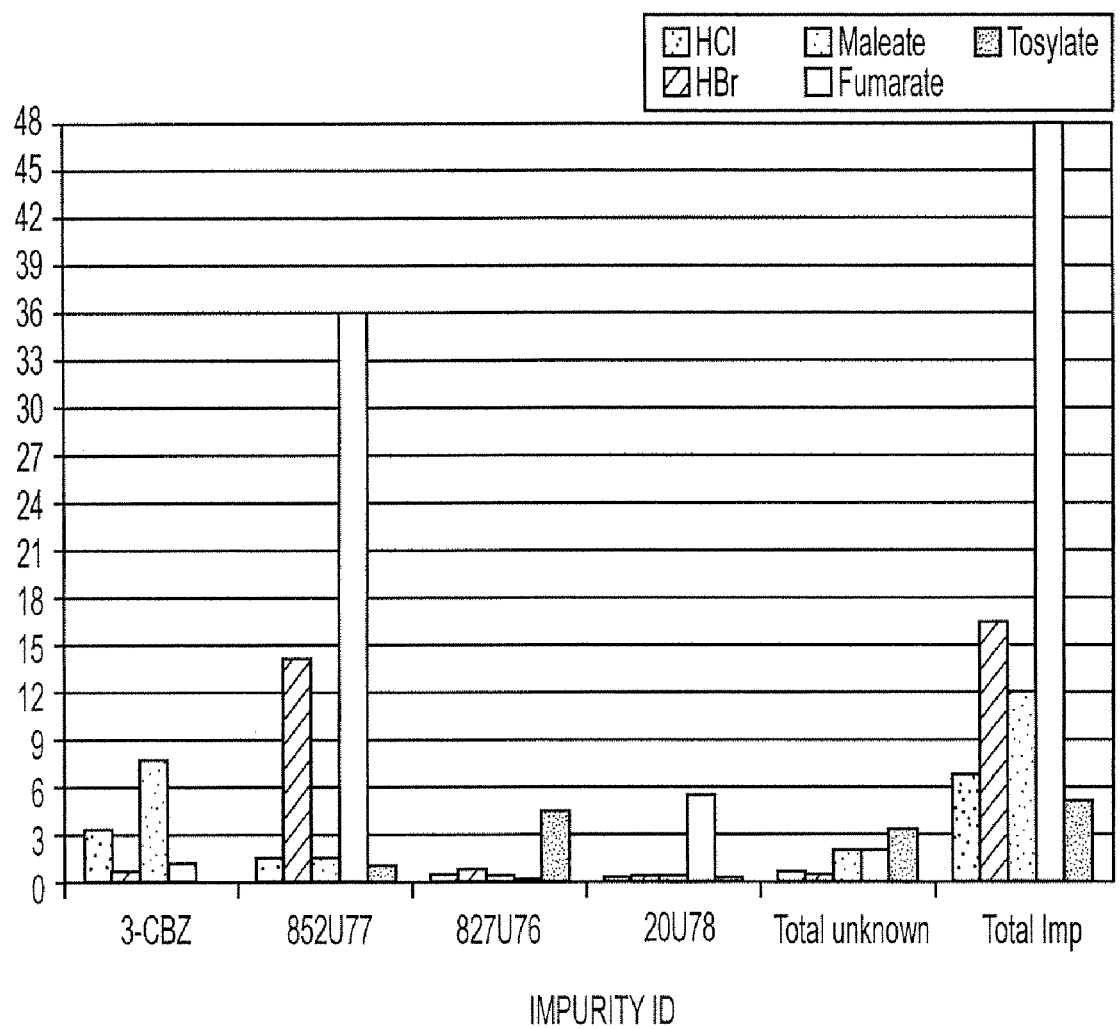
FIG. 9 is a bar graph showing the % impurities for the bupropion salts mixed with excipients and treated for 32 days in closed vials ans spiked with water, isopropyl alcohol (IPA) and ethanol (EtOH).
Figure 10:
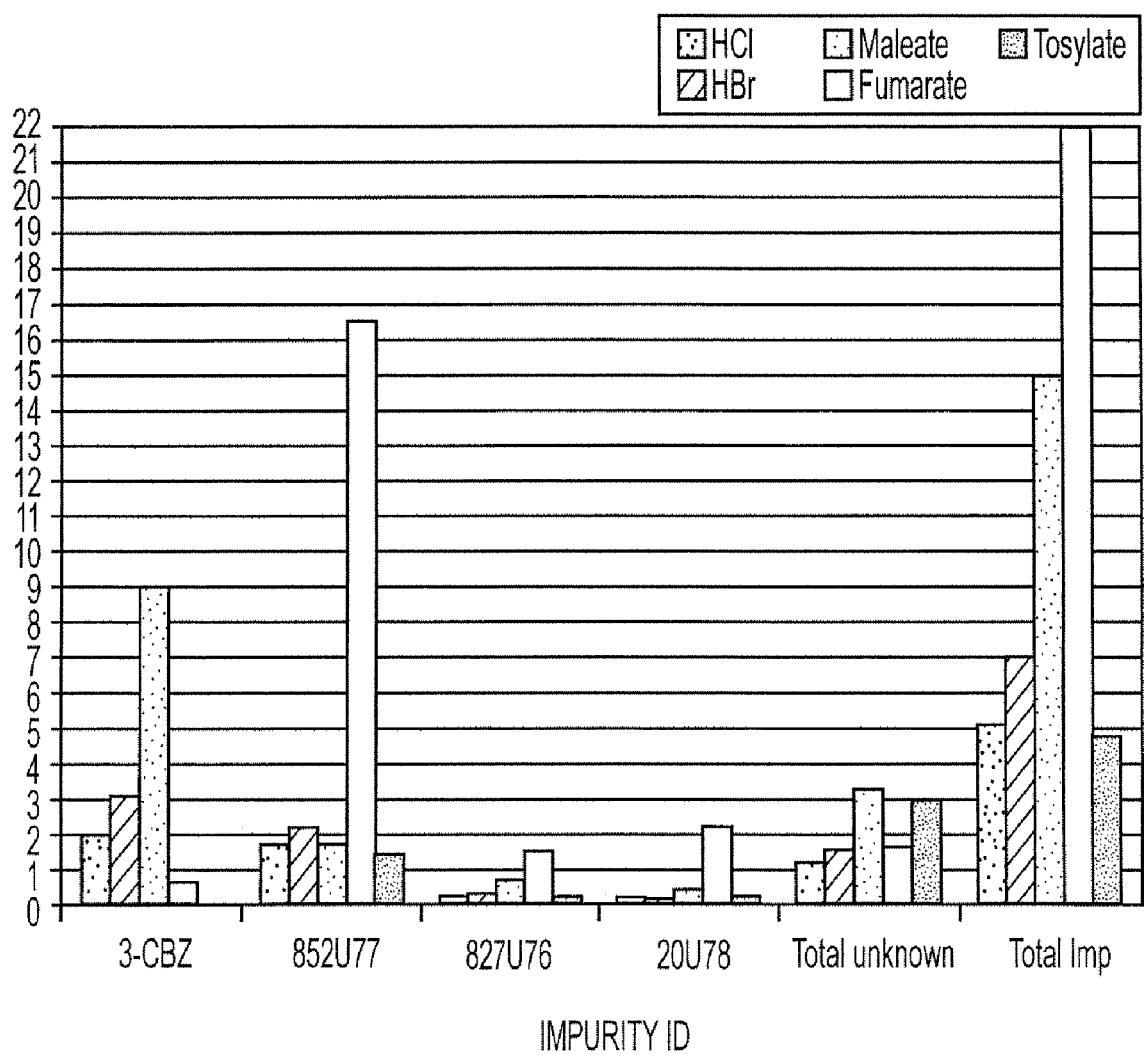
FIG. 10 is a bar graph showing the % impurities for the bupropion salts mixed with excipients and treated for 32 days in closed vials and spiked with isopropyl alcohol (IPA) and ethanol (EtOH).

The 10, 20 and 32 days stability time points for the maleate, tosylate, HBr, and fumarate salts were continued in parallel to Bupropion HCl. The results are shown in FIGS. 3-10. The assay and impurity results for 20-days in closed vials for these five salts were compared for salt plus excipients and are presented FIGS. 3 and 4. FIGS. 5-7 show the results for the drug salts (DS) kept for 32 days in closed vials and spiked with water, water-isopropyl alcohol (IPA)-ethanol (EtOH) and IPA-EtOH.

Figure 3:
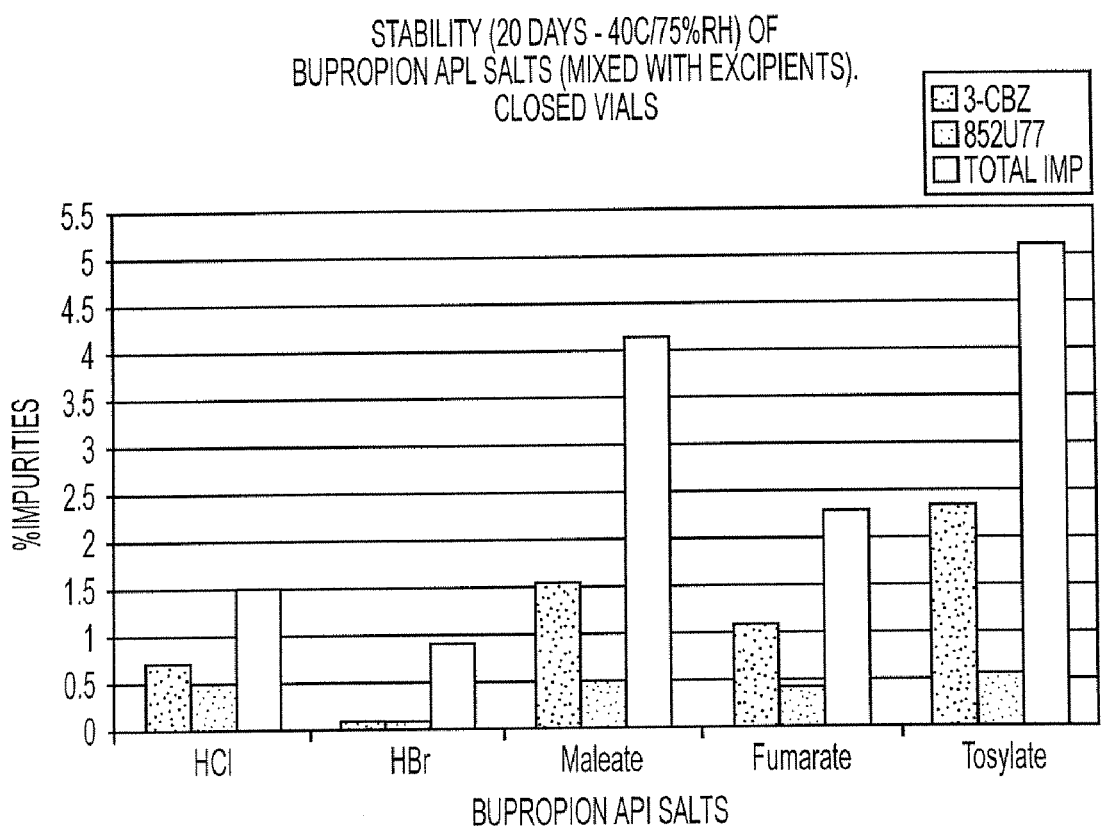
FIG. 3 is a bar graph showing the results of stability testing on the bupropion salts mixed with excipients in closed vials over 20 days at 40° C./75% relative humidity (RH).

In the closed vial assays, it is of note that the impurities (3-CBZ, 852U77 & total) in the HBr salt were the lowest compared to all of the other salts including HCl (see FIG. 3). The levels of 852U77 in the other salts were comparable with HCl, however, the levels of 3-CBZ and, in particular levels of the total impurities were more with the other salts than HCl. In the assay results (% potency), the tosylate and the HCl salts had similar potency after the 20 days in a closed vial (FIG. 4). In the assay study, the order of stability for the bupropion salts was as follows: HBr>HCl≈tosylate>fumarate>maleate).

The stability of the salts was then evaluated under more aggressive conditions. The drug salts (DS) and excipients were spiked with water, water plus EtOH and IPA and EtOH and IPA. As can be seen from the results shown in FIGS. 5-7, the order of stability (assay) of the salts can be summarised as follows:

Stability with water: tosylate>maleate>HCl>HBr>fumarate.
Stability with IPA & EtOH: HCl>HBr>tosylate>maleate>fumarate Tosylate and maleate salts were more stable than other salts when exposed directly to water, and less stable when exposed to the organic solvents IPA & EtOH.

The HCl and HBr salts were more stable than other salts when exposed directly to IPA & EtOH and less stable with water. The fumarate salt was neither stable in water nor in the organic solvents IPA & EtOH.

The level of the impurities (known, unknown & total) varied in each of the salts under the conditions of this experiment. The content of each of the major impurities (3CBZ & 52U77) and the total impurities was as follows (FIGS. 8-10):

In water, 3-CBZ: HCl>HBr≈maleate≈fumarate
852U77: fumarate>HBr>maleate>HCl
Total imp. fumarate>HBr>HCl>tosylate>maleate
In IPA/EtOH:
3-CBZ: maleate>HBr>HCl>Fumarate
852U77: fumarate>HBr≈HCl≈maleate≈tosylate
Total imp. fumarate>maleate>HBr>HCl>tosylate Based on the forced degradation stability studies conducted on the above bupropion salts, the stability of oxalate, citrate, succinate and tartarate were shown to be very poor for the DS and the spiked DS (20 days: discoloration, Low assay & high level of degradation impurities). The HBr, tosylate, maleate and to some extent fumarate salts are good candidates for further studies. Among the latter salts, HBr was the best candidate due to its superior stability in a closed container, lowest water content, non-hygroscopic and its easy preparation.

The tosylate salt also showed good stability, although it was not as pure as the HBr, HCl or maleate. The tosylate salt, however, does not have an acceptable toxicity profile.

It also was found that the presence of the organic solvents ethanol and isopropyl alcohol have significant impact on the stability of these salts.

Example 4

Comparative Forced Degradation Studies of Bupropion HCl and Bupropion HBr API Salts The stability of bupropion HCl and bupropion HBr API salts were further evaluated under the accelerated conditions of 40oC/75% RH in a stability chamber. The samples were exposed to the above conditions in a closed bottle for few days, and then subjected to HPLC analysis. The amount of the main degradation products present after treatment were compared with those amounts that were present initially.

Accurately quantities of each API were weighed individually in 50-mL amber glass bottles as shown in the Table 5. The bottles were closed and placed in the stability chamber at 40oC/75% RH. The samples were analysed after 14 and 24 days (study-1) and 10 days (study II), in a quantitative manner by direct treatment of the whole content of the bottle as per the HPLC standard test method (P05.901.10).

As shown in the Table 6, the resulting degradation products in both bupropion HCl and bupropion HBr were either similar or better for the HBr salt.

The above study was repeated on two batches of each of the APIs for 10 days. As shown in table 7, the level of impurities in the case of bupropion HBr salt was lower than bupropion HCl, also the assay value for the latter was lower than that for the HBr salt.

Example 5

Bupropion HBr Extended Release (XL) Tablets

The aim of this example was to describe the development of bupropion HBr XL (174 and 348 mg). Granulation, tabletting and coating procedures are all described thoroughly in this example. In vitro testing was conducted on the cores, the EC coated cores and the final coated tablets in order to determine which formulation gave the desired results.

From their structural formulae, it is observable that the difference between bupropion HCl and bupropion HBr is the salt. This, of course, results in a different molecular weight. However, these differences were taken into account in the present study, and modifications were made in order to obtain in vitro correlation results to the bupropion HCl using dissolution studies.

It was previously observed that when 150 mg of bupropion HCl was tested for its release of bupropion, the base value that was released was 130 mg. However, when 150 mg of bupropion HBr was tested, the base value released was only 112 mg. Thus, the amount of bupropion HBr had to be increased in order to increase the base value from 112 mg to 130 mg, which was the target. Studies showed that 174 mg of bupropion HBr gave a base value release of 130 mg and is therefore why 174 mg was used as opposed to 150 mg bupropion HBr.

Bupropion HBr XL—Granulation Process

Figure 11:
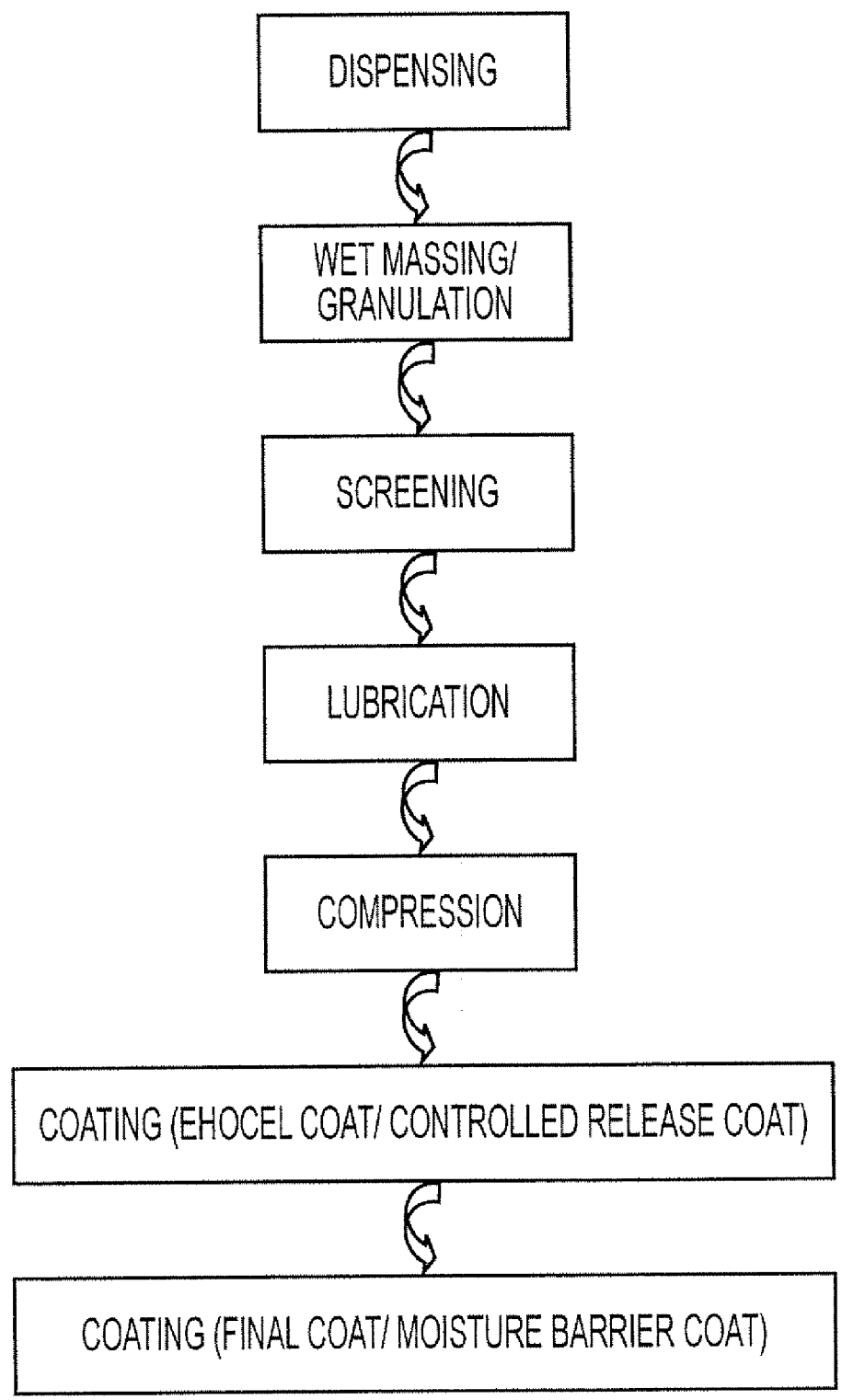
FIG. 11 is a flow chart showing the overall process for the development of bupropion HBr XL tablets.

A summary of the manufacturing process used for the preparation of bupropion HBr XL tablets is shown in FIG. 11.

The following materials were used in the granulation of the immediate release core of the bupropion HBr EA tablets: bupropion HBr, polyvinyl alcohol (PVA) and purified water. Once granulated, lubricant (Compritol 888) was added to complete the formulation.

Each Trial was divided into 5 parts. The percentage of API in each formulation was 93.75%; the percentage of PVA in each formulation was 3.125%. A summary of the breakdown of each trial per part is described in Table 8.

The PVA was dissolved into the purified water using a magnetic stirrer and a clear colourless solution was made.

Figure 12:
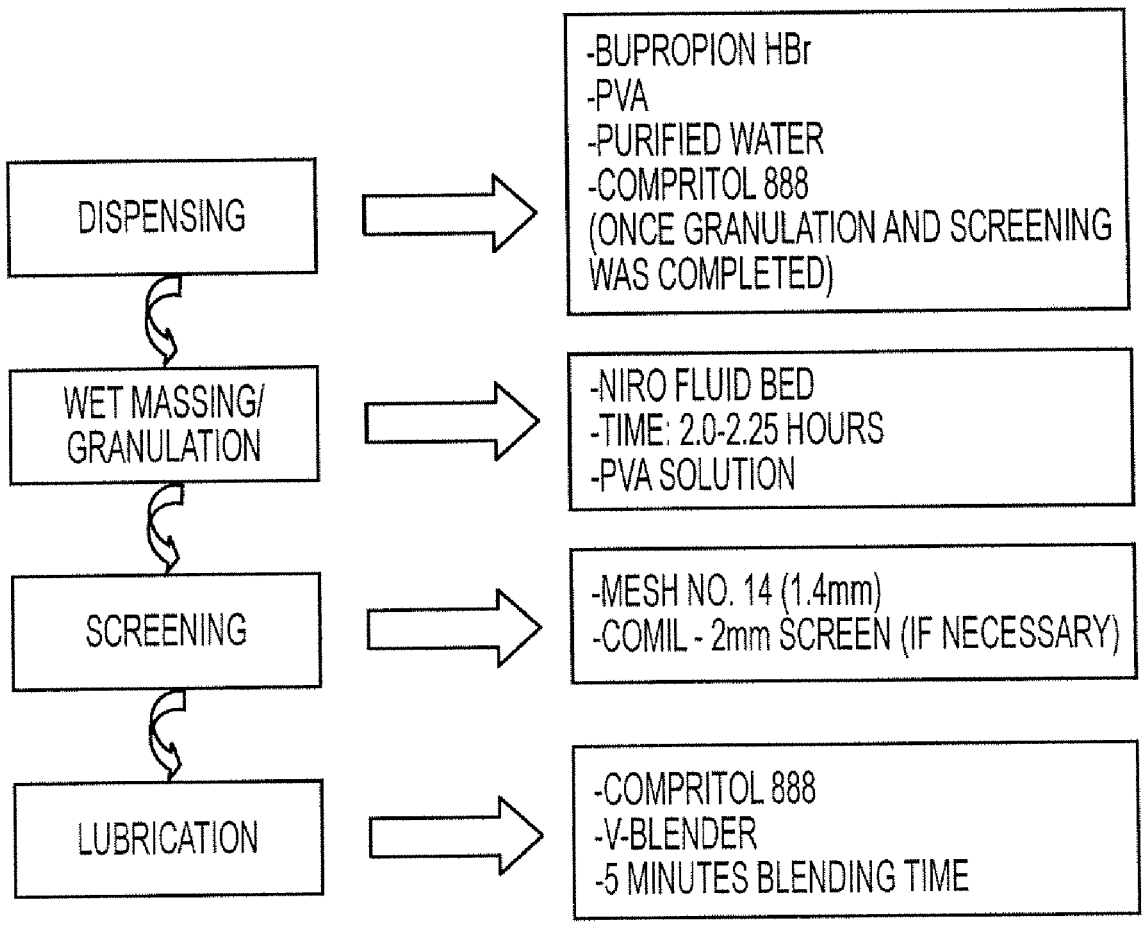
FIG. 12 is a flow chart demonstrating the granulation process of the bupropion HBr XL and EA tablets.

The NIRO Fluid Bed was used to granulate the bupropion HBr Granules with the PVA solution in a process known as wet massing. FIG. 12 shows a summary of the granulation procedure.

The Bupropion HBr was loaded into the fluid bed and granulation was initiated. The specifications that were used as guidelines are listed in Table 9.

Loss on Drying was determined after each granulation using the Moisture Analyzer. A 1 g sample was taken and loaded into the moisture analyzer. The sample ran for 5 minutes at a temperature of 105° C.

Upon completion of each batch part's granulation, the five parts were combined together. They were hand screened using Mesh No. 14 (1.4 mm) and any oversized granulation was passed through the Comil fitted with a 2 mm screen.

Compritol 888 was used as a lubricant in the formulation. The screened bupropion HBr granules and the Compritol 888 were loaded into the V-blender and were blended for 5 minutes. The Compritol 888 made up 3.125% of the formulation. The final granule batch size is described in Table 10.

Bupropion HBr XL—Tabletting Process

The Beta Press was used to compress the Bupropion HBr tablets. Depending on the dose of the tablet, 174 mg or 348 mg, different tooling sets were used. The 7 mm punches were used to compress the 174 mg tablets and 9 mm and 10 mm punches were used to compress the 348 mg tablets. Tooling was polished prior to each run.

The tablet weights were determined as being 185.6 mg for the 174 mg dose tablets and 371.2 mg for the 348 mg dose tablets. These adjustments to tablet weight were made in order to compensate for the fact that bupropion HBr was being used in place of bupropion HCl. The individual tablet weights had a control limit of±5%, and the average tablet weight had a control limit of±3% (using ten tablets).

A hardness tester was used to determine the load required to diametrically break the tablets (crushing strength) into two equal halves. A predetermined range set the specifications for hardness, which was 6.0-12.0 SC for both the 174 mg and 348 mg tablets.

Friability was determined using tablets that equaled a weight of 6.5 g in a friability tester for 4 minutes at 25 rpm. Tablets were de-dusted before and after testing. A weight loss of less than 0.8% was used as the criteria in order to accept or reject a batch.

Table 11 summarizes the specifications of the tablet press set-up. All the specifications were kept within the range and at the setting that was assigned, throughout all of the batches.

Table 12 summarizes the specifications that were kept constant throughout the compression of all the batches.

Figure 13:
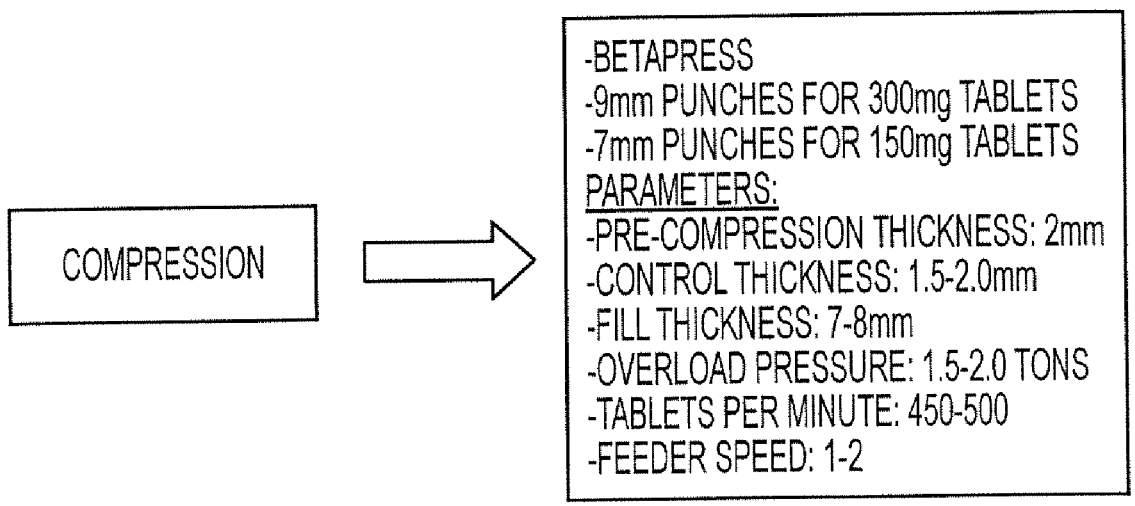
FIG. 13 is a flow chart showing the overall tabletting process of bupropion HBr XL.

The flow chart shown in FIG. 12 describes the steps that led up to and including the tabletting process. FIG. 13 shows a summary of the tabletting procedure.

Bupropion HBr XL—Coating Process

Figure 14:
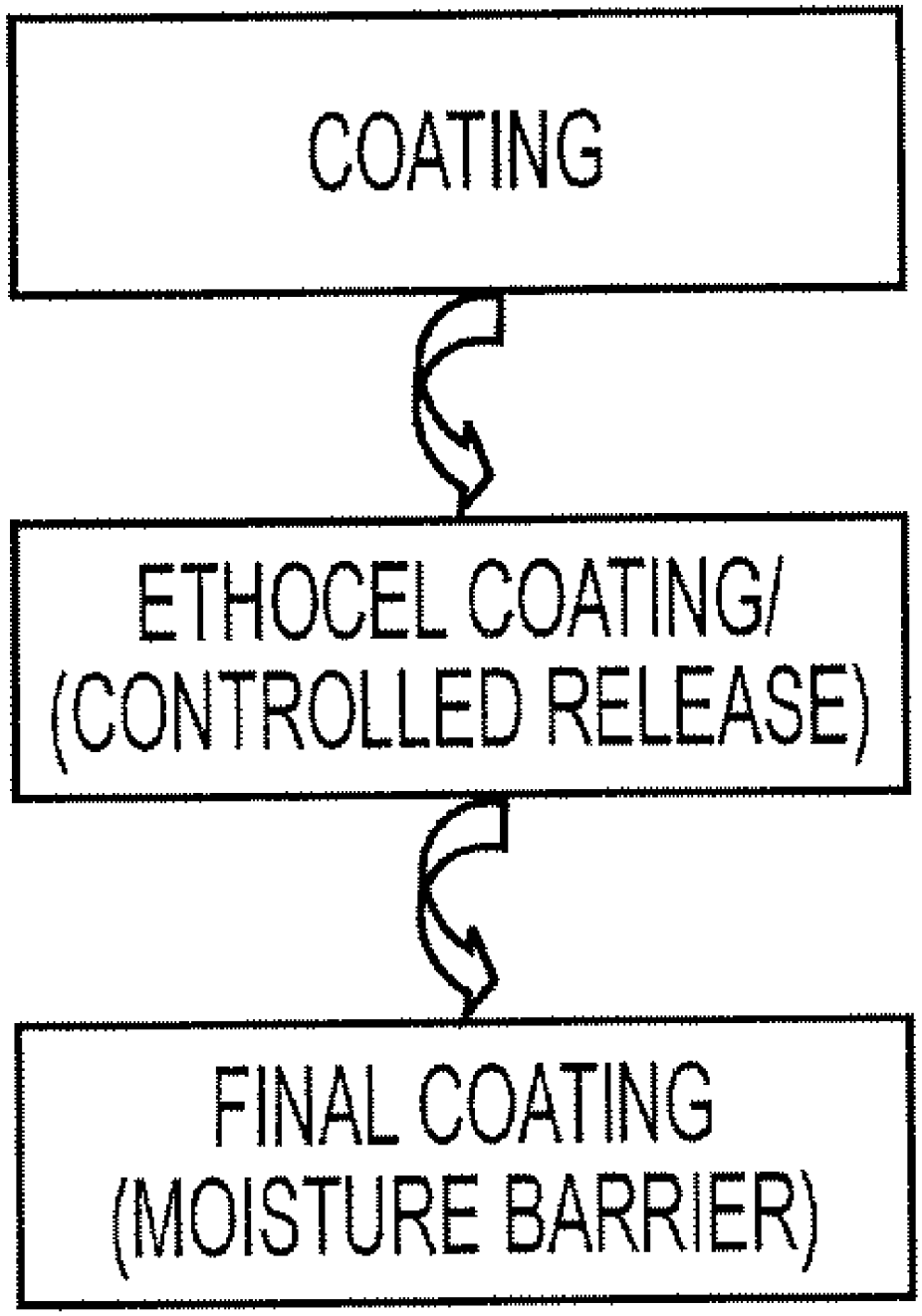
FIG. 14 is a flow chart showing the overall coating process of bupropion HBr XL.

A summary of the coating process used for the coating of the Bupropion HBr XL tablets is shown in FIG. 14. The first coat is an Ethocel coat that controls the release, which is followed by a final coat that acts as a moisture barrier.

For the Ethocel coating and final coating of the Bupropion HBr XL tablets, the 15 inches O'Hara Labcoat II System was used. An attached spraying nozzle and a propeller mixer were also used.

Several Ethocel coating solutions were developed and used to coat the Bupropion HBr tablets. The Ethocel coating layer was placed on the tablets containing one of the formulations listed in Table 13.

In formulation 1, ethyl Alcohol 95% and IPA 99% were combined together in a stainless steel container. While stirring, PEG 4000 was added and allowed to dissolve. Once dissolved, Ethocel was added and left to stir for 30 minutes. Then, Povidone was added to the solution and was mixed for an overnight period (15-20 hours).

In formulation 2, PEG4000 was placed into a beaker with the Dibutyl Sebacate and was stirred until it dissolved. Ethyl Alcohol 95% was added accordingly in order to allow the PEG 4000 to completely dissolve. In a separate stainless steel container, the remaining Ethyl Alcohol 95% was placed and, while being stirred, Ethocel was added and stirred for 30 minutes. Following that, Povidone was added and allowed to stir for an overnight period (15-20 hours).

In formulation 3, Ethyl Alcohol 95% was placed in a stainless steel container. While stirring, PEG 4000 was added and allowed to dissolve. Once dissolved, Ethocel was added and left to stir for 30 minutes. Then, Povidone was added to the solution and was mixed for an overnight period (15-20 hours).

Two Final coating solutions were developed and used to coat the Bupropion HBr tablets after they had been first coated with the Ethocel coat.

One of the following formulations shown in Table 14 was used to coat the tablets with a final coat.

In Formulation A, the purified water was placed in a glass beaker and Chroma-Tone DEB 5156-CLE was added and allowed to mix for 15 minutes. The Eudragit was passed through a Mesh screen (no. 60) prior to use. Following this, the Eudragit was added to the beaker and was stirred for 15 more minutes.

In Formulation B, part 1 of the Purified Water was placed into a glass beaker and PEG 4000 was added to it and allowed to mix until it was completely dissolved (5 minutes). The Triethyl Citrate was then added and left to mix for another 5 minutes. Once dissolved, the solution was then added to the Eudragit Suspension and left to stir for 45 minutes. The Eudragit was passed through a Mesh screen (no. 60) prior to use. In a separate beaker, part 2 of the purified water was added to the Syloid 244FP and mixed until it was completely dissolved (10 minutes). Finally the Syloid Suspension was added to the Eudragit Suspension and left to stir for another 10 minutes.

Table 15 summarizes the specifications that were monitored in the Ethocel coating process and their ranges.

Table 16 summarizes the specifications that were monitored in the final coating process and their ranges.

In-Vitro Studies on the Bupropion HBr Cores

Dissolution was performed on the Bupropion HBr cores, on the different weight gains of Ethocel coated cores and on the different weight gains of final coated tablets. USP-1 method was used to conduct these studies. The dissolution test was performed using 900 mL of 0.1N HCl and at a speed of 75 rpm. Samples were taken at every hour for 16 hours. The dissolution profiles were obtained by plotting the cumulative percent of API dissolved against sampling time points. Sink conditions were maintained throughout all the experiments.

On several trials, USP-3 method was used to conduct the dissolution studies. These dissolution tests were performed for 16 hours total with the following breakdown: 2 hours using 900 mL of Simulated Gastric Fluid (SGF) at pH 1.2 with 0.5% of Sodium Lauryl Sulfate (SLS), followed by 2 hours in 900 mL of Acetate Buffer at a pH of 4.5, followed by 12 hours in 900 mL of Phosphate Buffer Simulated Intestinal Fluid (SIF) at a pH of 6.8. These results were plotted with the in-vivo data and the Bupropion HCl data in order for a comparison to be made.

Study on Batch BUP-HBr-XL-009-5

Figure 15:
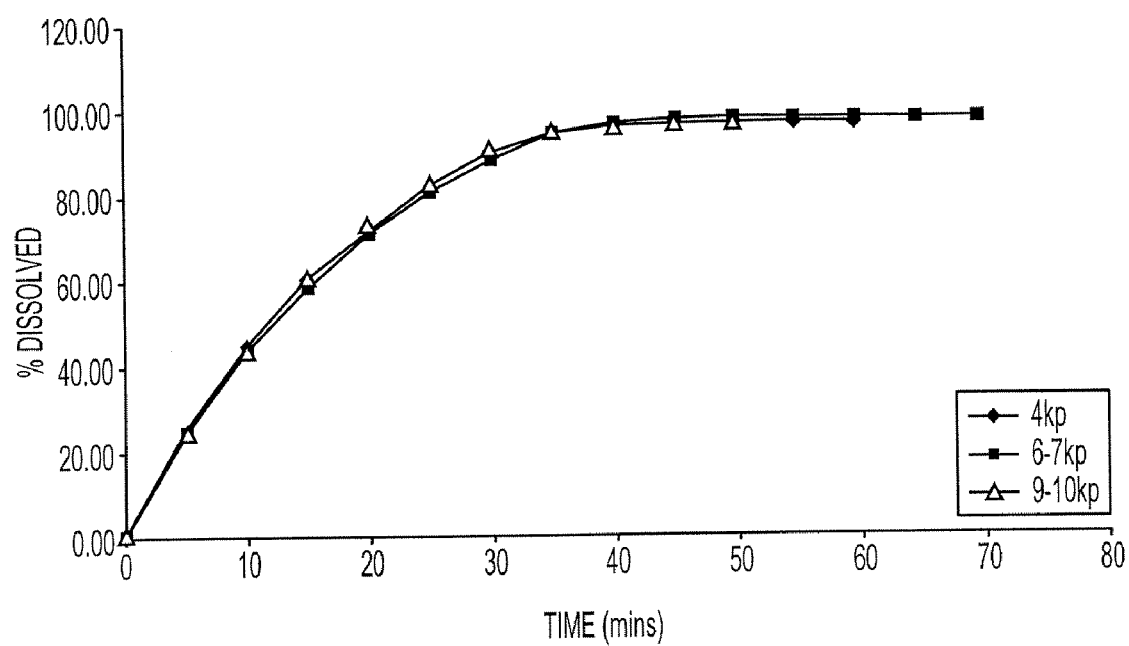
FIG. 15 is a dissolution profile of the 4 kp, 6-7 kp and 9-10 kp tablets, comparing the effects of hardness on dissolution in the study on Batch BUP-HBr-XL-009-5.
Figure 16:
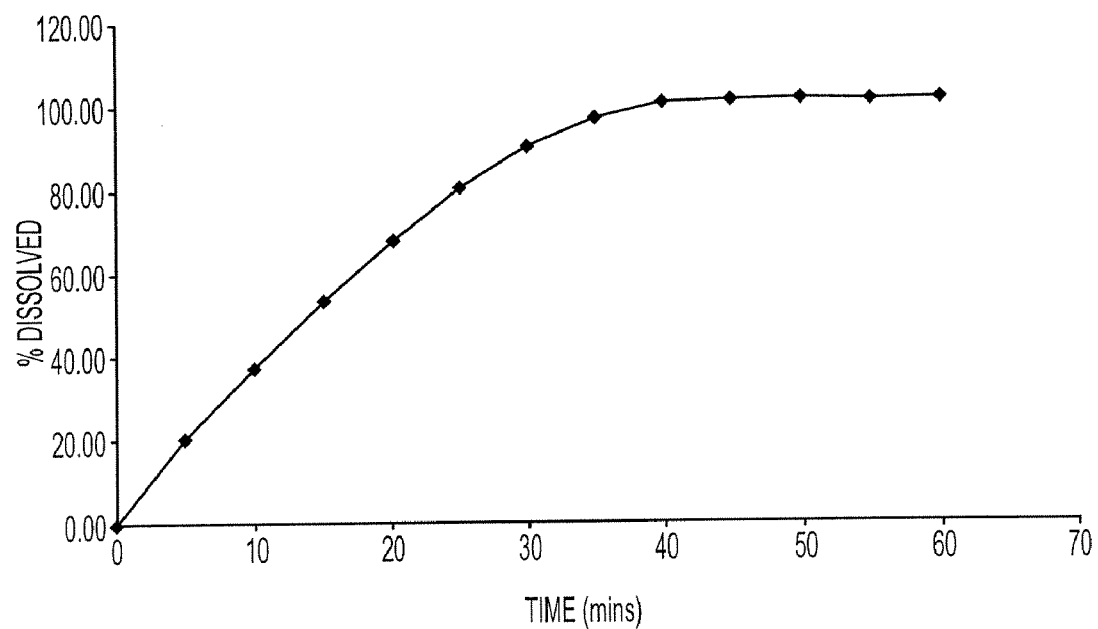
FIG. 16 is a dissolution profile of the 348 mg Bupropion HBr cores which have been compressed using 9 mm tooling in the study on Batch BUP-HBr-XL-009-5.

The formulation was granulated using NIRO Fluid Bed. After granulation was completed, the batch was screened and then prior to compression the lubricant (Compritol 888) was added. The final blend was compressed into 348 mg tablets using the Beta press with 9 mm and 10 mm standard, round, concave tooling. Table 17 describes the amounts of each material in the granulation of the 348 mg tablets. A first compression run was done to produce tablets with different hardness values so as to determine the effects of hardness, if any, on the dissolution (FIG. 15). Dissolution was conducted on the 348 mg cores in order to determine their release (FIG. 16).

The granulation results show that the average granulation time is 2.0 hours and the average LOD % is 0.345%. Tables 18 and 19 summarize the theoretical and actual values of the parameters that were monitored in the compression process using the 9 mm and 10 mm tooling, respectively.

In order to determine the tablet hardness for this study, tablets of different hardness values were compressed and dissolution was conducted on them to see the difference.

Tablets with a hardness of 4 kp, 6-7 kp and 9-10 kp were compressed and the dissolution profiles of each were shown in FIG. 15. It was observed that there was no significant difference between the three different hardness ranges.

The dissolution profiles of the 348 mg (FIG. 16) and 174 mg cores (FIG. 17) showed that the cores were releasing approximately 100 percent of API in an hour.

Figure 17:
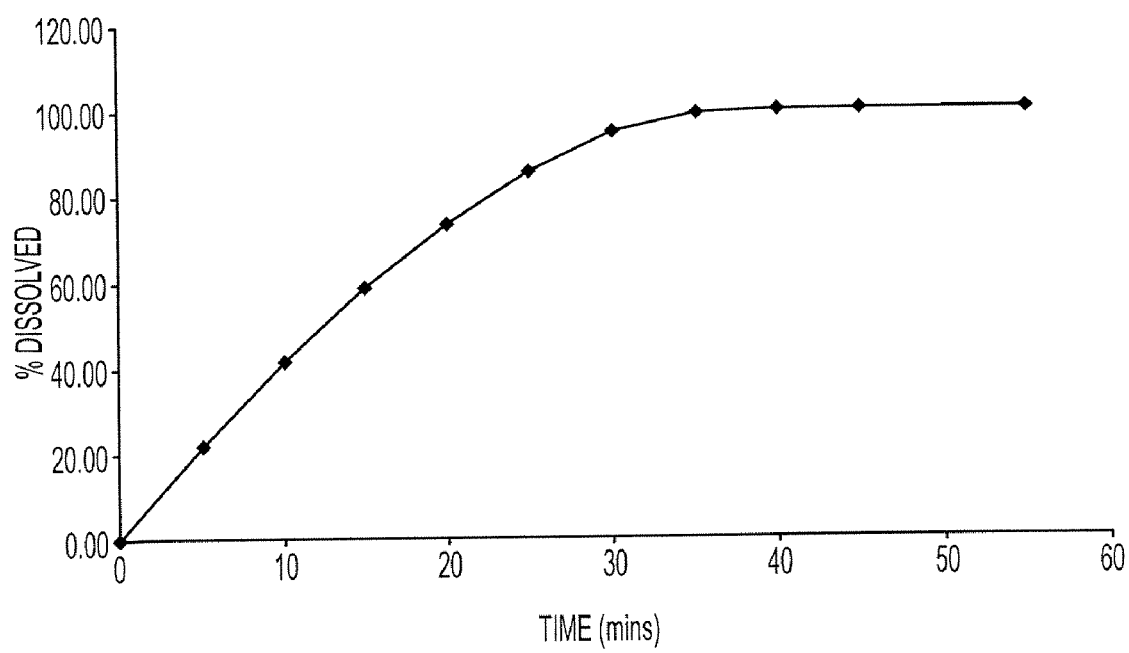
FIG. 17 is a dissolution profile of the 348 mg Bupropion HBr cores which have been compressed using 10 mm tooling in the study on Batch BUP-HBr-XL-009-5.

Dissolution of the 10 mm, 348 mg cores was done also in order to see if these tablets released faster when compared to the 9 mm cores due to their larger surface area (FIG. 17).

Figure 18:
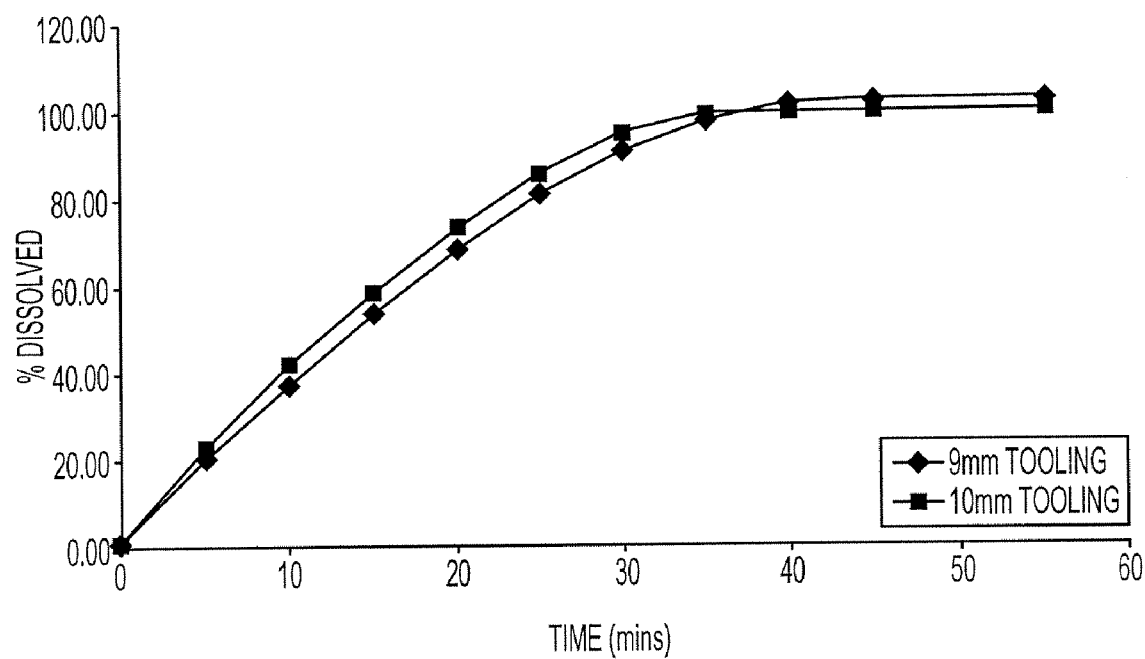
FIG. 18 is a dissolution profile comparison of the 9 mm and 10 mm diameter 348 mg Bupropion HBr cores in the study on Batch BUP-HBr-XL-009-5.

When the dissolution results of the 9 mm and 10 mm cores were compared (FIG. 18), the 10 mm cores showed no difference from the 9 mm cores. Thus, the 10 mm cores were no longer manufactured or used in this study.

Study on Batch BUP-HBr-XL-021-5

Figure 19:
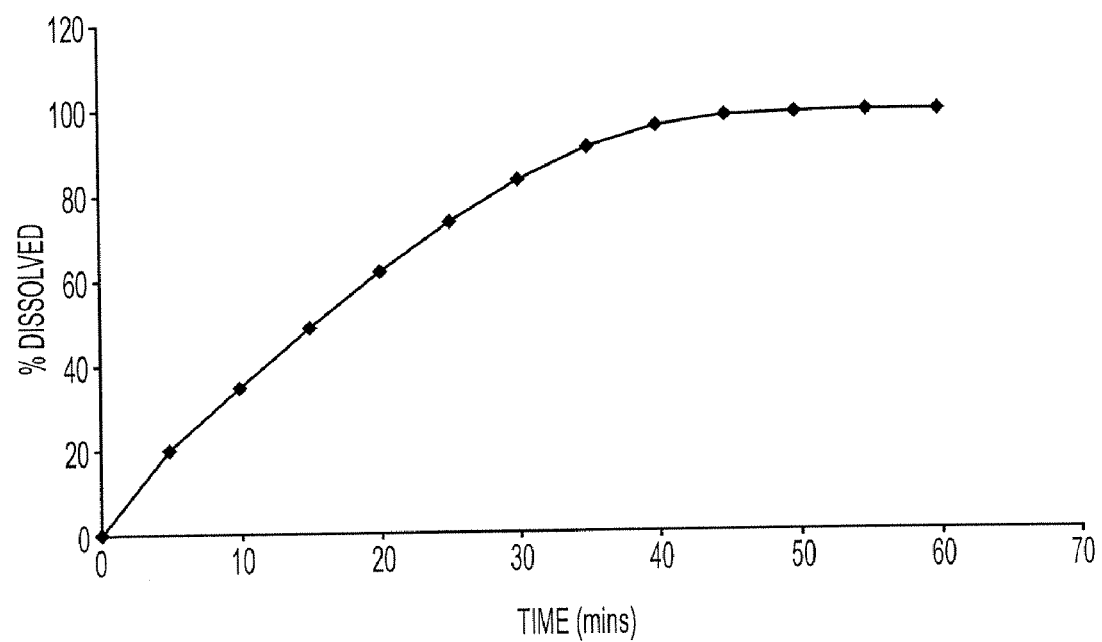
FIG. 19 is a dissolution profile of the 174 mg in the study on Batch BUP-HBr-XL-021-5.

The Formulation was granulated using NIRO Fluid Bed. The final blend was compressed into 174 mg tablets using the Beta press with 7 mm standard, round, concave, stainless steel tooling. Table 20 describes the amounts of each material in the granulation of the 174 mg tablets. It was noted that the 348 and the 174 mg tablets had the same composition and amounts of each material; the only variation was the tablet weight, which was adjusted at the compression stage. Dissolution was conducted on the 174 mg cores in order to see their release (FIG. 19).

The granulation results show that the granulation time is 2 hours 6 minutes and the average LOD % is 0.26%. Table 21 summarizes the theoretical and actual values of the parameters that were monitored in the compression process using the 7 mm tooling.

The dissolution profile of the 174 mg (FIG. 19) showed that the cores were releasing approximately 100 percent of API in an hour.

Study on Batch BUP-HBr-XL-348 mg-013-5

Using 348 mg tablets, an Ethocel coating followed by a Final coating, were sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 22.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 25 minutes to coat the tablets with a weight gain of 32 mg. Tablet weights were taken and recorded in Table 23 at 28 mg, 30 mg, 32 mg, and 34 mg weight gains.

Figure 20:
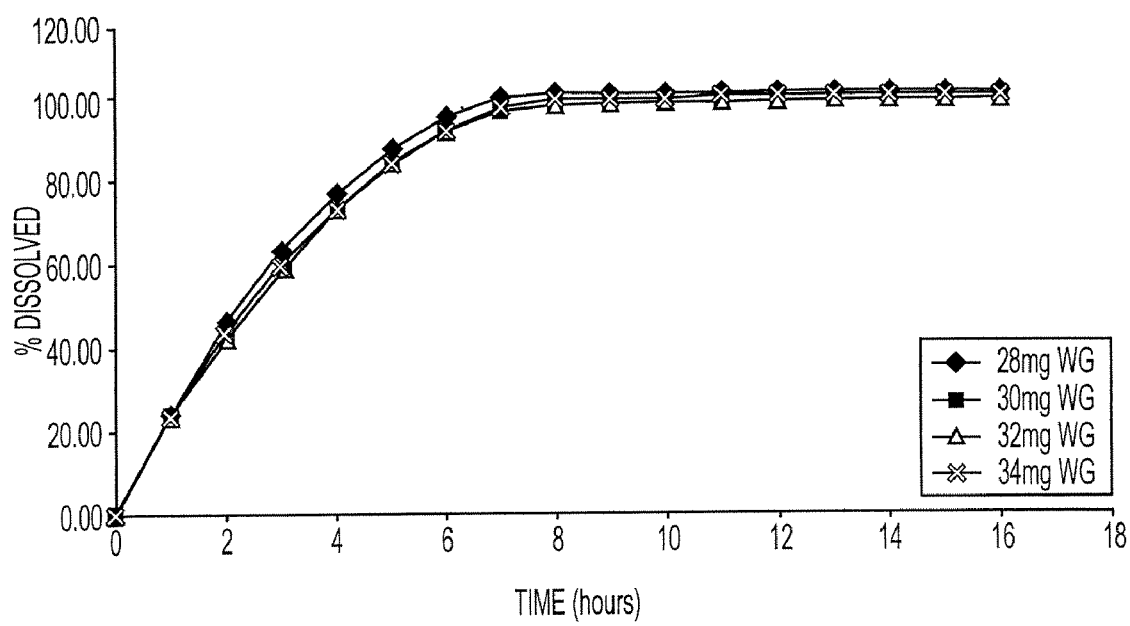
FIG. 20 is a dissolution profile of BUP-HBr-XL-348 mg-013-5 (28 mg, 30 mg, 32 mg and 34 mg weight gains).

The dissolution profile (FIG. 20) shows that the tablets with the 34 mg weight gain of EC coating released Bupropion HBr the slowest when compared to the others and that the tablets with the 28 mg weight gain released Bupropion HBr the fastest when compared to the other weight gains.

The materials used in the final coating, their percent contribution to the total solution, the amounts of each in the batch, the amount of solid contribution in grams and the percentage of the solids in the solution were all listed in Table 24.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

After this trial run, Chroma-Tone was no longer used due to the formulation problems it caused. First, it limited the composition of the formulation due to its inflexibility, as Syloid, PEG and Triethyl Citrate ratios could not be varied. Second, the solution foamed and coagulated, which in turn caused the process for making the coating solution to be changed from the original so that it did not re-coagulate. Chroma-Tone can, however, still be considered an option for the formulation but different grades and mixtures would need to be used and made in order to accommodate the Bupropion HBr XL tablets.

It took 31 minutes to add a 7 mg weight gain of the final coating solution to the tablets.

Tablet weights were taken and recorded in Table 25 at 4 mg, 5 mg, 6 mg and 7 mg weight gains.

Figure 21:
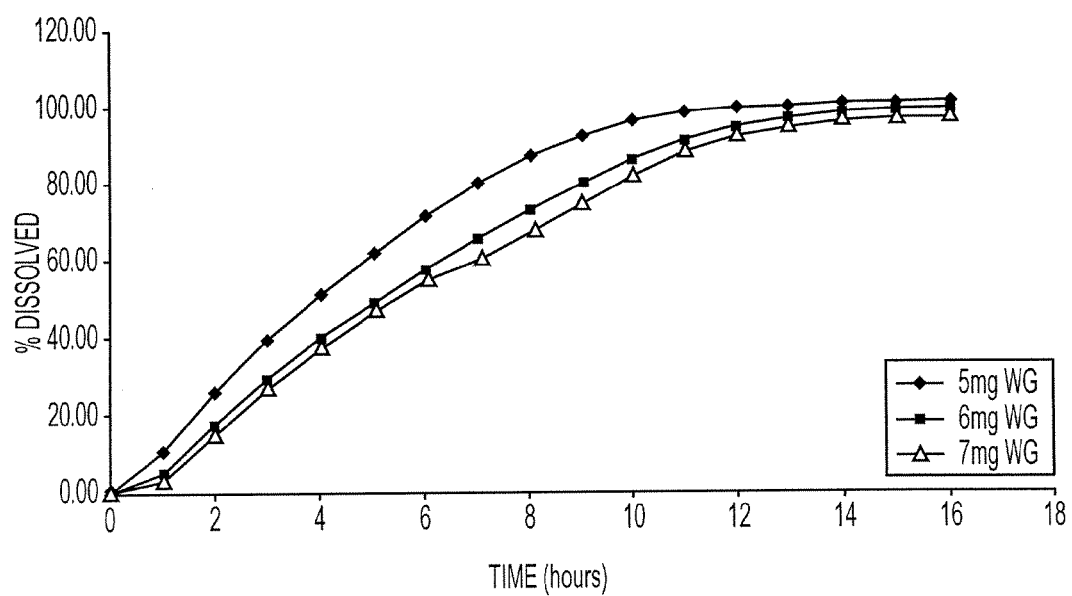
FIG. 21 is a dissolution profile of BUP-HBr-XL-348 mg-013-5 (5 mg, 6 mg, and 7 mg weight gains).

The dissolution profile (FIG. 21) shows that the tablets with the 7 mg weight gain of Final coating released the slowest when compared to the other two weight gains (5 mg and 6 mg weight gains).

Study on Batch BUP-HBr-XL-348 mg-018-5

Using 348 mg tablets, an Ethocel coating followed by a final coating, were sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 26.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

The coating process of this trial took 2 hours and 13 minutes to obtain a 32 mg weight gain. Tablet weights were taken and recorded in Table 27 at 26 mg, 28 mg, 30 mg, and 32 mg weight gains.

Figure 22:
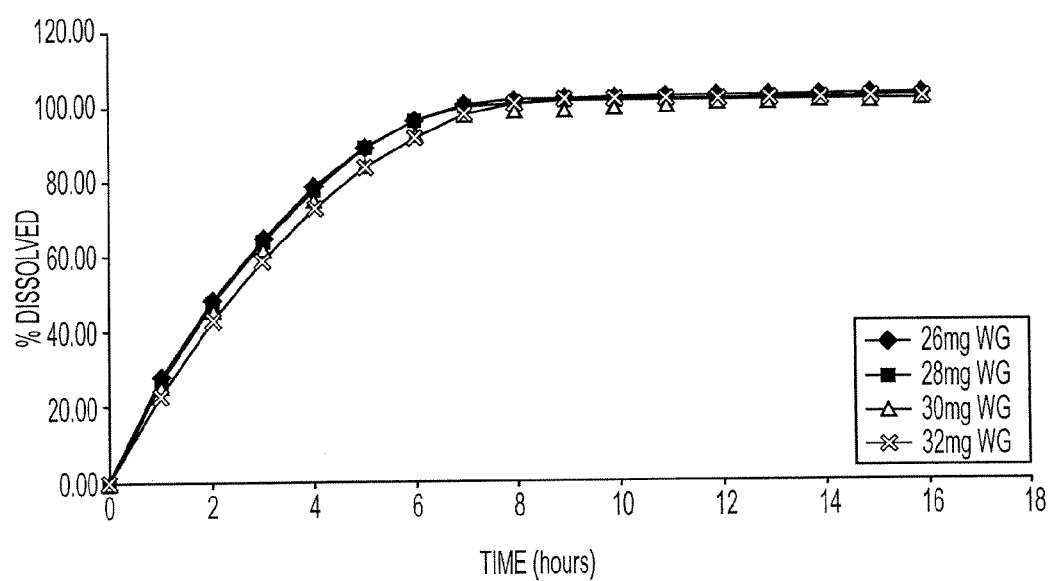
FIG. 22 is a dissolution profile of BUP-HBr-XL-348 mg-018-5 (26 mg, 28 mg, 30 mg and 32 mg weight gains).

FIG. 22 shows that the tablets with the 30 mg and 32 mg weight gain of EC coating solution released at almost the same rate. The tablets with the 32 mg weight gain released slower than the tablets with the 30 mg weight gain in the first 5 hours of dissolution. After 6 hours, the tablets with the 32 mg weight gain released slightly faster than those with a 30 mg weight gain. The f2 similarity factor confirmed that the release rate of both weight gains was similar (91.32%).

The materials used in the final coating, their percent contribution to the total solution, the amounts of each in the batch, the amount of solid contribution in grams and the percentage of the solids in the solution were all listed in Table 28.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 41 minutes to add a 7 mg weight gain of the final coating solution to the tablets. Tablet weights were taken and recorded in Table 29 at 4 mg, 5 mg, 6 mg, and 7 mg weight gains.

Figure 23:
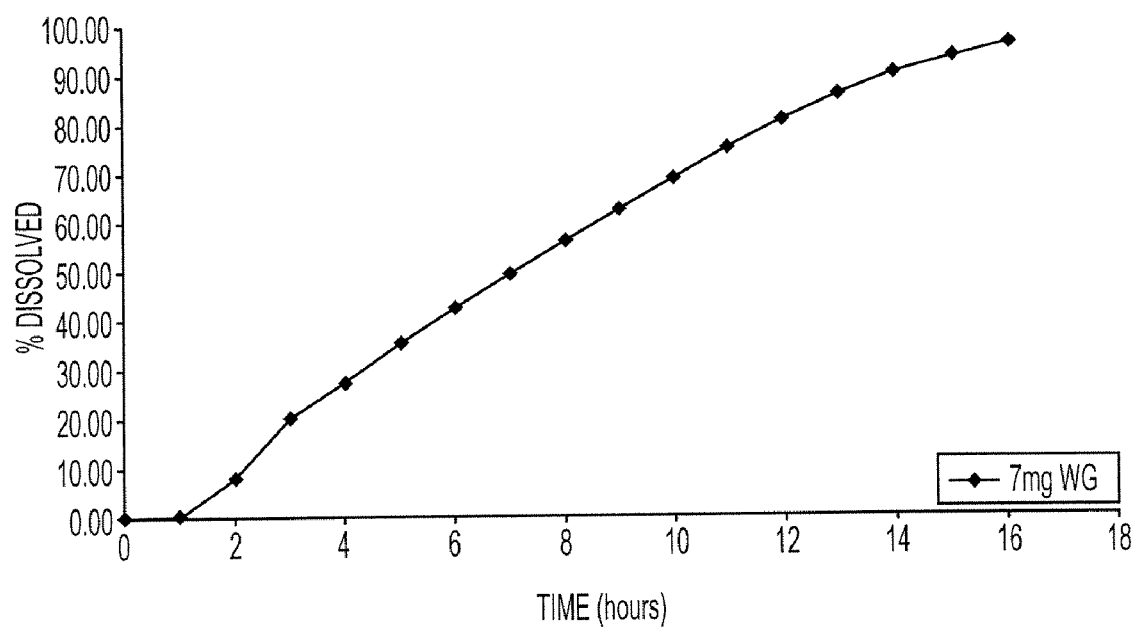
FIG. 23 is a dissolution profile of BUP-HBr-XL-348 mg-018-5 (7 mg weight gain).

FIG. 23 shows the release profile of the tablets with the 7 mg weight gain of Final coating.

Study on Batch BUP-HBr-XL-174 mg-022-5

Using 174 mg tablets, an Ethocel coating followed by a final coating, were sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 30.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 4 hours and 30 minutes to add a 30 mg weight gain of the EC coating solution to the tablets. Tablet weights were taken at 20 mg, 22 mg, 24 mg, 26 mg, 28 mg, 29 mg, and 30 mg weight gains and were recorded in Table 31.

Figure 24:
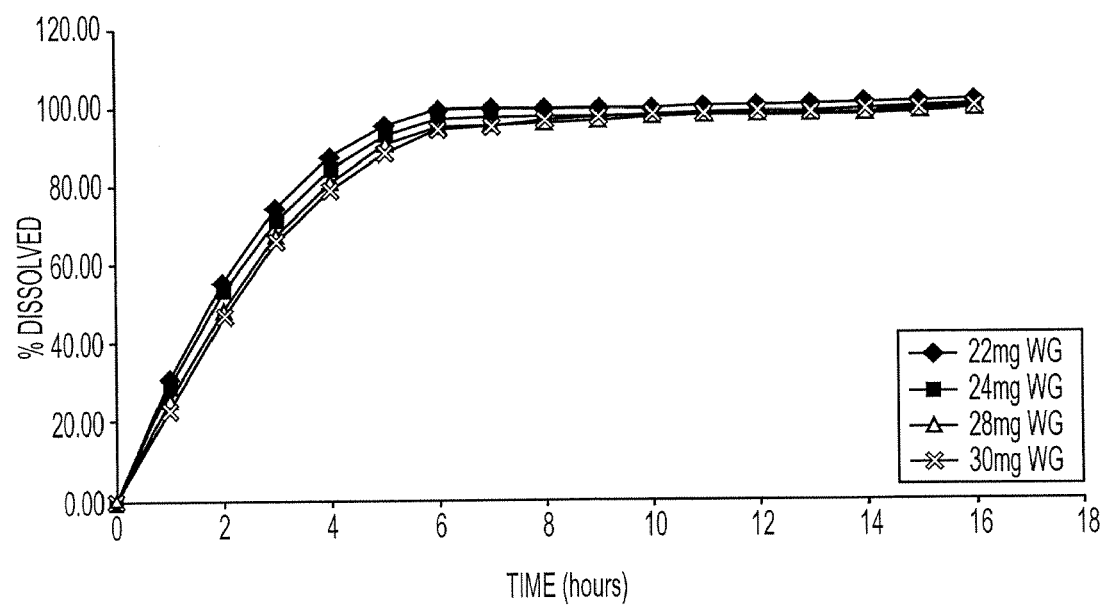
FIG. 24 is a dissolution profile of BUP-HBr-XL-174 mg-022-5 (22 mg, 24 mg, 28 mg and 30 mg weight gains).

FIG. 24 shows the % dissolved of each of the samples with different weight gains of EC coating (22 mg, 24 mg, 28 mg and 30 mg weight gains). From the graph, it was evident that the tablets with the 30 mg weight gain of EC coating released slower than the other weight gains. When the release rates of the tablets with the 30 mg and the 28 mg weight gains were compared, there was only a slight difference noticed in the release. The f2 similarity factor confirmed the similarity of the two releases (92.34%).

The materials used in the final coating, their percent contribution to the total solution, the amounts of each in the batch, the amount of solid contribution in grams and the percentage of the solids in the solution were all listed in Table 32.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 1 hour and 26 minutes to add a 7 mg weight gain of the final coating solution to the tablets. Tablet weights were taken and recorded in Table 33 at 4 mg, 5 mg, 6 mg, and 7 mg weight gains.

Figure 25:
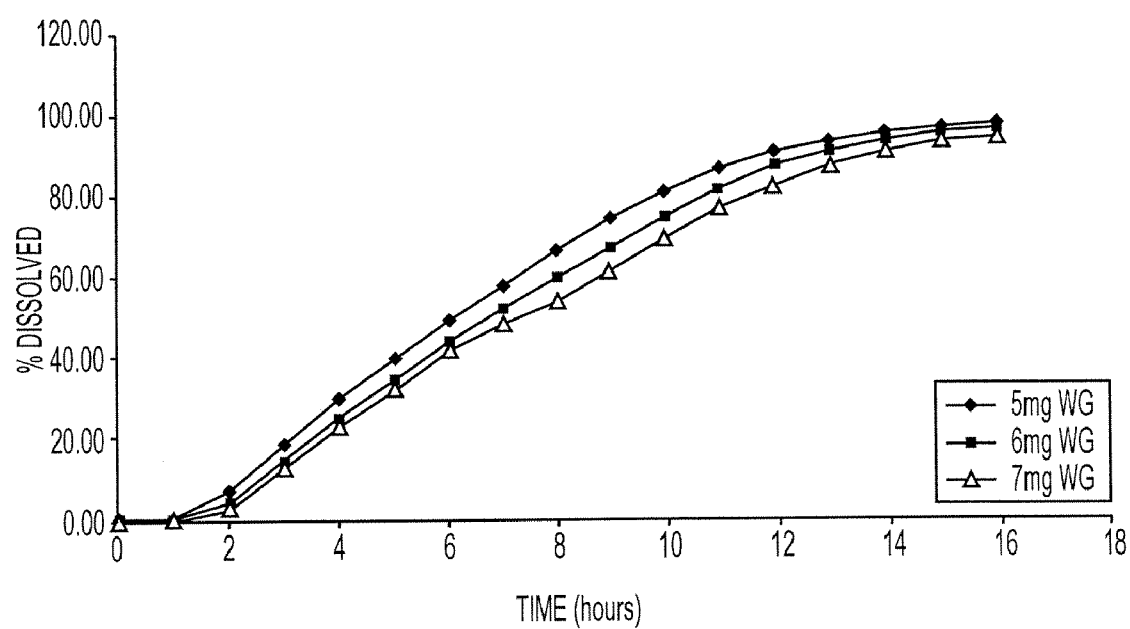
FIG. 25 is a dissolution profile of BUP-HBr-XL-174 mg-022-5 (5 mg, 6 mg, and 7 mg weight gains).

The dissolution profile (FIG. 25) shows that the tablets with the 7 mg weight gain of final coating released the slowest, in comparison to the 5 mg and the 6 mg weight gains.

Study on Batch BUP-HBr-XL-348 mg-023-5

Using 348 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 34.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 16 minutes to add a 32 mg weight gain of the EC coating solution to the tablets. Tablet weights were taken at 26 mg, 28 mg, 30 mg, and 32 mg weight gains and were recorded in Table 35.

Figure 26:
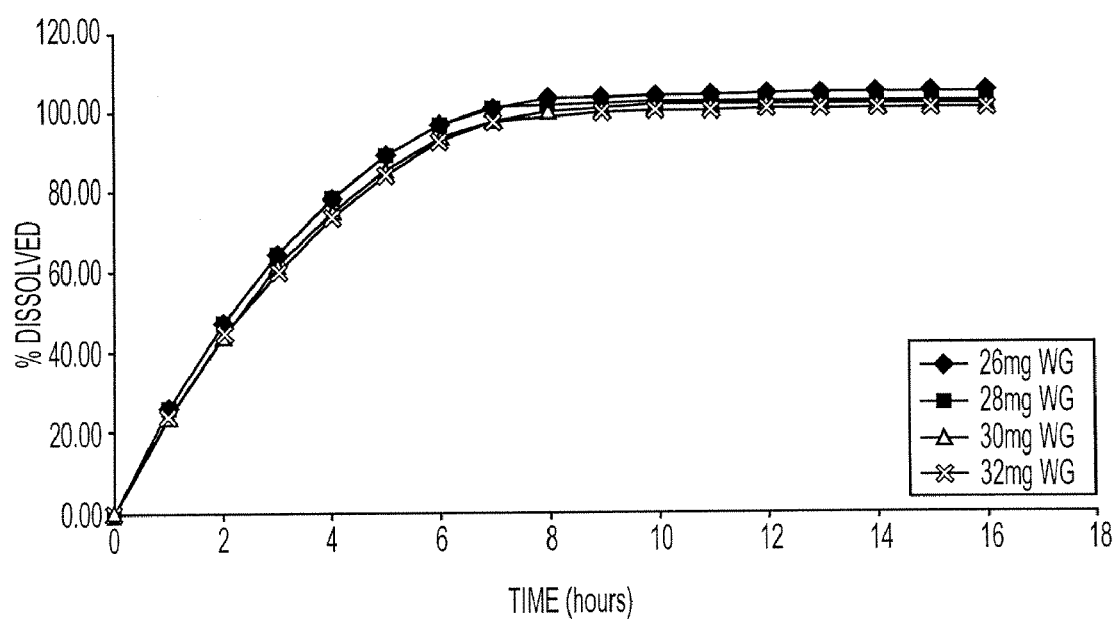
FIG. 26 is a dissolution profile of BUP-HBr-XL-348 mg-023-5 (26 mg, 28 mg, 30 mg and 32 mg weight gains).

The dissolution profile (FIG. 26) shows that the tablets with the 32 mg weight gain of EC coating, when compared to the tablets with the 26 mg, 28 mg and the 30 mg weight gain of EC coating, released at the slowest rate.

Study on Batch BUP-HBr-XL-348 mg-025-5

Using 348 mg tablets, an Ethocel coating followed by a final coating, were sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 36.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 13 minutes to add a 32 mg weight gain of the EC coating solution to the tablets. Tablet weights were taken at 26 mg, 28 mg, 30 mg, and 32 mg weight gains and were recorded in Table 37.

Figure 27:
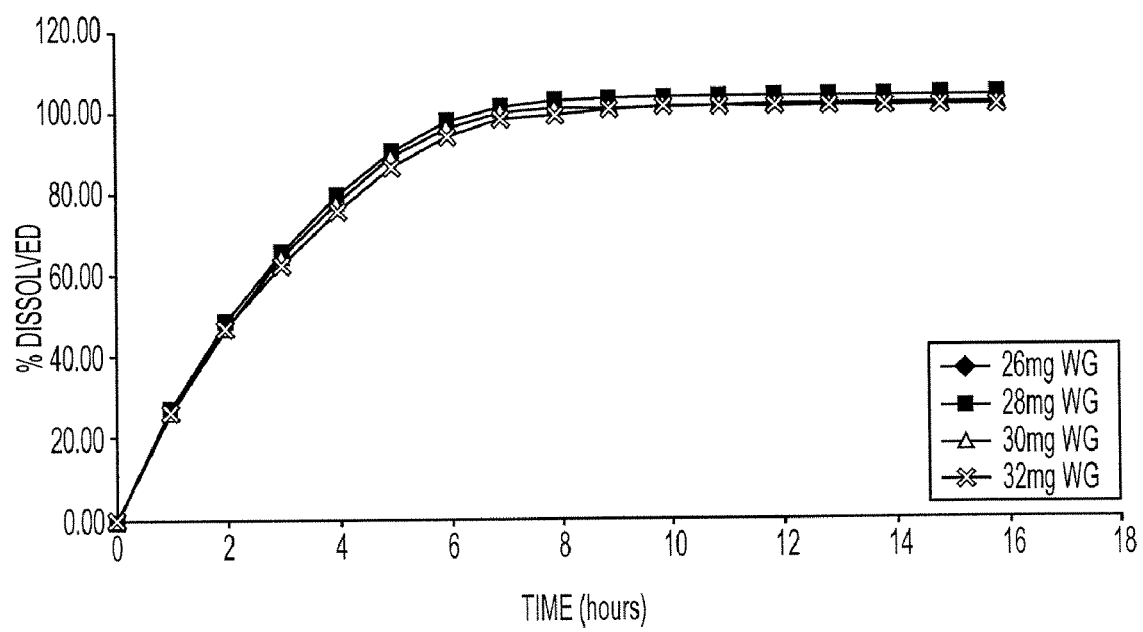
FIG. 27 is a dissolution profile of BUP-HBr-XL-348 mg-025-5 (26 mg, 28 mg, 30 mg, and 32 mg mg weight gains).

The dissolution profile (FIG. 27) shows that the tablets with the 32 mg weight gain of EC coating when compared to those with 26 mg weight gain released slower in the beginning and then faster after 7 hours. When comparing the tablets with 32 mg weight gain of EC coating to those with 30 mg weight gain of EC coating, the tablets with the 32 mg weight gain released slower up until 10 hours. The f2 similarity factor showed that the release of the tablets with the 30 mg and 32 mg weight gains were in fact similar (93.72%).

The materials used in the final coating, their percent contribution to the total solution, the amounts of each in the batch, the amount of solid contribution in grams and the percentage of the solids in the solution were all listed in Table 38.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

The coating solution was altered for this batch by changing the percentage of solid from each of the solid components in the solution. The percentage of Eudragit solid contribution was decreased from 65% to 56.5%. The percentage of Syloid, Carbowax and Triethyl Citrate were increased from 25%, 6.65% and 3.39% to 30%, 9% and 4.5%, respectively.

It took 40 minutes to add a 7 mg weight gain of the final coating solution to the tablets. Tablet weights were taken and recorded (Table 39) at 4 mg, 5 mg, 6 mg, and 7 mg weight gains.

Figure 28:
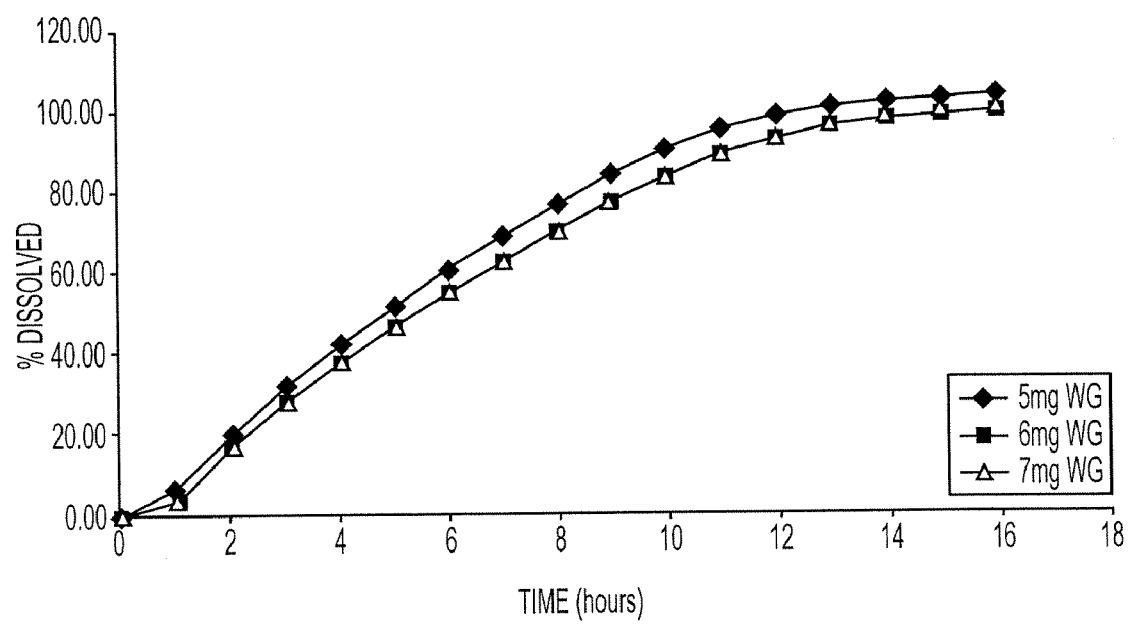
FIG. 28 is a dissolution profile of BUP-HBr-XL-348 mg-025-5 (5 mg, 6 mg, and 7 mg weight gains).

The dissolution profile (FIG. 28) shows that the tablets with the 7 mg weight gains released the slowest of the three samples tested. However, f2 calculation showed that the tablets with the 6 mg weight gain released similarly to those with the 7 mg weight gain of Final coating (93.33%).

Study on Batch BUP-HBr-XL-348 mg-026-5

Using 348 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 40.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 11 minutes to add a 32 mg weight gain of the EC coating solution to the tablets. Tablet weights were taken at 26 mg, 28 mg, 30 mg, and 32 mg weight gains and were recorded in Table 41.

Figure 29:
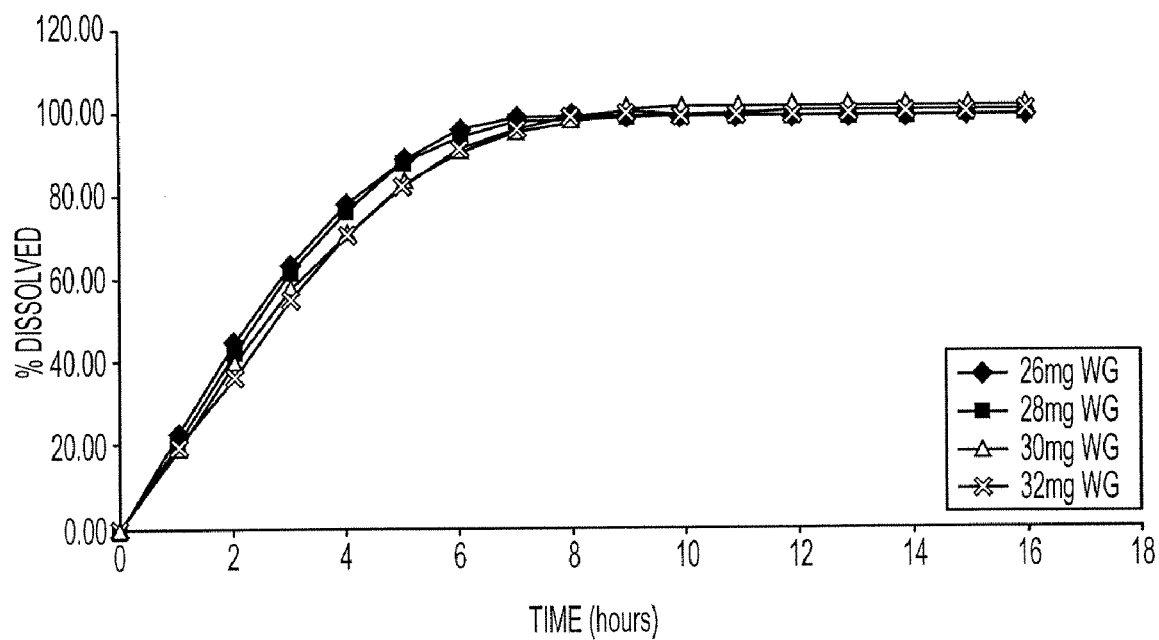
FIG. 29 is a dissolution profile of BUP-HBr-XL-348 mg-026-5 (26 mg, 28 mg, 30 mg, and 32 mg weight gains).

The dissolution profile (FIG. 29) shows that the tablets with the 32 mg weight gain of EC coating released the slowest when compared to the other three samples with lower weight gains of EC coating (26 mg, 28 mg and 30 mg).

Study on Batch BUP-HBr-XL-174 mg-027-5

Using 174 mg tablets, an Ethocel coating followed by a final coating, were sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 42.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 3 hours and 29 minutes to add a 32 mg weight gain of the EC coating solution to the tablets. Tablet weights were taken at 22 mg, 24 mg, and 26 mg weight gains and were recorded in Table 43.

Figure 30:
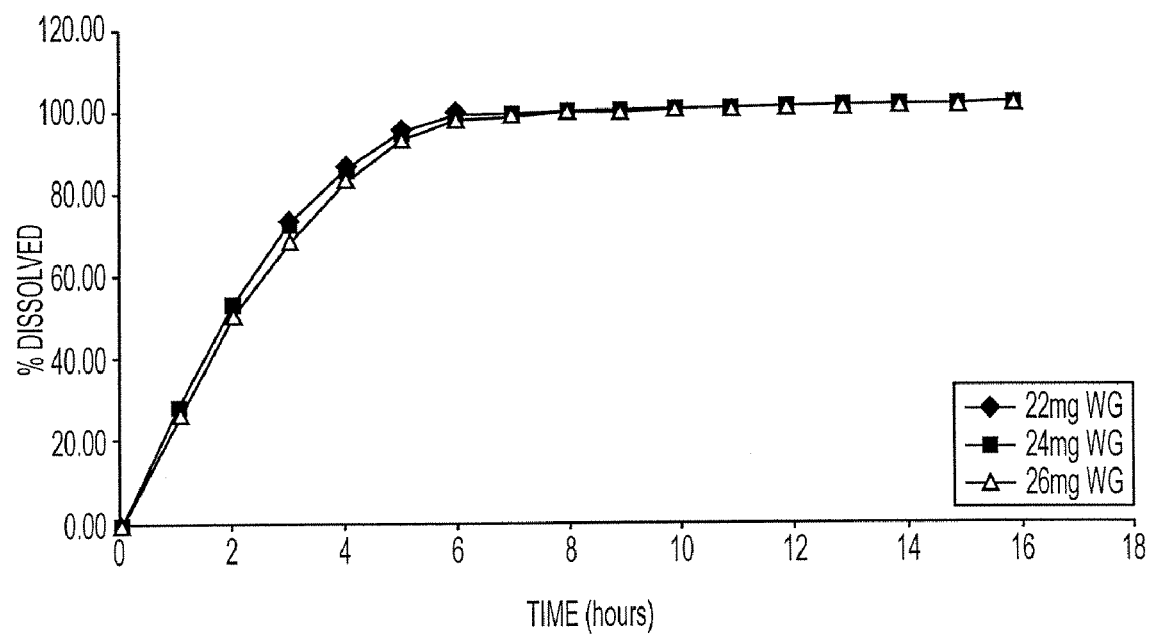
FIG. 30 is a dissolution profile of BUP-HBr-XL-174 mg-027-5 (22 mg, 24 mg, and 26 mg weight gains).

The dissolution profile (FIG. 30) shows that the tablets with the 26 mg weight gain of EC coating released the slowest of the three samples tested.

The materials used in the final coating, their percent contribution to the total solution, the amounts in each in the batch, the amount of solid contribution in grams and the percentage of the solids in the solution were all listed in Table 44.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 1 hour and 17 minutes to add a 7 mg weight gain of the final coating solution to the tablets. Tablet weights were taken and recorded in Table 45 at 4 mg, 5 mg, 6 mg, and 7 mg weight gains.

Figure 31:
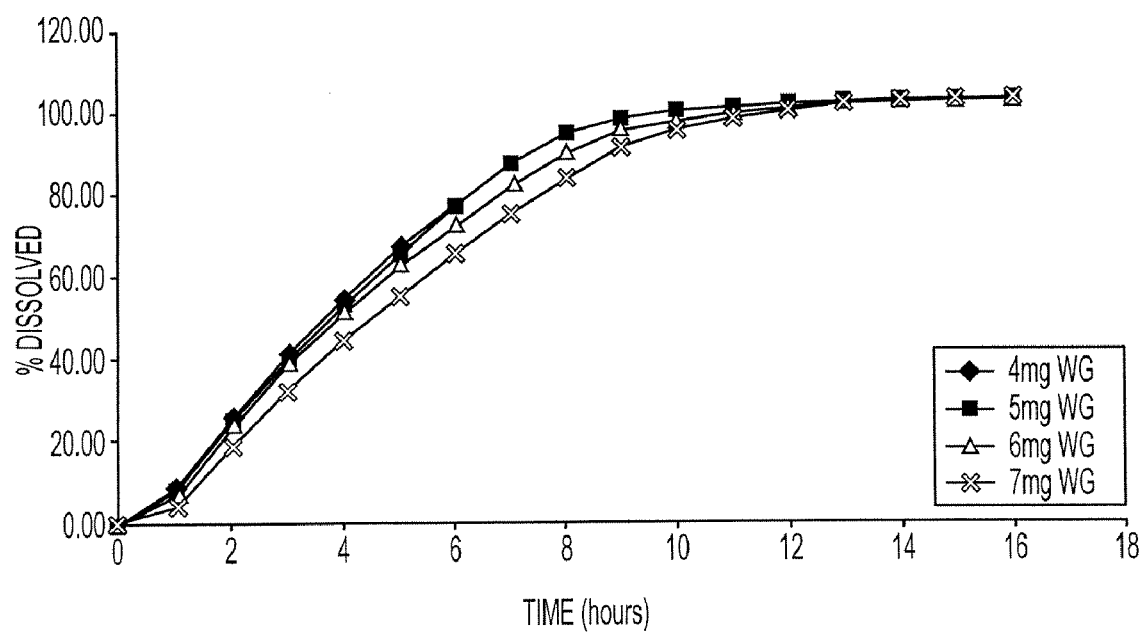
FIG. 31 is a dissolution profile of BUP-HBr-XL-174 mg-027-5 (4 mg, 5 mg, 6 mg, and 7 mg weight gains).

The dissolution profile (FIG. 31) shows that the tablets with the 7 mg weight gain of final coating initially released slower that the tablets with 4 mg, 5 mg and 6 mg weight gains. However, at approximately 12 hours, all 4 samples were releasing similarly.

Example 6

Bupropion HBr Enhanced Absorption (EA) Tablets

This example describes the development of bupropion EA "Enhanced Absorption" tablets (150 mg and 300 mg). Granulation, tabletting and coating procedures are all described thoroughly in this example. In vitro testing was conducted on the EC coated cores in order to determine which formulation gave the desired results.

Bupropion HBr was used in this study and its only difference to Bupropion HCl is the salt. A major advantage of an enhanced absorption composition can be lessening the amount of drug in the composition, which in turn can lead to a reduction of side effects.

Figure 32:
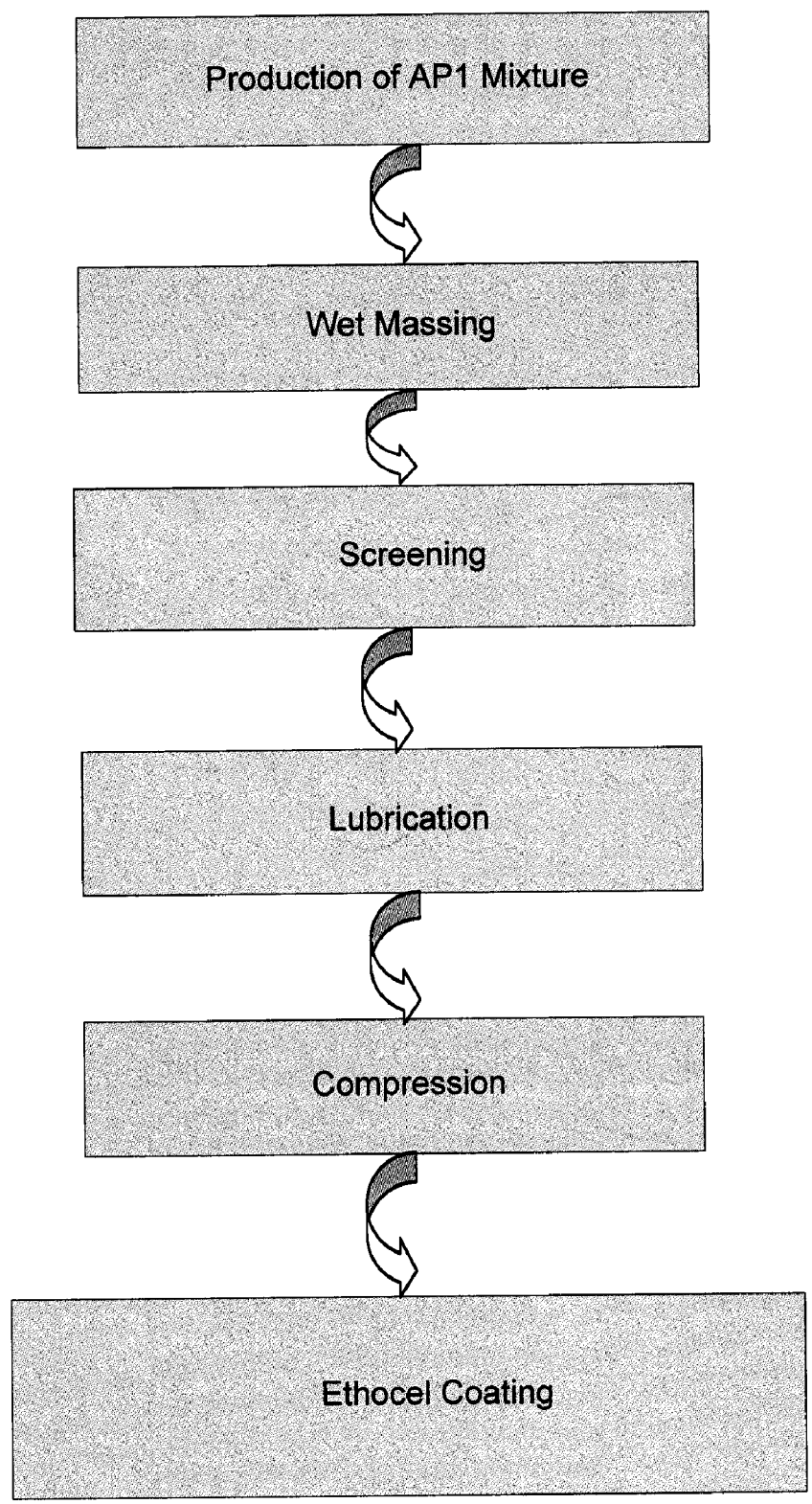
FIG. 32 is a flow chart showing the overall process for the development of bupropion HBr EA tablets.

The overall process for the development of bupropion HBr EA tablets is shown in FIG. 32.

Bupropion HBr EA—Granulation Process

Figure 33:
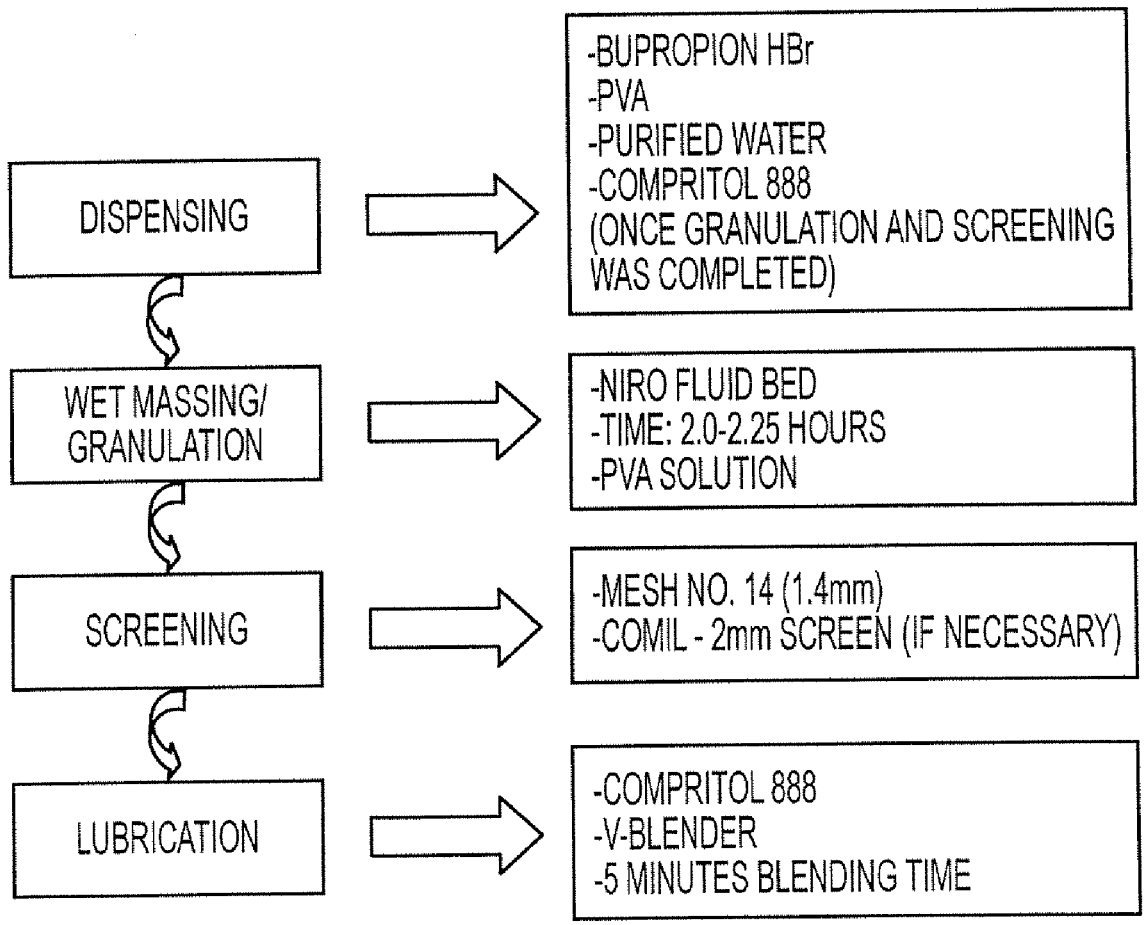
FIG. 33 is a flow chart demonstrating the granulation process of the bupropion HBr EA tablets.
Figure 34:
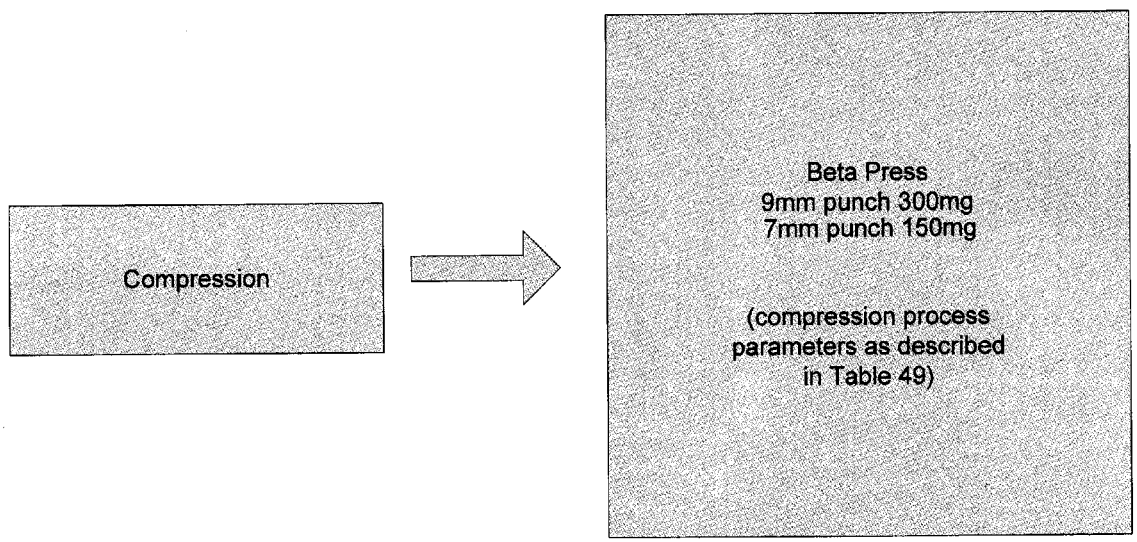
FIG. 34 is a flow chart showing the compression process of the 300 mg and 150 mg bupropion HBr EA Tablets.

A summary of the granulation process of the bupropion HBr EA tablets is shown in FIG. 33.

The following materials were used in the granulation of the immediate release core of the bupropion HBr EA tablets: bupropion HBr, polyvinyl alcohol and purified water. Once granulated, lubricant (Compritol 888) was added to complete the formulation. It must be noted that the granulation procedure for the bupropion HBr XL and Bupropion HBr EA are the same.

Each trial was divided into 5 parts. The percentage of API in each formulation was 93.75% and the percentage of PVA in each formulation was 3.125%. A summary of the breakdown of each trial per part was described in Table 46.

The Polyvinyl Alcohol was dissolved into the purified water using a magnetic stirrer and a clear colourless solution was made.

The NIRO Fluid Bed was used to granulate the Bupropion HBr Granules with the PVA solution in a process known as wet massing.

The Bupropion HBr was loaded into the fluid bed and granulation was initiated. The specifications that were used as guidelines were listed in Table 47.

Loss on Drying was determined after each granulation using the Moisture Analyzer. A 1 g sample was taken and loaded into the moisture analyzer. The sample ran for 5 minutes at a temperature of 105° C.

Upon completion of each batch part's granulation, the five parts were combined together. They were hand screened using Mesh No. 14 (1.4 mm) and any oversized granulation was passed through the Comil fitted with a 2 mm screen.

Compritol 888 was used as a lubricant in the formulation. The screened Bupropion HBr granules and the Compritol 888 were loaded into the V-blender and were blended for 5 minutes. The Compritol 888 made up 3.125% of the formulation. The final granule batch size was described in Table 48.

Bupropion HBr EA—Tabletting Process

The Beta Press was used to compress the Bupropion HBr tablets. Depending on the dose of the tablet, 150 mg or 300 mg, different tooling sets were used. The 7 mm punches were used to compress the 150 mg tablets and 9 mm punches were used to compress the 300 mg tablets. Tooling was polished prior to each run.

The tablet weights were determined as being 160.0 mg for the 150 mg dose tablets and 320.0 mg for the 300 mg dose tablets. These adjustments to tablet weight were made in order to compensate for the fact that bupropion HBr was being used in place of bupropion HCl. Prior investigations showed that bupropion HBr tablets with the above stated weights gave in vitro results similar to those of the 150 mg and 300 mg bupropion HCl tablets. The individual tablet weights had a control limit of ±5%, and the average tablet weight had a control limit of ±3% (using ten tablets).

A hardness tester was used to determine the load required to diametrically break the tablets (crushing strength) into two equal halves. A predetermined range set the specifications for hardness, which was 6.0-12.0 SC for both the 174 mg and 348 mg tablets.

Friability was determined using tablets that equaled a weight of 6.5 g in a friability tester for 4 minutes at 25 rpm. Tablets were de-dusted before and after testing. A weight loss of less than 0.8% was used as the criteria in order to accept or reject a batch.

Table 49 summarizes the specifications of the tablet press set-up. All the specifications were kept within the range and at the setting that was assigned, throughout all of the batches.

Table 50 summarizes the specifications that were kept constant throughout the compression of all the batches.

Bupropion HBr EA—Coating Process

Figure 35:
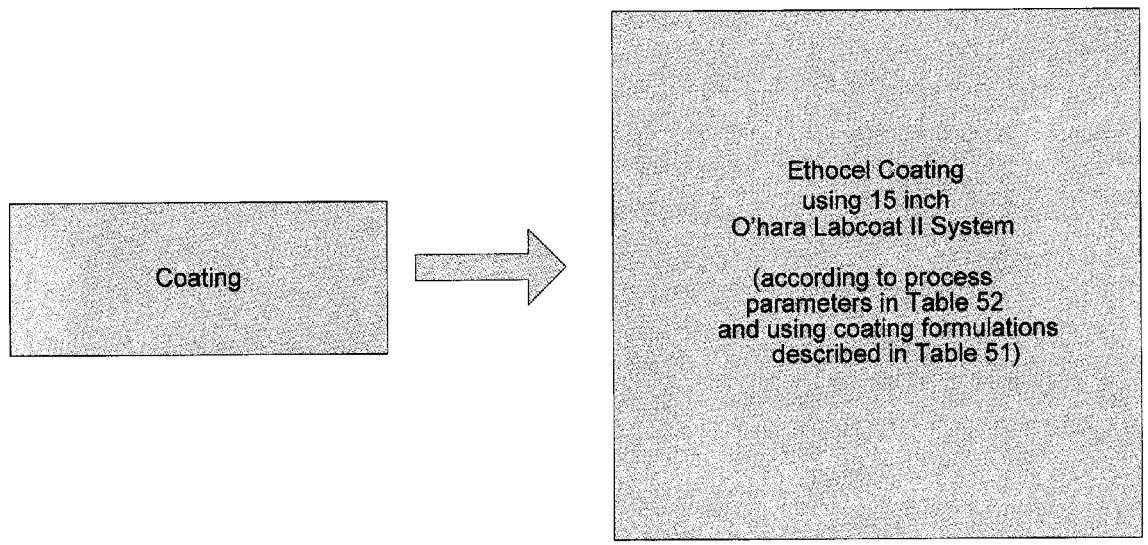
FIG. 35 is a flow chart showing the coating process of 150 mg and 300 mg bupropion HBr EA Tablets with an ETHO-CEL™ Coating.

A summary of the coating process of the 150 mg and 300 mg bupropion HBr EA tablets with an Ethocel Coating is shown in FIG. 35.

For the Ethocel coating of the Bupropion HBr EA tablets, the 15 inches O'Hara Labcoat II System was used. An attached spraying nozzle and a propeller mixer were also used.

Several Ethocel coating solutions were developed and used to coat the Bupropion HBr tablets. An Ethocel coating layer was placed on the tablets containing one of the formulations listed in Table 51.

In formulation 1, Ethyl Alcohol 200 proof was weighed out in a stainless steel container. While stirring, PEG 4000 was added and allowed to dissolve. Once dissolved, Ethocel was added and left to stir for 30 minutes. Then, Povidone was added to the solution and was mixed for an overnight period (15-20 hours).

In formulation 2, PEG4000 was placed into a beaker with the Dibutyl Sebacate and was stirred until it dissolved. This was added to the Ethyl Alcohol 200 proof that had already been weighed out in a stainless steel container. Following this, Ethocel was added and stirred for 30 minutes. Thereafter, Povidone was added and allowed to stir for an overnight period (15-20 hours).

In formulation 3, Ethyl Alcohol 200 proof was placed in a stainless steel container. While stirring, Dibutyl Sebacate was added and allowed to dissolve. Once dissolved, Ethocel was added and left to stir for 30 minutes. Then, Povidone was added to the solution and was mixed for an overnight period (15-20 hours).

In formulation 4, Ethyl Alcohol 95% USP was weighed out in a stainless steel container. While stirring, PEG 4000 was added and allowed to dissolve. Once dissolved, Ethocel was added and left to stir for 30 minutes. Then, Povidone was added to the solution and was mixed for an overnight period (15-20 hours).

Table 52 summarizes the specifications that were monitored in the coating process and their ranges.

In-Vitro Studies on the Bupropion HBr Cores

Dissolution was performed on the Bupropion HBr cores and on the different weight gains of Ethocel coated cores. USP-1 method was used to conduct these studies. The dissolution test was performed using 900 mL of 0.1N HCl and at a speed of 75 rpm. Samples were taken at every hour for 16 hours. The dissolution profiles were obtained by plotting the cumulative percent of API dissolved against sampling time points. Sink conditions were maintained throughout all the experiments.

On several trials, USP-3 method was used to conduct the dissolution studies. These dissolution tests were performed for 16 hours total with the following breakdown: 2 hours using 900 mL of Simulated Gastric Fluid (SGF) at pH 1.2 with 0.5% of Sodium Lauryl Sulfate (SLS), followed by 2 hours in 900 mL of Acetate Buffer at a pH of 4.5, followed by 12 hours in 900 mL of Phosphate Buffer Simulated Intestinal Fluid (SIF) at a pH of 6.8. These results were plotted with the in-vitro data and the Bupropion HCl data in order for a comparison to be made.

Study on Batch BUP-HBr-XL-016-5

Figure 36:
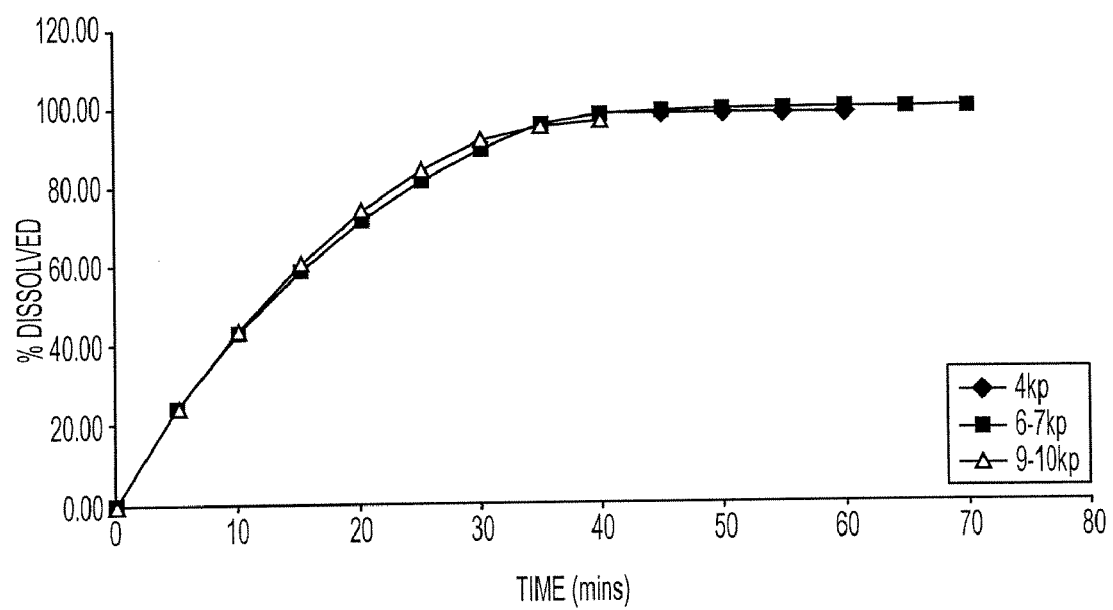
FIG. 36 is a dissolution profile of the of tablet cores at different hardness levels (4 kp, 6-7 kp and 9 kp) in the study on Batch BUP-HBr-XL-016-5.
Figure 37:
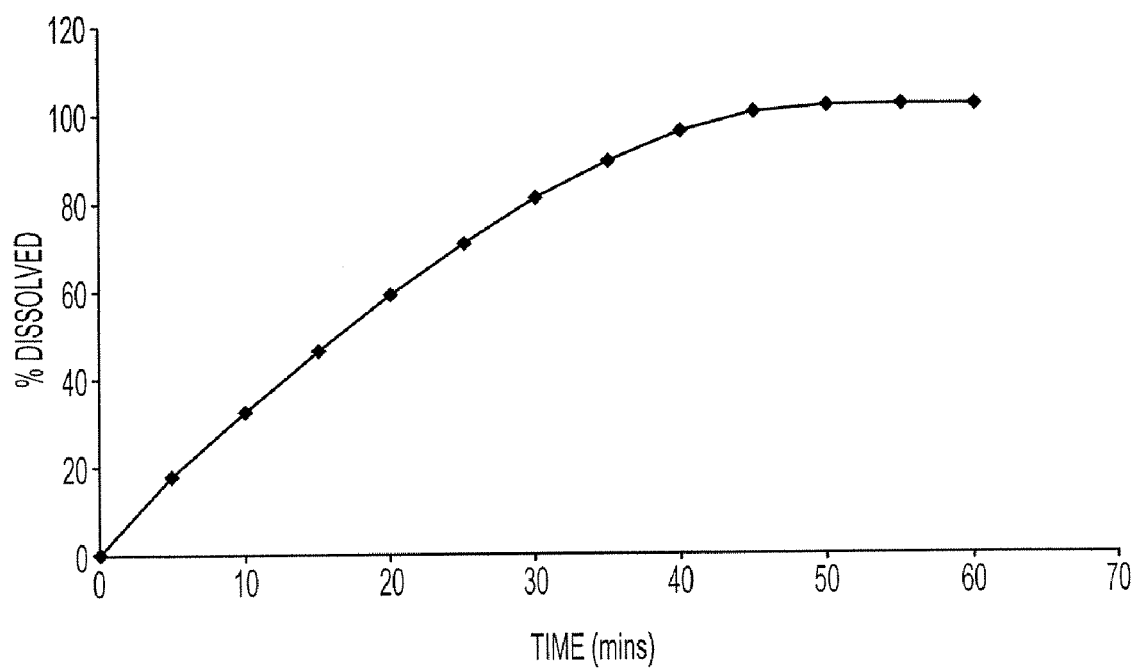
FIG. 37 is a dissolution profile of the 300 mg Bupropion HBr EACores in the study on Batch BUP-HBr-XL-016-5.
Figure 38:
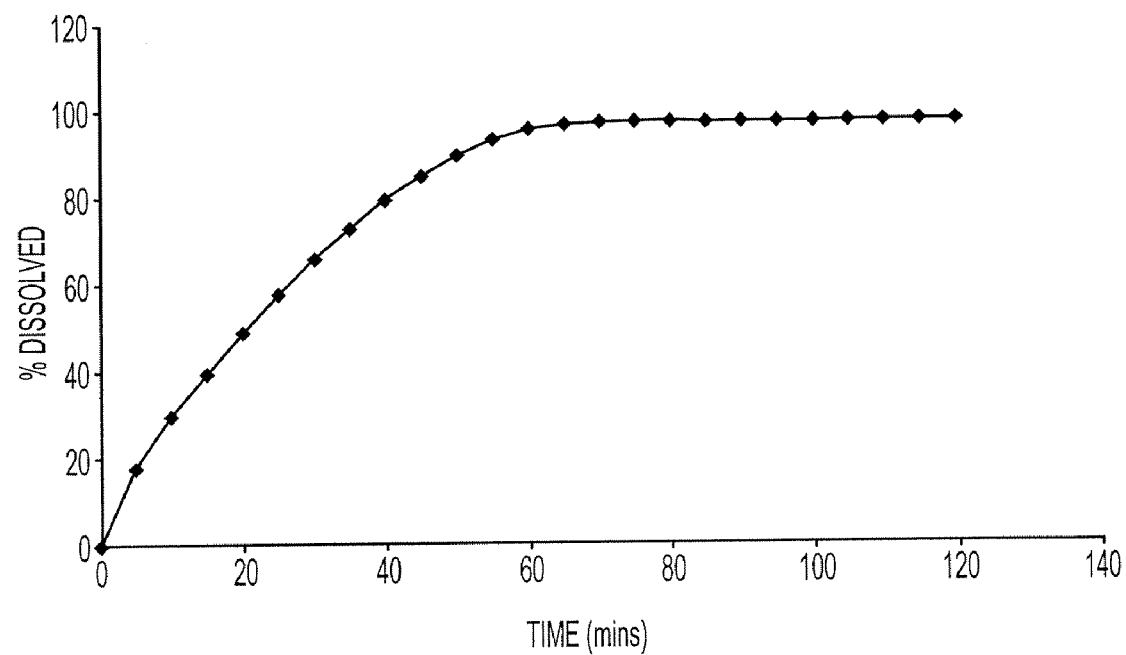
FIG. 38 is a dissolution profile of the 150 mg Bupropion HBr Cores in the study on Batch BUP-HBr-XL-016-5.

The formulation was granulated using NIRO Fluid Bed. The final blend was compressed into 300 mg tablets using the Beta press with 9 mm round, concave tooling and into 150 mg tablets with 7 mm round, concave tooling. Table 53 describes the amounts of each material in the granulation of the 300 mg tablets and Table 54 describes the amounts for the 150 mg tablets. It was noted that they were the same; the only variation was the tablet weight, which was adjusted at the compression stage. A first compression run was done to produce tablets with different hardness values so as to determine the effects of hardness, if any, on the dissolution (FIG. 36). Dissolution was conducted on the 300 mg and 150 mg cores in order to determine their release (FIGS. 37 and 38, respectively). After granulation was completed, the batch was screened and then prior to compression, the lubricant (Compritol 888) was added.

The granulation results show that the average granulation time is 2.0 hours and the average LOD % is 0.342%. Table 55 and Table 56 summarize the theoretical and actual values of the parameters that were monitored in the compression process using the 9 mm and 7 mm tooling respectively.

FIG. 36 shows that the different hardness ranges did not drastically affect the dissolution profiles. The dissolution profiles of the 300 mg (FIG. 37) and 150 mg cores (FIG. 38) show that the cores were releasing approximately 100 percent of API in an hour.

Study on Batch BUP-HBr-EA-300 mg-001-5

Using 300 mg Bupropion HBr core tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 57.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 4 minutes to coat the tablets with a weight gain of 54 mg. Tablet weights were taken and recorded in Table 58 at 44 mg, 46 mg, 48 mg, 50 mg 52 mg, and 54 mg weight gains.

Figure 39:
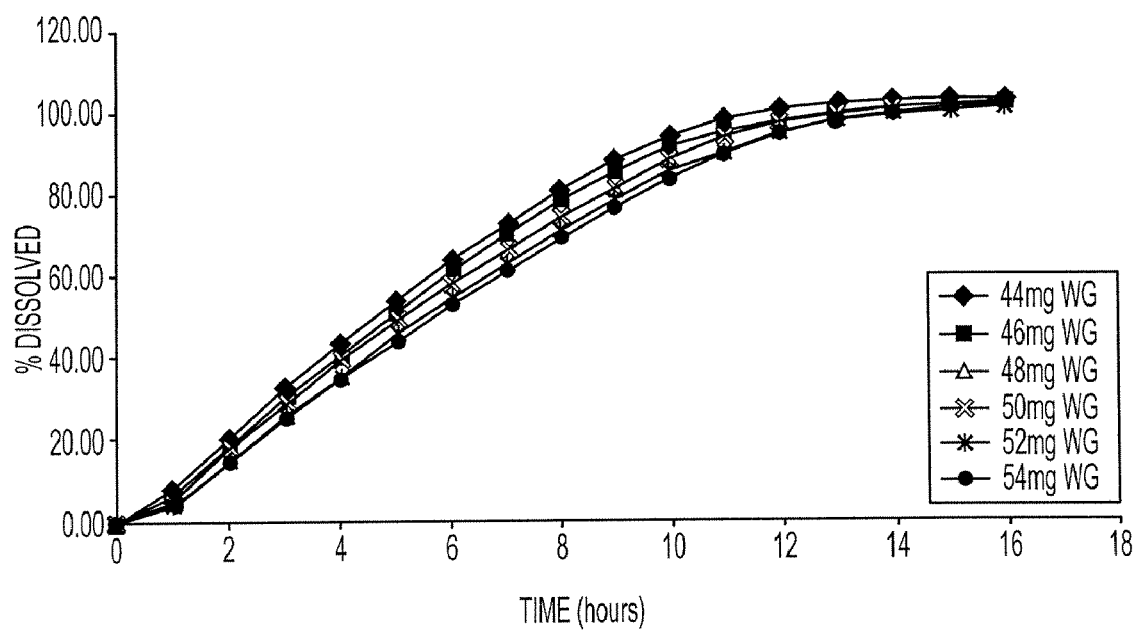
FIG. 39 is a dissolution profile of BUP-HBr-EA-300 mg-001-5 (44 mg, 46 mg, 48 mg, 50 mg 52 mg, and 54 mg weight gains).

The dissolution profile (FIG. 39) shows that the tablets with the 44 mg weight gain released the fastest and the tablets with the 54 mg weight gain released the slowest from the 6 different weight gains that were tested.

Figure 40:
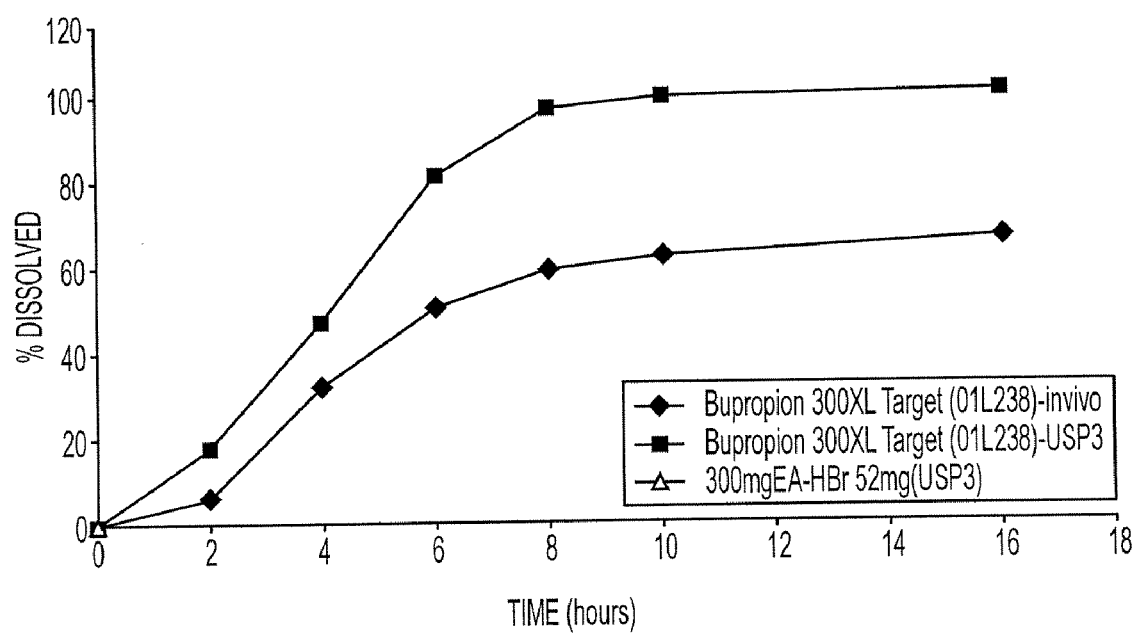
FIG. 40 is a comparative USP3 dissolution profile of Bupropion HBr 300 mg EA Tablets with 52 mg weight gain to the in vivo and the in vitro profiles of the target (Bupropion HCl 300 mg).

Dissolution using USP3 was also conducted on this trial, using the tablet with the 52 mg weight gain. The dissolution profile was plotted as time in hours versus % Dissolved, and was plotted alongside the in vivo data and the Bupropion HCl data in order for a comparison to be made. The results (FIG. 40) showed that the trial did not match the in vivo data, nor did it match the Bupropion HCl data.

Study on Batch BUP-HBr-EA-150 mg-002-5

Using 150 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 59.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

The coating process of this trial took 4 hours and 38 minutes to obtain a 36 mg weight gain. Tablet weights were taken and recorded in Table 60 at 18 mg, 20 mg, 22 mg, 24 mg, 26 mg, 28 mg, 30 mg, 32 mg, 34 mg and 36 mg weight gains.

Figure 41:
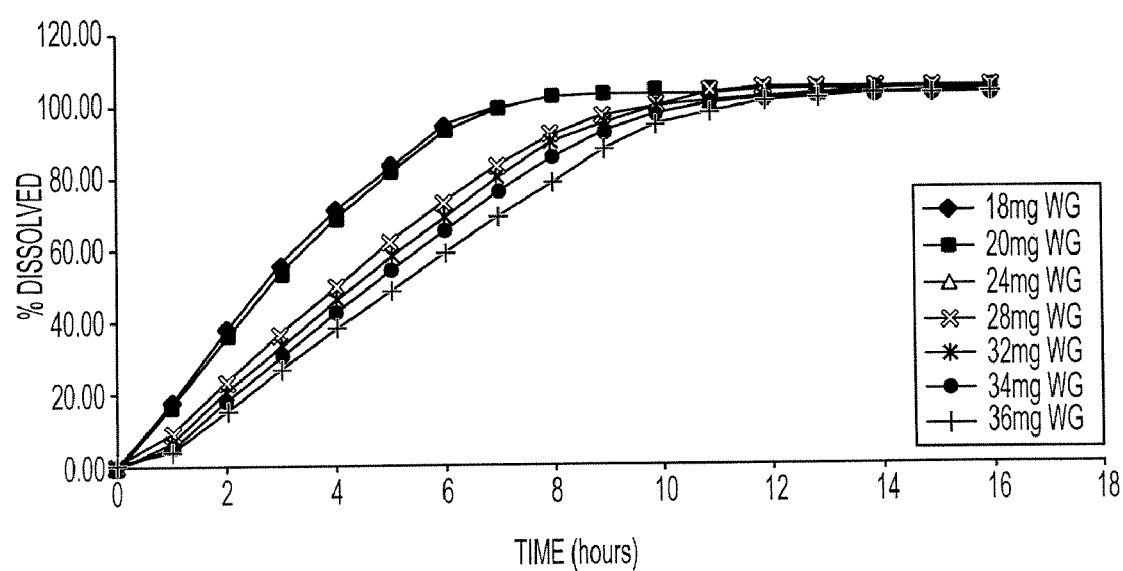
FIG. 41 is a dissolution profile of BUP-HBr-EA-150 mg-002-5 (18 mg, 20 mg, 22 mg, 24 mg, 26 mg, 28 mg, 30 mg, 32 mg, 34 mg and 36 mg weight gains).

The dissolution profile (FIG. 41) shows that the tablets with the 18 mg and 20 mg weight gains of EC coating released the fastest of all the weight gains tested. It was the tablets with the 36 mg weight gain that released the slowest when compared to all the other weight gains.

Study on Batch BUP-HBr-EA-300 mg-003-5

Using 300 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 61.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 13 minutes to add a 54 mg weight gain of the EC coating solution to the tablets. Tablet weights were taken at 44 mg, 46 mg, 48 mg, 50 mg, 52 mg, and 54 mg weight gains and were recorded in Table 62.

Figure 42:
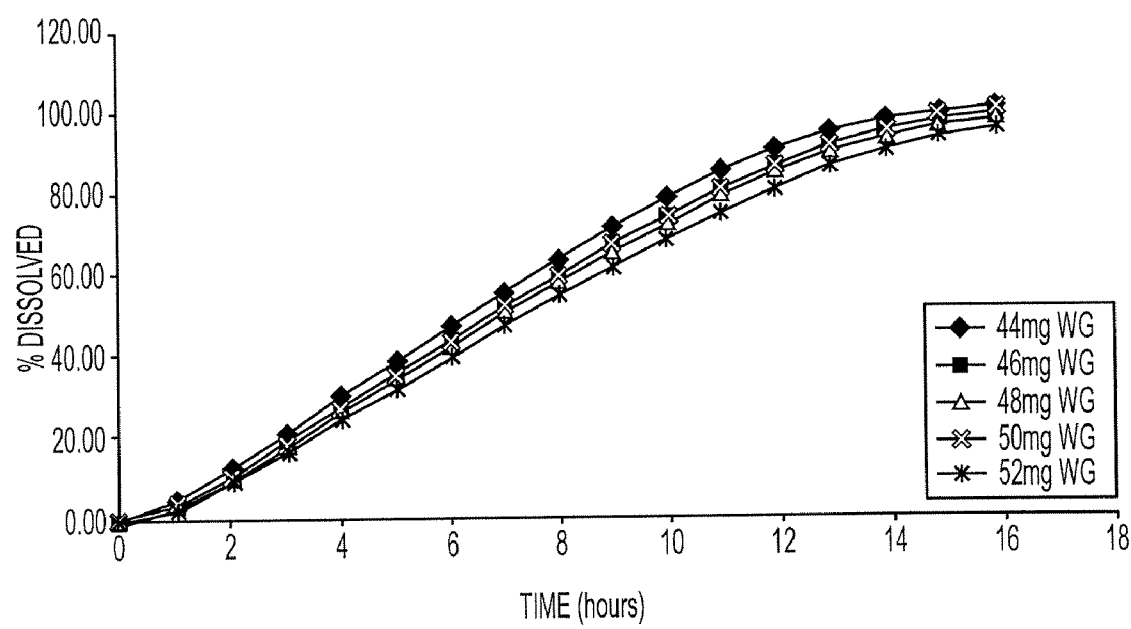
FIG. 42 is a dissolution profile of BUP-HBr-EA-300 mg-003-5 (44 mg, 46 mg, 48 mg, 50 mg, 52 mg, and 54 mg weight gains).

The dissolution profile (FIG. 42) shows that the tablets with the 52 mg weight gain of EC coating released the slowest when compared to the other profiles with different weight gains.

Study on Batch BUP-HBr-EA-300 mg-004-5

Using 300 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 63.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 13 minutes to add a 54 mg weight gain of the EC coating solution to the tablets. Tablet weights were taken at 44 mg, 46 mg, 48 mg, 50 mg, 52 mg, and 54 mg weight gains and were recorded in Table 64.

Figure 43:
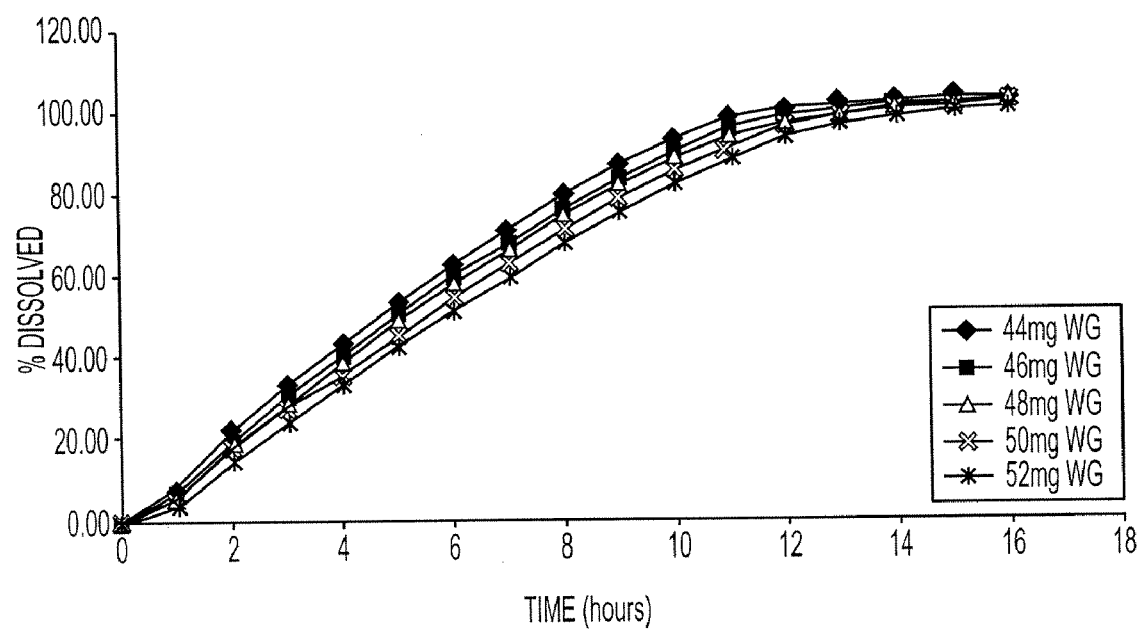
FIG. 43 is a dissolution profile of BUP-HBr-EA-300 mg-004-5 (44 mg, 46 mg, 48 mg, 50 mg, 52 mg, and 54 mg weight gains).

The dissolution profile (FIG. 43) shows that the tablets with the 52 mg weight gain released the slowest when compared to the other profile and the tablets with the 44 mg weight gain of EC coating released the fastest.

Study on Batch BUP-HBr-EA-300 mg-005-5

Using 300 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 65.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 14 minutes to add a 54 mg weight gain of the EC coating solution to the tablets. Tablet weights were taken at 44 mg, 46 mg, 48 mg, 50 mg, 52 mg, and 54 mg weight gains and were recorded in Table 66.

Figure 44:
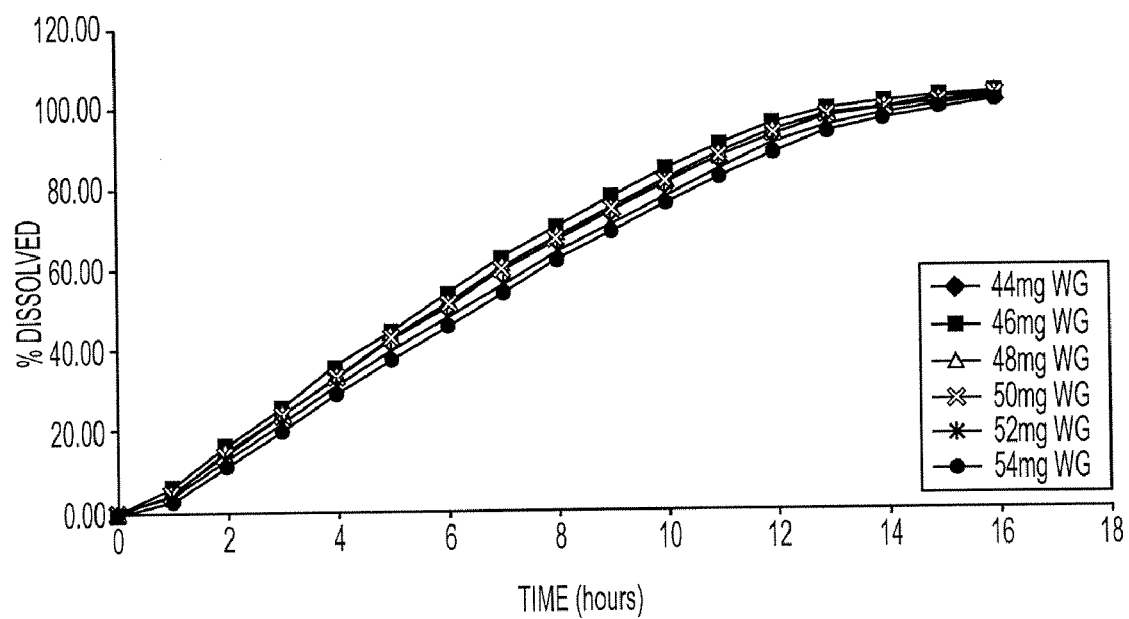
FIG. 44 is a dissolution profile of BUP-HBr-EA-300 mg-005-5 (44 mg, 46 mg, 48 mg, 50 mg, 52 mg, and 54 mg weight gains).

FIG. 44 shows that the tablets with the 54 mg weight gain released the slowest when compared to the other profiles and that the tablets with the 44 mg weight gain of EC coating released the fastest of the six profiles.

Study on Batch BUP-HBr-EA-150 mg-006-5

Using 150 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 67.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

The coating process of this trial took 4 hours and 36 minutes to obtain a 36 mg weight gain. Tablet weights were taken and recorded in Table 68 at 18 mg, 20 mg, 22 mg, 24 mg, 26 mg, 28 mg, 30 mg, 32 mg, 34 mg and 36 mg weight gains.

Figure 45:
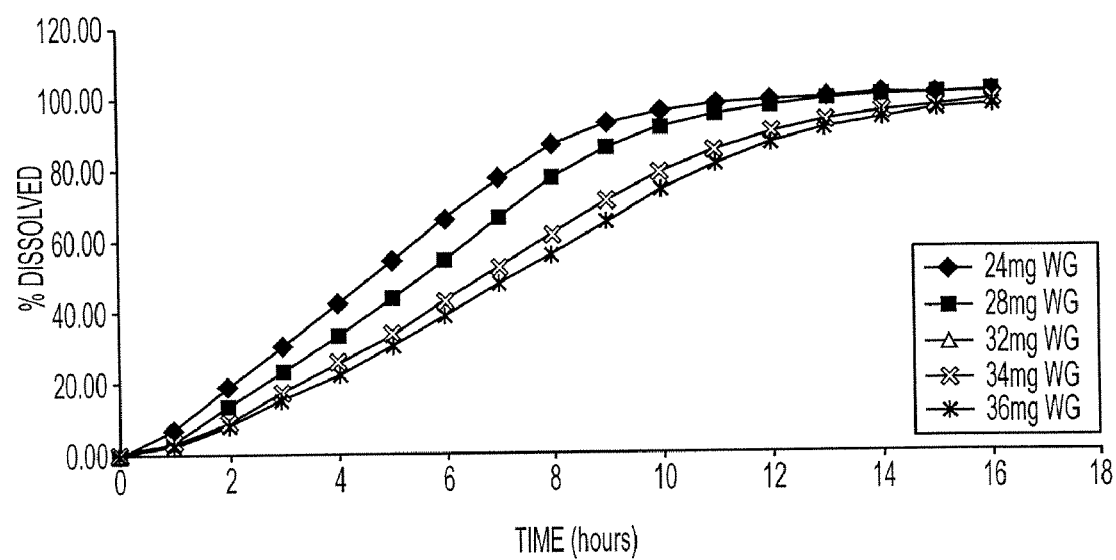
FIG. 45 is a dissolution profile of BUP-HBr-EA-150 mg-006-5 (24 mg, 28 mg, 32 mg, 34 mg and 36 mg weight gains).

The dissolution profile (FIG. 45) shows that the tablets with the 36 mg weight gain of EC coating released the slowest when compared to the other four profiles (24 mg, 28 mg, 32 mg and 34 mg weight gains).

Figure 46:
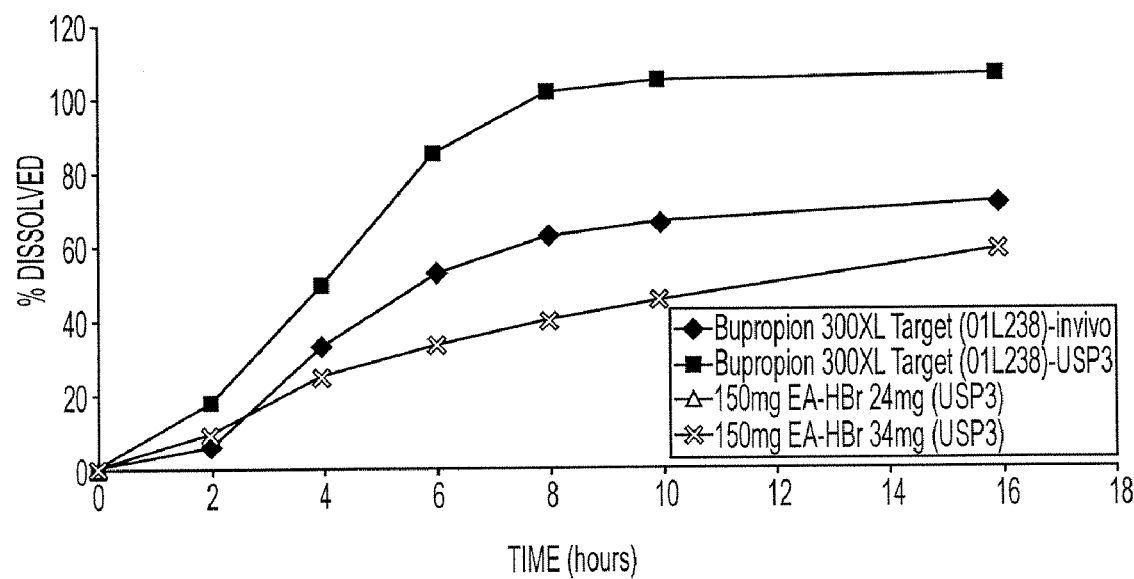
FIG. 46 is a comparative USP3 dissolution profile of bupropion HBr 150 mg EA Tablets with 24 and 34 mg weight gains to the in vivo and the in vitro profiles of the target (bupropion HCl 300 mg).

Dissolution using USP3 was also conducted with this trial, in order to see if the results were close to the in vivo data and the in vitro data of the Bupropion HCl 300 mg target. The dissolution profile (FIG. 46) shows that the 150 mg Bupropion HBr EA tablets with 24 mg weight gain was close to the in vivo profile.

Study on Batch BUP-HBr-EA-150 mg-007-5

Using 150 mg tablets, an Ethocel coating was sprayed onto the tablets using the O'Hara Labcoat II Coating Equipment.

The materials used in the Ethocel (EC) coating, their percent contribution to the total solution, the amounts of each in the batch and the percentage of the solids in the solution were all listed in Table 69.

Example 7

Comparative Forced Degradation Studies on Bupropion HCL and Bupropion HBR Drug Products The Bupropion HCl and HBr tablets (EC coated and the EC+moisture barrier coated) were placed individually on an open dish, and exposed to the accelerated conditions of 40° C./75% RH in the stability chamber. After 13 and 20 days, the samples were assayed and impurity analysis was performed as per the method HPLC P05.901.10.

Figure 47:
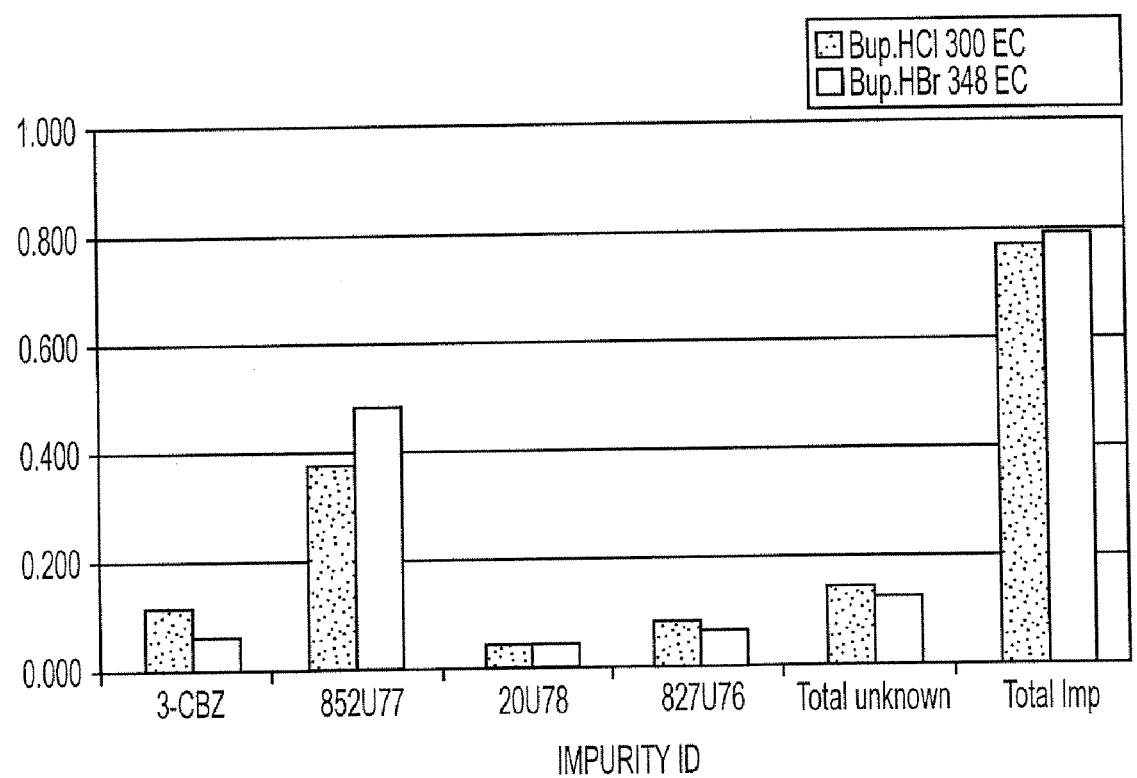
FIG. 47 is a bar graph showing the % impurities for the bupropion HCl XL 300 mg and bupropion HBr 348 mg EC coated tablets at 40° C. and 75% relative humidity.
Figure 48:
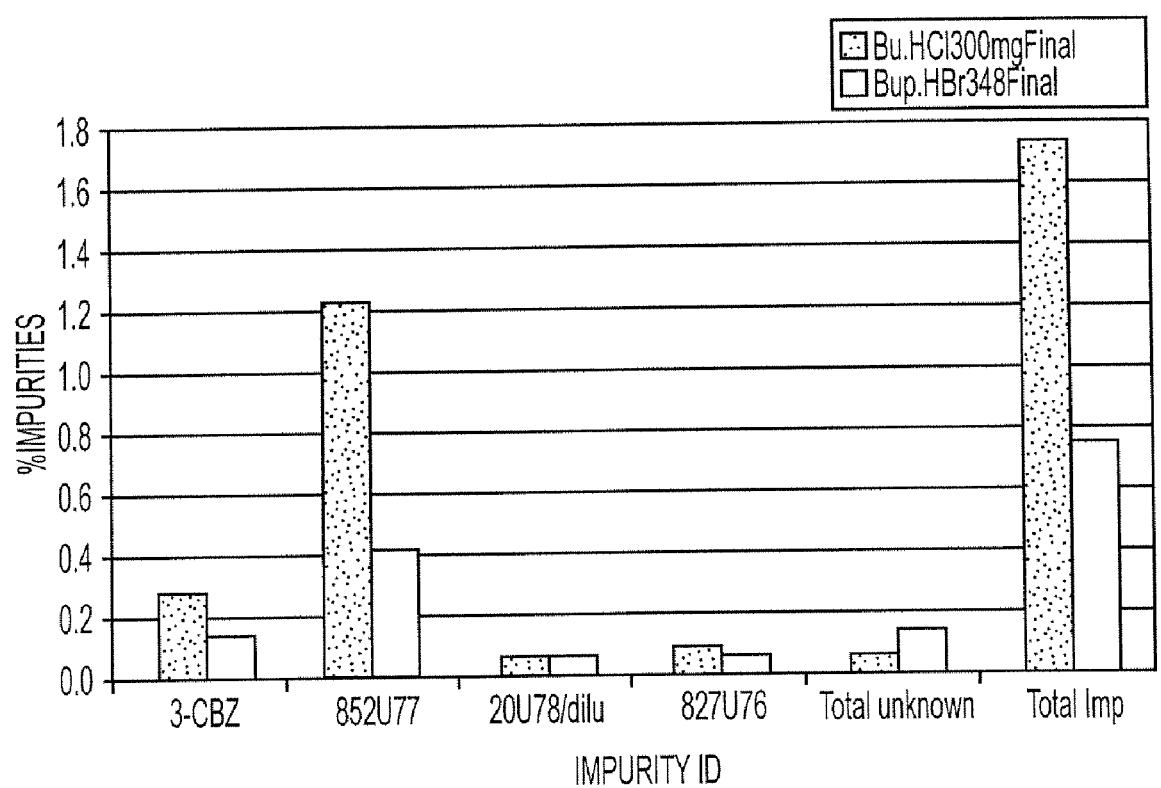
FIG. 48 is a bar graph showing the % impurities for the bupropion HCl 300 mg (Wellbutrin XL) and bupropion HBr 348 mg XL final tablets at 40° C. and 75% relative humidity.

Table 70 and FIG. 47 show the 13 and 20 days results of the forced degradation study on both Bupropion HCl and HBr EC coated tablets. For the Bupropion HCl product, the main degradation impurities 3-CBZ and 852U77 were 0.12% and 0.38% respectively, whereas, for the Bupropion HBr, these values were 0.07% and 0.49% respectively. The other degradation impurities and the total unknowns were very similar for both products; however, the assay value for the HBr product was higher than the HCl. The difference in the assay and the impurity levels were more significant in the final drug products. As shown in the Table 71 and FIG. 48, for the same period of the study the assay of the Bupropion HCl was lower (95.5%) and the level of the degradation and total unknowns were higher (3-CBZ: 0.28%, 852U77: 1.23%, 827U76: 0.10% and total 1.73%) than the Bupropion HBr (3-CBZ: 0.12%, 852U77: 0.41%, 827U76: 0.05% and total 0.75%).

Example 8

Figure 49:
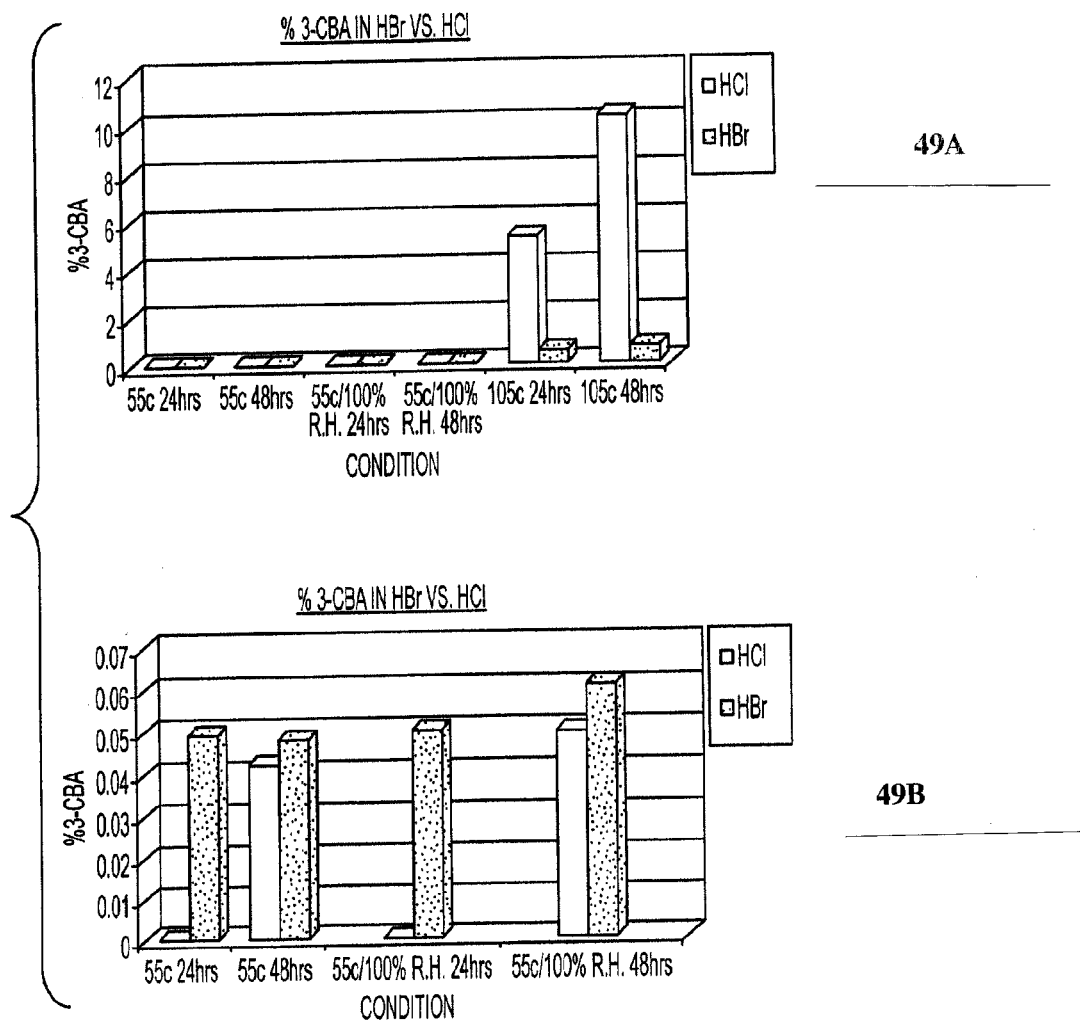
FIGS. 49A and 49B contain bar graphs showing the % of 3-CBA formed in forced degradation studies of bupropion hydrochloride (HCl) vs. bupropion HBr in the presence of excipients.
Figure 50:
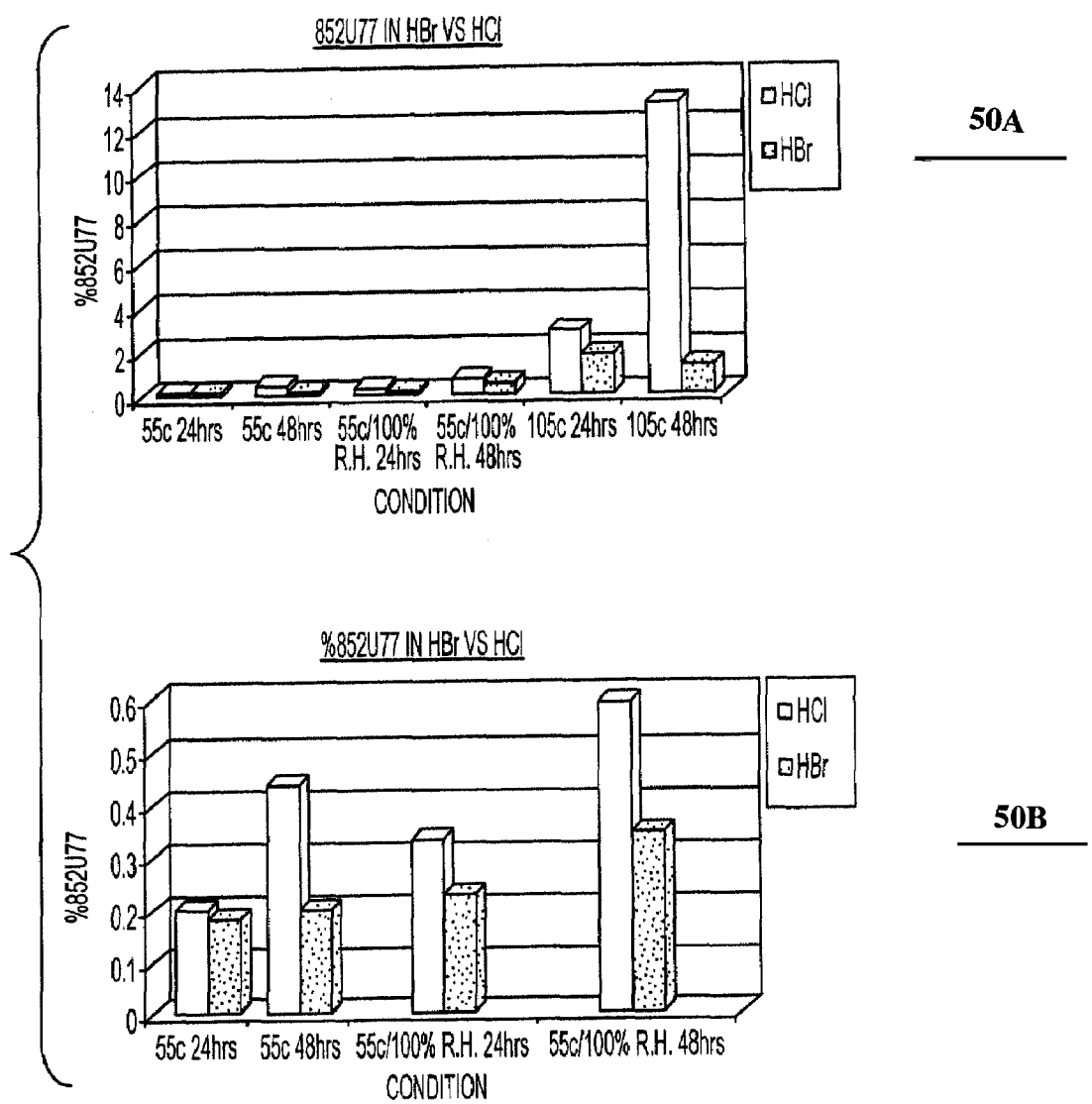
FIGS. 50A and 50B contain bar graphs showing the % of 852U77 formed in forced degradation studies of bupropion HCl vs. bupropion HBr in the presence of excipients.
Figure 51:
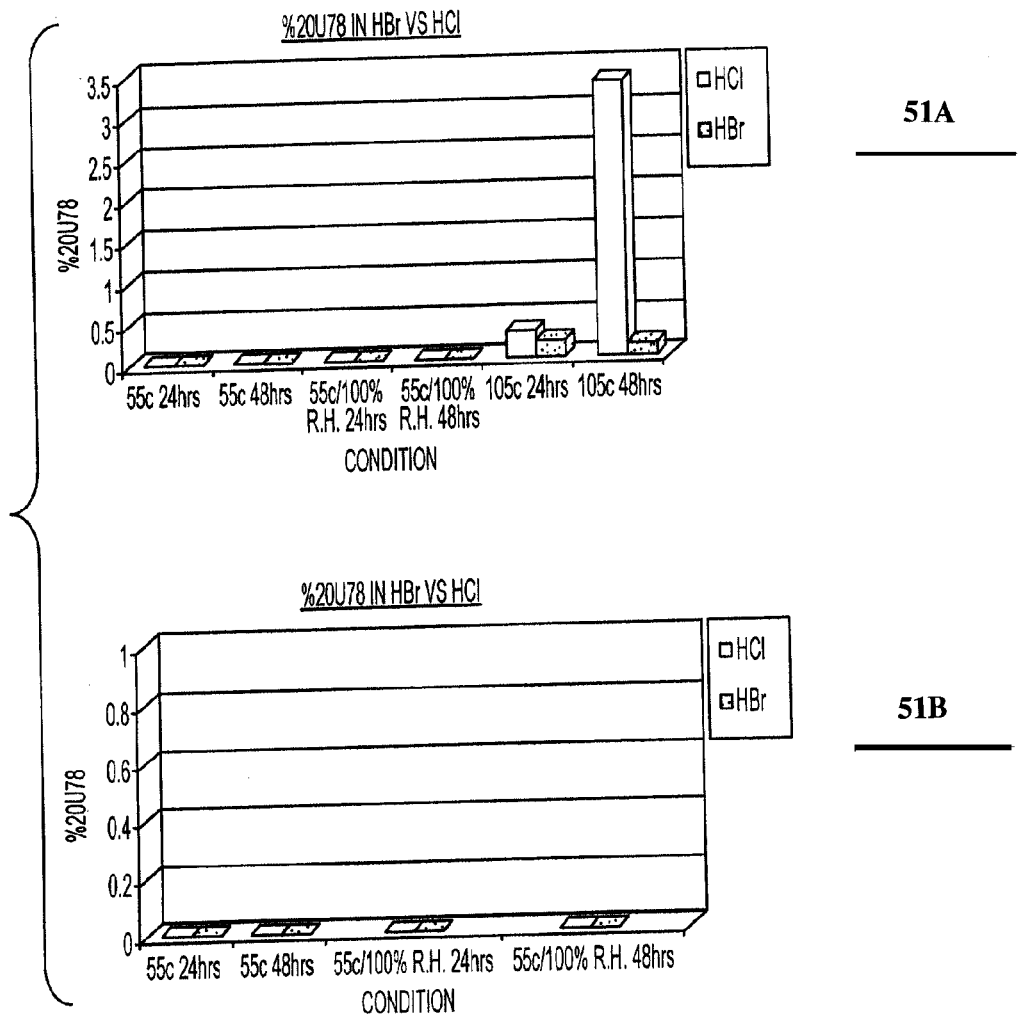
Figure 52:
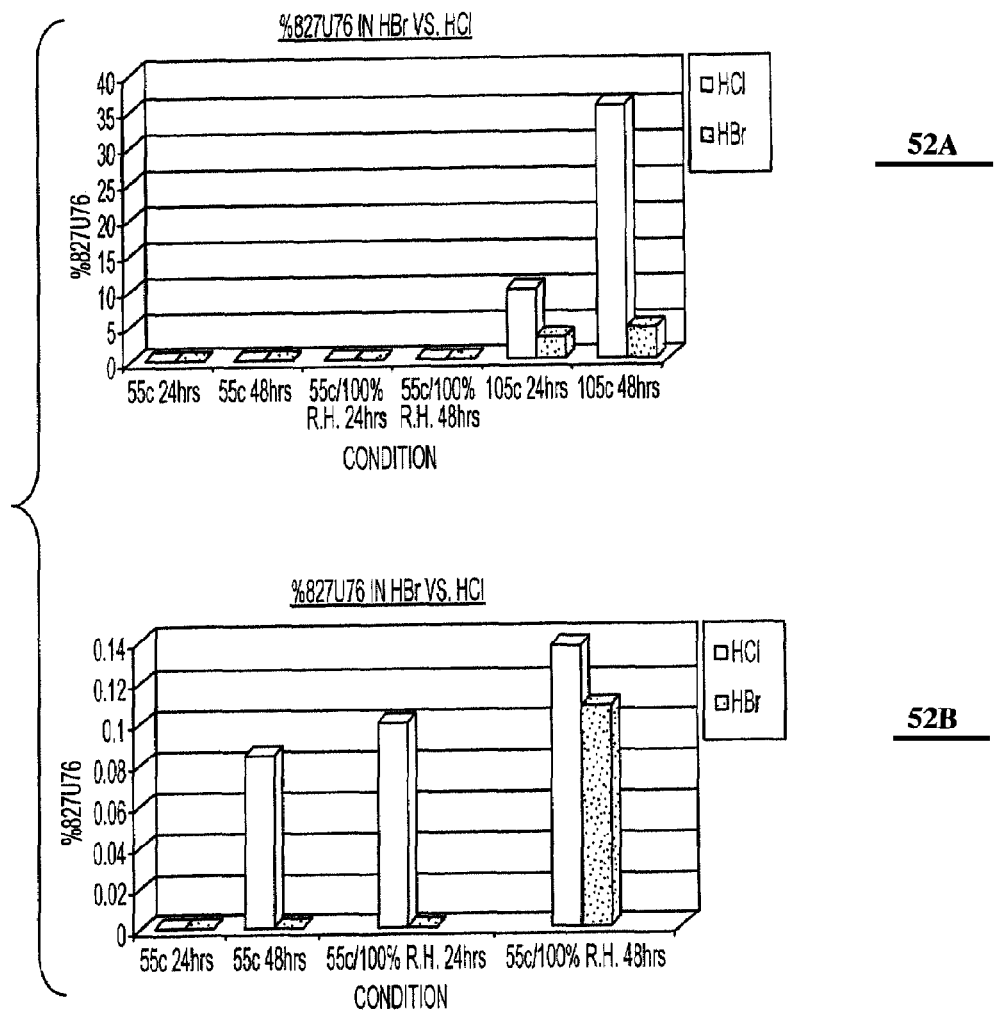
FIGS. 52A and 52B contain bar graphs showing the % of 827U76 formed in forced degradation studies of bupropion HCl vs. bupropion HBr in the presence of excipients.
Figure 53:
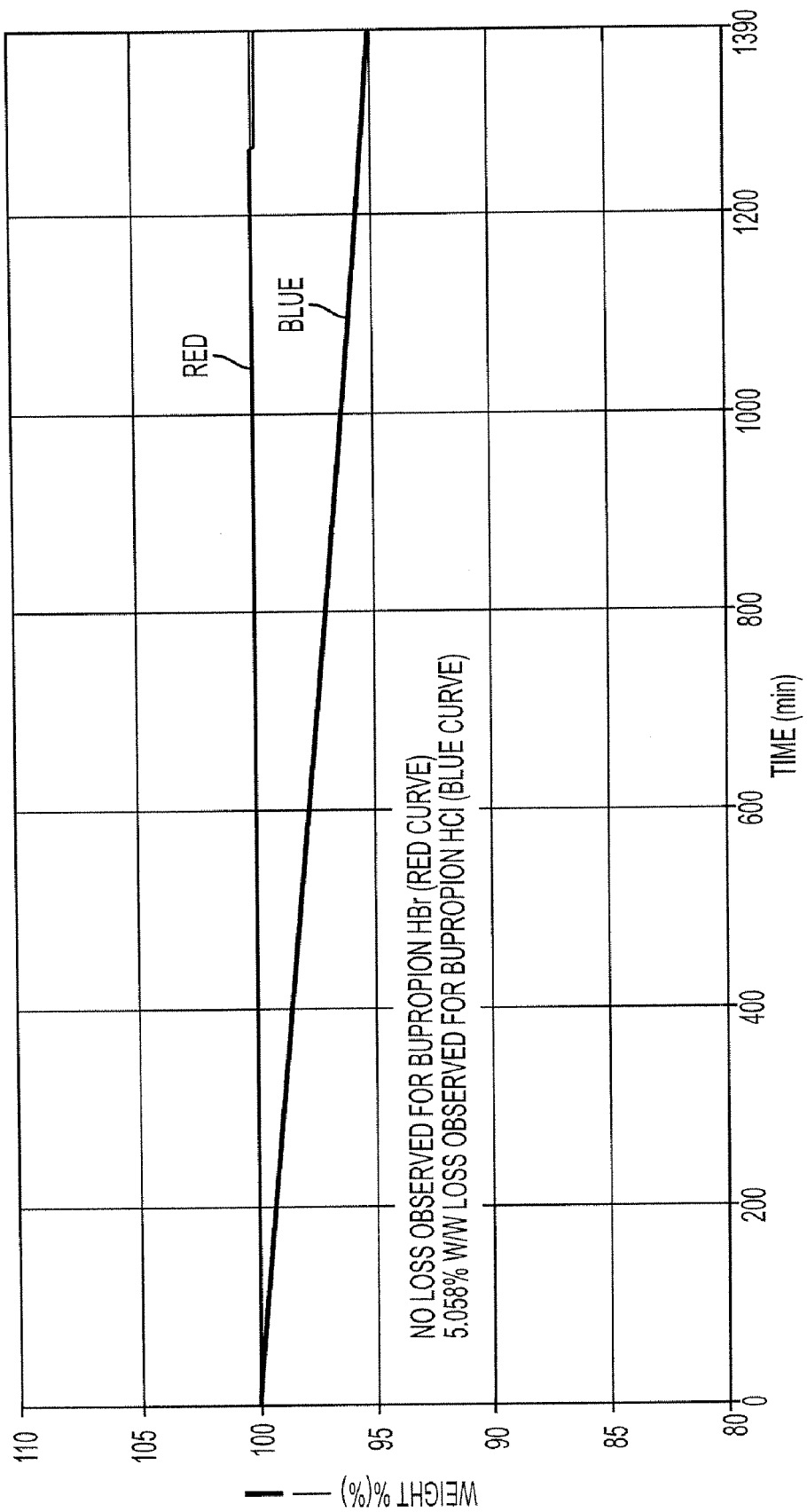
FIG. 53 is a graph showing the loss of API in a thermal gravimetric analysis (TGA) experiment at 100° C. of bupropion HCl vs. bupropion HBr.

Further Forced Degradation Studies on Bupropion HBR and Bupropion HCL in the Presence of Excipients Further forced degradation studies were carried out at 55oC, at 55oC and 100% relative humidity, at 100oC, and at 105 oC on both the HCl and HBr Bupropion salts in the presence of excipients. The average weight of the excipients and the weight of the active pharmaceutical ingredient (API) present in the samples are presented in Table 72. The results from this study are presented in FIGS. 49-53. FIG. 49 shows the amount of 3-CBA impurity in the various samples. FIG. 50 shows the amount of 852U77 impurity in the various samples. FIG. 51 shows the amount of 20U78 impurity in the various samples. FIG. 52 shows the amount of 827U76 impurity in the various samples. FIG. 53 is a graph showing the loss of each salt over time in a TGA experiment at 100 oC. These results indicate that at elevated temperatures, a disproportionation of the HCl salt occurs with concomitant loss of gaseous HCl. This disproportionation did not occur with the HBr salt.

It is clear from the results that bupropion HBr shows significant improvements in stability compared to bupropion HCl. The degradation of bupropion HBr was slower as indicated by the formation of less amounts of impurities compared to bupropion HCl.

Example 9

Preparation of Further Bupropion HBR EA Tablets

Using procedures as described in Example 6, further bupropion EA tablets were prepared using the quantities listed in Table 73.

Example 10

Accelerated Stability Study of Bupropion HBR

The stability of bupropion HBr was evaluated under the accelerated conditions of 40 oC+2 oC and 75%+5% RH in a stability chamber. The samples were prepared in closed bottles and placed in the stability chamber. HPLC analysis was conducted on the samples prior to placing them in the stability chamber (time 0), and after 3 months and 6 months. The amounts of the main degradation products present at time 0 were compared with those amounts present after 3 months and 6 months. As shown in Table 74-76 three different batches of bupropion HBr were tested. For each sample tested, at each time period, two different HPLC assays were run. The first assay labelled chromatographic purity A, measured the percentage of three impurities 3'chloropropiophenone, 3'-Chloro-2-bromopropiophenone and 3'-Chlorobenzoic acid. The second assay, labelled chromatographic purity B, measured the percentage of 2-N-(tert-Butyl)-aminopropiophenone, a single unknown impurity and the total unknown impurities. Finally a total percentage of impurities (known and unknown) was reported for each sample. From the data presented it can be seen that there is a slight increase in the impurity 3'-chloropropiophenone. While slight fluctuations were seen in the percentage of other impurities there was no trend showing an increase of these impurities at the 3- and 6-month time periods as measured. The total percentage of impurities for each of the HBr samples did not change at either the 3-month or the 6-month time periods. These results indicate that the HBr salt of bupropion was highly stable under the accelerated stability test conditions.

Example 11

Shelf Life Stability Program

The stability of bupropion HBr was studied over a longer term under conditions meant to approximate standard storage or shelf conditions. Samples were prepared in closed containers and subjected to long-term storage at 25oC+2 oC and 60%+5% RH in a stability chamber. The samples were analyzed by HPLC prior to being placed in the stability chamber (time 0) and after 3 months and 6 months. The amounts of the main degradation products present at time 0 were compared with the amounts present at 3 months and 6 months. As shown in Table 77-79 three different batches of bupropion HBr were tested. As in Example 10 each sample was tested under two HPLC assay conditions to identify 6 impurities or groups of impurities as described in Example 10. From the results shown in tables 77-79 it can be seen that the percentage of the impurity 3'-chloropropiophenone increased slightly over time. While the other impurities fluctuated slightly they did not show an increasing trend over time. These results demonstrate the stability of bupropion HBr under standard shelf conditions over an extended period of time.

Example 12

Preparation and Stability Study of Bupropion HBR Polymorphic Forms I, II and III Bupropion hydrobromide polymorphic forms I, II and III were prepared in the following manner and their stability was studied under the conditions described below:

Form I:

A 250 ml flask equipped with overhead stirrer and gas inlet was charged with 34 g of bupropion base and 138 ml of isopropanol. The solution was maintained under stirring while 13 g of gaseous HBr was introduced through the gas inlet in a time of 20' while the internal temperature of the mixture raises from 25 to 40oC. During the gas addition a heavy white precipitate formed. At the end of the gas addition the temperature of the mixture was raised to reflux (80oC), to get complete solution of the suspended solid. The temperature was then lowered to 25oC in 1 hour and further lowered to 0-5oC in 1 additional hour. The precipitate obtained was filtered and washed with 20 ml of cold isopropanol. The discharged wet solid was dried under vacuum (30 mmHg) in a static drier at 50oC for 16 hours. 34 g of bupropion hydrobromide form I were obtained.

Figure 60:
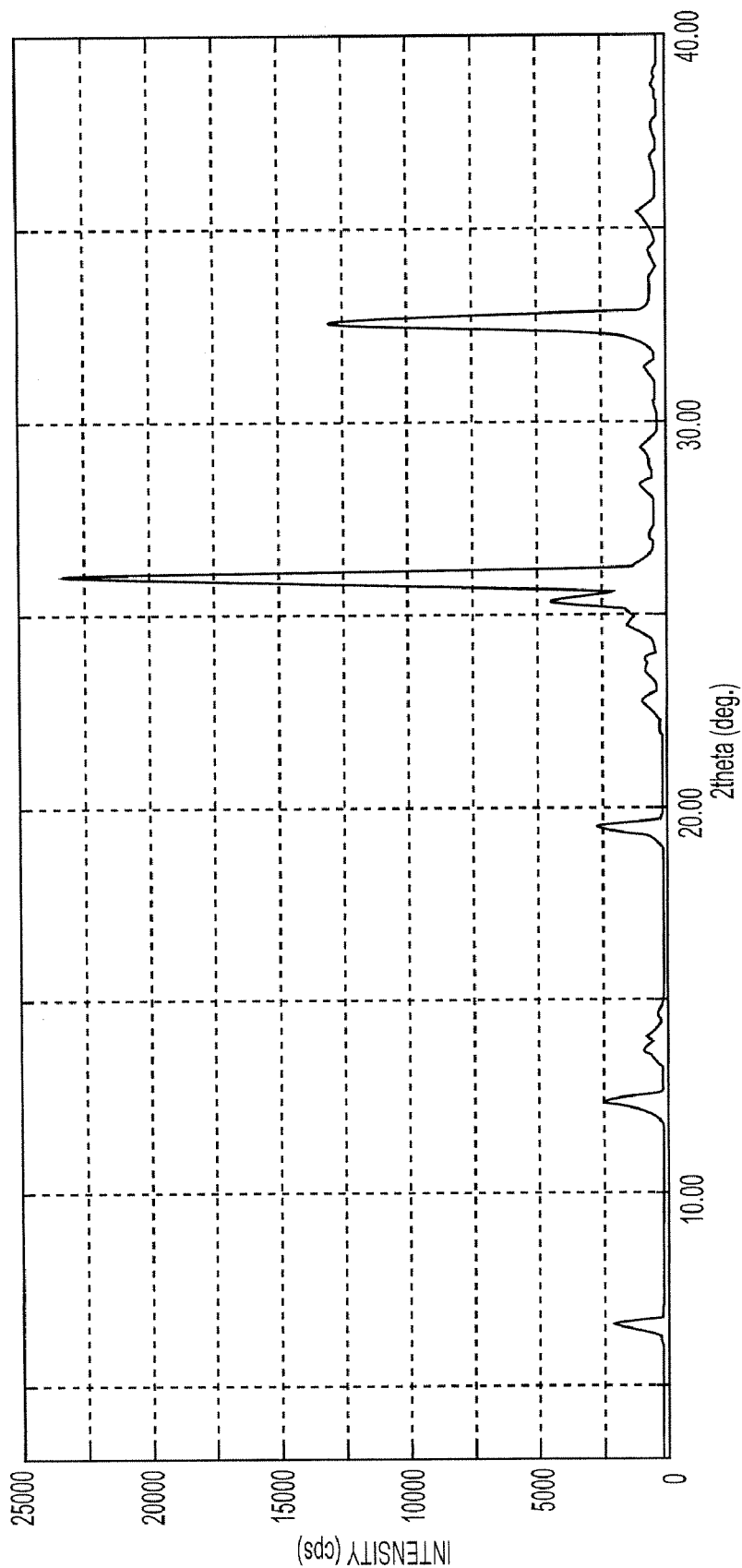
FIG. 60 is a graph of the relative PXRD of a sample of bupropion hydrobromide polymorphic form I after 6 months under the ICH (International Conference on Harmonisation of Technical Requirements for Registration of Pharmaceuticals for Human Use) conditions (40° C., 75% R.H.).

Samples of bupropion HBr form I were subjected to the conditions for the accelerated stability study as described in Example 10 and the shelf life stability study as described in Example 11. PXRD studies carried out after 3 months and 6 months for each sample gave the same results. The PXRD profile of one of the samples after 6 months in the accelerated stability condition is provided in FIG. 60.

Figure 61:
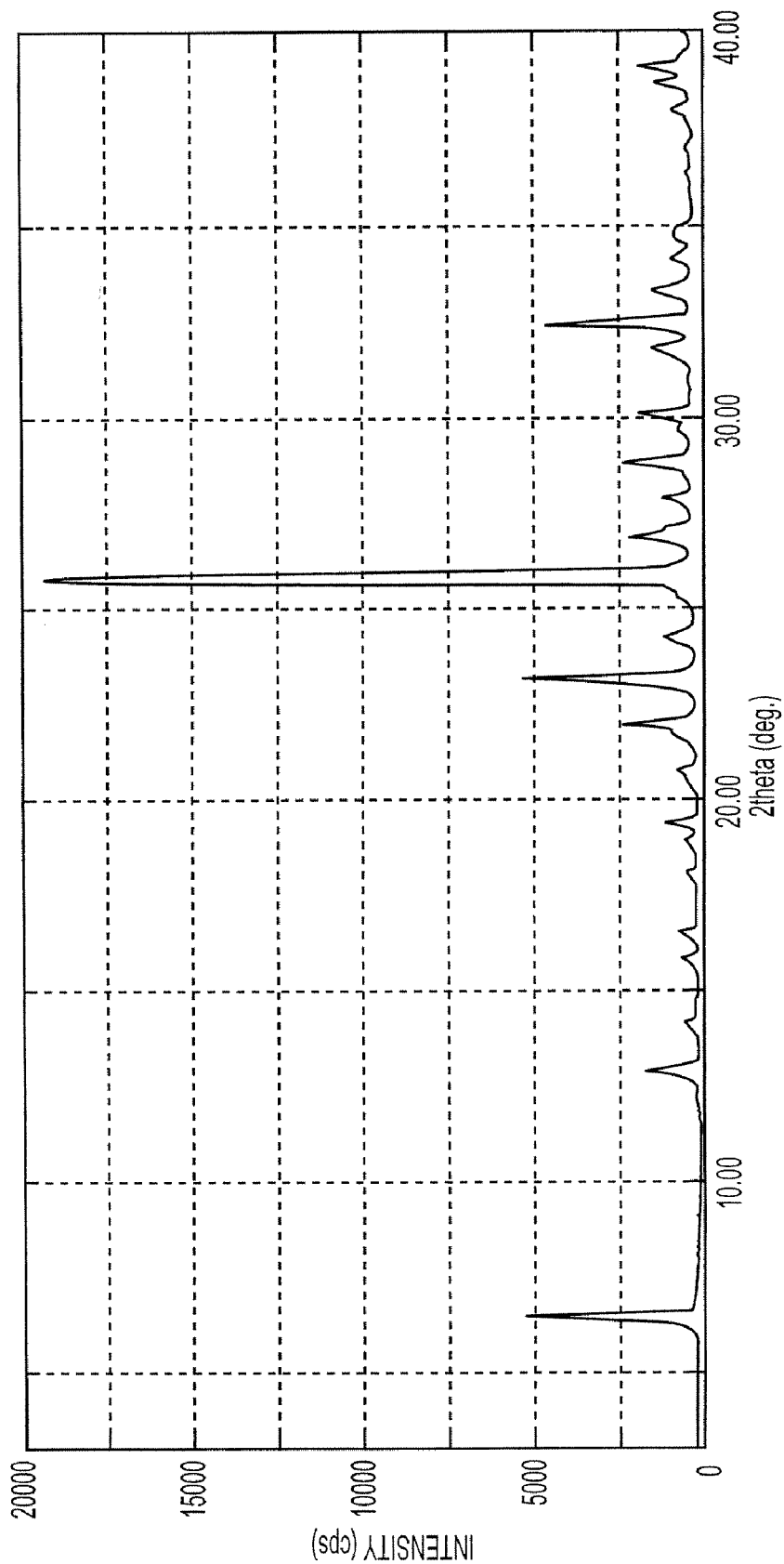
FIG. 61 is a graph of the PXRD of a sample of bupropion hydrobromide polymorphic form II after 1 month under ICH conditions (40° C., 75% R.H.).

Form II:

10 g of bupropion HBr form I were dissolved in a mixture of 170 ml of acetone and 7 ml of water. The mixture was brought to reflux with dissolution of the solid. The solution was then cooled to room temperature. After one night the precipitate formed was filtered and dried at 40oC under vacuum (30 mmHg) for 12 hours. 2.4 g of bupropion HBr form II were obtained. A sample of the product was prepared for an accelerated stability test, in ICH (International Conference on Harmonisation of Technical Requirements for Registration of Pharmaceuticals for Human Use) conditions (40oC/75% r.h.), by sealing the product in polyethylene bags, which in turn were placed in aluminium bags containing silica and sealed and placed in the stability chamber in ICH conditions (40oC/75% r.h.). The crystalline form was checked after maintaining the product under these conditions for 1 month. The PXRD profile shown in FIG. 61 shows that the compound is still in form II. This demonstrates the stability of crystal form II under these conditions.

Figure 62:
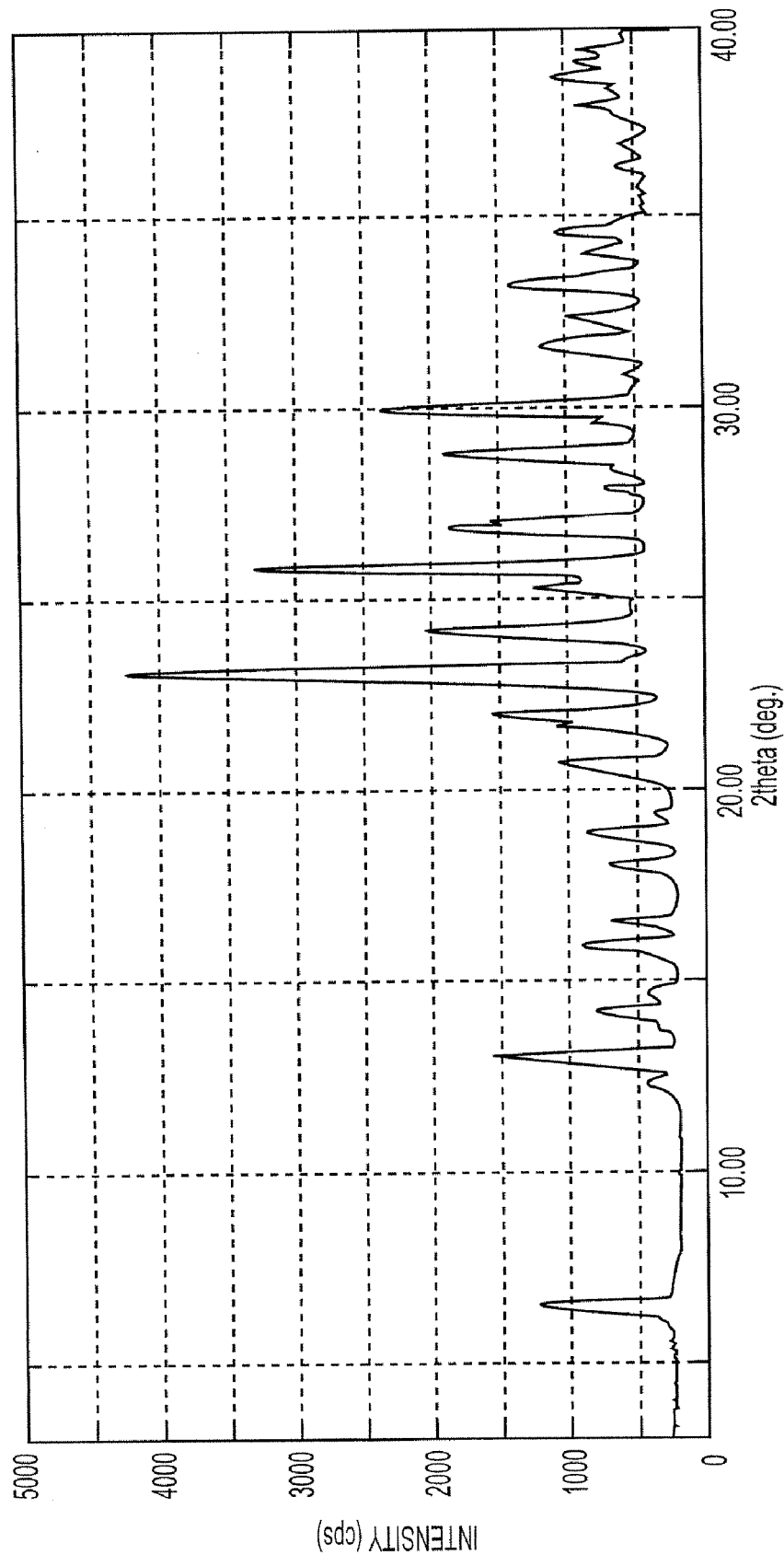
FIG. 62 is a graph of the PXRD of a sample of bupropion hydrobromide polymorphic form III after 1 month under ICH conditions (40° C., 75% R.H.).

Form III:

20 g of bupropion hydrobromide form 1 and 96 ml of absolute ethanol were placed in a 250 ml flask. The mixture was brought to reflux obtaining complete dissolution of the solid. The solution was then cooled to room temperature without stirring and left in these conditions for 18 hours. The resulting crystalline solid was then filtered and dried under vacuum (30 mmHg) at 50oC for 4 hours. 11.2 g of bupropion HBr form III were obtained. A sample of the product was prepared for stability testing by sealing the product in polyethylene bags, which in turn were placed in aluminium bags containing silica and sealed, and placed in the stability chamber in ICH conditions (40 oC/75% r.h.). The crystalline form was checked after maintaining the product in these conditions for 1 month. The PXRD profile shown in FIG. 62 demonstrates that the product is not stable in this form under these conditions, as the majority of the product changed to form II.

Example 13

HBr—SR Tablets for 100 and 150 mg Strength as Alternate to HCl—SR

Formulation to be based on options used during the development of the Wellbutrin HCl SR 100 and 150 mg.

Bupropion HCl was replaced with HBr and adjusted to obtain same amount Bupropion base.

Filler materials adjusted accordingly in order to obtain the same tablet core weights.

e.g. 150 mg HCl=130 mg base=174 mg HBr 100 mg=86.7=116

HBr Granulation Process:

Bupropion HBr is granulated with an aqueous solution containing Polyvinyl Alcohol and Stabilizing agent such as Oxalic acid or Succinic acid or Aspartic acid or other suitable acid compounds, in a Fluid bed granulator.

The dry granules are than mixed with water soluble polymer or mixtures of hydrophobic/hydrophilic polymers at various viscosity grades. In trials used Hypromellose (Hydroxypropyl methylcelluloseK4M CR grade) as well as Hydroxypropyl Cellulose (HPC) at quantities to obtain target release.

Microcrystalline Cellulose (MCC) was used as filler and binding material. Could be replaced with Lactose. For final lubrication Glyceryl Behenate (Compritol 888 ATO) was used. Other suitable lubricant such as Stearic Acid, Sodium Fumarate are suitable.

The compressed tablets are then coated with a non-functional colored film coating solution.

Formulation example: mg/unit (Target weight 400 mg) for 174 mg strength (equivalent to 150 mg HCl)

| | |
|---|---|
| Bupropion HBr | 174 mg |
| Polyvinyl Alcohol | 16 |
| Stabilizer | 20 |
| HPMC (HPC) | 40 |
| MCC | 144 |
| Glyceryl Behenate | 6 |

Coating: Opadry provided by Colorcon, approximately 3-4% weight gain

Above formulation(s) are evaluated without use of stabilizers.

Example 14

Further Stability Studies

Stability of Bupropion HBr 348 Mg Tablets

In these studies, the stability of bupropion HBr tablets (Lot # Bup-HBr-XL-348-025-5 (7, 30 and 90 counts) were tested after storage at 40 degrees C. and 75% relative humidity as described previously for 348 mg tablets prepared as described above and having the tablet composition shown in Table 99. These experiments evaluated the results of accelerated stability of the bupropion HBr XL 348 mg tablets packaged in 7, 30 and 90 counts based on a comparison of the changes in physical appearance, assay, the level of the known degradation impurities and the dissolution profiles of the 1, 2, 3 and 6M time points within the initial data.

No significant changes were observed in physical appearance, and the assay values of the tablets for all counts, however, as expected, there were gradual increase in the levels of two major known degradation impurities (3-CBZ and 852U77) and going from 7 to 90 counts, the percentages of the latter two impurities were varied. The dissolution profiles of the drug product for all counts were lower at the first month for all time points in comparison with the initial profile, however, other stability time points varied, for example:

7 Counts: the 2M and 3M were similar to the initial and 6M similar to the 1M.

30 Counts: The 6M was similar to the 1M and lower than the initial, the 2 & 4 hours time points for 2M and 3M were similar to the initial, however, the 8 & 16 hours time points were lower than the corresponding values.

90 Counts: Essentially lower dissolution profiles were observed for 2M, 3M, and 6M in comparison with the initial profiles These results are contained in FIG. 63.

Example 15

Additional Stability Testing of 150 mg, 300 mg Bupropion HBr Tablets (Lot # Bup-Hbr-Ea-150-002-5 and Bup-Hbr-300-001-5)

The same criteria were used to evaluate the stability of Bupropion HBr EA 150 and 300 mg drug products for the 90 counts. Similar results were obtained for the two drug products as compared with the bupropion HBr XL 348 XL 348 mg tablet-90 counts, however, better disolution stability data were observed, i.e., no significant differences of the dissolution profiles for 1M, 2M, 3M, & 6M were observed for the two EA products in comparison with their corresponding initials, except the 6M dissolution data for the 300 mg which showed slightly lower values. These results are in FIG. 64.

Example 16

Additional Open Dish-Closed Bottle Stability Studies

Experiments were conducted comparing the stability of bupropion HBr XL 174 mg core, Bupropion HBr XL 348 core, Bupropion HCl XL 150 mg Core and Bupropion HCl XL 300 mg core over 10 and 20 days under open bottle and closed bottle conditions. These studies were again effected at 40 degrees C. and 75% relative humidity. Degradation was again assessed by assaying for known impurities 3-CBZ and 852U77. As before the bupropion HBr cores were less subject to degradation than the bupropion HCl cores under open and closed bottle conditions. These results are contained in FIG. 65.

Example 17

Dissolution of Bupropion Formulations According to the Invention in Different USP-3 Media The dissolution of bupropion HBr formulations according to the invention were assessed in three USP-3 media, i.e., SGF pH 1.2, Acetate Buffer pH 4.5 and Phosphate Buffer pH 6.8 over a period of 16 hours. These results are contained in FIG. 66. Particularly Bupropion HBr XL 348 mg tablets (final), Lot # Bup-HBr-XL-012-5; Wellbutrin XL 300 mg tablets (final), Lot # 05A116; Bupropion HBr XL 348 mg tablets EC1 Lot # Bup-HBr-XL-012-5 (EC 32 mg wg) and Wellbutrin XL 300 mg tablets (EC10-Lot # 05D047 were assessed in SGF media pH 1.2 for 2 hours, Acetate Buffer pH 4.5 for 2 hours, and Phosphate Buffer SIF pH 6.8 for a total of 10 hours. The results are contained in the FIG. 66-68.

Additionally, FIG. 66 contains the results of dissolution testing of a bupropion HBr formulation according to the invention, i.e., bupropion HBr 348 mg, lot # 05E304, versus BupHCl 300 mg (Bup 300XL Target) lot# 01L238 in vivo and BUP 300XL Target in USP3-0.5% SLS media over times ranging from 0 to 16 hours.

Additionally the same Figure tabulates the results of these dissolution experiments comparing % drug release over time for bupropion HBr 348 mg Lot # 05E304 in USP-3 media (SGF pH 1.2 and 0.5% SLS after 2 hours, Acetate Buffer pH 4.5 after 2 hours and Phosphate Buffer pH 6.8 after a total of 16 hrs.

Also, FIG. 68 contains comparative dissolution profiles for Bupropion HBr XL 348 mg final, Wellbutrin XL EC, tablets in different USP-3 media (SGF pH 1.2, acetate buffer pH 4.5 and phosphate buffer pH 6.8) compared against in vivo data for Bupropion HCl 150 mg XL target (Lot 02A063) over a period of 16 hours.

TABLE 1

Assay of bupropion salts by HPLC

| Test | Maleate | Tosylate | Fumarate | HBr | Succinate | Tartrate acid | Tartrate neutral | Citrate |
|---|---|---|---|---|---|---|---|---|
| Assay | 99.7% | 97.4% | 89.8% | 99.7% | 97.6 | 84.9% | 51.7%* | 85.0% |

TABLE 2 moisture content and pH of aqueous solutions:

| | Original (Initial APIs) | | After re crystallization (R&D) | | Tested after 2 Months |
|---|---|---|---|---|---|
| | | pH | Tested after 1 day | | |
| Sample ID | KF | (aq. 0.5%) | KF | pH (aq. 0.5%) | KF |
| Bup-HCl | 0.0 | 5.90 | | | |
| Bup-Maleate | 0.10 | 4.29 | | | |
| Bup-Tosylate | 1.71* | 5.56 | 023 | 5.88 | 0.18 |
| Bup-Fumarate | 0.09 | 3.84 | | | |
| Bup-HBr | 0.00 | 5.92 | | | |
| Bup-Succinate | 0.13 | 4.82 | | | |
| Bup-Tartrate | 0.18 | 3.62 | | | |
| Bup-Tartrate neutral | 0.14 | 3.62 | | | |
| Bup-Citrate (I) | 0.23 | 3.89 | | | |

*KF after 3M = 1.80%
Bup = bupropion

TABLE 3

Solubility & other physical properties: Bupropion HBr vs Bupropion HCl.

| | Solubility (mg/ml) | | |
|---|---|---|---|
| Sample ID | Water | EtOH | IPA |
| Bupropion HCl | 270 | 80 | 10 |
| Bupropion HBr | 143 | 92 | 12 |

| Sample ID | PS (Malvern) | | Moisture Content (KF) | pH (aq. 0.5%) | MP (DSC) |
|---|---|---|---|---|---|
| Bupropion HCl (Erregierre) | 10% | 32 μm | 0.01% | 5.90 | 243.6C |
| | 50% | 102 μm | | | |
| | 90% | 276 μm | | | |
| Bupropion HBr (Chemi) | 10% | 72 μm | 0.00% | 5.92 | 234.1C |
| | 50% | 245 μm | | | |
| | 90% | 657 μm | | | |

TABLE 4

40° C./75% RH
Close Vial

| (DS + Placebo)[1] | (DS + Placebo)[1] + Water[2] | (DS + Placebo)[1] + (Water + EtOH + IPA)[3] | (DS + Placebo)[1] + (IPA + EtOH)[4] |
|---|---|---|---|

[1] 300 mg of the drug substance was placed in a 2 mL vial, then 100 mg placebo (almost double of the required amount) was added, and mixed well.
[2] Two drops of water was added to the spiked placebo and mixed well with a spatula, then closed with a cup.
[3] A mixture of equal volume of water, EtOH and IPA was prepared. Two drops of the latter mixture was added to the spiked placebo, and mixed well with a spatula, then closed with a cup.
[4] A mixture of equal volume of EtOH and IPA was prepared. Two drops of the latter mixture was added to the spiked placebo, and mixed well with a spatula, then closed with a cup.

TABLE 5

| API ID | Lot # | Quantity/bottle | # of glass bottle 40° C./75% RH | Stability pulling time (Day) |
|---|---|---|---|---|
| Bupropion HBr | STN07492 | 348 mg | 2 | 14 & 24 |
| Bupropion HCl | STN06973 | 300 mg | 2 | 14 & 24 |
| Bupropion HBr | STN07491 | 348 mg | 1 | 10 |
| | STN07492 | 348 mg | 1 | 10 |
| Bupropion HCl | STN06973 | 300 mg | 1 | 10 |
| | STN06978 | 300 mg | 1 | 10 |

TABLE 6

Closed glass bottle stability studies (40° C./75% RH) on Bupropion-HBr & HCl APIs.

| | Bupropion HBr, Lot# STN07492 | | | Bupropion HCl, L# STN06973 | | |
|---|---|---|---|---|---|---|
| Tests | Initial | 14-Days | 24 Days | Initial | 14-Days | 24 Days |
| % Assay | 99.6 | 98.8 | 99.5 | 100.4 | 98.5 | 98.5 |
| % Impurities | | | | | | |
| 3-CBZ | 0.007 | 0.015 | 0.022 | 0.002 | 0.019 | 0.082 |
| 852U77 | 0.009 | 0.058 | 0.052 | 0.003 | 0.010 | 0.023 |
| 20U78/dilu | 0.044 | 0.048 | 0.038 | 0.043 | 0.038 | 0.040 |
| 827U76 | ND | 0.012 | 0.016 | ND | ND | 0.102 |
| Total | 0.098 | 0.105 | 0.104 | 0.044 | 0.038 | 0.049 |
| unknown | | | | | | |
| Total (%) | 0.16 | 0.23 | 0.23 | 0.09 | 0.11 | 0.30 |

TABLE 7

Closed glass bottle stability studies (40 C/75% RH) on Bupropion HCl & Bupropion HBr APIs.

| | Bupropion HBr, Lot# STN07491 | | Bupropion HBr, Lot# STN07492 | |
|---|---|---|---|---|
| Tests | Initial | 10-Days | Initial | 10 Days |
| % Assay | 99.5 | 98.2 | 99.6 | 99.2 |
| % Impurities | | | | |
| 3-CBZ | 0.011 | 0.070 | 0.007 | 0.031 |
| 852U77 | ND | 0.125 | ND | 0.055 |
| 20U78/dilu | 0.041 | 0.051 | 0.041 | 0.044 |
| 827U76 | ND | 0.039 | ND | ND |

TABLE 7-continued

Closed glass bottle stability studies (40 C/75% RH) on Bupropion HCl & Bupropion HBr APIs.

| Total unknown | 0.129 | 0.129 | 0.194 | 0.15 |
|---|---|---|---|---|
| Total (%) | 0.17 | 0.42 | 0.23 | 0.24 |

| | Bupropion HCl, Lot# STN06973 | | Bupropion HCl, Lot# STN06978 | |
|---|---|---|---|---|
| Tests | Initial | 10-Days | Initial | 10 Days |
| % Assay | 99.4 | 96.3 | 99.1 | 96.5 |
| % Impurities | | | | |
| 3-CBZ | 0.003 | 0.110 | 0.002 | 0.278 |
| 852U77 | ND | 0.047 | ND | 0.124 |
| 20U78/dilu | 0.040 | 0.047 | 0.04 | 0.057 |
| 827U76 | ND | 0.045 | ND | 0.141 |
| Total unknown | 0.053 | 0.187 | 0.165 | 0.137 |
| Total (%) | 0.10 | 0.44 | 0.21 | 0.74 |

TABLE 8

Each trial's contents and amounts of each material per part

| | Amount (g) | | | | |
|---|---|---|---|---|---|
| Materials | Part 1 | Part 2 | Part 3 | Part 4 | Part 5 |
| Bupropion HBr | 2062.5 | 2062.5 | 2062.5 | 2062.5 | 2062.5 |
| PVA | 68.75 | 68.75 | 68.75 | 68.75 | 68.75 |
| Purified Water | 1452.5 | 1452.5 | 1452.5 | 1452.5 | 1452.5 |

TABLE 9

Summary of specifications for granulation procedure.

| Specification | Range | Target |
|---|---|---|
| Fan Speed | Slow | Slow |
| Air Volume (CMH) | 60–65 | 65 |
| Exhaust Temperature (° C.) | 35–45 | 40 |
| Supply Temperature (° C.) | 60–65 | 65 |
| Product Temperature (° C.) | 35–55 | 45 |
| Atomizing Air Pressure (Bar/psi) | 35 | 35 |
| Pump Speed (rpm) | 18 | 18 |
| Liquid Flow Rate (g/min) | 13 | 13 |
| Bed Dew Point (MMWC) | 0 | 0 |
| Filter Dew Point (MMWC) | 100–300 | 200 |

TABLE 10

The amount of lubricant in the final formulation was 343.75 g, which was 3.125% of the total.

| Materials | Amount (g) |
|---|---|
| Part 1 | 2131.25 |
| Part 2 | 2131.25 |
| Part 3 | 2131.25 |
| Part 4 | 2131.25 |
| Part 5 | 2131.25 |
| Compritol 888 | 343.75 |
| Total | 11000.0 |

TABLE 11

Summary of Specifications for Tablet Press Set-up.

| Parameters | Settings/Ranges |
|---|---|
| Pre-Compression Thickness (mm) | 2 |
| Control Thickness (mm) | 1.5 |
| Fill Thickness (mm) | 7–8 |
| Overload Pressure (Tons) | 1.5–2.0 |
| Tablets per minute | 450–500 |
| Feeder Speed | 1–2 |
| Feeder Control | Auto |

TABLE 12

Summary of specifications for compression

| Parameters | Specification for 174 mg Tablet | Specification for 348 mg Tablet |
|---|---|---|
| Individual Tablet Weight (mg) | 185.6 ± 5% (176.3 mg-194.9 mg) | 371.2 ± 5% (352.6 mg-389.8 mg) |
| Average Tablet Weight (mg) | 185.6 ± 3% (180.0 mg-191.2 mg) | 371.2 ± 3% (360.1 mg-382.3 mg) |
| Tablet Hardness (SC) | 6.0-12.0 | 6.0-12.0 |
| Tablet Thickness (mm) | 5.0-6.0 | 4.5-5.0 |
| Friability (%) | <0.8 | <0.8 |

TABLE 13

Formulations used as the Ethocel coating on the 174 mg and 348 mg Bupropion HBr cores.

| FORMULATION 1 | FORMULATION 2 | FORMULATION 3 |
|---|---|---|
| Ethocel (Ethyl Cellulose) Standard 100 Premium | Ethocel (Ethyl Cellulose) Standard 100 Premium | Ethocel (Ethyl Cellulose) Standard 100 Premium |
| Povidone USP (Kollidone 90F) | Povidone USP (Kollidone 90F) | Povidone USP (Kollidone 90F) |
| Polyethylene Glycol 4000 | Polyethylene Glycol 4000 | Polyethylene Glycol 4000 |
| Ethyl Alcohol 95% USP | Dibutyl Sebacate | Ethyl Alcohol 95% USP |
| Isopropyl Alcohol (IPA) | Ethyl Alcohol 95% USP | |

TABLE 14

Formulations used as the Final Coats on the 174 mg and 348 mg Bupropion HBr tablets.

| FORMULATION A | FORMULATION B |
|---|---|
| Eudragit L30D-55 | Eudragit L30D-55 |
| Chroma-Tone DEB 5156-CLE | Syloid 244FP |
| Purified Water | Polyethylene Glycol 4000 |
| | Triethyl Citrate |
| | Purified Water |

TABLE 15

Summary of Specifications that were kept constant in the Ethocel coating Process.

| Process Parameters | Operational Ranges | Target |
|---|---|---|
| Inlet Temperature for coating (° C.) | SV: 40 ± 5 PV: 40 ± 5 | 40 |
| Inlet Temperature for Drying (° C.) | 30-35 | 35 |

TABLE 15-continued

Summary of Specifications that were kept constant in the Ethocel coating Process.

| Process Parameters | Operational Ranges | Target |
|---|---|---|
| Exhaust Temperature | 30 ± 10 | 30 |
| Product Temperature | 25-35 | 28 |
| ΔP Differential Pressure (W.C) | (−0.1)-(−0.12) | −0.10 |
| Supply Air Flow (CFM) | 200 ± 50 | 200 |
| Pan Speed (rpm) | 2.5-12 | 5.0 |
| Atomizing Air (psi) | 35-40 | 35 |
| Pattern Air (psi) | 20-30 | 25 |
| Spray Rate (g/min) | 5-15 | 6.0 |

TABLE 16

Summary of Specifications that were kept constant in the Final coating Process.

| Process Parameters | Operational Ranges | Target |
|---|---|---|
| Inlet Temperature for coating (° C.) | SV: 50 ± 5 PV: 50 ± 5 | 50 |
| Inlet Temperature for Drying (° C.) | 40 ± 5 | 40 |
| Exhaust Temperature | 35 ± 5 | 38 |
| Product Temperature | 35 ± 2 | 35 |
| ΔP Differential Pressure (W.C) | (−0.1)-(−0.12) | −0.10 |
| Supply Air Flow (CFM) | 200 ± 50 | 200 |
| Pan Speed (rpm) | 2.5-15 | 12.0 |
| Atomizing Air (psi) | 25-35 | 35 |
| Pattern Air (psi) | 20-30 | 25 |
| Spray Rate (g/min) | 5-15 | 13.0 |

TABLE 17

Materials used in one part of the batch, the percentage of each constituent, the amount per tablet and the amount per batch, for BUP-HBr-XL-009-5

| Materials | % | mg/tablet | Batch Quantity (g) |
|---|---|---|---|
| Bupropion HBr | 93.75 | 348.00 | 1993.75 |
| PVA | 3.125 | 11.60 | 68.75 |
| Compritol 888 | 3.125 | 11.60 | 68.75 |
| Total | 100.00 | 371.2 mg | 2131.25 |

TABLE 18

Results obtained using 9 mm tooling for batch BUP-HBr-XL-009-5.

| Parameters | Theoretical | Actual |
|---|---|---|
| Average Individual Tablet Weight | 371.2 mg | 371.5 mg |
| Average Hardness | 6.0-12.0 SC | 10.77 SC |
| Average Thickness | 5.0-6.0 mm | 5.60 mm |
| Friability | <0.8% | 0% |

TABLE 19

Results obtained using 10 mm tooling for batch BUP-HBr-XL-009-5.

| Parameters | Theoretical | Actual |
|---|---|---|
| Average Individual Tablet Weight | 371.2 mg | 366.5 mg |
| Average Hardness | 6.0-12.0 SC | 7.50 SC |
| Average Thickness | 5.0-6.0 mm | 4.97 mm |
| Friability | <0.8% | 0% |

TABLE 20

Materials used in one part of the batch, the percentage of each constituent, the amount per tablet and the amount per batch for batch BUP-HBr-XL-021-5.

| Materials | % | mg/tablet | Batch Quantity (g) |
|---|---|---|---|
| Bupropion HBr | 93.75 | 174.00 | 1993.75 |
| PVA | 3.125 | 5.80 | 68.75 |
| Compritol 888 | 3.125 | 5.80 | 68.75 |
| Total | 100.00 | 185.60 | 2131.25 |

TABLE 21

Results obtained using 7 mm tooling for batch BUP-HBr-XL-021-5.

| Parameters | Theoretical | Actual |
|---|---|---|
| Average Individual Tablet Weight | 185.6 mg | 186.8 mg |
| Average Hardness | 6.0-12.0 SC | 9.23 SC |
| Average Thickness | 4.5-5.0 mm | 4.70 mm |
| Friability | <0.8% | 0% |

TABLE 22

Materials used in the EC coating and their quantities for batch BUP-HBr-XL-348-013-5.

| Materials | % Contribution to Total Solution | Batch Quantity (g) | % of Solids in Solution |
|---|---|---|---|
| Ethocel (Ethyl Cellulose) Standard 100 Premium | 3.60 | 77.44* | 38.74 |
| Povidone USP (Kollidone 90F) | 4.600 | 99.22* | 49.64 |
| PEG 4000 | 1.07 | 23.23* | 11.62 |
| Ethyl Alcohol 95% USP | 86.44 | 1859.50 | N/A |
| Isopropyl Alcohol 99% USP | 4.54 | 97.87 | N/A |
| Total | 100.00 | 2151.00 | 100.00 |

*Total solid component of the formulation included 77.44 g of Ethocel, 99.22 g of Povidone and 23.23 g of PEG 4000, which gave a total solid amount of 199.89 g. The solid component of the formulation made up 9% of the total solution and the remaining 91% was made up of liquid.

TABLE 23

Theoretical and Actual Tablet weights at 28 mg, 30 mg, 32 mg and 34 mg weight gains for batch BUP-HBr-XL-348-013-5.

| Weight Gain (mg) | Theoretical Weight (mg) | Actual Weight (mg) |
|---|---|---|
| 28.0 | 400.0 | 401.3 |
| 30.0 | 402.0 | 402.6 |
| 32.0 | 404.0 | 404.5 |
| 34.0 | 406.0 | 406.8 |

TABLE 24

Materials used in the Final coating and their quantities for batch BUP-HBr-XL-348-013-5.

| Materials | % Contribution to Total Solution | Batch Quantity (g) | Amount of Solid (g) | % of Solids in Solution |
|---|---|---|---|---|
| Eudragit L30 D-55 | 22.73 | 104.8 | 31.44 | 65.00* |
| Chroma-Tone | 3.66 | 16.90 | 16.90 | 35.00** |

TABLE 24-continued

Materials used in the Final coating and their quantities for batch BUP-HBr-XL-348-013-5.

| Materials | % Contribution to Total Solution | Batch Quantity (g) | Amount of Solid (g) | % of Solids in Solution |
|---|---|---|---|---|
| DEB 5156-CLE | | | | |
| Purified Water (1) | 21.78 | 100.40 | N/A | N/A |
| Purified Water (2) | 51.89 | 239.20 | N/A | N/A |
| Total | 100.00 | 460.95 | 48.34*** | 100.00 |

*The percentage of Eudragit, solid, that contributed to the total amount of solid was 65%.
**The percentage of Chroma-Tone, solid, that contributed to the total amount of solid was 35%.
***The Total amount of solid (48.34 g) was 10.5% of the total solution.

TABLE 25

Theoretical and Actual Tablet weights at 4 mg, 5 mg, 6 mg and 7 mg weight gains.

| Weight Gain (mg) | Theoretical Weight (mg) | Actual Weight (mg) |
|---|---|---|
| 4.0 | 410.0 | 410.5 |
| 5.0 | 411.0 | 410.8 |
| 6.0 | 412.0 | 412.4 |
| 7.0 | 413.0 | 413.9 |

TABLE 26

Materials used in the EC coating and their quantities for batch BUP-HBr-XL-348 mg-018-5.

| Materials | % Contribution to Total Solution | Batch Quantity (g) | % of Solids in Solution* |
|---|---|---|---|
| Ethocel (Ethyl Cellulose) Standard 100 Premium | 3.42 | 73.57 | 38.00 |
| Povidone USP (Kollidone 90F) | 4.41 | 94.86 | 49.00 |
| PEG 4000 | 1.17 | 25.17 | 13.00 |
| Ethyl Alcohol 95% USP | 86.45 | 1859.53 | N/A |
| Isopropyl Alcohol 99% USP | 4.55 | 97.87 | N/A |
| Total | 100.00 | 2151.00 | 100.00 |

*Total solid included 73.57 g of Ethocel, 94.86 g of Povidone and 25.17 g of PEG 4000. This gave a total of 193.6 g total solid amount.

TABLE 27

Theoretical and Actual Tablet weights at 26 mg, 28 mg, 30 mg, and 32 mg weight gains for batch BUP-HBr-XL-348 mg-018-5.

| Weight Gain (mg) | Theoretical Weight (mg) | Actual Weight (mg) |
|---|---|---|
| 26.0 | 398.0 | 397.7 |
| 28.0 | 400.0 | 399.5 |
| 30.0 | 402.0 | 401.5 |
| 32.0 | 404.0 | 404.0 |

TABLE 28

Materials used in the Final coating and their quantities for batch BUP-HBr-XL-348 mg-018-5.

| Materials | % Contribution to Total Solution | Batch Quantity (g) | Amount of Solid (g) | % of Solids in Solution |
|---|---|---|---|---|
| Eudragit L30D D-55 | 22.75 | 104.86 | 31.46 | 65.00* |
| Syloid 244FP | 2.62 | 12.08 | 12.08 | 25.00** |
| Carbowax 4000 | 0.70 | 3.22 | 3.22 | 6.65** |
| Triethyl Citrate | 0.36 | 1.64 | 1.64 | 3.39** |
| Purified Water (1) | 33.84 | 156.00 | N/A | N/A |
| Purified Water (2) | 39.73 | 183.15 | N/A | N/A |
| Total | 100.00 | 460.95 | 48.40*** | 100.00 |

*The percentage of Eudragit, solid, that contributed to the total amount of solid was 65%.
**The percentage of Syloid, Carbowax 4000 and Triethyl Citrate that contributed to the total amount of solid was 25%, 6.65% and 3.39%, respectively. This gave a total of 35%.
***The total amount of solid (48.4 g) was 10.5% of the total solution.

TABLE 29

Theoretical and Actual Tablet weights at 4 mg, 5 mg, 6 mg, and 7 mg weight gains for batch BUP-HBr-XL-348 mg-018-5.

| Weight Gain (mg) | Theoretical Weight (mg) | Actual Weight (mg) |
|---|---|---|
| 4.0 | 408.0 | 408.5 |
| 5.0 | 409.0 | 409.3 |
| 6.0 | 410.0 | 410.7 |
| 7.0 | 411.0 | 411.1 |

TABLE 30

Materials used in the EC coating and their quantities for batch BUP-HBr-XL-174 mg-022-5.

| Materials | % Contribution to Total Solution | Batch Quantity (g) | % of Solids in Solution* |
|---|---|---|---|
| Ethocel (Ethyl Cellulose) Standard 100 Premium | 3.60 | 116.12 | 40.00 |
| Povidone USP (Kollidone 90F) | 4.32 | 139.34 | 48.00 |
| PEG 4000 | 1.08 | 34.84 | 12.00 |
| Ethyl Alcohol 95% USP | 86.45 | 2788.54 | N/A |
| Isopropyl Alcohol 99% USP | 4.55 | 146.76 | N/A |
| Total | 100.00 | 3225.60 | 100.00 |

*Total Solid included 116.12 g of Ethocel, 139.34 g of Povidone and 34.84 g of PEG 4000. This gave a total solid amount of 290.3 g.

TABLE 31

Theoretical and Actual Tablet weights at 20 mg, 22 mg, 24 mg, 26 mg, 28 mg, 29 mg, and 30 mg weight gains for batch BUP-HBr-XL-174 mg-022-5.

| Weight Gain (mg) | Theoretical Weight (mg) | Actual Weight (mg) |
|---|---|---|
| 20.0 | 206.0 | 206.1 |
| 22.0 | 208.0 | 207.8 |
| 24.0 | 210.0 | 210.2 |
| 26.0 | 212.0 | 211.5 |
| 28.0 | 214.0 | 213.7 |
| 29.0 | 215.0 | 214.9 |
| 30.0 | 216.0 | 216.5 |

TABLE 32

Materials used in the Final coating and their quantities for batch BUP-HBr-XL-174 mg-022-5.

| Materials | % Contribution to Total Solution | Batch Quantity (g) | Amount of Solid (g) | % of Solids in Solution |
|---|---|---|---|---|
| Eudragit L30D D-55 | 22.75 | 104.86 | 31.46 | 65.0* |
| Syloid 244FP | 2.62 | 12.08 | 12.08 | 25.0** |
| Carbowax 4000 | 0.70 | 3.22 | 3.22 | 6.65** |
| Triethyl Citrate | 0.36 | 1.64 | 1.64 | 3.39** |
| Purified Water (1) | 33.84 | 156.00 | N/A | N/A |
| Purified Water (2) | 39.73 | 183.15 | N/A | N/A |
| Total | 100.00 | 460.95 | 48.40*** | 100.00 |

*The percentage of Eudragit, solid, that contributed to the total amount of solid was 65%.
**The percentage of Syloid, Carbowax 4000 and Triethyl Citrate that contributed to the total amount of solid was 25%, 6.65% and 3.39%, respectively. This gave a total of 35%.
***The Total amount of solid (48.4 g) was 10.5% of the total solution.

TABLE 33

Theoretical and Actual Tablet weights at 4 mg, 5 mg, 6 mg, and 7 mg weight gains for batch BUP-HBr-XL-174 mg-022-5.

| Weight Gain (mg) | Theoretical Weight (mg) | Actual Weight (mg) |
|---|---|---|
| 4.0 | 219.0 | 219.4 |
| 5.0 | 220.0 | 220.2 |
| 6.0 | 221.0 | 221.2 |
| 7.0 | 222.0 | 223.0 |

TABLE 34

Materials used in the EC coating and their quantities for batch BUP-HBr-XL-348 mg-023-5.

| Materials | % Contribution to Total Solution | Batch Quantity (g) | % of Solids in Solution* |
|---|---|---|---|
| Ethocel (Ethyl Cellulose) Standard 100 Premium | 3.69 | 79.37 | 42.71 |
| Povidone USP (Kollidone 90F) | 3.69 | 79.37 | 42.71 |
| PEG 4000 | 1.26 | 27.11 | 14.58 |
| Dibutyl Sebacate, NF | 0.36 | 7.75 | N/A |
| Ethyl Alcohol 95% USP | 91.00 | 1957.4 | N/A |
| Total | 100.00 | 2151.00 | 100.00 |

*Total Solid includes 79.37 g of Ethocel, 79.37 g of Povidone, 27.11 g of PEG 4000 and 7.75 g of Dibutyl Sebacate. This gave a total solid amount of 193.6 g.

TABLE 35

Theoretical and Actual Tablet weights at 26 mg, 28 mg, 30 mg, and 32 mg weight gains for batch BUP-HBr-XL-348 mg-023-5.

| Weight Gain (mg) | Theoretical Weight (mg) | Actual Weight (mg) |
|---|---|---|
| 26.0 | 398.0 | 399.3 |
| 28.0 | 400.0 | 401.0 |
| 30.0 | 402.0 | 401.7 |
| 32.0 | 404.0 | 402.7 |

TABLE 36

Materials used in the EC coating and their quantities for batch BUP-HBr-XL-348 mg-025-5.

| Materials | % Contribution to Total Solution | Batch Quantity (g) | % of Solids in Solution* |
|---|---|---|---|
| Ethocel (Ethyl Cellulose) Standard 100 Premium | 3.69 | 79.40 | 41.00 |
| Povidone USP (Kollidone 90F) | 3.78 | 81.30 | 42.00 |
| PEG 4000 | 1.53 | 32.90 | 17.00 |
| Ethyl Alcohol 95% USP | 91.00 | 1957.40 | N/A |
| Total | 100.00 | 2151.00 | 100.00 |

*Total Solid included 79.40 g of Ethocel, 81.30 g of Povidone and 32.90 g of PEG 4000. This gave a total solid amount of 193.6 g.

TABLE 37

Theoretical and Actual Tablet weights at 26 mg, 28 mg, 30 mg, and 32 mg weight gains for batch BUP-HBr-XL-348 mg-025-5.

| Weight Gain (mg) | Theoretical Weight (mg) | Actual Weight (mg) |
|---|---|---|
| 26.0 | 398.0 | 397.8 |
| 28.0 | 400.0 | 400.6 |
| 30.0 | 402.0 | 401.4 |
| 32.0 | 404.0 | 402.2 |

TABLE 38

Materials used in the Final coating and their quantities for batch BUP-HBr-XL-348 mg-025-5.

| Materials | % Contribution to Total Solution | Batch Quantity (g) | Amount of Solid (g) | % of Solids in Solution |
|---|---|---|---|---|
| Eudragit L30D D-55 | 19.77 | 91.13 | 27.34 | 56.50* |
| Syloid 244FP | 3.15 | 14.52 | 14.52 | 30.00** |
| Carbowax 4000 | 0.95 | 4.36 | 4.36 | 9.00** |
| Triethyl Citrate | 0.47 | 2.17 | 2.17 | 4.50** |
| Purified Water (1) | 21.70 | 100.00 | N/A | N/A |
| Purified Water (2) | 53.96 | 248.77 | N/A | N/A |
| Total | 100.00 | 460.95 | 48.39*** | 100.00 |

*The percentage of Eudragit, solid, that contributed to the total amount of solid was 65%.
**The percentage of Syloid, Carbowax 4000 and Triethyl Citrate that contributed to the total amount of solid was 30%, 9% and 4.5%, respectively. This gave a total of 43.5%.
***The Total amount of solid (48.39 g) was 10.5% of the total solution.

TABLE 39

Theoretical and Actual Tablet weights at 4 mg, 5 mg, 6 mg, and 7 mg weight gains for batch BUP-HBr-XL-348 mg-025-5.

| Weight Gain (mg) | Theoretical Weight (mg) | Actual Weight (mg) |
|---|---|---|
| 4.0 | 408.0 | 408.3 |
| 5.0 | 409.0 | 408.8 |
| 6.0 | 410.0 | 409.5 |
| 7.0 | 411.0 | 411.1 |

TABLE 40

Materials used in the EC coating and their quantities for batch BUP-HBr-XL-348 mg-026-5.

| Materials | % Contribution to Total Solution | Batch Quantity (g) | % of Solids Solution* |
|---|---|---|---|
| Ethocel (Ethyl Cellulose) Standard 100 Premium | 3.69 | 79.37 | 41.00 |
| Povidone USP (Kollidone 90F) | 3.69 | 79.37 | 41.00 |
| PEG 4000 | 0.36 | 7.75 | 4.00 |
| Dibutyl Sebacate, NF | 1.26 | 27.11 | 14.00 |
| Ethyl Alcohol 95% USP | 91.00 | 1957.4 | N/A |
| Total | 100.00 | 2151.00 | 100.00 |

*Total Solid included 79.37 g of Ethocel, 79.37 g of Povidone, 7.75 g of PEG 4000 and 27.11 g of Dibutyl Sebacate. This gave a total solid amount of 193.6 g.

TABLE 41

Theoretical and Actual Tablet weights at 26 mg, 28 mg, 30 mg, and 32 mg weight gains for batch BUP-HBr-XL-348 mg-026-5.

| Weight Gain (mg) | Theoretical Weight (mg) | Actual Weight (mg) |
|---|---|---|
| 26.0 | 398.0 | 398.8 |
| 28.0 | 400.0 | 400.5 |
| 30.0 | 402.0 | 402.5 |
| 32.0 | 404.0 | 403.6 |

TABLE 42

Materials used in the EC coating and their quantities for batch BUP-HBr-XL-174 mg-027-5.

| Materials | % Contribution to Total Solution | Batch Quantity (g) | % of Solid in Solution* |
|---|---|---|---|
| Ethocel (Ethyl Cellulose) Standard 100 Premium | 3.69 | 138.87 | 41.00 |
| Povidone USP (Kollidone 90F) | 3.78 | 142.25 | 42.00 |
| PEG 4000 | 1.53 | 57.58 | 17.00 |
| Ethyl Alcohol 95% USP | 91.00 | 3424.63 | N/A |
| Total | 100.00 | 3763.33 | 100.00 |

*Total Solid included 138.87 g of Ethocel, 142.25 g of Povidone and 57.58 g of PEG 4000. This gave a total solid amount of 338.7 g.

TABLE 43

Theoretical and Actual Tablet weights at 22 mg, 24 mg, and 26 mg weight gains for batch BUP-HBr-XL-174 mg-027-5.

| Weight Gain (mg) | Theoretical Weight (mg) | Actual Weight (mg) |
|---|---|---|
| 22.0 | 208.0 | 207.7 |
| 24.0 | 210.0 | 210.8 |
| 26.0 | 212.0 | 212.4 |

TABLE 44

Materials used in the Final coating and their quantities for batch BUP-HBr-XL-174 mg-027-5.

| Materials | % Contribution to Total Solution | Batch Quantity (g) | Amount of Solid (g) | % of Solids in Solution |
|---|---|---|---|---|
| Eudragit L30D D-55 | 19.77 | 182.27 | 54.68 | 56.5* |
| Syloid 244FP | 3.15 | 29.03 | 29.03 | 30.0** |
| Carbowax 4000 | 0.95 | 8.71 | 8.71 | 9.0** |
| Triethyl Citrate | 0.47 | 4.35 | 4.35 | 4.5** |
| Purified Water (1) | 21.70 | 200.00 | N/A | N/A |
| Purified Water (2) | 53.98 | 497.26 | N/A | N/A |
| Total | 100.00 | 921.62 | 96.77*** | 100.00 |

*The percentage of Eudragit, solid, that contributed to the total amount of solid was 56.5%.
**The percentage of Syloid, Carbowax 4000 and Triethyl Citrate that contributed to the total amount of solid was 30.0%, 9.0% and 4.5%, respectively. This gave a total of 43.5%.
***The Total amount of solid (9.77 g) was 10.5% of the total solution.

TABLE 45

Theoretical and Actual Tablet weights at 4 mg, 5 mg, 6 mg, and 7 mg weight gains for batch BUP-HBr-XL-174 mg-027-5.

| Weight Gain (mg) | Theoretical Weight (mg) | Actual Weight (mg) |
|---|---|---|
| 4.0 | 216.0 | 216.6 |
| 5.0 | 217.0 | 217.6 |
| 6.0 | 218.0 | 217.8 |
| 7.0 | 219.0 | 219.8 |

TABLE 46

Each trial's contents and amounts of each material per part for EA formulation.

| | Amount (g) | | | | |
|---|---|---|---|---|---|
| Materials | Part 1 | Part 2 | Part 3 | Part 4 | Part 5 |
| Bupropion HBr | 2062.5 | 2062.5 | 2062.5 | 2062.5 | 2062.5 |
| PVA | 68.75 | 68.75 | 68.75 | 68.75 | 68.75 |
| Purified Water | 1452.5 | 1452.5 | 1452.5 | 1452.5 | 1452.5 |

TABLE 47

Summary of specifications for granulation procedure for EA formulations.

| Specification | Setting/Range | Target |
|---|---|---|
| Fan Speed | Slow | Slow |
| Air Volume (CMH) | 60-65 | 65 |
| Exhaust Temperature (° C.) | 35-45 | 40 |
| Supply Temperature (° C.) | 60-65 | 65 |
| Product Temperature (° C.) | 35-55 | 45 |
| Atomizing Air Pressure (Bar/psi) | 35 | 35 |
| Pump Speed (rpm) | 18 | 18 |
| Liquid Flow Rate (g/min) | 13 | 13 |
| Bed Dew Point (MMWC) | 0 | 0 |
| Filter Dew Point (MMWC) | 100-300 | 200 |

TABLE 48

The amount of lubricant in the final EA formulation was 343.75 g, which was 3.125% of the total.

| Materials | Amount (g) |
| --- | --- |
| Bupropion HBr Granules | 10656.25 |
| Compritol 888 | 343.75 |
| Total | 11000 |

TABLE 49

Summary of Specifications for Tablet Press Set-up for the EA formulation.

| Parameters | Settings/Ranges |
| --- | --- |
| Pre-Compression Thickness (mm) | 2 |
| Control Thickness (mm) | 1.5 |
| Fill Thickness (mm) | 7-8 |
| Overload Pressure (Tons) | 1.5-2.0 |
| Tablets per minute | 450-500 |
| Feeder Speed | 1-2 |
| Feeder Control | Auto |

TABLE 50

Summary of specifications for compression for the EA formulation.

| Parameters | Specification for 150 mg Tablet | Specification for 300 mg Tablet |
| --- | --- | --- |
| Individual Tablet Weight (mg) | 160.0 ± 5% (152.0 mg-168.0 mg) | 320.0 ± 5% (304.0 mg-336.0 mg) |
| Average Tablet Weight (mg) | 160.0 ± 3% (155.2 mg-164.8 mg) | 320.0 ± 3% (310.4 mg-329.6 mg) |
| Tablet Hardness (SC) | 6.0-12.0 | 6.0-12.0 |
| Tablet Thickness (mm) | 5.0-6.0 | 4.5-5.0 |
| Friability (%) | <0.8 | <0.8 |

TABLE 51

Formulations used as the Ethocel coating on the 150 mg and 300 mg Bupropion HBr EA cores.

| FORMULATION 1 | FORMULATION 2 | FORMULATION 3 | FORMULATION 4 |
| --- | --- | --- | --- |
| Ethocel (Ethyl Cellulose) Standard 100 Premium | Ethocel (Ethyl Cellulose) Standard 100 Premium | Ethocel (Ethyl Cellulose) Standard 100 Premium | Ethocel (Ethyl Cellulose) Standard 100 Premium |
| Povidone USP (Kollidone 90F) | Povidone USP (Kollidone 90F) | Povidone USP (Kollidone 90F) | Povidone USP (Kollidone 90F) |
| Polyethylene Glycol 4000 | Polyethylene Glycol 4000 | Dibutyl Sebacate | Polyethylene Glycol 4000 |
| Ethyl Alcohol 200 proof | Dibutyl Sebacate Ethyl Alcohol 200 proof | Ethyl Alcohol 200 proof | Ethyl Alcohol 95% USP |

TABLE 52

Summary of Specifications that were kept constant in the Coating Process for the EA formulations.

| Process Parameters | Ranges | Target |
| --- | --- | --- |
| Inlet Temperature for coating (° C.) | SV: 50 ± 5 PV: 50 ± 5 | 50 |

TABLE 52-continued

Summary of Specifications that were kept constant in the Coating Process for the EA formulations.

| Process Parameters | Ranges | Target |
| --- | --- | --- |
| Inlet Temperature for Drying (° C.) | 40 ± 5 | 40 |
| Exhaust Temperature | 35 ± 5 | 35 |
| Product Temperature | 35 ± 2 | 35 |
| ΔP Differential Pressure (W.C) | (−0.1)-(−0.12) | −0.10 |
| Supply Air Flow (CFM) | 200 ± 50 | 200 |
| Pan Speed (rpm) | 2.5-15 | 12.0 |
| Atomizing Air (psi) | 25-35 | 35 |
| Pattern Air (psi) | 20-30 | 25 |
| Spray Rate (g/min) | 5-15 | 13 |

TABLE 53

Materials used in the batch, the percentage of each constituent, the amount per 300 mg EA tablet and the amount per batch.

| Materials | % | mg/tablet | Batch Quantity (g) |
| --- | --- | --- | --- |
| Bupropion HBr | 93.75 | 300.00 | 1993.75 |
| PVA | 3.125 | 10.00 | 68.75 |
| Compritol 888 | 3.125 | 10.00 | 68.75 |
| Total | 100.00 | 320.0 mg | 2131.25 |

TABLE 54

Materials used in the batch, the percentage of each constituent, the amount per 150 mg EA tablet and the amount per batch.

| Materials | % | mg/tablet | Batch Quantity (g) |
| --- | --- | --- | --- |
| Bupropion HBr | 93.75 | 150.00 | 1993.75 |
| PVA | 3.125 | 5.00 | 68.75 |
| Compritol 888 | 3.125 | 5.00 | 68.75 |
| Total | 100.00 | 160.0 mg | 2131.25 |

TABLE 55

Results obtained using 9 mm tooling (EA formulations).

| Parameters | Theoretical | Actual |
| --- | --- | --- |
| Average Individual Tablet Weight | 372.0 mg | 371.5 mg |
| Average Hardness | 6.0-12.0 SC | 10.77 SC |
| Average Thickness | 5.0-6.0 mm | 5.60 mm |
| Friability | <0.8% | 0% |

TABLE 56

Results obtained using 7 mm tooling (EA formulations).

| Parameters | Theoretical | Actual |
| --- | --- | --- |
| Average Individual Tablet Weight | 372.0 mg | 366.5 mg |
| Average Hardness | 6.0-12.0 SC | 7.50 SC |
| Average Thickness | 5.0-6.0 mm | 4.97 mm |
| Friability | <0.8% | 0% |

TABLE 57

Materials used in the EC coating and their quantities for batch BUP-HBr-EA-300 mg-001-5.

| Materials | % Contribution to Total Solution | Batch Quantity (g) | % of Solids in Solution |
|---|---|---|---|
| Ethocel (Ethyl Cellulose) Standard 100 Premium | 4.94 | 185.62* | 55.00 |
| Povidone USP (Kollidone 90F) | 2.52 | 94.50* | 28.00 |
| PEG 4000 | 0.77 | 28.69* | 8.50 |
| Dibutyl Sebacate | 0.77 | 28.69* | 8.50 |
| Ethyl Alcohol Anhydrous (200 Proof) | 91.0 | 3412.5 | N/A |
| Total | 100.00 | 3750.00 | 100.00 |

*Total solid component of the formulation included all the material except for the Ethyl Alcohol. This formulation consisted of a total solid amount of 337.5 g, which made up 9% of the total solution. The remaining 91% was made up of the Ethyl Alcohol 200 proof (liquid).

TABLE 58

Theoretical and Actual EA Tablet weights at 44 mg, 46 mg, 48 mg, 50 mg, 52 mg and 54 mg weight gains for batch BUP-HBr-EA-300 mg-001-5.

| Weight Gain (mg) | Theoretical Weight (mg) | Actual Weight (mg) |
|---|---|---|
| 44.0 | 364.0 | 362.9 |
| 46.0 | 366.0 | 365.6 |
| 48.0 | 368.0 | 366.6 |
| 50.0 | 370.0 | 369.3 |
| 52.0 | 372.0 | 371.7 |
| 54.0 | 374.0 | 374.8 |

TABLE 59

Materials used in the EC coating and their quantities for batch BUP-HBr-EA-150 mg-002-5.

| Materials | % Contribution to Total Solution | Batch Quantity (g) | % of Solids in Solution |
|---|---|---|---|
| Ethocel (Ethyl Cellulose) Standard 100 Premium | 4.94 | 232.03* | 55.0 |
| Povidone USP (Kollidone 90F) | 2.52 | 118.12* | 28.0 |
| PEG 4000 | 0.77 | 35.86* | 8.5 |
| Dibutyl Sebacate | 0.77 | 35.86* | 8.5 |
| Ethyl Alcohol Anhydrous (200 Proof) | 91.0 | 4265.63 | N/A |
| Total | 100.00 | 4687.50 | 100.00 |

*Total solid included 232.03 g of Ethocel, 118.12 g of Povidone, 35.86 g of PEG 4000 and 35.86 g of Dibutyl Sebacate. This gave a total solid amount of 421.87 g.

TABLE 60

Theoretical and Actual Tablet weights at 18 mg, 20 mg, 22 mg, 24 mg, 26 mg, 28 mg, 30 mg, 32 mg, 34 mg, and 36 mg weight gains for batch BUP-HBr-EA-150 mg-002-5.

| Weight Gain (mg) | Theoretical Weight (mg) | Actual Weight (mg) |
|---|---|---|
| 18.0 | 178.0 | 178.2 |
| 20.0 | 180.0 | 181.0 |
| 22.0 | 182.0 | 181.8 |
| 24.0 | 184.0 | 184.3 |
| 26.0 | 186.0 | 185.8 |
| 28.0 | 188.0 | 188.1 |
| 30.0 | 190.0 | 190.7 |
| 32.0 | 192.0 | 192.5 |
| 34.0 | 194.0 | 193.7 |
| 36.0 | 196.0 | 195.5 |

TABLE 61

Materials used in the EC coating and their quantities for batch BUP-HBr-EA-300 mg-003-5.

| Materials | % Contribution to Total Solution | Batch Quantity (g) | % of Solids in Solution |
|---|---|---|---|
| Ethocel (Ethyl Cellulose) Standard 100 Premium | 4.94 | 185.62* | 55.00 |
| Povidone USP (Kollidone 90F) | 2.52 | 94.50* | 28.00 |
| Dibutyl Sebacate | 1.54 | 57.38* | 17.00 |
| Ethyl Alcohol Anhydrous (200 Proof) | 91.0 | 3412.5 | N/A |
| Total | 100.00 | 3750.0 | 100.00 |

*Total Solid included 185.62 g of Ethocel, 94.50 g of Povidone and 57.38 g of Dibutyl Sebacate. This gave a total solid amount of 337.5 g.

TABLE 62

Theoretical and Actual Tablet weights at 44 mg, 46 mg, 48 mg, 50 mg, 52 mg, and 54 mg weight gains for batch BUP-HBr-EA-300 mg-003-5.

| Weight Gain (mg) | Theoretical Weight (mg) | Actual Weight (mg) |
|---|---|---|
| 44.0 | 364.0 | 364.7 |
| 46.0 | 366.0 | 365.8 |
| 48.0 | 368.0 | 367.7 |
| 50.0 | 370.0 | 369.7 |
| 52.0 | 372.0 | 371.9 |
| 54.0 | 374.0 | 372.9 |

TABLE 63

Materials used in the EC coating and their quantities for batch BUP-HBr-EA-300 mg-004-5.

| Materials | % Contribution to Total Solution | Batch Quantity (g) | % of Solids in Solution |
|---|---|---|---|
| Ethocel (Ethyl Cellulose) Standard 100 Premium | 4.94 | 185.62* | 55.00 |
| Povidone USP (Kollidone 90F) | 2.52 | 94.50* | 28.00 |
| PEG 4000 | 1.54 | 57.38* | 17.00 |
| Ethyl Alcohol Anhydrous (200 Proof) | 91.00 | 3412.50 | N/A |
| Total | 100.00 | 3750.00 | 100.00 |

*Total Solid amount included 185.62 g of Ethocel, 94.50 g of Povidone and 57.38 g of PEG 4000. This gave a total solid amount of 337.5 g.

TABLE 64

Theoretical and Actual Tablet weights at 44 mg, 46 mg, 48 mg, 50 mg, 52 mg, and 54 mg weight gains for batch BUP-HBr-EA-300 mg-004-5.

| Weight Gain (mg) | Theoretical Weight (mg) | Actual Weight (mg) |
|---|---|---|
| 44.0 | 364.0 | 363.6 |
| 46.0 | 366.0 | 365.5 |
| 48.0 | 368.0 | 368.5 |
| 50.0 | 370.0 | 370.2 |
| 52.0 | 372.0 | 372.6 |
| 54.0 | 374.0 | 374.3 |

TABLE 65

Materials used in the EC coating and their quantities for batch BUP-HBr-EA-300 mg-005-5.

| Materials | % Contribution to Total Solution | Batch Quantity (g) | % of Solids in Solution |
|---|---|---|---|
| Ethocel (Ethyl Cellulose) Standard 100 Premium | 4.94 | 185.62* | 55.00 |
| Povidone USP (Kollidone 90F) | 2.52 | 94.50* | 28.00 |
| PEG 4000 | 0.77 | 28.69* | 8.50 |
| Dibutyl Sebacate | 0.77 | 28.69* | 8.50 |
| Ethyl Alcohol Anhydrous (200 Proof) | 91.00 | 3412.50 | N/A |
| Total | 100.00 | 3750.0 | 100.00 |

*Total Solids included 185.62 g of Ethocel, 94.50 g of Povidone, 28.69 g of PEG 4000 and 28.69 g of Dibutyl Sebacate. This gave a total solid amount of 337.50 g. Therefore, solids made 9% contribution to the Total solution, and the remaining 91% was made up by the liquid component (Ethyl Alcohol Anhydrous).

TABLE 66

Theoretical and Actual Tablet weights at 44 mg, 46 mg, 48 mg, 50 mg, 52 mg, and 54 mg weight gains for batch BUP-HBr-EA-300 mg-005-5.

| Weight Gain (mg) | Theoretical Weight (mg) | Actual Weight (mg) |
|---|---|---|
| 44.0 | 364.0 | 364.9 |
| 46.0 | 366.0 | 366.3 |
| 48.0 | 368.0 | 368.5 |
| 50.0 | 370.0 | 371.7 |
| 52.0 | 372.0 | 372.9 |
| 54.0 | 374.0 | 373.7 |

TABLE 67

Materials used in the EC coating and their quantities for batch BUP-HBr-EA-300 mg-006-5.

| Materials | % Contribution to Total Solution | Batch Quantity (g) | % of Solids in Solution |
|---|---|---|---|
| Ethocel (Ethyl Cellulose) Standard 100 Premium | 4.94 | 232.03* | 55.00 |
| Povidone USP (Kollidone 90F) | 2.52 | 118.12* | 28.00 |
| Dibutyl Sebacate | 1.54 | 71.72* | 17.00 |
| Ethyl Alcohol Anhydrous (200 Proof) | 91.0 | 4265.63 | N/A |
| Total | 100.00 | 4687.50 | 100.00 |

*Total solid included 232.03 g of Ethocel, 118.12 g of Povidone and 71.72 g of Dibutyl Sebacate. This gave a total solid amount of 421.87 g. The Solid component of the coating solution made up 9% of the total solution. The remaining 91% of the solution was made up by the Ethyl Alcohol Anhydrous (liquid component).

TABLE 68

Theoretical and Actual Tablet weights at 18 mg, 20 mg, 22 mg, 24 mg, 26 mg, 28 mg, 30 mg, 32 mg, 34 mg, and 36 mg weight gains for batch BUP-HBr-EA-150 mg-006-5.

| Weight Gain (mg) | Theoretical Weight (mg) | Actual Weight (mg) |
|---|---|---|
| 18.0 | 178.0 | 178.2 |
| 20.0 | 180.0 | 180.3 |
| 22.0 | 182.0 | 181.8 |
| 24.0 | 184.0 | 184.6 |
| 26.0 | 186.0 | 185.8 |
| 28.0 | 188.0 | 188.8 |
| 30.0 | 190.0 | 190.9 |
| 32.0 | 192.0 | 191.6 |
| 34.0 | 194.0 | 194.1 |
| 36.0 | 196.0 | 196.7 |

TABLE 69

Materials used in the EC coating and their quantities for batch BUP-HBr-EA-150 mg-007-5.

| Materials | % Contribution to Total Solution | Batch Quantity (g) | % of Solids Solution* |
|---|---|---|---|
| Ethocel (Ethyl Cellulose) Standard 100 Premium | 4.94 | 232.03 | 55.00 |
| Povidone USP (Kollidone 90F) | 2.52 | 118.12 | 28.00 |
| PEG 4000 | 1.54 | 71.72 | 17.00 |
| Ethyl Alcohol 95% USP | 91.00 | 4265.63 | N/A |
| Total | 100.00 | 4687.50 | 100.00 |

*Total Solid included 232.03 g of Ethocel, 118.12 g of Povidone and 71.72 g of PEG 4000. This gave a total solid amount of 421.87 g.

TABLE 70

Open-dish stability studies (40 C./75% RH) on Bupropion HCl & Bupropion HBr EC Coated Tablets

| | Open dish stability (40 C./75% RH) | | |
|---|---|---|---|
| Tests | Initial | 13 Days | 20 Days |
| Bupropion HBr XL 348 mg coated EC Tablets (EC-32 mg WG.), Lot# Bup-HBr-XL-012-5 (EC-32 mg wg.) | | | |
| % Assay | 101.2 | 99.6 | 99.9 |
| % Impurities | 0.021 | 0.056 | 0.067 |
| 3-CBZ | | | |
| 852U77 | 0.029 | 0.350 | 0.486 |
| 20U78/dilu | 0.054 | 0.046 | 0.047 |
| 827U76 | ND | 0.056 | 0.062 |
| Total unknown | 0.356 | 0.059 | 0.123 |
| Total | 0.46 | 0.57 | 0.79 |
| Bupropion HCl XL 300 mg coated EC tablets (EC, Lot# 05D047) | | | |
| % Assay | 100.4 | 100.2 | 96.2 |
| % Impurities | 0.015 | 0.089 | 0.117 |
| 3-CBZ | | | |
| 852U77 | 0.041 | 0.337 | 0.378 |
| 20U78/dilu | 0.038 | 0.046 | 0.045 |
| 827U76 | 0.023 | 0.071 | 0.080 |
| Total unknown | 0.118 | 0.112 | 0.145 |
| Total | 0.24 | 6.66 | 0.77 |

TABLE 71

Open dish-stability studies (40 C./75% RH) on Bupropion HCl & HBr Final Coated Tablets

| | Bupropion HBr XL 348 mg coated tablets (final 8 mg wg), Lot# Bup-HBr-XL-012-5 (EC32 mg wg-final 8 mg wg.) | | | Wellbutrin (Bupropion HCl) XL 300 mg tablets Lot# 05A116 | | |
|---|---|---|---|---|---|---|
| Tests | Initial | 13-Days | 20 Days | Initial | 13 Days | 20 Days |
| % Assay | 97.7 | 103.0 | 98.6 | 98.1 | 95.6 | 95.5 |
| % Impurities | | | | | | |
| 3-CBZ | 0.021 | 0.091 | 0.119 | 0.032 | 0.171 | 0.279 |
| 852U77 | 0.039 | 0.505 | 0.412 | 0.193 | 0.974 | 1.228 |
| 20U78/dilu | 0.051 | 0.055 | 0.048 | 0.042 | 0.055 | 0.062 |
| 827U76 | ND | 0.046 | 0.054 | 0.028 | 0.082 | 0.096 |
| Total unknown | 0.476 | 0.110 | 0.112 | 0.083 | 0.033 | 0.06 |
| Total (%) | 0.58 | 0.80 | 0.75 | 0.38 | 1.32 | 1.73 |

TABLE 72

Average weight of excipients and weight of the API present in the forced degradation samples for Example 8

| Component | Average weight in mgs present in samples used for Forced deg study | |
|---|---|---|
| API | 348 - HBr | 350 - HCl |
| Precirol | 162 | |
| Mannitol | 413 | |
| Avicel pH101 | 154 | |
| L-HPC | 20 | |
| Kollidon | 20 | |
| Citric acid | 31 | |
| Ethylcellulose E45 | 54 | |
| ATBC | 16 | |

TABLE 73

BUPROPION HBr EA COATING SOLUTION FORMULATION/mg/TABLET FOR PIVOTAL BATCHES

| Item # | Material | Qty. Required (kg) | % of Batch | Mg/tablet |
|---|---|---|---|---|
| 150 mg EA Coated Tablets - Pivotal Coating Formulation/Batch Size ||||||
| RE0233 | Ethylcellulose 100, NF | 4.210 | 4.95% | 19.80 |
| RE0067 | Povidone, USP | 2.140 | 2.52% | 10.06 |
| RE0331 | Polyethylene Glycol 4000, NF | 0.435 | 0.51% | 2.05 |
| RE0103 | Dibutyl Sebacate, NF | 0.870 | 1.02% | 4.09 |
| RS0010 | Dehydrated Alcohol, 200 proof, USP | 73.475 | 86.44% | N/A |
| RS0006 | Ethyl Alcohol, 95%, USP | 3.870 | 4.56% | N/A |
| | COOATING SOLUTION TOTAL (kg) | 85 kg | 100% | 36 mg Range: (38–40 mg) |
| *RE0223 | Carnauba Wax, NF | 0.010 kg | N/A | 0.05 mg/tablet |
| 300 mg EA Coated Tablets - Pivotal Coating Formulation/Batch Size ||||||
| RE0233 | Ethylcellulose 100, NF | 5.450 | 4.95% | 23.12 |
| RE0067 | Povidone, USP | 2.770 | 2.52% | 11.75 |
| RE0331 | Polyethylene Glycol 4000, NF | 0.560 | 0.51% | 2.38 |
| RE0103 | Dibutyl Sebacate, NF | 1.120 | 1.02% | 4.75 |
| RS0010 | Dehydrated Alcohol, 200 proof, USP | 95.070 | 86.43% | N/A |
| RS0006 | Ethyl Alcohol, 95%, USP | 5.030 | 4.57% | N/A |
| | COATING SOLUTION TOTAL (kg) | 110 kg | 100% | 42 mg/tablet Range: (40–44 mg) |
| *RE0223 | Carnauba Wax, NF | 0.010 kg | N/A | 0.05 mg/tablet |

Note:
Where applicable, percentages and mg/tablet totals have been rounded to two decimal places.
*Carnauba Wax not included as part of coating solution formulation. Trace amounts applied after completion of the coating process.

The patent and non-patent references cited in this patent specification are incorporated by reference in their entireties to the extent that their disclosures are not inconsistent with the explicit or implicit teachings of this application especially the definitions.

TABLE 74

ACCELERATED STABILITY PROGRAM

Product: Bupropion.HBr FV0092  Batch No.: D00894  Start date: 20/12/04  Temperature: 40° C. ± 2° C. R.H.: 75% ± 5%

| Analysis | Specification | time 0 | 3 month | 6 months |
|---|---|---|---|---|
| Description | white or almost white crystalline powder | conform | conform | conform |
| Identification | IR, HPLC (positive) | positive | positive | positive |
| Water content (K.F.) | NMT 0.5% | 0.05 | 0.07 | 0.08 |
| Chromatographic purity A) | 1) NMT 0.1% 2) NMT 0.1% | 1) n.d. 2) n.d. | 1) n.q. 2) n.d. | 1) 0.05 2) n.d. |

TABLE 74-continued

ACCELERATED STABILITY PROGRAM

Product: Bupropion.HBr FV0092  Batch No.: D00894  Start date: 20/12/04  Temperature: 40° C. ± 2° C. R.H.: 75% ± 5%

| Analysis | Specification | time 0 | 3 month | 6 months |
|---|---|---|---|---|
| (HPLC) Chromatographic purity B) | 3) NMT 0.1% 4) NMT 0.1% 5) NMT 0.1% | 3) n.q. 4) 0.04 5) 0.04 | 3) n.q. 4) 0.03 5) 0.04 | 3) n.q. 4) 0.04 5) n.q. |
| (HPLC) Chromatographic purity (HPLC: A + B) | 6) NMT 0.3% Total impurities NMT 0.5% | 6) 0.04 0.1 | 6) 0.06 0.1 | 6) 0.02 0.1 |
| Assay (HPLC) | 98.0–102.0% on d.b. | 99.6 | 99.6 | 99.7 |

Impurities:
1) 3'-Chloropropiophenone;
2) 3'-Chloro-2-bromopropiophenone;

TABLE 74-continued

ACCELERATED STABILITY PROGRAM

Product:
Bupropion.HBr  Batch No.:  Start date:  Temperature: 40° C. ± 2° C.
FV0092         D00894      20/12/04     R.H.: 75% ± 5%
Analysis       Specification            time 0   3 month   6 months 3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 75

ACCELERATED STABILITY PROGRAM

Product:
Bupropion.HBr  Batch No.:  Start date:  Temperature: 40° C. ± 2° C.
FV0092         D00895      20/12/04     R.H.: 75% ± 5%

| Analysis | Specification | time 0 | 3 month | 6 months |
|---|---|---|---|---|
| Description | white or almost white crystalline powder | conform | conform | conform |
| Identification | IR, HPLC (positive) | positive | positive | positive |
| Water content (K.F.) | NMT 0.5% | 0.04 | 0.07 | 0.07 |
| Chromatographic purity A) (HPLC) | 1) NMT 0.1% | 1) n.d. | 1) n.q. | 1) 0.05 |
| | 2) NMT 0.1% | 2) n.d. | 2) n.d. | 2) n.d. |
| | 3) NMT 0.1% | 3) n.q. | 3) 0.05 | 3) n.q. |
| Chromatographic purity B) (HPLC) | 4) NMT 0.1% | 4) 0.04 | 4) 0.03 | 4) 0.04 |
| | 5) NMT 0.1% | 5) 0.04 | 5) 0.04 | 5) n.q. |
| | 6) NMT 0.3% | 6) 0.04 | 6) 0.05 | 6) 0.02 |
| Chromatographic purity (HPLC: A + B) | Total impurities NMT 0.5% | 0.1 | 0.1 | 0.1 |
| Assay (HPLC) | 98.0–102.0% on d.b. | 99.2 | 100.7 | 99.7 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;

TABLE 75-continued

ACCELERATED STABILITY PROGRAM

Product:
Bupropion.HBr  Batch No.:  Start date:  Temperature: 40° C. ± 2° C.
FV0092         D00895      20/12/04     R.H.: 75% ± 5%
Analysis       Specification            time 0   3 month   6 months 5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 76

ACCELERATED STABILITY PROGRAM

Product:
Bupropion.HBr  Batch No.:  Start date:  Temperature: 40° C. ± 2° C.
FV0092         D00896      20/12/04     R.H.: 75% ± 5%

| Analysis | Specification | time 0 | 3 month | 6 months |
|---|---|---|---|---|
| Description | white or almost-white crystalline powder | conform | conform | conform |
| Identification | IR, HPLC (positive) | positive | positive | positive |
| Water content (K.F.) | NMT 0.5% | 0.06 | 0.11 | 0.04 |
| Chromatographic purity A) (HPLC) | 1) NMT 0.1% | 1) n.d. | 1) n.q. | 1) 0.05 |
| | 2) NMT 0.1% | 2) n.d. | 2) n.d. | 2) n.d. |
| | 3) NMT 0.1% | 3) n.q. | 3) n.q. | 3) n.q. |
| Chromatographic purity B) (HPLC) | 4) NMT 0.1% | 4) 0.04 | 4) 0.03 | 4) 0.04 |
| | 5) NMT 0.1% | 5) 0.05 | 5) 0.04 | 5) n.q. |
| | 6) NMT 0.3% | 6) 0.05 | 6) 0.05 | 6) n.q. |
| Chromatographic purity (HPLC: A + B) | Total impurities NMT 0.5% | 0.1 | 0.1 | 0.1 |
| Assay (HPLC) | 98.0–102.0% on d.b. | 99.3 | 100.0 | 100.4 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 77

SHELF LIFE STABILITY PROGRAM

Product: Bupropion.HBr   Batch No.: D00894   Start date: 20/12/04   Temperature: 25° C. ± 2° C.; Relative Humidity: 60% ± 5%
FV0092

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.05 | 0.05 | 0.06 | 0.05 | 0.05 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.05 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0–102.0% on d.b. | 99.6 | 99.4 | 100.2 | 99.5 | 99.6 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1,2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 78

SHELF LIFE STABILITY PROGRAM

Product: Bupropion.HBr   Batch No.: D00895   Start date: 20/12/04   Temperature: 25° C. ± 2° C.; Relative Humidity: 60% ± 5%
FV0092

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.04 | 0.04 | 0.05 | 0.05 | 0.04 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.07 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0–102.0% on d.b. | 99.2 | 99.5 | 100.1 | 99.4 | 99.4 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1,2 and 3;

TABLE 78-continued

SHELF LIFE STABILITY PROGRAM

Product: Bupropion.HBr  Batch No.: D00895  Start date: Temperature: 25° C. ± 2° C.;
FV0092                                    20/12/04     Relative Humidity: 60% ± 5%

| Analysis | Specification | time 0 | 3 months | 6 months | 9 months | 12 months | 18 months | 24 months | 36 months |
|---|---|---|---|---|---|---|---|---|---|

LOQ = 0.02% for imp. 4 and 5;
LOD = 0.01% for imp. 1 and 3;
LOD = 0.04% for imp. 2;
LOD = 0.002% for imp. 4 and 5.

TABLE 79

SHELF LIFE STABILITY PROGRAM

Product: Bupropion.HBr  Batch No.: D00896  Start date: Temperature: 25° C. ± 2° C.;
FV0092                                    20/12/04     Relative Humidity: 60% ± 5%

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.06 | 0.04 | 0.04 | 0.04 | 0.03 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) n.q. | 3) | 3) | 3) |
| Chromatographic purity B) (HPLC) | 4) NMT 0.1% | 4) 0.04 | 4) 0.03 | 4) 0.04 | 4) n.d. | 4) 0.05 | 4) | 4) | 4) |
| | 5) NMT 0.1% | 5) 0.05 | 5) 0.04 | 5) n.q. | 5) n.q. | 5) 0.07 | 5) | 5) | 5) |
| | 6) NMT 0.3% | 6) 0.05 | 6) 0.05 | 6) n.q. | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.1 | | | |
| Assay (HPLC) | 98.0–102.0% on d.b. | 99.3 | 99.4 | 100.5 | 99.4 | 100.3 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1,2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 80

Bupropion Hydrobromide Polymorphs Table

| Trial | Solvent (Voll.) | Cosolvent (Voll.) | Yield (%) | Form | K.F. (%) | Notes |
|---|---|---|---|---|---|---|
| 085 | IPA + HBr gas | | | I | 0.07 | Standard procedure |
| 097 | Water 2 | / | 72 | I | 0.06 | |
| 098A | Methanol 2.4 | / | | II | 0.13 | |
| 098B | Acetone 17 | water 0.7 | 24 | II | 0.16 | |
| 099 | Ethanol abs. 4.8 | / | 56 | III | 0.12 | |
| 100 | IPA 15.1 | / | 77 | I | 0.11 | |
| 102 | AcOi-Pr 20 | MeOH 3.6 | 26 | I | 0.25 | |
| 108 | Acetonitrile 20 | / | 70 | I | 0.14 | |
| 109 | Dichloromethane 30 | / | 25 | II | 0.21 | |
| 110 | Water 2 | HBr 48% 1 | 83 | I | 0.12 | |
| 111 | IPA 6 | HBr 48% 1 | 69 | I | 0.32 | |
| 112 | MTBE 10 | MeOH 3 | 67 | I | 0.18 | |
| 113 | Toluene 10 | MeOH 1.25 | 40 | II | 0.39 | |
| 114 | DMC 10 | MeOH 1.75 | 67 | II | 0.17 | |

TABLE 80-continued

Bupropion Hydrobromide Polymorphs Table

| Trial | Solvent (Voll.) | Cosolvent (Voll.) | Yield (%) | Form | K.F. (%) | Notes |
|---|---|---|---|---|---|---|
| 115 | t-BuOH 20 | Water 0.55 | 74 | I | 0.15 | |
| 116 | Form I in rotavapor 100° C. 24 h | | | I | 0.45 | |
| 117 | IPA 10 | Water 0.125 | 88 | I | 0.32 | |
| 118 | Toluene 10 | MeOH 1.15 | 99 | I | 0.16 | |
| 119 | IPA 8 | MeOH 1.32 | 83 | I | 0.47 | |
| 120 | Sec-BuOH 25 | / | 89 | I | 0.13 | |
| 122 | Water 8 | / | | I | 1.3 | Spray dried |

TABLE 81

Polyethoxylated Fatty Acids
Although polyethylene glycol (PEG) itself does not function as a surfactant, a variety of PEG-fatty acid esters have useful surfactant properties. Examples of polyethoxylated fatty acid monoester surfactants commercially available are shown here in Table 81.
PEG-Fatty Acid Monoester Surfactants

| Compound | Commercial Product (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400-1000 monostearate | Cithrol MS series (Croda) | >10 |
| PEG-1 stearate | Nikkol MYS-1EX (Nikko), Coster KI (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200ML (Stepan), LIPOPEG 2L (LIPO Chem.) | 9.3 |
| PEG-4 oleate | Mapeg ® 200 MO (PPG), Kessco ® PEG200 MO (Stepan), | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stepan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco ® PEG300 ML (Stepan) | 11.4 |
| PEG-7 laurate | Lauridac 7 (Condea) | 13 |
| PEG-6 stearate | Kessco ® PEG300 MS (Stepan) | 9.7 |
| PEG-8 laurate | Mapeg ® 400 ML (PPG), LIPOPEG 4DL(Lipo Chem.) | 13 |
| PEG-8 oleate | Mapeg ® 400 MO (PPG), Emulgante A8 (Condea); Kessco PEG 400 MO (Stepan) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor 59 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600ML (Stepan) | 15 |
| PEG-12 oleate | Kessco ® PEG 600MO (Stepan) | 14 |
| PEG-12 ricinoleate | (CAS #9004-97-1) | >10 |
| PEG-12 stearate | Mapeg ® 600 MS (PPG), Kessco ® PEG 600MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet 0-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf) | >10 |

TABLE 82

PEG-Fatty Acid Diesters
Polyethylene glycol (PEG) fatty acid diesters are also suitable for use as surfactants in the compositions of the present invention. Representative PEG-fatty acid diesters are shown here in Table 82.
PEG-Fatty Acid Diester Surfactants

| Compound | Commercial Product (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7<br>6 |
| PEG-4 dioleate | Mapeg ® 200 DO (PPG), | 6 |
| PEG-4 distearate | Kessco ® 200 DS (Stepan) | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |

TABLE 82-continued

PEG-Fatty Acid Diesters
Polyethylene glycol (PEG) fatty acid diesters are also suitable for
use as surfactants in the compositions of the present invention.
Representative PEG-fatty acid diesters are shown here in Table 82.
PEG-Fatty Acid Diester Surfactants

| Compound | Commercial Product (Supplier) | HLB |
|---|---|---|
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO(Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO(Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

TABLE 83

PEG-Fatty Acid Mono- and Di-ester Mixtures
In general, mixtures of surfactants are also useful in the present
invention, including mixtures of two or more commercial surfactant
products. Several PEG-fatty acid esters are marketed commercially
as mixtures or mono- and diesters. Representative surfactant
mixtures are shown here in Table 83.
PEG-Fatty Acid Mono-and Diester Mixtures

| Compound | Commercial Product (Supplier) |
|---|---|
| PEG 4-150 mono, dilaurate | Kessco ® PEG 200-6000 mono, dilaurate (Stepan) |
| PEG 4-150 mono, dioleate | Kessco ® PEG 200-6000 mono, dioteate (Stepan) |
| PEG 4-150 mono, distearate | Kessco ® 200-6000 mono, distearate (Stepan) |

TABLE 84

Polyethylene Glycol Glycerol Fatty Acid Esters
Suitable PEG glycerol fatty acid esters are shown here in Table 84.
PEG Glycerol Fatty Acid Esters

| Compound | Commercial Product (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

TABLE 85

Alcohol - Oil Transesterification Products
A large number of surfactants of different degrees of lipophilicity
or hydrophilicity can be prepared by reaction of alcohols or
polyalcohols with a variety of natural and/or hydrogenated oils.
In certain embodiments, the oils used are castor oil or hydrogenated
castor oil or an edible vegetable oil such as corn oil, olive oil,
peanut oil, palm kernel oil, apricot kernel oil, or almond oil. Examples
of alcohols include glycerol, propylene glycol, ethylene glycol,
polyethylene glycol, sorbitol, and pentaerythritol. Representative
surfactants of this class suitable for use in the present invention
are shown here in Table 85.
Transesterification Products of Oils and Alcohols

| Compound | Commercial Product (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6–7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko), Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6–7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |

TABLE 85-continued

Alcohol - Oil Transesterification Products
A large number of surfactants of different degrees of lipophilicity or hydrophilicity can be prepared by reaction of alcohols or polyalcohols with a variety of natural and/or hydrogenated oils. In certain embodiments, the oils used are castor oil or hydrogenated castor oil or an edible vegetable oil such as corn oil, olive oil, peanut oil, palm kernel oil, apricot kernel oil, or almond oil. Examples of alcohols include glycerol, propylene glycol, ethylene glycol, polyethylene glycol, sorbitol, and pentaerythritol. Representative surfactants of this class suitable for use in the present invention are shown here in Table 85.
Transesterification Products of Oils and Alcohols

| Compound | Commercial Product (Supplier) | HLB |
|---|---|---|
| PEG-60 corn glycerides | Crovol M70 (Croda) | 15 |
| PEG-60 almond glycerides | Crovol A70 (Croda) | 15 |
| PEG-4 caprylic/capric triglyceride | Labrafac ® Hydro (Gattefosse), | 4–5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Huls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/ tetracaprate | Liponate PE-810 (Lipo Chem.), Crodamol PTC (Croda) | <10 |
| Pentaerythrityl tetraoctanoate | Nikkol Pentarate 408 (Nikko) | |

TABLE 86

Polyglycerized Fatty Acids
Polyglycerol esters of fatty acids are also suitable surfactants for the present invention. Examples of suitable polyglyceryl esters are shown here in Table 86.
Polyglycerized Fatty Acids

| Compound | Commercial Product (Supplier) | HLB |
|---|---|---|
| Polyglyceryl-2 stearate | Nikkol DGMS (Nikko) | 5–7 |
| Polyglyceryl-2 oleate | Nikkol DGMO (Nikko) | 5–7 |
| Polyglyceryl-2 isostearate | Nikkol DGMIS (Nikko) | 5–7 |
| Polyglyceryl-3 oleate | Caprol ® 3GO (ABITEC), Drewpol 3-1-O (Stepan) | 6.5 |
| Polyglyceryl-4 oleate | Nikkol Tetraglyn 1-O (Nikko) | 5–7 |
| Polyglyceryl-4 stearate | Nikkol Tetraglyn 1-S (Nikko) | 5–6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | |
| Polyglyceryl-10 linoleate | Nikkol Decaglyn I-LN (Nikko) | 12 |
| Polyglyceryl-6 pentaoleate | Nikkol Hexaglyn S-O (Nikko) | <10 |
| Polyglyceryl-3 dioleate | Cremophor G032 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decagtyn 7-O (Nikko) | 3 |
| Polyglyceryl-10 tetraoleate | Caprol ® 10G40 (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-10 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3–20 |

TABLE 87

Propylene Glycol Fatty Acid Esters
Esters of propylene glycol and fatty acids are suitable surfactants for use in the present invention. Examples of surfactants of this class are given here in Table 87.
Propylene Glycol Fatty Acid Esters

| Compound | Commercial Product (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3–4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-06 (Eastman) | <10 |
| Propylene glycol dicaprylate/dicaprate | Captex ® 200 (ABITEC), Miglyol ® 840 (Huls), Neobee ® M-20 (Stepan) | >6 |
| Propylene glycol dioctanoate | Captex ® 800 (ABITEC) | |
| Propylene glycol caprylate/caprate | LABRAFAC PG (Gattefosse) | >6 |

TABLE 87-continued

Propylene Glycol Fatty Acid Esters

Esters of propylene glycol and fatty acids are suitable surfactants for use in the present invention. Examples of surfactants of this class are given here in Table 87.

Propylene Glycol Fatty Acid Esters

| Compound | Commercial Product (Supplier) | HLB |
|---|---|---|
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

TABLE 88

Mixtures of Propylene Glycol Esters-Glycerol Esters

In general, mixtures of surfactants are also suitable for use in the present invention. In particular, mixtures of propylene glycol fatty acid esters and glycerol fatty acid esters are suitable and are commercially available. Examples of these surfactants are shown here in Table 88.

Glycerol/Propylene Glycol Fatty Acid Esters

| Compound | Commercial Product (Supplier) | HLB |
|---|---|---|
| Oleic | ATMOS 300, ARLACEL 186 (ICI) | 3–4 |
| Stearic | ATMOS 150 | 3–4 |

TABLE 89

Mono- and Diglycerides

Another class of surfactants is the class of mono- and diglycerides. These surfactants are generally lipophilic. Examples of these surfactants are given here in Table 89.

Mono- and Diglyceride Surfactants

| Compound | Commercial Product (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3–4 |
| Glyceryl monooleate (C18:1) | PECEOL (Gattefosse), Hodag GMO-D, Nikkol MGO (Nikko) | 3–4 |
| Glyceryl monooleate | RYLO series (Danisco), DIMODAN series (Danisco), EMULDAN (Danisco), ALDO ® MOFG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3–4 |
| Glycerol monooleate/linoleate | OLICINE (Gattefosse) | 3–4 |
| Glycerol monolinoleate | Maisine (Gattefosse), MYVEROL 18-92, Myverol 18-06 (Eastman) | 3–4 |
| Glyceryl ricinoleate | Softigen ® 701 (Huls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS. (ABITEC), Myvaplex (Eastman), IMWITOR ® 191 (Huls), CUTINA GMS, Aldo ® MS (Lonza), Nikkol MGS series (Nikko) | 5–9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grunau GmbH) | <10 |
| Glyceryl laurate | Inwitor ® 312 (Huls), Monomuls ® 90-45 (Grunau GmbH), Aldo ® MLD (Lonza) | 4 |

TABLE 89-continued

Mono- and Diglycerides
Another class of surfactants is the class of mono- and diglycerides. These surfactants are generally lipophilic. Examples of these surfactants are given here in Table 89.
Mono- and Diglyceride Surfactants

| Compound | Commercial Product (Supplier) | HLB |
| --- | --- | --- |
| Glyceryl citrate/lactate/oleate/linoieate | Imwitor ® 375 (Huls) | <10 |
| Glyceryl caprylate | Imwitor ® 308 (Huls), Capmul ® MCMC8 (ABITEC) | 5–6 |
| Glyceryl caprylate/caprate | Capmul ® MCM (ABITEC) | 5–6 |
| Caprylic acid mono, diglycerides | Imwitor ® 988 (Huls) | 5–6 |
| Caprylic/capric glycerides | Imwitor ® 742 (Huls) | <10 |
| Mono-and diacetylated monoglycerides | Myvacet ® 9-45, Myvacet ® 9-40, Myvacet ® 9-08 (Eastman), Lamegin ® (Grunau) | 3.8–4 |
| Glyceryl monostearate | Aldo ® MS, Arlacel 129 (ICI), LIPO GMS (Lipo Chem.), Imwitor ® 191 (Huls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | |
| Distearin | (Larodan) | <10 |
| Glyceryl dilaurate (C12) | Capmul ® GDL (ABITEC) | 3–4 |
| Glyceryl dioleate | Capmul ® GDO (ABITEC) | 3–4 |
| Glycerol esters of fatty acids | GELUCIRE 39/01 (Gattefosse), GELUCIRE 43/01 (Gattefosse) GELUCIRE 37/06 (Gattefosse) | 16 |
| Dipalmitolein (C16:1) 1,2 and 1,3-diolein (C18:1) | (Larodan) | <10 |
| Dielaidin (C18:1) | (Larodan) | <10 |
| Dilinolein (C18:2) | (Larodan) | <10 |

TABLE 90

Sterol and Sterol Derivatives

Sterols and derivatives of sterols are suitable surfactants for use in the present invention. These surfactants can be hydrophilic or lipophilic. Examples of surfactants of this class are shown here in Table 90.
Sterol and Sterol Derivative Surfactants

| Compound | Commercial Product (Supplier) | HLB |
| --- | --- | --- |
| Cholesterol, sitosterol, lanosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-S (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

TABLE 91

Polyethylene Glycol Sorbitan Fatty Acid Esters
A variety of PEG-sorbitan fatty acid esters are available and are suitable for use as surfactants in the present invention. In general, these surfactants are hydrophilic, although several lipophilic surfactants of this class can be used. Examples of these surfactants are shown here in Table 91.
PEG-Sorbitan Fatty Acid Esters

| Compound | Commercial Product (Supplier) | HLB |
| --- | --- | --- |
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PBG-6 sorbitan monostearate | Nikkol TS106 (Nikko) | 11 |

TABLE 91-continued

Polyethylene Glycol Sorbitan Fatty Acid Esters
A variety of PEG-sorbitan fatty acid esters are available and are suitable for use as surfactants in the present invention. In general, these surfactants are hydrophilic, although several lipophilic surfactants of this class can be used. Examples of these surfactants are shown here in Table 91.
PEG-Sorbitan Fatty Acid Esters

| Compound | Commercial Product (Supplier) | HLB |
|---|---|---|
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040, (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

TABLE 92

Polyethylene Glycol Alkyl Ethers
Ethers of polyethylene glycol and alkyl alcohols are suitable surfactants for use in the present invention. Examples of these surfactants are shown here in Table 92.
Polyethylene Glycol Alkyl Ethers

| Compound | Commercial Product (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

TABLE 93

Sugar Esters
Esters of sugars are suitable surfactants for use in the present invention. Examples of such surfactants are shown here in Table 93.
Sugar Ester Surfactants

| Compound | Commercial Product (Supplier) | HLB |
|---|---|---|
| Sucrose distearate | SUCRO ESTER 7 (Gattefosse), Crodesta F-10 (Croda) | 3 |
| Sucrose distearate/monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

TABLE 94

Polyethylene Glycol Alkyl Phenols
Several hydrophilic PEG-alkyl phenol surfactants are available, and are suitable for use in the present invention. Examples of these surfactants are shown here in Table 94.
Polyethylene Glycol Alkyl Phenol Surfactants

| Compound | Commercial Product (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

TABLE 95

Polyoxyethylene-Polyoxypropylene Block Copolymers
The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including Synperonic PE series (ICI); Pluronic ® series (BASF), Emkalyx, Lutrol (BASF), Supronic, Monolan, Pluracare, and Plurodac. The generic term for these polymers is "poloxamer" (CAS 9003-11-6). These polymers have the formula:
$$HO(C_2H_4O)_a(C_3H_6O)_b(C_2H_4O)_aH$$
where "a" and "b" denote the number of polyoxyethylene and polyoxypropylene units, respectively. Examples of suitable surfactants of this class are shown here in Table 95. Since the compounds are widely available, commercial sources are not listed in the Table. The compounds are listed by generic name, with the corresponding "a" and "b" values.
POE-POP Block Copolymers

| Compound | a, b values in $HO(C_2H_4O)_a (C_3H_6O)_b (C_2H_4O)_aH$ | | HLB |
|---|---|---|---|
| Poloxamer 105 | a = 11 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |

TABLE 95-continued

Polyoxyethylene-Polyoxypropylene Block Copolymers
The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including Synperonic PE series (ICI); Pluronic ® series (BASF), Emkalyx, Lutrol (BASF), Supronic, Monolan, Pluracare, and Plurodac. The generic term for these polymers is "poloxamer" (CAS 9003-11-6). These polymers have the formula:
$HO(C_2H_4O)_a(C_3H_6O)_b(C_2H_4O)_aH$
where "a" and "b" denote the number of polyoxyethylene and polyoxypropylene units, respectively. Examples of suitable surfactants of this class are shown here in Table 95. Since the compounds are widely available, commercial sources are not listed in the Table. The compounds are listed by generic name, with the corresponding "a" and "b" values.
POE-POP Block Copolymers

| Compound | a, b values in $HO(C_2H_4O)_a (C_3H_6O)_b (C_2H_4O)_aH$ | | HLB |
|---|---|---|---|
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

TABLE 96

Sorbitan Fatty Acid Esters
Sorbitan esters of fatty acids are suitable surfactants for use in the present invention. Examples of these surfactants are shown here in Table 96.
Sorbitan Fatty Acid Ester Surfactants

| Compound | Commercial Product (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

TABLE 97

Lower Alcohol Fatty Acid Esters
Esters of lower alcohols ($C_2$ to $C_4$) and fatty acids ($C_8$ to $C_{18}$) are suitable surfactants for use in the present invention. Examples of these surfactants are shown here in Table 97.
Lower Alcohol Fatty Acid Ester Surfactants

| Compound | Commercial Product (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

TABLE 98

Ionic Surfactants
Ionic surfactants, including cationic, anionic and zwitterionic surfactants, are suitable hydrophilic surfactants for use in the present invention. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown here in Table 98. For simplicity, typical counterions are shown in the entries in the Table. It will be appreciated by one skilled in the art, however, that any bioacceptable counterion can be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.
Ionic Surfactants

| Compound | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glycol cheno deoxycholate | |
| Sodium cholylsarcosinate | |
| Sodium N-methyl taurocholate | |
| Sodium lithocholate | |

TABLE 98-continued

Ionic Surfactants

Ionic surfactants, including cationic, anionic and zwitterionic surfactants, are suitable hydrophilic surfactants for use in the present invention. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown here in Table 98. For simplicity, typical counterions are shown in the entries in the Table. It will be appreciated by one skilled in the art, however, that any bioacceptable counterion can be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

Ionic Surfactants

| Compound | HLB |
|---|---|
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

TABLE 99

BUPROPION HBr XL TABLETS, 348 mg
TABLET COMPOSITION (mg/tablet)
Table 1: Core Tablets

| Item # | Material | Qty. Required (kg) | % of Tablet Tablet Core Formulation | 348 mg Strength Target Weight 371.2 mg/tablat |
|---|---|---|---|---|
| RS0009 | Polyvinyl Alcohol | 2.25 kg dispensed 2.00 kg used | 3.125% | 11.6 mg/tablet |
| RA0057 | Bupropion HBr | 60.00 | 93.750% | 348 mg/tablet |
| RE0200 | Glyceryl Behenate, NF | 2.00 | 3.125% | 11.6 mg/tablet |
| RS0003 | *Purified Water, USP | 47.75 | 0 | 0 |
| | Theoretical Batch Size: kg | 64.00 | 100% | 371.2 mg/tablet |

*Evaporated during granulating process and not included in tablet core composition.

TABLE 100

Table 2: Coated/Printed Tablets
348 mg XL Coated/Printed Tablets - Pivotal Coating Formulation/Batch Size

| Item # | Material | Qty. Required (kg) | % of Batch | Applied Solids Mg/tablet Target Weight Gain: 32 mg (Range: 30–34 mg/tablet) |
|---|---|---|---|---|
| RE0233 | Ethylcellulose 100, NF | 3.230 | 4.61% | 16.406 mg |
| RE0067 | Povidone, USP | 2.000 | 2.86% | 10.159 mg |
| RE0331 | Polyethylene Glycol 4000, NF | 0.720 | 1.03% | 3.657 mg |
| RE0103 | Dibutyl Sebacate, NF | 0.350 | 0.50% | 1.778 mg |
| *RS0010 | *Dehydrated Alcohol, 200 proof, USP | 57.300 | 81.86% | 0 |
| *RS0006 | *Ethyl Alcohol, 95% USP | 6.400 | 9.14% | 0 |
| | COATING SOLUTION TOTAL (kg) | 70 kg | 100% | 32 mg/tablet |
| **RE0223 | **Carnauba Wax, NF | 0.010 kg | N/A | Trance Amounts |
| RE0234 | Opacode Black Ink S-1-8090 or S-1-17823 | 1.00 | 50% | Trace Amounts to brand tablets with logo on one side BR 348 |
| ***RS0001 | ***Isopropyl Alcohol | 1.00 | 50% | Used for cleaning design and transfer rolls only |

Note:
Where applicable, percentages and mg/tablet totals have been rounded to two decimal places.
*Evaporated during coating process.
**Carnauba Wax not included as part of coating solution formulation, trace amounts applied after completion of the coating process.
***Isopropyl Alcohol used for cleaning only. Only trace amounts of black ink to brand tablets with specific logo is applied to one side of tablet. Weight of this material applied to tablet cannot be measured.

TABLE 101

Table 3: BUPROPION HBr XL TABLETS, 348 mg:
OVERALL FINAL PRINTED TABLET COMPOSITION/WEIGHT

| Material | 348 mg (+32 mg Coating)/ Overall % of Final Tablet Camposition |
|---|---|
| Polyvinyl, Alcohol | 11.6 mg (2.88%) |
| Bupropion, HBr (API) | 348 mg (86.29%) |
| Purified Water, USP | 0 |
| Glyceryl Behenate, NF | 11.6 mg (2.88%) |
| Ethylcellulose 100, NF | 16.406 mg (4.07%) |
| Povidone USP | 10.159 mg (2.52%) |
| Polyethylene Glycol 4000, NF | 3.657 mg (0.91%) |
| Dibutyl Sebacate, NF | 1.778 mg (0.44%) |
| Dehydrated Alcohol, 200 proof, USP | 0 |
| Ethyl Alcohol, 95% USP | 0 |
| Camauba Wax, NF | 0.058 mg/tablet (0.01%) (based on 172,413 tablets for coating pan-load) |
| Opacode Black Ink S-1-8090 or S-1-17823 | Trace Amounts |
| Isopropyl Alcohol | 0 |
| Final Printed Tablet Weight (mg) | 403.258 mg/tablet (100%) |

NOTE:
Bupropion HBr XL Tablets, 174 mg and 348 mg have the same tablet core formulation and coating formulation (composition). The only difference in percentage of material per tablet is due to the differences in core tablet weight and coating weight gain. Total quantity of Carnauba Wax applied to tablets will vary based on coating pan-load. The percent (%) Composition of each ingredient in final tablet formulation, is based on final target coating weight gain and target amount of Carnauba Wax for calculation.

TABLE 102

BUPROPION HBr XL TABLETS, 174 mg TABLET COMPOSITION (mg/tablet)
*Table 1: Core Tablets*

| Item # | Material | Qty. Required (kg) | % of Tablet Core Formulation | Tablet 174 mg Strength Target Weight 185.6 mg/tablet |
|---|---|---|---|---|
| RS0009 | Polyvinyl Alcohol | 2.25 kg dispensed 2.00 kg used | 3.125% | 5.8 mg/tablet |
| RA0057 | Bupropion HBr | 60.00 | 93.750% | 174 mg/tablet |
| RE0200 | Glyceryl Behenate, NF | 2.00 | 3.125% | 5.8 mg/tablet |
| RS0003 | *Purified Water, USP | 47.75 | 0 | 0 |
| | Theoretical Batch Size: kg | 64.00 | 100% | 185.6 mg/tablet |

*Evaporated during granulating process and not included in tablet core composition.

TABLE 103

*Table 2: Coated/Printed Tablets*
*174 mg XL Coated/Printed Tablets - Pivotal Coating Formulation/Batch Size*

| Item # | Material | Qty. Required (kg) | % of Batch | Applied Solids Mg/tablet Target Weight Gain: 30 mg (Range: 28–32 mg/tablet) |
|---|---|---|---|---|
| RE0233 | Ethylcellulose 100, NF | 3.230 | 4.61% | 15.381 mg |
| RE0067 | Povidone USP | 2.000 | 2.86% | 9.524 mg |
| RE0331 | Polyethylene Glycol 4000, NF | 0.720 | 1.03% | 3.428 mg |
| RE0103 | Dibutyl Sebacate, NF | 0.350 | 0.50% | 1.667 mg |
| *RS0010 | *Dehydrated Alcohol, 200 proof, USP | 57.300 | 81.86% | 0 |
| RS0006 | *Ethyl Alcohol, 95%, USP | 6.400 | 9.14% | 0 |
| | COATING SOLUTION TOTAL (kg) | 70 kg | 100% | 30 mg/tablet |
| *RE0223 | **Carnauba Wax, NF | 0.010 kg | N/A | Trance Amounts |
| RE0234 | Opacode Block Ink S-1-8090 or S-1-17823 | 1.00 | 50% | Trace Amounts to brand tablets with logo on one side BR 174 |
| ***RS0001 | ***Isopropyl Alcohol | 1.00 | 50% | Used for cleaning design and transfer rolls only |

Note:
Where applicable, percentages and mg/tablet totals have been rounded to two decimal places.
*Evaporated during coating process.
**Carnauba Wax not included as part of coating solution formulation, trace amounts applied after completion of the coating process.
***Isopropyl Alcohol used for cleaning only. Only trace amounts of black ink to brand tablets with specific logo is applied to one side of tablet. Weight of this material applied to tablet cannot be measured.

TABLE 104

*Table 3: BUPROPION HBr XL TABLETS, 174 mg: OVERALL FINAL PRINTED TABLET COMPOSITION/WEIGHT*

| Material | 174 mg (+30 mg Coating)/ Overall % of Final Tablet Composition |
|---|---|
| Polyvinyl Alcohol | 5.8 mg (2.69%) |
| Bupropion HBr (API) | 174 mg (80.68%) |
| Purified Water, USP | 0 |
| Glyceryl Behenate, NF | 5.8 mg (2.69%) |
| Ethylcellulose 100, NF | 15.381 mg (7.13%) |
| Povidone, USP | 9.524 mg (4.42%) |
| Polyethylene Glycol 4000, NF | 3.428 mg (1.59%) |
| Dibutyl Sebacate, NF | 1.667 mg (0.77%) |

TABLE 104-continued

Table 3: BUPROPION HBr XL TABLETS, 174 mg:
OVERALL FINAL PRINTED TABLET COMPOSITION/WEIGHT

| Material | 174 mg (+30 mg Coating)/ Overall % of Final Tablet Composition |
|---|---|
| Dehydrated Alcohol, 200 proof, USP | 0 |
| Ethyl Alcohol, 95%, USP | 0 |
| Carnauba Wax, NF | 0.058 mg/tablet (0.03%) (based on 172,413 tablets for coating pan-load) |
| Opacode Black Ink S-1-8090 or S-1-17823 | Trace Amounts |
| Isopropyl Alcohol | 0 |
| Final Printed Tablet Weight (mg) | 215.658 mg/tablet (100%) |

NOTE:
Bupropion HBr XL Tablets, 174 mg and 348 mg have the same tablet core formulation and coating formulation (composition). The only difference in percentage of material per tablet is due to the differences in core tablet weight and coating weight gain. Total quantity of Carnauba Wax applied to tablets will vary based on coating pan-load. The percent (%) Composition of each ingredient in final tablet formulation, is based on final target coating weight gain and target amount of Carnauba Wax for calculation.

TABLE 105(1)

ACCELERATED STABILITY
ACCELERATED STABILITY PROGRAM

| Product: Bupropion.HBr FV0092 Analysis | Batch No.: D00894 Specification | Start date: 20/12/04 time 0 | Temperature: 40° C. ± 2° C. R.H.: 75% ± 5% 3 month 6 months |
|---|---|---|---|
| Description | white or almost white crystalline powder | conform | conform conform |
| Identification | IR, HPLC (positive) | positive | positive positive |
| Water content (K.F.) | NMT 0.5% | 0.05 | 0.07 0.08 |
| Chromatographic purity A) (HPLC) | 1) NMT 0.1% 2) NMT 0.1% 3) NMT 0.1% | 1) n.d. 2) n.d. 3) n.q. | 1) n.q. 1) 0.05 2) n.d. 2) n.d. 3) n.q. 3) n.q. |
| Chromatographic purity B) (HPLC) | 4) NMT 0.1% 5) NMT 0.1% 6) NMT 0.3% | 4) 0.04 5) 0.04 6) 0.04 | 4) 0.03 4) 0.04 5) 0.04 5) n.q. 6) 0.06 6) 0.02 |
| Chromatographic purity (HPLC: A + B) | Total impurities NMT 0.5% | 0.1 | 0.1 0.1 |
| Assay (HPLC) | 98.0–102.0% on d.b. | 99.6 | 99.6 99.7 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 105(2)

ACCELERATED STABILITY PROGRAM

| Product: Bupropion.HBr FV0092 Analysis | Batch No.: D00895 Specification | Start date: 20/12/04 time 0 | Temperature: 40° C. ± 2° C. R.H.: 75% ± 5% 3 month 6 months |
|---|---|---|---|
| Description | white or almost white crystalline powder | conform | conform conform |
| Identification | IR, HPLC (positive) | positive | positive positive |
| Water content (K.F.) | NMT 0.5% | 0.04 | 0.07 0.07 |
| Chromatographic purity A) (HPLC) | 1) NMT 0.1% 2) NMT 0.1% 3) NMT 0.1% | 1) n.d. 2) n.d. 3) n.q. | 1) n.q. 1) 0.05 2) n.d. 2) n.d. 3) 0.05 3) n.q. |
| Chromatographic purity B) (HPLC) | 4) NMT 0.1% 5) NMT 0.1% 6) NMT 0.3% | 4) 0.04 5) 0.04 6) 0.04 | 4) 0.03 4) 0.04 5) 0.04 5) n.q. 6) 0.05 6) 0.02 |
| Chromatographic purity (HPLC: A + B) | Total impurities NMT 0.5% | 0.1 | 0.1 0.1 |
| Assay (HPLC) | 98.0–102.0% on d.b. | 99.2 | 100.7 99.7 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each); 6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 105(3)

ACCELERATED STABILITY PROGRAM

| Product: Bupropion.HBr FV0092 Analysis | Batch No.: D00896 Specification | Start date: 20/12/04 time 0 | Temperature: 40° C. ± 2° C. R.H.: 75% ± 5% 3 month 6 months |
|---|---|---|---|
| Description | white or almost white crystalline powder | conform | conform conform |
| Identification | IR, HPLC (positive) | positive | positive positive |
| Water content (K.F.) | NMT 0.5% | 0.06 | 0.11 0.04 |
| Chromatographic purity A) (HPLC) | 1) NMT 0.1% 2) NMT 0.1% 3) NMT 0.1% | 1) n.d. 2) n.d. 3) n.q. | 1) n.q. 1) 0.05 2) n.d. 2) n.d. 3) n.q. 3) n.q. |
| Chromatographic purity B) (HPLC) | 4) NMT 0.1% 5) NMT 0.1% 6) NMT 0.3% | 4) 0.04 5) 0.05 6) 0.05 | 4) 0.03 4) 0.04 5) 0.04 5) n.q. 6) 0.05 6) n.q. |
| Chromatographic | Total impurities | 0.1 | 0.1 0.1 |

TABLE 105(3)-continued

ACCELERATED STABILITY PROGRAM

Product: Bupropion.HBr FV0092  
Batch No.: D00896  
Start date: 20/12/04  
Temperature: 40° C. ± 2° C.  
R.H.: 75% ± 5%

| Analysis | Specification | time 0 | 3 month | 6 months |
|---|---|---|---|---|
| purity (HPLC: A + B) | NMT 0.5% | | | |
| Assay (HPLC) | 98.0–102.0% on d.b. | 99.3 | 100.0 | 100.4 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 105(4)

SHELF LIFE
SHELF LIFE STABILITY PROGRAM

Product: Bupropion.HBr FV0092  
Batch No.: D00894  
Start date: 20/12/04  
Temperature: 25° C. ± 2° C.;  
Relative Humidity: 60% ± 5%

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.05 | 0.05 | 0.06 | 0.05 | 0.05 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.05 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0–102.0% on d.b. | 99.6 | 99.4 | 100.2 | 99.5 | 99.6 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 105(5)

SHELF LIFE STABILITY PROGRAM

Product: Bupropion.HBr FV0092  Batch No.: D00895  Start date: 20/12/04  Temperature: 25° C. ± 2° C.; Relative Humidity: 60% ± 5%

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.04 | 0.04 | 0.05 | 0.05 | 0.04 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.07 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0–102.0% on d.b. | 99.2 | 99.5 | 100.1 | 99.4 | 99.4 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 105(6)

SHELF LIFE STABILITY PROGRAM

Product: Bupropion.HBr FV0092  Batch No.: D00896  Start date: 20/12/04  Temperature: 25° C. ± 2° C.; Relative Humidity: 60% ± 5%

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.06 | 0.04 | 0.04 | 0.04 | 0.03 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) n.q. | 3) | 3) | 3) |
| Chromatographic purity B) (HPLC) | 4) NMT 0.1% | 4) 0.04 | 4) 0.03 | 4) 0.04 | 4) n.d. | 4) 0.05 | 4) | 4) | 4) |
| | 5) NMT 0.1% | 5) 0.05 | 5) 0.04 | 5) n.q. | 5) n.q. | 5) 0.07 | 5) | 5) | 5) |
| | 6) NMT 0.3% | 6) 0.05 | 6) 0.05 | 6) n.q. | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.1 | | | |
| Assay (HPLC) | 98.0–102.0% on d.b. | 99.3 | 99.4 | 100.5 | 99.4 | 100.3 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

TABLE 105(6)-continued

SHELF LIFE STABILITY PROGRAM

Product: Bupropion.HBr  
FV0092  Batch No.: D00896

Start date: 20/12/04

Temperature: 25° C. ± 2° C.;  
Relative Humidity: 60% ± 5%

| Analysis | Specification | time 0 | 3 months | 6 months | 9 months | 12 months | 18 months | 24 months | 36 months |
|---|---|---|---|---|---|---|---|---|---|

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

We claim:

1. A modified release bupropion hydrobromide tablet suitable for oral administration having enhanced stability comprising:
   (a) a core comprising (i) a therapeutically effective amount of a bupropion hydrobromide salt, (ii) a binder, and (iii) a lubricant;
   (b) a controlled release polymeric coat which surrounds said core; and
   (c) a 3-CBZ degradation product;
   wherein said modified release bupropion hydrobromide tablet provides for the controlled release of said bupropion hydrobromide salt from said modified release bupropion hydrobromide tablet over a period of about 24 hours and has enhanced stability such that:
   (1) at about 13 days after formulation of said modified release bupropion hydrobromide tablet, said modified release bupropion hydrobromide tablet contains an increase in the amount of said 3-CBZ degradation product of no more than about 0.070 expressed in percent increase of 3-CBZ degradation product relative to the amount of 3-CBZ degradation product present in said modified release bupropion hydrobromide tablet at said tablet formulation, and
   (2) at about 20 days after formulation of said modified release bupropion hydrobrornide tablet, said modified release bupropion hydrobrornide tablet contains an increase in the amount of said 3-CBZ degradation product of no more than about 0.098 expressed in the percent increase of 3-CBZ degradation product relative to the amount of 3-CBZ degradation product present in said modified release bupropion hydrobromide tablet at said tablet formulation; and
   wherein said increase in the amount of said 3-CBZ degradation product in said modifted release bupropion hydrobrornide tablet is less than respective percent increase of 3-CBZ degradation product that is present in an otherwise identical modified release tablet comprising an equivalent molar amount of bupropion hydrochloride at about 13 days and at about 20 days after formulation of said identical modified release bupropion hydrochloride tablet when the modified release bupropion hydrochloride tablet and said modified release bupropion hydrobromide tablet are each stored for at least about 13 days or at least about 20 days, respectively, at about 40 degrees C. and at about 75% relative humidity after tablet formulation.

2. The modified release bupropion hydrobromide tablet of claim 1, wherein said bupropion hydrobromide salt is present in an amount ranging from between about 40% to about 99% dry weight of said core, said binder is present in an amount ranging from between about 0.5% to about 25% dry weight of said core, and said lubricant is present in an amount ranging from between about 1% to about 6% dry weight of said core.

3. The modified release bupropion hydrobrornide tablet of claim 1, wherein the increase in the amount of said 3-CBZ degradation product contained in said modified release bupropion hydrobromide tablet after said modified release bupropion hydrobromide tablet formulation is stored for about 13 days is no more than about 0.035 percent and wherein the increase in the amount of said 3-CBZ degradation product contained in said modified release bupropion hydrobromide tablet after said modified release bupropion hydrobrornide tablet formulation is stored for about 20 days is no more than about 0.046 percent, and wherein said respective percent increases in 3-CBZ degradation product at about 13 days and at about 20 days in said modified release bupropion hydrobromide tablet are less than the respective percent increases in 3-CBZ degradation product in the otherwise identical modified release bupropion hydrochloride tablet after storage of the modified release bupropion hydrochloride tablet for about 13 and 20 days after formulation when each are stored after tablet formulation at about 40 degrees C. and at about 75% relative humidity.

4. A method of treating a depressive condition in a subject in need of bupropion administration comprising administering once daily to said subject a stable bupropion hydrobromide release tablet according to claim 1.

5. A method of treating a depressive condition in a subject in need of bupropion administration comprising administering once daily to said subject a stable bupropion hydrobromide release tablet according to claim 2.

6. A method of treating a depressive condition in a subject in need of bupropion administration comprising administering once daily to said subject a stable bupropion hydrobromide release tablet according to claim 3.

7. A method of treating a subject diagnosed with a depressive condition in need of bupropion administration comprising administering the stable bupropion hydrobromide modified release tablet according to claim 1.

8. A method of treating a subject diagnosed with a depressive condition in need of bupropion administration comprising administering the stable bupropion hydrobromide modified release tablet according to claim 3.

9. A method of treating a depressive condition in a subject in need of bupropion administration comprising administering once daily to said subject the stable bupropion hydrobromide modified release tablet according to claim 3.

* * * * *

UNITED STATES PATENT AND TRADEMARK OFFICE
CERTIFICATE OF CORRECTION

| | |
|---|---|
| PATENT NO. | : 7,241,805 B2 |
| APPLICATION NO. | : 11/475252 |
| DATED | : July 23, 2007 |
| INVENTOR(S) | : Werner Oberegger et al. |

It is certified that error appears in the above-identified patent and that said Letters Patent is hereby corrected as shown below:

On the title page
- (73) Assignee: Insert --Biovail Laboratories International S.R.L., Barbados, West Indies--, Delete "Biovail Laboratories, Inc., Mississauga, Ontario (CA)"

Signed and Sealed this

Twenty-first Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,241,805 B2 Page 1 of 1
APPLICATION NO. : 11/475252
DATED : July 10, 2007
INVENTOR(S) : Werner Oberegger et al.

It is certified that error appears in the above-identified patent and that said Letters Patent is hereby corrected as shown below:

On the title page
- (73) Assignee: Insert --Biovail Laboratories International S.R.L., Barbados, West Indies--, Delete "Biovail Laboratories, Inc., Mississauga, Ontario (CA)"

This certificate supersedes Certificate of Correction issued August 21, 2007.

Signed and Sealed this

Eighteenth Day of September, 2007

JON W. DUDAS
*Director of the United States Patent and Trademark Office*